United States Patent
Gyorkos et al.

(10) Patent No.: US 7,897,607 B2
(45) Date of Patent: Mar. 1, 2011

(54) CYCLIC COMPOUNDS

(75) Inventors: Albert Charles Gyorkos, Westminster, CO (US); Christopher Peter Corrette, Boulder, CO (US); Suk Young Cho, Boulder, CO (US); Timothy Mark Turner, Boulder, CO (US); Kazuyoshi Aso, Osaka (JP); Masakuni Kori, Osaka (JP); Michiyo Mochizuki, Osaka (JP); Kevin Ronald Condroski, Boulder, CO (US); Christopher Stephen Siedem, Boulder, CO (US); Steven Armen Boyd, Boulder, CO (US)

(73) Assignee: Takeda Pharmaceutical Company Limited, Osaka (JP)

( * ) Notice: Subject to any disclaimer, the term of this patent is extended or adjusted under 35 U.S.C. 154(b) by 472 days.

(21) Appl. No.: 10/593,891

(22) PCT Filed: Apr. 6, 2005

(86) PCT No.: PCT/US2005/013583
§ 371 (c)(1),
(2), (4) Date: Apr. 5, 2007

(87) PCT Pub. No.: WO2005/099688
PCT Pub. Date: Oct. 27, 2005

(65) Prior Publication Data
US 2007/0179165 A1 Aug. 2, 2007

(51) Int. Cl.
*C07D 487/04* (2006.01)
*A61K 31/519* (2006.01)

(52) U.S. Cl. .................... 514/265.1; 544/280
(58) Field of Classification Search ............... 544/280; 514/265.1
See application file for complete search history.

(56) References Cited

U.S. PATENT DOCUMENTS

| 6,653,300 | B2 | 11/2003 | Bebbington et al. |
| 2004/0209917 | A1 | 10/2004 | Hartz et al. |
| 2004/0229891 | A1 | 11/2004 | Hartz et al. |

FOREIGN PATENT DOCUMENTS

| EP | 0 164 204 | 12/1985 |
| EP | 0 456 323 | 11/1991 |
| EP | 0 685 467 | 12/1995 |
| EP | 1 300 396 | 4/2003 |
| EP | 1 439 175 | 7/2004 |
| EP | 1 439 176 | 7/2004 |
| WO | 98/24782 | 6/1998 |
| WO | 99/54311 | 10/1999 |
| WO | 03/011293 | 2/2003 |
| WO | 03/035639 | 5/2003 |
| WO | 03/035640 | 5/2003 |
| WO | 03/047577 | 6/2003 |
| WO | 03/076414 | 9/2003 |
| WO | 2004/029204 | 4/2004 |

OTHER PUBLICATIONS

Wolff, Manfred E. "Burger's Medicinal Chemistry and Drug Discovery, 5ed, vol. 1" John Wiley & Sons, 1995, pp. 975-977.*
Banker, G.S. et al, "Modern Pharmaceutics, 3ed." Marcel Dekker, New York, 1996, pp. 451 and 596.*
Secrist et al. Journal of Organic Chemistry (1978), 43(20), 3937-41.*
A. Sutherland et al., "Versatile Synthesis of 3,5-Disubstituted 2-Fluoropyridines and 2-Pyridones", J. Org. Chem., vol. 68, pp. 3352-3355, 2003.

* cited by examiner

*Primary Examiner*—Kahsay T Habte
(74) *Attorney, Agent, or Firm*—Wenderoth, Lind & Ponack, LLP.

(57) ABSTRACT

There is provided a CRF receptor antagonist comprising a compound of the formula (I):

A-W—Ar   (I)

wherein, A is a group represented by the formula (A1) or (A2):

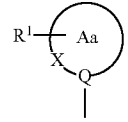

(A1)

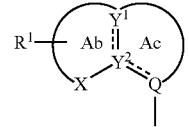

(A2)

(wherein, ring Aa is a 5- or 6-membered ring which may be further substituted; ring Ab is a 5- or 6-membered ring which may be further substituted; ring Ac is a 5- or 6-membered ring which may be substituted; $R^1$ is optionally substituted alkyl, substituted amino, substituted hydroxy, etc.; X is carbonyl, —O—, —S—, etc.; $Y^1$, $Y^2$ and Q are independently optionally substituted carbon or nitrogen; ⚌ is a single or double bond);
W is a bond, optionally substituted methylene, optionally substituted imino, —O—, —S—, etc.; Ar is optionally substituted aryl or optionally substituted heteroaryl; or a salt thereof or a prodrug thereof.

10 Claims, No Drawings

CYCLIC COMPOUNDS

This application is the National Phase filing of International Patent Application No. PCT/JP2005/13583, filed Apr. 6, 2005.

TECHNICAL FIELD

The present invention relates to novel cyclic compounds having CRF (corticotropin releasing factor) antagonistic activity and pharmaceutical compositions containing them.

BACKGROUND ART

Corticotropin-releasing factor (hereinafter, abbreviated as "CRF") is a neuropeptide composed of 41 amino acids that serves as the primary hypothalamic factor stimulating the release of adrenocorticotropic hormone (ACTH) from the pituitary gland. First, the structure thereof was determined from sheep hypothalamus and, thereafter, the presence thereof was confirmed also in rat and human, and the structure thereof was determined [Science, 213, 1394(1981); Proc. Natl. Acad. Sci USA, 80, 4851(1983); EMBO J. 5, 775(1983)]. The amino acid sequence is the same in human and rat, but differed in 7 amino acids in ovine. CRF is synthesized as a carboxy-terminal of prepro CRF, cut and secreted. The CRF peptide and a mRNA thereof are present at the largest amount in the hypothalamus and pituitary gland, and are widely distributed in the brain such as cerebral cortex, cerebellum, hippocampus and corpus amygdaloideum. In addition, in peripheral tissues, the existence has been confirmed in placenta, adrenal gland, lung, liver, pancreas, skin and digestive tract [J. Clin. Endocrinol. Metab., 65, 176(1987); J. Clin. Endocrinol. Metab., 67, 768(1988); Regul. Pept., 18, 173(1987), Peptides, 5 (Suppl. 1), 71(1984)]. CRF acts via two receptor subtypes, CRF1 and CRF2, which are 7-transmembrane G protein-coupled receptors. It is reported that CRF1 is present mainly in the cerebral cortex, cerebellum, olfactory bulb, pituitary gland and tonsil nucleus. On the other hand, the CRF2 receptor has three isoforms, CRF2α, CRF2β and CRF2γ. It was made clear that the CRF2α receptor is distributed mainly in the hypothalamus, septal area and choroids plexus, and the CRF2β receptor is present mainly in peripheral tissues such as skeletal muscle and is distributed in blood vessels in the brain [J. Neurosci. 15, 6340(1995); Endocrinology, 137, 72(1996); Biochim. Biophys. Acta, 1352, 129(1997); Pharmacological reviews, 55, 21 (2003)]. Since each receptor differs in distribution in a living body, it is suggested that a role thereof is also different [Trends. Pharmacol. Sci. 23, 71(2002)].

As a physiological action of CRF, the action on the endocrine system is known in which CRF is produced and secreted in response to stress in the hypothalamus and acts on the pituitary gland to promote the release of ACTH [Recent Prog. Horm. Res., 39, 245(1983)]. In addition to the action on the endocrine system, CRF acts as a neurotransmitter or a neuroregulating factor in the brain, and integrates electrophysiology, autonomic nerve and conducts to stress [Brain Res. Rev., 15, 71(1990); Pharmacol. Rev., 43, 425(1991)]. When CRF is administered in a cerebral ventricle of an experimental animal such as a rat, anxiety conduct is observed, and much more anxiety conduct is observed in a CRF-overexpressing mouse as compared with a normal animal [Brain Res., 574, 70(1992); J. Neurosci., 10, 176(1992); J. Neurosci., 14, 2579 (1994)]. In addition, α-helical CRF(9-41) of a peptidergic CRF receptor antagonist exerts an anti-anxiety action in an animal model [Brain Res., 509, 80(1990); J. Neurosci., 14, 2579(1994)]. Blood pressure, heart rate and body temperature of a rat are increased by stress or CRF administration, but the α-helical CRF(9-41) of a peptidergic CRF antagonist inhibits the increase in blood pressure, heart rate and body temperature due to stress [J. Physiol., 460, 221(1993)]. The α-helical CRF(9-41) of a peptidergic CRF receptor antagonist inhibits abnormal conducts due to withdrawal of a dependent drug such as alcohol and cocaine [Psychopharmacology, 103, 227(1991); Pharmacol. Rev. 53, 209(2001)]. In addition, it has been reported that learning and memory are promoted by CRF administration in a rat [Nature, 375, 284(1995); Neuroendocrinology, 57, 1071(1993); Eur. J. Pharmacol., 405, 225(2000)].

Since CRF is associated with stress response in a living body, there are clinical reports regarding stress-associated depression or anxiety. The CRF concentration in cerebrospinal fluid of a depressed patient is higher as compared with that of a normal person [Am. J. Psychiatry, 144, 873(1987)], and the mRNA level of CRF in hypothalamus of a depressed patient is increased as compared with that of a normal person [Am. J. Psychiatry, 152, 1372(1995)]. The CRF binding site in the cerebral cortex of a patient who committed suicide as a result of depression was decreased [Arch. Gen. Psychiatry, 45, 577(1988)]. The increase in the plasma ACTH concentration due to CRF administration is small in a depressed patient [N. Engl. J. Med., 314, 1329 (1986)]. In a patient with panic disorder, the increase of plasma ACTH concentration due to CRF administration is small [Am. J. Psychiatry, 143, 896 (1986)]. The CRF concentration in the cerebrospinal fluid of a patient with anxiety induced by stress such as obsessive-compulsive neurosis, post-psychic trauma stress disorder, Tourette's syndrome and the like is higher as compared with that of a normal person [Arch. Gen. Psychiatry, 51, 794(1994); Am. J. Psychiatry, 154, 624(1997); Biol. Psychiatry, 39, 776(1996)]. The CRF concentration in the cerebrospinal fluid of schizophrenics is higher as compared with that of a normal person [Brain Res., 437, 355(1987); Neurology, 37, 905(1987)]. Thus, it has been reported that there is abnormality in the living body response system via CRF in stress-associated mental disease.

The action of CRF on the endocrine system can be presumed by the characteristics of CRF gene-introduced animal and actions in an experimental animal. In a CRF-overexpressing mouse, excessive secretions of ACTH and adrenal cortex steroid occur, and abnormalities analogous to Cushing's syndrome such as atrophy of muscle, alopecia, infertility and the like are observed [Endocrinology, 130, 3378(1992)]. CRF inhibits ingestion in an experimental animal such as a rat [Life Sci., 31, 363 (1982); Neuropharmacology, 22, 337(1983)]. In addition, α-helical CRF(9-41) of a peptidergic CRF antagonist inhibited decrease of ingestion due to stress loading in an experimental model [Brain Res. Bull., 17, 285(1986)]. CRF inhibited weight gain in a hereditary obesity animal [Physiol. Behav., 45, 565(1989)]. In a nervous orexia inactivity patient, the increase of ACTH in plasma upon CRF administration is small [J. Clin. Endocrinol. Metab., 62, 319(1986)]. It has been suggested that a low CRF value is associated with obesity syndrome [Endocrinology, 130, 1931(1992)]. There has been suggested a possibility that ingestion inhibition and weight loss action of a serotonin reuptake inhibiting agent are exerted via release of CRF [Pharmacol. Rev., 43, 425(1991)].

CRF is centrally or peripherally associated with the digestive tract movement involved in stress or inflammation [Am. J. Physiol. Gastrointest. Liver Physiol. 280, G315(2001)]. CRF acts centrally or peripherally, weakens the shrinkability of the stomach, and decreases the gastric excreting ability [Regulatory Peptides, 21, 173(1988); Am. J. Physiol., 253, G241(1987)]. In addition, α-helical CRF (9-41) of a peptidergic CRF antagonist has a restoring action for hypofunction of the stomach by abdominal operation [Am. J. Physiol., 258, G152(1990)]. CRF inhibits secretion of a bicarbonate ion in the stomach, decreases gastric acid secretion and inhibits ulcer due to cold restriction stress [Am. J. Physiol., 258, G152(1990)]. Furthermore, α-helical CRF (9-41) of a peptidergic CRF antagonist shows the inhibitory action on gastric acid secretion decrease, gastric excretion decrease, small intestinal transport decrease and large intestinal transport enhancement due to restriction stress [Gastroenterology, 95, 1510(1988)]. In a healthy person, mental stress increases gas and abdominal pain due to anxiety and intestine dilation, and CRF decreases the threshold of discomfort [Gastroenterology, 109, 1772(1995); Neurogastroenterol. Mot., 8, 9[1996]. In a irritable bowel syndrome patient, large intestinal movement is excessively enhanced by CRF administration as compared with a healthy person [Gut, 42, 845(1998)].

It has been reported from studies on experimental animals and clinical studies that CRF is induced by inflammation and is involved in a inflammatory reaction. In an inflammatory site of an experimental animal and in the joint fluid of a rheumatoid arthritis patient, production of CRF is topically increased [Science, 254, 421(1991); J. Clin. Invest., 90, 2555 (1992); J. Immunol., 151, 1587(1993)]. CRF induces degranulation of mast cells and enhances the blood vessel permeability [Endocrinology, 139, 403(1998); J. Pharmacol. Exp. Ther., 288, 1349(1999)]. CRF can be detected also in a thyroid gland of autoimmune thyroiditis patient [Am. J. Pathol. 145, 1159(1994)]. When CRF is administered to an experimental autoimmune cerebrospinal meningitis rat, the progression of symptoms such as paralysis was remarkably inhibited [J. Immunil., 158, 5751(1997)]. In a rat, the immune response activity such as T-lymphocyte proliferation and the natural killer cell activity is reduced by CRF administration or stress loading [Endocrinology, 128, 1329(1991)].

From the above-mentioned reports, it is expected that a CRF receptor antagonistic compound would exert an excellent effect for treating or preventing various diseases in which CRF is involved.

As a CRF antagonist, for example, peptide CRF receptor antagonists are reported in which part of the amino acid sequence of CRF or associated peptides of a human or other mammal is altered or deleted, and they are reported to show a pharmacological action such as ACTH release-inhibiting action and anti-anxiety action [Science, 224, 889(1984); J. Pharmacol. Exp. Ther., 269, 564(1994); Brain Res. Rev., 15, 71(1990)]. However, from a pharmacokinetic point of view such as chemical stability and absorbability for oral administration in a living body, bioavailability and intracerebral transferability, peptide derivatives have a low utility value as a drug.

As a cyclic compound, WO02/62795 discloses dihydropyrazolo[3,4-b]pyridine derivatives [ethyl 4-(6-chloro-2,2,4-trimethyl-3,4-dihydro-2H-1,4-benzoxazin-8-yl)-6-propyl-2,4-dihydro-1H-pyrazolo[3,4-b]pyridine-5-carboxylate, etc.: glycogen synthase kinase-3 beta (GSK-3β) inhibitor]; WO02/22074 and WO01/12607 disclose 3-aryl-4-quinolone derivatives [7-methoxy-3-(4-methoxyphenyl)-1-methyl-5-phenylquinolin-4(1H)-one, 8-methoxy-3-(4-methoxyphenyl)-1-methyl-5-phenylquinolin-4(1H)-one, etc.: prevention for post-angioplasty intraluminal restenosis, proliferation of clonogenic cells in malignant tumours]; WO99/62520 discloses 3,4-dihydro-2H-1,4-benzoxazine derivatives [4-(8-benzyl-4-methyl-3,4-dihydro-2H-1,4-benzoxazin-6-yl)-2,4-dioxobutanoic acid, etc.: treatment for HIV infection]; Bulletin des SCB (1997), 106(7-8), 467-474 discloses quinazoline derivatives [ethyl 1,7-dimethyl-4-oxo-3,5-diphenyl-1,2,3,4-tetrahydroquinazoline-6-carboxylate: synthesis]; Zhongguo Yaowu Huaxue Zazhi (1995), 5(3), 187-191 discloses 4-quinolone-3-carboxylic acid derivatives [1-cyclobutyl-6,8-difluoro-7-(4-methylpiperazin-1-yl)-4-oxo-5-phenoxy-1,4-dihydroquinoline-3-carboxylic acid: antibacterial agent]; J. Med. Chem., (1993), 36(19), 2801-9 discloses 4-quinolone-3-carboxylic acid derivatives [1-cyclopropyl-7-(2,6-dimethylpyridin-4-yl)-6,8-difluoro-4-oxo-5-(phenylthio)-1,4-dihydroquinoline-3-carboxylic acid: topoisomerase II inhibitor]; EP0343574 discloses 4-quinolone derivatives [1-ethyl-8-methoxy-5-phenylquinolin-4 (1H)-one, etc.: a cardiac]; JP-A S63-258855 discloses 4-quinolone-3-carboxylic acid derivatives [1-cyclopropyl-6,8-difluoro-7-(4-methylpiperazin-1-yl)-4-oxo-5-(phenylthio)-1,4-dihydroquinoline-3-carboxylic acid: animal drug]; EP272914 discloses benzoxazinylpyridazinone derivatives [4,6-dimethyl-8-(4-methyl-6-oxo-1,4,5,6-tetrahydropyridazin-3-yl)-2H-1,4-benzoxazin-3(4H)-one, 4,6-dimethyl-8-(6-oxo-1,4,5,6-tetrahydropyridazin-3-yl)-2H-1,4-benzoxazin-3(4H)-one, 2,2,4-trimethyl-8-(6-oxo-1,4,5,6-tetrahydropyridazin-3-yl)-2H-1,4-benzoxazin-3(4H)-one, etc.: a cardiac]; J. Med. Chem., (1972), 15(3), 237-241 discloses 4-quinolone-3-carboxylic acid derivatives [8-chloro-1-methyl-4-oxo-5-phenyl-1,4-dihydroquinoline-3-carboxylic acid: dehydrogenase inhibitor]; DE10021568 discloses pyrimidinyl phthalazinyl sulfoxide derivatives [8-[(4,6-dimethoxypyrimidin-2-yl)sulfinyl]-4-methyl-2-phenylphthalazin-1(2H)-one, etc.: agricultural chemical]; Acta. Chemica. Sloveniva (2000), 47(2), 187-203 discloses pyrazolo[3,4-d]pyrimidine derivatives [3-[(1,5-dimethyl-3-oxo-2-phenyl-2,3-dihydro-1H-pyrazol-4-yl)amino]-6-methyl-1,7-dihydro-4H-pyrazolo[3,4-d]pyrimidin-4-one: synthesis]; WO03/39131 discloses pyrazolo[4,3-d]pyrimidine derivatives [6-(4-bromophenyl)-1-(4-methoxyphenyl)-5-methyl-7-oxo-6,7-dihydro-1H-pyrazolo[4,3-d]pyrimidine-3-carbonitrile: Factor Xa inhibition]; JP-A H11-501923 discloses pyrazolo[3,4-d]pyrimidine derivatives [3,6-d]benzyl-1-cyclopentyl-1,7-dihydro-4H-pyrazolo[3,4-d]pyrimidin-4-one: c-GMP phosphodiesterase inhibition]; Bulletin de la Soc. Chim. de France (1995), 132(7), 67580 discloses pyrazolo[3,4-d]pyrimidine derivatives [methyl (6-tert-butoxy-4-oxo-1,3-diphenyl-1,4-dihydro-5H-pyrazolo[3,4-d]pyrimidin-5-yl) acetate: synthesis]; and WO98/54116 discloses pyrrolo[2,3-d]pyrimidine derivatives [1,3,6-trimethyl-5-phenyl-1H-pyrrolo[2,3-d]pyrimidine-2,4(3H,7H)-dione: cancer].

DISCLOSURE OF INVENTION

Summary of the Invention

According to the present invention, there is provided: (1) A compound represented by the formula:

A—W—Ar (I)

wherein, A is a group represented by the formula (A1) or (A2):

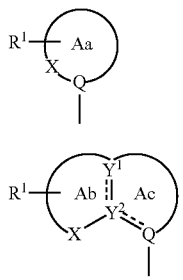

(A1)

(A2)

wherein, ring Aa is a 5- or 6-membered ring which may have one or two further heteroatoms selected from oxygen, sulfur and nitrogen at a position other than Q and X, and may be further substituted with one or more substituents in addition to $R^1$;

ring Ab is a 5- or 6-membered ring which may have one or two further heteroatoms selected from oxygen, sulfur and nitrogen at a position other than $Y^1$, $Y^2$ and X, and may be further substituted with one or more substituents in addition to $R^1$;

ring Ac is a 5- or 6-membered ring which may have one or two further heteroatoms selected from oxygen, sulfur and nitrogen at a position other than $Y^1$, $Y^2$ and Q, and may be substituted with one or more substituents;

$R^1$ is an optionally substituted hydrocarbyl, a substituted amino, an optionally substituted cyclic amino, a substituted hydroxy, a substituted sulfanyl, an optionally substituted sulfinyl, or an optionally substituted sulfonyl;

X is carbonyl, —O—, —S—, —SO—, or —$SO_2$—;

$Y^1$, $Y^2$ and Q are independently optionally substituted carbon or nitrogen;

⋯ is a single or double bond;

W is a bond, an optionally substituted methylene, an optionally substituted ethylene, an optionally substituted imino, —O—, —S—, —SO—, or —$SO_2$—;

Ar is an optionally substituted aryl or an optionally substituted heteroaryl;

provided that when the group represented by the formula (A2) is a group represented by the formula:

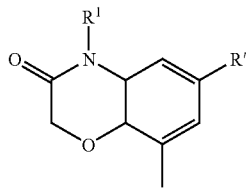

wherein R' is hydrogen, chloro or an optionally substituted alkoxy and $R^1$ is as defined above; and W is a bond, then Ar is not thiazolyl substituted with one or two substituents or condensed with dihydroimidazole;

and excluding the following compounds:

(i) a compound represented by the formula:

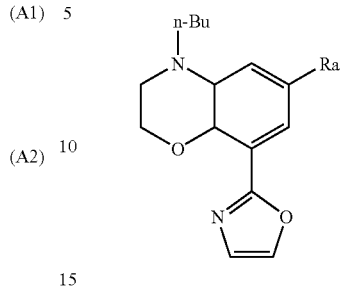

wherein Ra is a substituted carbamoyl, (ii) a compound represented by the formula:

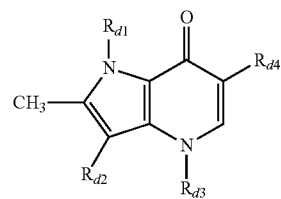

wherein $R_{d1}$ and $R_{d3}$ is each hydrocarbyl, $R_{d2}$ and $R_{d4}$ is each carboxy optionally substituted with hydrocarbyl, (iii) a compound represented by the formula:

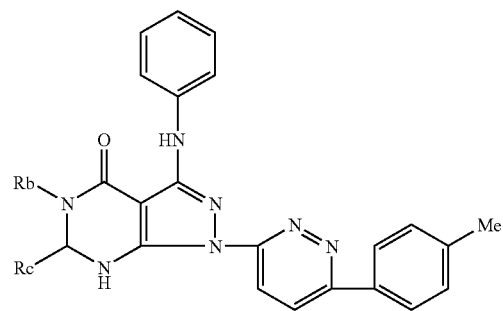

wherein Rb is hydrogen, amino or phenyl, Rc is $C_{1-4}$ alkyl, a substituted phenyl or an optionally substituted heteroaryl, (iv) ethyl 4-(6-chloro-2,2,4-trimethyl-3,4-dihydro-2H-1,4-benzoxazin-8-yl)-6-propyl-2,4-dihydro-1H-pyrazolo[3,4-b]pyridine-5-carboxylate, 7-methoxy-3-(4-methoxyphenyl)-1-methyl-5-phenylquinolin-4(1H)-one, 8-methoxy-3-(4-methoxyphenyl)-1-methyl-5-phenylquinolin-4(1H)-one, 4-(8-benzyl-4-methyl-3,4-dihydro-2H-1,4-benzoxazin-6-yl)-2,4-dioxobutanoic acid, ethyl 1,7-dimethyl-4-oxo-3,5-diphenyl-1,2,3,4-tetrahydroquinazoline-6-carboxylate, 1-cyclobutyl-6,8-difluoro-7-(4-methylpiperazin-1-yl)-4-oxo-5-phenoxy-1,4-dihydroquinoline-3-carboxylic acid, 1-cyclopropyl-7-(2,6-dimethylpyridin-4-yl)-6,8-difluoro-4-oxo-5-(phenylthio)-1,4-dihydroquinoline-3-carboxylic acid, 1-ethyl-8-methoxy-5-phenylquinolin-4(1H)-one, 1-cyclopropyl-6,8-difluoro-7-(4-methylpiperazin-1-yl)-4-oxo-5-(phenylthio)-1,4-dihydroquinoline-3-carboxylic acid, 4,6-dimethyl-8-(4-methyl-6-oxo-1,4,5,6-tetrahydropyridazin-3- yl)-2H-1,4-benzoxazin-3(4H)-one, 4,6-dimethyl-8-(6-oxo-1,4,5,6-tetrahydropyridazin-3-yl)-2H-1,4-benzoxazin-3(4H)-one, 2,2,4-trimethyl-8-(6-oxo-1,4,5,6-tetrahydropyridazin-3-yl)-2H-1,4-benzoxazin-3(4H)-one, 8-chloro-1-methyl-4-oxo-5-phenyl-1,4-dihydroquinoline-3-carboxylic acid, 8-[(4,6-dimethoxypyrimidin-2-yl)sulfinyl]-4-methyl-2-phenylphthalazin-1(2H)-one, 3-[(1,5-dimethyl-3-oxo-2-phenyl-2,3-dihydro-1H-pyrazol-4-yl)amino]-6-methyl-1,7-dihydro-4H-pyrazolo[3,4-d]pyrimidin-4-one, 6-(4-bromophenyl)-1-(4-methoxyphenyl)-5-methyl-7-oxo-6,7-dihydro-1H-pyrazolo[4,3-d]pyrimidine-3-carbonitrile, 3,6-dibenzyl-1-cyclopentyl-1,7-dihydro-4H-pyrazolo[3,4-d]pyrimidin-4-one, methyl (6-tert-butoxy-4-oxo-1,3-diphenyl-1,4-dihydro-5H-pyrazolo[3,4-d]pyrimidin-5-yl)acetate, 1,3,6-trimethyl-5-phenyl-1H-pyrrolo[2,3-d]pyrimidine-2,4(3H,7H)-dione, ethyl 4-({2-[(2,2-dimethylpropanoyl)amino]-6-methyl-4-oxo-4,7-dihydro-1H-pyrrolo[2,3-d]pyrimidin-5-yl}thio)benzoate and methyl 4-{2-[2-amino-7-benzyl-3-(isopropoxymethyl)-4-oxo-4,7-dihydro-3H-pyrrolo[2,3-d]pyrimidin-5-yl]vinyl}benzoate; or a salt thereof, (2) A prodrug of the compound according to the above-mentioned (1), (3) The compound according to the above-mentioned (1) wherein A is a group represented by the formula (A1), (4) The compound according to the above-mentioned (3) wherein ring Aa is a 5- or 6-membered unsaturated nitrogen-containing heterocyclic ring which may have one or two further heteroatoms selected from oxygen, sulfur and nitrogen at a position other than Q and X, and which may be further substituted with one or more substituents in addition to $R^1$, (5) The compound according to the above-mentioned (1) wherein $R^1$ is an optionally substituted branched $C_{3-10}$ alkyl or an optionally substituted $C_{6-10}$ aryl, (6) The compound according to the above-mentioned (1) wherein $R^1$ is a substituted amino or an optionally substituted cyclic amino, (7) The compound according to the above-mentioned (3) wherein the group represented by the formula (A1) is a group represented by the formula selected from

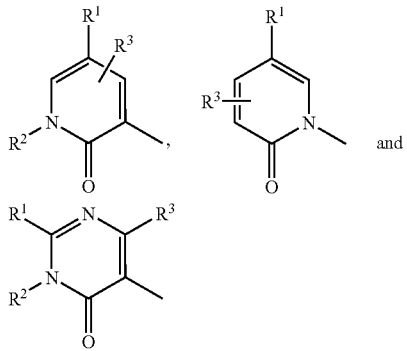

wherein, $R^1$ is as defined in the above-mentioned (1); $R^2$ is hydrogen, an optionally substituted hydrocarbyl, an optionally substituted carboxy, or an optionally substituted acyl; and $R^3$ is hydrogen, halogen, cyano, nitro, an optionally substituted hydrocarbyl, an optionally substituted amino, an optionally substituted hydroxy, an optionally substituted carboxy, an optionally substituted phosphoryl, an optionally substituted sulfanyl, an optionally substituted sulfinyl, an optionally substituted sulfonyl or acyl, (8) The compound according to the above-mentioned (1) wherein A is a group represented by the formula (A2), (9) The compound according to the above-mentioned (1) wherein ring Ab is a 5- or 6-membered saturated or unsaturated nitrogen-containing heterocyclic ring which may have one or two further heteroatoms selected from oxygen, sulfur and nitrogen at a position other than $Y^1$, $Y^2$ and X, and may be further substituted with one or more substituents in addition to $R^1$; ring Ac is a 5- or 6-membered unsaturated ring which may have one or two further heteroatoms selected from oxygen, sulfur and nitrogen at a position other than $Y^1$, $Y^2$ and Q, and may be substituted with one or more substituents,

(10) The compound according to the above-mentioned (1) wherein the group represented by the formula (A2) is a group represented by the formula selected from

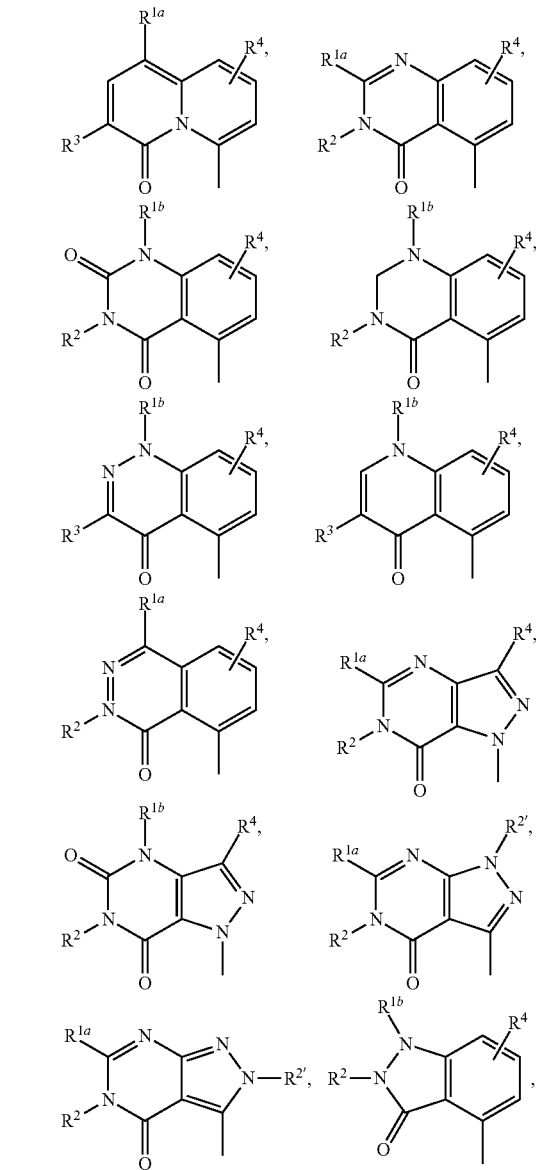

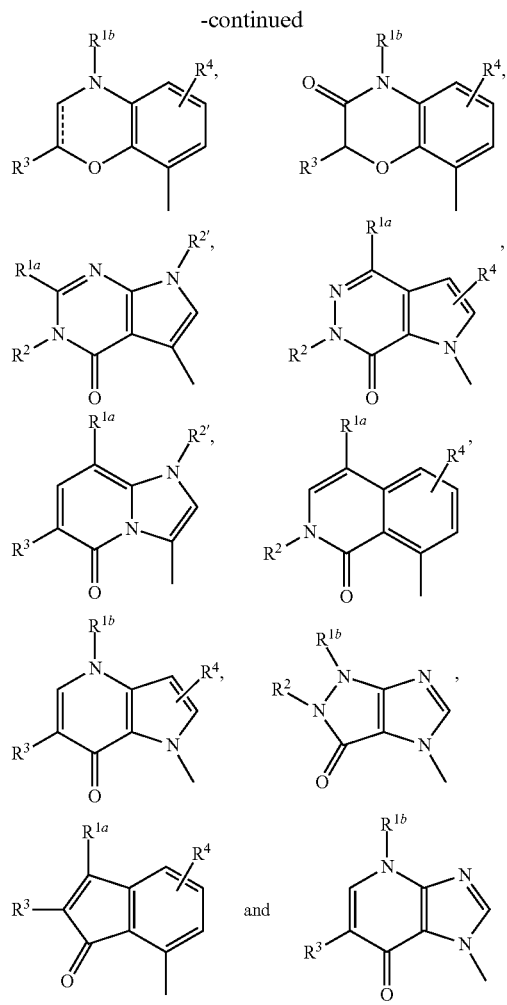

wherein R¹ᵃ is an optionally substituted hydrocarbyl, a substituted amino, an optionally substituted cyclic amino, a substituted hydroxy, an optionally substituted acyl, a substituted sulfanyl, an optionally substituted sulfinyl, or an optionally substituted sulfonyl; R¹ᵇ is an optionally substituted hydrocarbyl or an optionally substituted acyl; R² and R²' are independently hydrogen, an optionally substituted hydrocarbyl, an optionally substituted carboxy, or an optionally substituted acyl;

R³ and R⁴ are independently hydrogen, halogen, cyano, nitro, an optionally substituted hydrocarbyl, an optionally substituted amino, an optionally substituted hydroxy, an optionally substituted carboxy, an optionally substituted phosphoryl, an optionally substituted sulfanyl, an optionally substituted sulfinyl, an optionally substituted sulfonyl or acyl, and ⁞ is as defined in the above-mentioned (1),

(11) The compound according to the above-mentioned (1) wherein W is a bond, an optionally substituted methylene, an optionally substituted ethylene, or an optionally substituted imino,

(12) The compound according to the above-mentioned (1) wherein W is a bond,

(13) The compound according to the above-mentioned (1) wherein Ar is an optionally substituted phenyl, an optionally substituted pyridyl or an optionally substituted pyrimidinyl,

(14) The compound according to the above-mentioned (1) wherein X is carbonyl,

(15) The compound according to the above-mentioned (1), wherein the compound is 3-(2,4-dimethylphenyl)-6-dipropylamino-1,5-dimethyl-1,5-dihydro-4H-pyrazolo[3,4-d]pyrimidin-4-one, 5-(2,4-dimethylphenyl)-3-methyl-1-(1-propylbutyl)quinolin-4(1H)-one, 1-(dipropylamino)-6-mesityl-3-methyl-4H-quinolizin-4-one, 2-(dipropylamino)-5-mesityl-3,7-dimethyl-3,7-dihydro-4H-pyrrolo[2,3-d]pyrimidin-4-one, 1-(2,4-dimethylphenyl)-4-(1-ethylpropoxy)-6-methyl-1,6-dihydro-7H-pyrrolo[2,3-c]pyridazin-7-one, 5-mesityl-3-methyl-1-(1-propylbutyl)cinnolin-4(1H)-one, or 1-(1-ethylpropyl)-4-mesityl-2-methyl-1,2-dihydro-3H-indazol-3-one,

(16) A method for treating or preventing a disease wherein a CRF receptor is implicated, which comprises administering to a subject in need thereof an effective amount of a compound represented by the formula:

$$A\text{-}W\text{—}Ar \qquad (I')$$

wherein, A is a group represented by the formula (A1) or (A2)

(A1)

(A2)

wherein, ring Aa is a 5- or 6-membered ring which may have one or two further heteroatoms selected from oxygen, sulfur and nitrogen at a position other than Q and X, and may be further substituted with one or more substituents in addition to R¹; ring Ab is a 5- or 6-membered ring which may have one or two further heteroatoms selected from oxygen, sulfur and nitrogen at a position other than Y¹, Y² and X, and may be further substituted with one or more substituents in addition to R¹; ring Ac is a 5- or 6-membered ring which may have one or two further heteroatoms selected from oxygen, sulfur and nitrogen at a position other than Y¹, Y² and Q, and may be substituted with one or more substituents; R¹ is an optionally substituted alkyl, an optionally substituted cycloalkyl, an optionally substituted cycloalkenyl, a substituted amino, an optionally substituted cyclic amino, a substituted hydroxy, a substituted sulfanyl, an optionally substituted sulfinyl, or an optionally substituted sulfonyl; X is carbonyl, —O—, —S—, —SO—, or —SO₂—; Y¹, Y² and Q are independently optionally substituted carbon or nitrogen; ⁞ is a single or double bond;

W is a bond, an optionally substituted methylene, an optionally substituted ethylene, an optionally substituted imino, —O—, —S—, —SO—, or —SO$_2$—;

Ar is an optionally substituted aryl or an optionally substituted heteroaryl;

or a salt thereof or a prodrug thereof,

(17) The method according to the above-mentioned (16) wherein the disease being treated or prevented is selected from affective disorder, depression or anxiety,

(18) A medicine comprising the compound according to the above-mentioned (1) or a prodrug thereof,

(19) The medicine according to the above-mentioned (18) which is a corticotropin releasing factor antagonist,

(20) The medicine according to the above-mentioned (18) which is an agent for treating or preventing affective disorder, depression or anxiety, and

(21) Use of the compound according to the above-mentioned (1) or a prodrug thereof for manufacturing an agent for preventing or treating affective disorder, depression or anxiety.

DETAILED DESCRIPTION OF THE PREFERRED EMBODIMENTS

In the present specification, the term "hydrocarbyl" means a univalent group containing only carbon and hydrogen.

In the above formula (I), A represents a group represented by the formula (A1) or (A2)

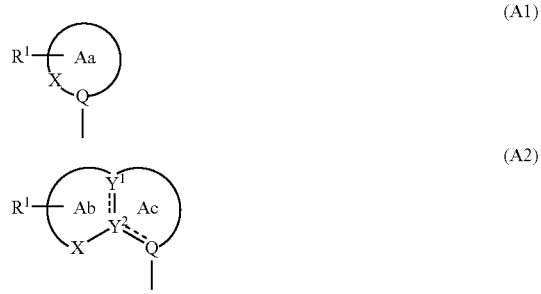

In the formulas (A1) and (A2), ring Aa of the formula (A1) and rings Ab and Ac of the formula (A2) are a 5- or 6-membered ring which may have one or two further heteroatoms selected from oxygen, sulfur and nitrogen at a position other than $Y^1$, $Y^2$, Q and X, and may be substituted with one or more substituents. Preferably the rings Aa and Ab are a 5- or 6-membered nitrogen-containing heterocyclic ring which may have one or two further heteroatoms selected from oxygen, sulfur and nitrogen at a position other than $Y^1$, $Y^2$, Q and X, and may be further substituted with one or more substituents in addition to $R^1$. The ring Ac is preferably a 5- or 6-membered unsaturated ring which may have one or two further heteroatoms selected from oxygen, sulfur and nitrogen at a position other than $Y^1$, $Y^2$, and Q, and may be further substituted with one or more substituents.

Examples of the "5- or 6-membered ring" in the "5- or 6-membered ring which may have one or two further heteroatoms selected from oxygen, sulfur and nitrogen at a position other than $Y^1$, $Y^2$, Q and X, and may be substituted with one or more substituents in addition to $R^1$" for rings Aa and Ab include a 5- or 6-membered aromatic heterocyclic or homocyclic ring such as furan, thiophene, pyrrole, imidazole, pyrazole, thiazole, oxazole, isothiazole, isoxazole, thiadiazole, oxadiazole, triazole, tetrazole, pyridine, pyrazine, pyrimidine, pyridazine, thiazine, triazine, and benzene etc., and a 5- or 6-membered non-aromatic ring such as tetrahydrofuran, tetrahydrothiophene, pyrrolidine, pyrroline, imidazolidine, imidazoline, pyrazolidine, pyrazoline, thiazolidine, thiazoline, isothiazolidine, isothiazoline, oxazolidine, oxazoline, isoxazolidine, isoxazoline, piperidine, piperazine, oxazine, oxadiazine, thiazine, thiadiazine, dihydrooxazine, morpholine, thiomorpholine, pyran, dihydropyran, tetrahydropyran, thiopyran (thiin), dihydrothiopyran, tetrahydrothiopyran, cyclopentane, cyclopentene, cyclohexane, cyclohexene, etc., and oxo compound thereof such as di- or tetrahydrofuranone, tetrahydrothiophenone, pyrrolinone, pyrrolidinone, imidazolinone, imidazolidinone, pyrazolidinone, pyrazolinone, thiazolidinone, thiazolinone, oxazolidinone, oxazolinone, isothiazolidinone, isothiazolinone, isoxazolidinone, isoxazolinone, thiadiazolidinone, oxadiazolinone, triazolidinone, triazolinone, pyridinone, pyrazinone, pyrimidinone, pyridazinone, thiazinone, triazinone, piperidinone, piperazinone, pyranone, dihydropyranone, tetrahydropyranone, thiopyranone, dihydrothiopyranone, tetrahydrothiopyranone, cyclopentanone, cyclopentenone, cyclohexanone, cyclohexenone, thiin-1-oxide, thiin-1,1-dioxide, dihydrothiin-1-oxide, dihydrothiin-1,1-dioxide, tetrahydrothiin-1-oxide, tetrahydrothiin-1,1-dioxide and the like.

Examples of the "5- or 6-membered ring" in the "5- or 6-membered ring which may have one or two further heteroatoms selected from oxygen, sulfur and nitrogen at a position other than $Y^1$, $Y^2$ and Q, and may be substituted with one or more substituents" for rings Ac include a 5- or 6-membered aromatic heterocyclic or homocyclic ring such as furan, thiophene, pyrrole, imidazole, pyrazole, thiazole, oxazole, isothiazole, isoxazole, thiadiazole, oxadiazole, triazole, tetrazole, pyridine, pyrazine, pyrimidine, pyridazine, thiazine, triazine, and benzene etc., and a 5- or 6-membered non-aromatic ring such as tetrahydrofuran, tetrahydrothiophene, pyrrolidine, pyrroline, imidazolidine, imidazoline, pyrazolidine, pyrazoline, thiazolidine, thiazoline, isothiazolidine, isothiazoline, oxazolidine, oxazoline, isoxazolidine, isoxazoline, piperidine, piperazine, oxazine, oxadiazine, thiazine, thiadiazine, dihydrooxazine, morpholine, thiomorpholine, pyran, dihydropyran, tetrahydropyran, thiopyran (thiin), dihydrothiopyran, tetrahydrothiopyran, cyclopentane, cyclopentene, cyclohexane, cyclohexene, and the like.

Examples of the substituent for "5- or 6-membered ring" in the "5- or 6-membered ring which may have one or two further heteroatoms selected from oxygen, sulfur and nitrogen at a position other than $Y^1$, $Y^2$, Q and X, and may be substituted with one or more substituents" for rings Aa, Ab and Ac include an optionally substituted hydrocarbyl, halogen, cyano, nitro, an optionally substituted heterocyclic group, an optionally substituted sulfinyl group, an optionally substituted sulfanyl group, an optionally substituted sulfonyl group, acyl, an optionally substituted amino, an optionally esterified or amidated carboxyl group, an optionally substituted phosphoryl group, and the like.

Examples of said "hydrocarbyl" in "an optionally substituted hydrocarbyl" include an aliphatic hydrocarbon group, an alicyclic hydrocarbon group, an alicyclic-aliphatic hydrocarbon group, an aromatic hydrocarbon group, an aromatic-aliphatic hydrocarbon group (an aralkyl group), and the like.

Examples of said aliphatic hydrocarbon group include a saturated aliphatic hydrocarbon group having 1-8 carbon atoms (e.g., alkyl group) such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; and an unsaturated aliphatic hydrocarbon group having 2-8 carbon atoms (e.g., alkenyl group, alkynyl group, alkadienyl group, alkadiynyl group, etc.) such as vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 2,4-hexadienyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl, 1-heptynyl, 1-octynyl, etc.

Examples of said alicyclic hydrocarbon group include a saturated alicyclic hydrocarbon group having 3-7 carbon atoms (e.g., cycloalkyl group, etc.) such as cyclopropyl, cyclobutyl, cyclopentyl, cyclohexyl, cycloheptyl, and the like; an unsaturated alicyclic hydrocarbon group having 3-7 carbon atoms (e.g., cycloalkenyl group, cycloalkadienyl group, etc.) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc.; a partly saturated and fused bicyclic hydrocarbon group [preferably, $C_{9-10}$ partly saturated and fused bicyclic hydrocarbon group, etc. (including those where the benzene ring is combined to a 5- or 6-membered non-aromatic cyclic hydrocarbon group)] such as 1-indenyl, 2-indenyl, 1-indanyl, 2-indanyl, 1,2,3,4-tetrahydro-1-naphthyl, 1,2,3,4-tetrahydro-2-naphthyl, 1,2-dihydro-1-naphthyl, 1,2-dihydro-2-naphthyl, 1,4-dihydro-1-naphthyl, 1,4-dihydro-2-naphthyl, 3,4-dihydro-1-naphthyl, 3,4-dihydro-2-naphthyl, etc.; and the like. Said alicyclic hydrocarbon group may be cross-linked.

Examples of said alicyclic-aliphatic hydrocarbon group include those where the above-mentioned alicyclic hydrocarbon group and the above-mentioned aliphatic hydrocarbon group are combined, for example, those having 4-14 carbon atoms such as cyclopropylmethyl, cyclopropylethyl, cyclobutylmethyl, cyclobutylethyl, cyclopentylmethyl, 2-cyclopentenylmethyl, 3-cyclopentenylmethyl, cyclopentylethyl, cyclohexylmethyl, 2-cyclohexenylmethyl, 3-cyclohexenylmethyl, cyclohexylethyl, cycloheptylmethyl, cycloheptylethyl, 2-(3,4-dihydro-2-naphtyl)ethyl, 2-(1,2,3,4-tetrahydro-2-naphtyl)ethyl, 2-(3,4-dihydro-2-naphtyl)ethenyl, etc. (e.g., $C_{3-7}$ cycloalkyl-$C_{1-4}$ alkyl group, $C_{3-7}$ cycloalkenyl-$C_{1-4}$ alkyl group, $C_{3-7}$ cycloalkyl-$C_{2-4}$ alkenyl group, $C_{3-7}$ cycloalkenyl-$C_{2-4}$ alkenyl group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl groups, etc.).

Examples of said aromatic hydrocarbon group include an aryl group having 6-10 carbon atoms (including that where a 5- to 6-membered non-aromatic hydrocarbon ring is fused with a phenyl group) such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; and the like.

Examples of said aromatic-aliphatic hydrocarbon group include an aralkyl group having 7-14 carbon atoms ($C_{6-10}$ aryl-$C_{1-4}$ alkyl group) such as phenyl-$C_{1-4}$ alkyl group, e.g., benzyl, phenethyl, 1-phenylethyl, 1-phenylpropyl, 2-phenylpropyl, 3-phenylpropyl, etc.; naphthyl-$C_{1-4}$ alkyl group such as α-naphthylmethyl, α-naphthylethyl, α-naphthylmethyl, β-naphthylethyl, etc.; $C_{6-10}$ aryl-$C_{2-4}$ alkenyl group such as phenyl-$C_{2-4}$ alkenyl group, e.g., styryl, cinnamyl, etc.; and the like.

The above-mentioned "hydrocarbyl" group may have a substituent at a substitutable position. Examples of such substituent include a halogen, nitro, cyano, oxo, (1) an optionally substituted heterocyclic group, (2) an optionally substituted sulfinyl group, (3) an optionally substituted sulfonyl group, (4) optionally substituted hydroxyl group, (5) optionally substituted sulfanyl group, (6) an optionally substituted amino group, (7) an acyl group, (8) an optionally esterified or amidated carboxyl group, (9) an optionally substituted phosphoryl group, or the like.

Examples of the substituent of above-mentioned (2) an optionally substituted sulfinyl group, (3) an optionally substituted sulfonyl group, (4) optionally substituted hydroxyl group, (5) optionally substituted sulfanyl group and (6) an optionally substituted amino group include an optionally substituted hydrocarbyl. Examples of "hydrocarbyl" of such optionally substituted hydrocarbyl include those exemplified above. Said hydrocarbyl may be substituted with one or more substituents at a substitutable position. Examples of such substituent of the optionally substituted hydrocarbyl as a substituent group include halogen, nitro, cyano, hydroxyl, sulfanyl, amino and carboxyl.

Examples of the acyl group of above-mentioned (7) include a formyl and a group where a carbonyl group is combined with a $C_{1-10}$ alkyl group, a $C_{2-10}$ alkenyl group, a $C_{2-10}$ alkynyl group, a $C_{3-7}$ cycloalkyl group, a $C_{5-7}$ cycloalkenyl group or an aromatic group (e.g., phenyl group, pyridyl group, etc.) (e.g., acetyl, propionyl, butyryl, isobytyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, etc.).

Examples of the ester group or amide group in the optionally esterified or amidated carboxyl group of above-mentioned (8) include an ester group where a carbonyloxy group is combined with an optionally substituted hydrocarbyl similar to the substituent of optionally substituted hydroxyl group of above-mentioned (4) or an amide group where a carbonyl group is combined with the optionally substituted amino group of above-mentioned (6).

Examples of the substituted phosphoryl group in the optionally substituted phosphoryl group of above-mentioned (9) include a group where phosphoryl is combined with a $C_{1-10}$ alkyl group, a $C_{2-10}$ alkenyl group, a $C_{2-10}$ alkynyl group, a $C_{3-7}$ cycloalkyl group, a $C_{5-7}$ cycloalkenyl group or an aromatic group (e.g., phenyl group, pyridyl group, etc.).

In the above formulas (A1) and (A2), $R^1$ is an optionally substituted alkyl, an optionally substituted cycloalkyl, an optionally substituted cycloalkenyl, a substituted amino, an optionally substituted cyclic amino, a substituted hydroxy, a substituted sulfanyl, optionally substituted sulfinyl, or optionally substituted sulfonyl.

Examples of the "alkyl" in the "optionally substituted alkyl" for $R^1$ include a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.

Examples of the "cycloalkyl" in the "optionally substituted cycloalkyl" for $R^1$ include a $C_{3-7}$ cycloalkyl group such as cyclopropyl, cyclobutyl, cyclopentyl, cyclohexyl, cycloheptyl, and the like.

Examples of the "cycloalkenyl" in the "optionally substituted cycloalkenyl" for $R^1$ include a $C_{3-7}$ cycloalkenyl group such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, etc.

The above-mentioned "alkyl", "cycloalkyl" and "cycloalkenyl" in $R^1$ may have a substituent similar to those exemplified with respect to the substituent of hydrocarbyl group which is a substituent of "5- or 6-membered ring" in the "5- or 6-membered ring which may have one or two further heteroatoms selected from oxygen, sulfur and nitrogen at a position other than $Y^1$, $Y^2$, Q and X, and may be substituted with one or more substituents" for rings Aa, Ab and Ac.

Examples of the "substituted amino" for $R^1$ include an amino group which is mono- or di-substituted with an optionally substituted hydrocarbyl group, an optionally substituted heterocyclic group or a group represented by the formula: —$COR^{1a}$ or $SO_2R^{1a}$ (wherein $R^{1a}$ represents hydrogen atom, an optionally substituted hydrocarbyl group, an optionally substituted heterocyclic group or an amino group which may be substituted with $C_{1-12}$ hydrocarbyl (e.g. alkyl, alkenyl, cycloalkyl, aryl, etc.). Preferably a $C_{1-10}$ acyl group (e.g., a $C_{2-7}$ alkanoyl, benzoyl, nicotinoyl, etc.)). Examples of said "hydrocarbyl group" in "an optionally substituted hydrocarbyl group" above include a $C_{1-8}$ alkyl group, a $C_{3-7}$ cycloalkyl group, a $C_{2-8}$ alkenyl group, a $C_{2-8}$ alkynyl group, a $C_{3-7}$ cycloalkenyl group, a $C_{6-10}$ aryl group that may have a $C_{1-4}$ alkyl group, etc., and examples of said "heterocyclic group" in "an optionally substituted heterocyclic group" above include an aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, etc., and a non-aromatic heterocyclic group such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc. These "hydrocarbyl group" and "heterocyclic group" may have a substituent similar to that of "the hydrocarbyl group" as a substituent of "5- or 6-membered ring" in the "5- or 6-membered ring which may have one or two further heteroatoms selected from oxygen, sulfur and nitrogen at a position other than $Y^1$, $Y^2$, Q and X, and may be substituted with one or more substituents" for rings Aa, Ab and Ac. Specific examples thereof include methylamino, dimethylamino, ethylamino, diethylamino, dipropylamino, dibutylamino, diallylamino, cyclohexylamino, phenylamino, N-methyl-N-phenylamino, acetylamino, propionylamino, benzoylamino, nicotinoylamino, and the like.

In addition, the two groups in said substituted amino groups may be combined to form a nitrogen-containing 5- to 7-membered ring.

Examples of the "cyclic amino" in the "optionally substituted cyclic amino" for $R^1$ include a 3- to 7-membered cyclic amino group such as aziridino, pyrrolidino, imidazolidino, oxazolidino, thiazolidino, piperidino, 1,2-dihydropyridyl, 1,2,3,6-tetrahydropyridyl, piperazino, morpholino, thiomorpholino and the like. The cyclic amino group may be substituted with 1 to 3 substituents selected from the group consisting of halogen, $C_{1-6}$ alkyl, $C_{2-6}$ alkenyl, $C_{1-6}$ alkoxy-$C_{1-6}$ alkyl, $C_{5-7}$ cycloalkyl, $C_{6-10}$ aryl (said aryl may have 1 or 2 substituents selected from halogen, $C_{1-6}$ alkyl, halogeno $C_{1-6}$ alkyl and $C_{1-6}$ alkoxy), $C_{7-14}$ aralkyl (said aralkyl may have 1 or 2 substituents selected from halogen, $C_{1-6}$ alkyl, halogeno $C_{1-6}$ alkyl and $C_{1-6}$ alkoxy), hydroxy, hydroxy-$C_{1-6}$ alkyl, $C_{6-10}$ aryloxy (said aryloxy may have 1 or 2 substituents selected from halogen, $C_{1-6}$ alkyl, halogeno $C_{1-6}$ alkyl and $C_{1-6}$ alkoxy), $C_{7-14}$ aralkyloxy, $C_{6-10}$ aryl-carbonyl, carboxyl, $C_{1-6}$ alkoxy-carbonyl, carbamoyl, $C_{6-10}$ aryl-carbamoyl, amino, $C_{6-10}$ aryl-carbonylamino, $C_{1-6}$ alkyl-carbonylamino, $C_{1-6}$ alkoxy-carbonylamino, $C_{6-10}$ arylthio, $C_{6-10}$ arylsulfonyl, cyano, 5- to 7-membered heterocyclic group and oxo.

Examples of the "substituted hydroxy" for $R^1$ include a hydroxy which is substituted with an optionally substituted hydrocarbyl (e.g., $C_{1-15}$ alkyl, $C_{1-15}$ alkenyl, $C_{1-15}$ alkynyl, $C_{1-15}$ cyclic hydrocarbon, each of which may be substituted with an optionally halogenated alkyl, amino, alkoxy, carbamoyl, aryl, heterocyclic group, hydroxy, etc. at a suitable position; preferably, $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc., which may be substituted at a suitable position with halogen, nitro, cyano, alkoxy, amino, substituted amino, or the like, a $C_{3-10}$ alkenyl group, a $C_{3-10}$ alkynyl group, a $C_{3-7}$ cycloalkyl group, a $C_{3-7}$ alkylcycloalkyl group, a $C_{5-7}$ cycloalkenyl group, a $C_{5-7}$ alkylcycloalkenyl group, an aromatic group (e.g., phenyl group, pyridyl group, etc.), benzyl group, or an alkylaromatic group (e.g. methylpyridyl group, etc.)); an optionally substituted heterocyclic group (e.g., a 5- to 10-membered saturated or unsaturated heterocyclic group including bicyclic ring such as piperidine, pyrrolidine, etc.) or an optionally substituted acyl (e.g., acyl formed by combining carbonyl with the above-mentioned optionally substituted hydrocarbyl).

Examples of the "substituted sulfanyl" for $R^1$ include a sulfanyl which is substituted with an optionally substituted hydrocarbyl (e.g., $C_{1-15}$ alkyl, $C_{1-15}$ alkenyl, $C_{1-15}$ alkynyl, $C_{1-15}$ cyclic hydrocarbon, each of which may be substituted with an optionally halogenated alkyl, amino, alkoxy, carbamoyl, aryl, heterocyclic group, hydroxy, etc. at a suitable position; preferably, $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc., which may be substituted at a suitable position with halogen, nitro, cyano, alkoxy, amino, substituted amino, or the like, a $C_{3-10}$ alkenyl group, a $C_{3-10}$ alkynyl group, a $C_{3-7}$ cycloalkyl group, a $C_{3-7}$ alkylcycloalkyl group, a $C_{5-7}$ cycloalkenyl group, a $C_{5-7}$ alkylcycloalkenyl group, an aromatic group (e.g., phenyl group, pyridyl group, etc.), benzyl group, or an alkylaromatic group (e.g. methylpyridyl group, etc.)); or an optionally substituted heterocyclic group (e.g., a 5- to 10-membered saturated or unsaturated heterocyclic group including bicyclic ring such as piperidine, pyrrolidine, etc.).

Examples of the "optionally substituted sulfinyl" for $R^1$ include a sulfinyl which may be substituted with an optionally substituted hydrocarbyl (e.g., $C_{1-15}$ alkyl, $C_{1-15}$ alkenyl, $C_{1-15}$ alkynyl, $C_{1-15}$ cyclic hydrocarbon, each of which may be substituted with an optionally halogenated alkyl, amino, alkoxy, carbamoyl, aryl, heterocyclic group, hydroxy, etc. at a suitable position; preferably, $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc., which may be substituted at a suitable position with halogen, nitro, cyano, alkoxy, amino, substituted amino, or the like, a $C_{3-10}$ alkenyl group, a $C_{3-10}$ alkynyl group, a $C_{3-7}$ cycloalkyl group, a $C_{3-7}$ alkylcycloalkyl group, a $C_{5-7}$ cycloalkenyl group, a $C_{5-7}$ alkylcycloalkenyl group, an aromatic group (e.g., phenyl group, pyridyl group, etc.), benzyl group, or an alkylaromatic group (e.g. methylpyridyl group, etc.)); or an optionally substituted heterocyclic group (e.g., a 5- to 10-membered saturated or unsaturated heterocyclic group including bicyclic ring such as piperidine, pyrrolidine, etc.).

Examples of the "optionally substituted sulfonyl" for $R^1$ include a sulfonyl which may be substituted with an optionally substituted hydrocarbyl (e.g., $C_{1-15}$ alkyl, $C_{1-15}$ alkenyl, $C_{1-15}$ alkynyl, $C_{1-15}$ cyclic hydrocarbon, each of which may be substituted with an optionally halogenated alkyl, amino, alkoxy, carbamoyl, aryl, heterocyclic group, hydroxy, etc. at a suitable position; preferably, $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc., which may be substituted at a suitable position with halogen, nitro, cyano, alkoxy, amino, substituted amino, or the like, a $C_{3-10}$ alkenyl group, a $C_{3-10}$ alkynyl group, a $C_{3-7}$ cycloalkyl group, a $C_{3-7}$ alkylcycloalkyl group, a $C_{5-7}$ cycloalkenyl group, a $C_{5-7}$ alkylcycloalkenyl group, an aromatic group (e.g., phenyl group, pyridyl group, etc.), benzyl group, or an alkylaromatic group (e.g. methylpyridyl group, etc.)); or an optionally substituted heterocyclic group (e.g., a 5- to 10-membered saturated or unsaturated heterocyclic group including bicyclic ring such as piperidine, pyrrolidine, etc.).

In the formulas (A1) and (A2), X represents carbonyl, —O—, —S—, —SO—, or —$SO_2$—, and preferably X is carbonyl.

In the formulas (A1) and (A2), $Y^1$, $Y^2$ and Q represent independently optionally substituted carbon or nitrogen. The substituent of the "optionally substituted carbon" for $Y^1$, $Y^2$ and Q includes, for example, an optionally substituted hydrocarbyl, preferably, $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc., which may be substituted at a suitable position with halogen, nitro, cyano, alkoxy, amino, substituted amino, or the like.

In the formulas (A1) and (A2), ⁝⁝⁝ is a single or double bond.

In the formula (A1), the ring Aa is preferably a 5- or 6-membered unsaturated nitrogen-containing heterocyclic ring which may have one or two further heteroatoms selected from oxygen, sulfur and nitrogen at a position other than Q and X, and may be further substituted with one or more substituents. Specifically, the group represented by the formula (A1) is preferably a group represented by the formula:

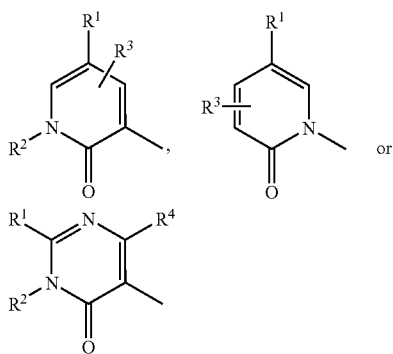

wherein, $R^1$ is as defined above; $R^2$ is hydrogen, an optionally substituted hydrocarbyl, an optionally substituted carboxy, or an optionally substituted acyl; and $R^3$ and $R^4$ are independently hydrogen, halogen, cyano, nitro, an optionally substituted hydrocarbyl, an optionally substituted amino, an optionally substituted hydroxy, an optionally substituted carboxy, an optionally substituted phosphoryl, an optionally substituted sulfanyl, an optionally substituted sulfinyl, an optionally substituted sulfonyl, or acyl.

The "optionally substituted hydrocarbyl" for $R^2$, $R^3$ and $R^4$ has the same meaning as defined in the optionally substituted hydrocarbyl as the substituent of "5- or 6-membered ring" in the "5- or 6-membered ring which may have one or two further heteroatoms selected from oxygen, sulfur and nitrogen at a position other than $Y^1$, $Y^2$, Q and X, and may be substituted with one or more substituents" for rings Aa, Ab and Ac.

Examples of the "optionally substituted carboxy" for $R^2$, $R^3$ and $R^4$ include carboxy, esterified carboxyl group (e.g., ester group where the carbonyloxy group is combined with $C_{1-8}$ alkyl group such as methyl, ethyl, propyl, isopropyl, butyl, etc. which may be substituted at a suitable position with halogen, nitro, cyano, alkoxy, amino, substituted amino, etc., a $C_{2-7}$ alkenyl group such as vinyl, allyl, etc., a $C_{3-7}$ cycloalkyl group, a $C_{3-7}$ alkylcycloalkyl group, a $C_{5-7}$ cycloalkenyl group, a $C_{5-7}$ alkylcycloalkyl group, an aromatic group (e.g., phenyl group, pyridyl group, etc.), benzyl group, or an alkylaromatic group (e.g. methylpyridyl group, etc.)) or amidated carboxyl group (e.g., amide group which may be substituted with $C_{1-6}$ alkyl group such as methyl, ethyl, propyl, isopropyl, butyl, etc).

Examples of the "acyl" in the "optionally substituted acyl" for $R^2$ and the "acyl" for $R^3$ and $R^4$ include a formyl and a group where the carbonyl group is combined with a $C_{1-10}$ alkyl group, a $C_{2-10}$ alkenyl group, a $C_{2-10}$ alkynyl group, a $C_{3-7}$ cycloalkyl group, a $C_{5-7}$ cycloalkenyl group or an aromatic group (e.g., phenyl group, pyridyl group, etc.) (e.g., acetyl, propionyl, butyryl, isobytyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, etc.) and the like. The "acyl" in the "optionally substituted acyl" for $R^2$ may have one or more substituents selected from halogen, nitro, cyano, alkoxy, amino, substituted amino, etc.

Examples of the "optionally substituted amino", "optionally substituted hydroxy", "optionally substituted phosphoryl", "optionally substituted sulfanyl", "optionally substituted sulfinyl" and "optionally substituted sulfonyl" for $R^3$ and $R^4$ are exemplified by those for the optionally substituted amino, optionally substituted hydroxy, optionally substituted phosphoryl, optionally substituted sulfanyl, optionally substituted sulfinyl and optionally substituted sulfonyl represented by $R^1$.

The optionally substituted carboxy for $R^3$ and $R^4$ includes an ester group and amide group, and examples thereof are exemplified by those for the optionally esterified or amidated carboxyl group as the substituent of hydrocarbyl group which is a substituent of "5- or 6-membered ring" in the "5- or 6-membered ring which may have one or two further heteroatoms selected from oxygen, sulfur and nitrogen at a position other than $Y^1$, $Y^2$, Q and X, and may be substituted with one or more substituents" for rings Aa, Ab and Ac.

In the formula (A2), preferably, the ring Ab is a 5- or 6-membered saturated or unsaturated nitrogen-containing heterocyclic ring which may have one or two further heteroatoms selected from oxygen, sulfur and nitrogen at a position other than $Y^1$, $Y^2$ and X, and may be further substituted with one or more substituents, and ring Ac is a 5- or 6-membered unsaturated ring which may have one or two further heteroatoms selected from oxygen, sulfur and nitrogen at a position other than $Y^1$, $Y^2$ and X, and may be substituted with one or more substituents. Specifically, the group represented by the formula (A2) is preferably a group represented by the formula:

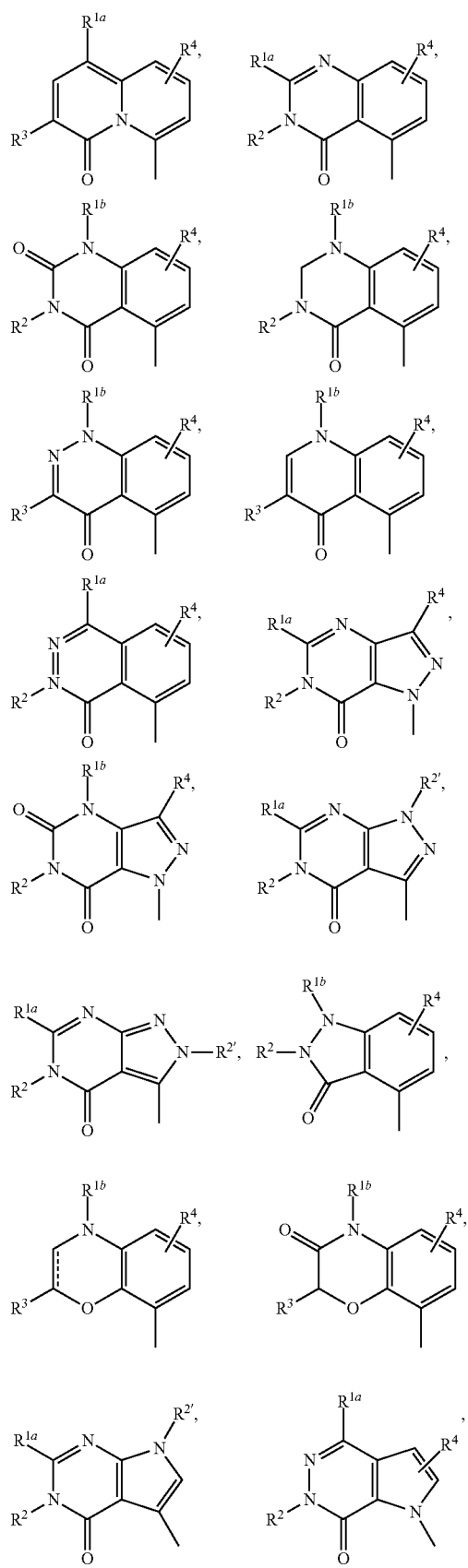

wherein $R^1$, $R^2$, $R^3$, $R^4$ and ⁚⁚ are as defined above, and $R^{2'}$ is hydrogen, an optionally substituted hydrocarbyl, an optionally substituted carboxy or an optionally substituted acyl.

The "optionally substituted hydrocarbyl", "optionally substituted carboxy" and "optionally substituted acyl" for $R^{2'}$ have the same meaning as defined in $R^2$.

In the formula (I), W represents a bond, an optionally substituted methylene, an optionally substituted ethylene, an optionally substituted imino, —O—, —S—, —SO—, or —SO$_2$—.

Examples of the substituent in the "optionally substituted methylene", "optionally substituted ethylene" and "optionally substituted imino" for W include H (unsubstituted), $C_{1-8}$ alkyl, $C_{1-8}$ dialkyl, $C_{3-7}$ cycloalkyl, $C_{2-8}$ alkenyl, $C_{2-8}$ alkynyl, $C_{3-7}$ cycloalkenyl, $C_{6-10}$ aryl that may have a $C_{1-4}$ alkyl group, oxo, hydroxy, alkoxy, and the like.

Preferably, W is a bond.

In the formula (I), Ar is an optionally substituted aryl or an optionally substituted heteroaryl. Examples of the "aryl" in the "optionally substituted aryl" for Ar include a $C_{6-10}$ aryl such as phenyl, naphthyl. The "heteroaryl" in the "optionally substituted heteroaryl" for Ar include, for example, a 5- or 6-membered nitrogen-containing aromatic heterocyclic ring which may have one or two further heteroatoms selected from oxygen, sulfur and nitrogen, such as furan, thiophene, pyrrole, imidazole, pyrazole, thiazole, oxazole, isothiazole, isoxazole, thiadiazole, oxadiazole, triazole, pyridine, pyrazine, pyrimidine, pyridazine, triazine.

Examples of the substituent in the "optionally substituted aryl" and "optionally substituted heteroaryl" for Ar include a halogen, nitro, cyano, (1) an optionally substituted heterocyclic group, (2) an optionally substituted sulfinyl group, (3) an optionally substituted sulfonyl group, (4) optionally substituted hydroxyl group, (5) optionally substituted sulfanyl group, (6) an optionally substituted amino group, (7) an acyl group, (8) an optionally esterified or amidated carboxyl group, (9) an optionally substituted phosphoryl group, or the like.

Examples of the substituent of above-mentioned (2) an optionally substituted sulfinyl group, (3) an optionally substituted sulfonyl group, (4) optionally substituted hydroxyl group, (5) optionally substituted sulfanyl group and (6) an optionally substituted amino group include an optionally substituted hydrocarbyl. Examples of the "hydrocarbyl" of such optionally substituted hydrocarbyl include those exemplified above. Said hydrocarbyl may be substituted by one or more substituents at a substitutable position. Examples of the substituent of the optionally substituted hydrocarbyl as a substituent group include halogen, nitro, cyano, hydroxyl, thiol, amino and carboxyl.

Examples of the acyl group of above-mentioned (7) include the same group as the acyl for $R^3$ and $R^4$.

Examples of the optionally esterified or amidated carboxyl group of above-mentioned (8) include ester group or amide group similar to those exemplified for $R^3$ and $R^4$.

Among these, preferable substituent in the "optionally substituted aryl" and "optionally substituted heteroaryl" for Ar is a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc. which may be substituted at a suitable position with halogen, nitro, cyano, alkoxy, amino, substituted amino, or the like; a $C_{3-7}$ cycloalkyl group, a $C_{3-7}$ alkylcycloalkyl group, a $C_{5-7}$ cycloalkenyl group, a $C_{5-7}$ alkylcycloalkenyl group, halogen, cyano, nitro, hydroxy, alkoxy, amino, substituted amino, and the like.

Ar is preferably an optionally substituted phenyl, an optionally substituted pyridyl or an optionally substituted pyrimidinyl.

As a preferred compound of the formula (I), a compound wherein (A2) is a group represented by structures C1 through C8;

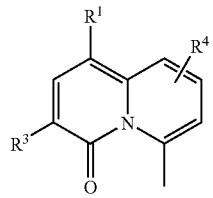
C1

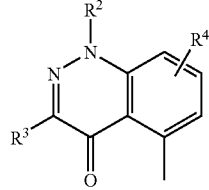
C2

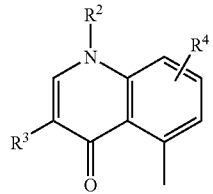
C3

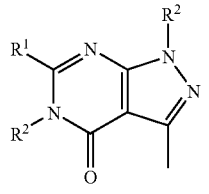
C4

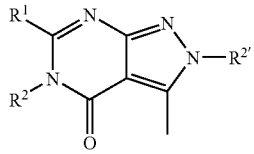
C5

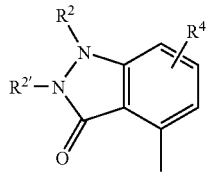
C6

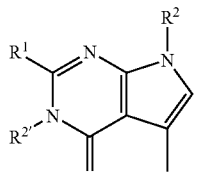
C7

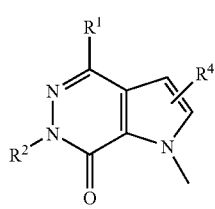
C8 in which $R^1$ is an optionally substituted alkyl, an optionally substituted cycloalkyl, an optionally substituted cycloalkenyl, a substituted amino, an optionally substituted cyclic amino or a substituted alkoxy; $R^2$, $R^{2'}$ is an optionally substituted $C_{3-10}$ alkyl (linear or branched); $R^3$ is halogen, optionally substituted carboxy, optionally substituted $C_{1-7}$ alkyl (linear or branched); $R^4$ is hydrogen, halogen, cyano, nitro, an optionally substituted hydrocarbyl, an optionally substituted amino, an optionally substituted hydroxy, an optionally substituted carboxy or acyl; W is a bond, Ar is a phenyl group having two or more substituents which may be the same or different and are selected from hydrogen, halogen, $C_{1-5}$ alkyl groups, $C_{1-5}$ alkoxy groups, $C_{1-5}$ alkylthio groups, cyano, trifluoromethyl and trifluoromethoxy groups; Ar is a heteroaryl optionally substituted with hydrogen, halogen, $C_{1-5}$ alkyl groups, $C_{1-5}$ alkoxy groups, $C_{1-5}$ alkylthio groups, cyano, trifluoromethyl and trifluoromethoxy groups.

Compound (I) may be in the form of a prodrug thereof. The prodrug of Compound (I) refers to a compound that is converted into Compound (I) by a reaction with an enzyme, gastric acid, or the like under a physiological condition in the living body, namely, (i) a compound that is converted into Compound (I) by an enzymatic oxidation, reduction, hydrolysis, or the like, and (ii) a compound that is converted into Compound (I) by hydrolysis with gastric acid or the like. Examples of a prodrug of Compound (I) to be used include a compound or its salt wherein hydroxyl group in Compound (I) is acylated, alkylated, phosphorylated, or converted into borate (e.g., a compound or its salt wherein hydroxyl group in Compound (I) is converted into acetyloxy, palmitoyloxy, propanoyloxy, pivaloyloxy, succinyloxy, fumaryloxy, alanyloxy, dimethylaminomethylcarbonyloxy, etc.), a compound or its salt wherein carboxyl group in Compound (I) is esterified or amidated (e.g., a compound or its salt wherein carboxyl group in Compound (I) is subjected to ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl)methyl esterification, cyclohexyloxycarbonyl esterification, or conversion into the methyl amide, etc.), or the like. These prodrugs can be produced according to a per se known method or its modified method.

Further, a prodrug of Compound (I) may be a compound or its salt that is converted into Compound (I) under physiological conditions as described in "Development of Drugs", Volume 7, Molecular Design, Hirokawa Shoten, 1990; pages 163-198.

General Synthetic Method

Production of a compound of formula (I) or a salt thereof of the present invention is discussed below. The following examples are given to illustrate the invention and are not intended to be inclusive in any manner. Alternative methods may be employed by one skilled in the art.

A process for preparing compound (I) or a salt thereof of the present invention is shown in the following methods.

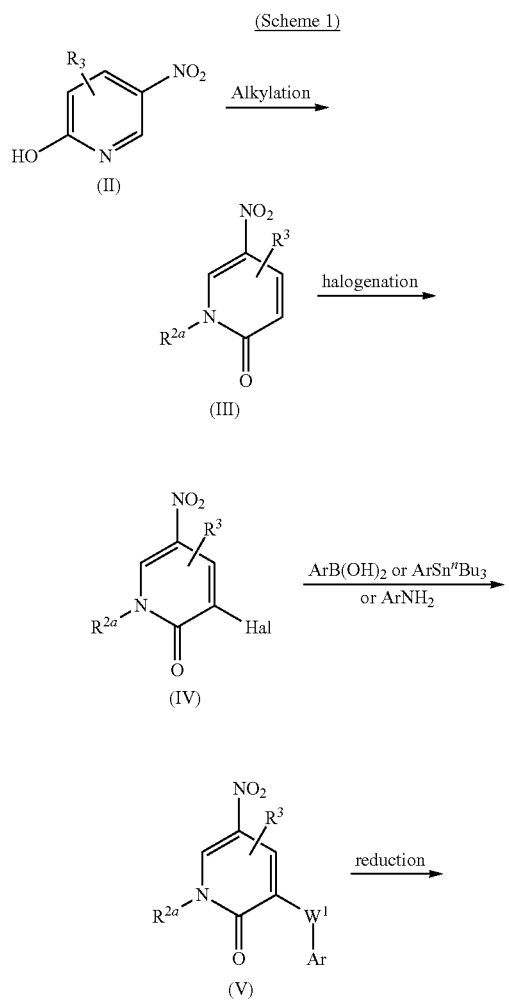

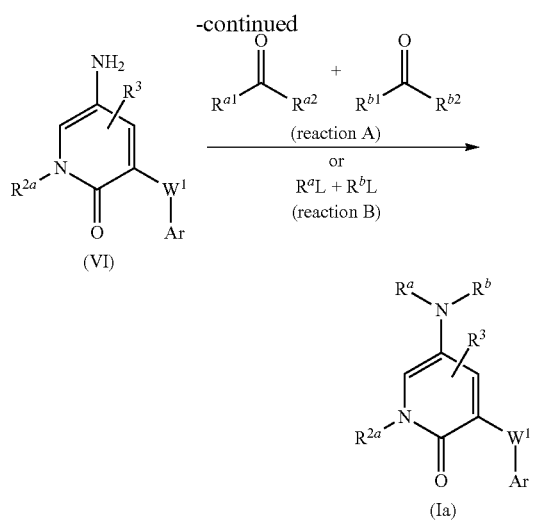

wherein $W^1$ is bond or NH, Hal is halogen, $R^{2a}$, $R^a$ and $R^b$ are independently optionally substituted hydrocarbyl groups, $R^a$ and $R^b$ may be optionally substituted cyclic form, $R^{2a}$, $R^{a1}$, $R^{a2}$, $R^{b1}$ and $R^{b2}$ are independently hydrogen or optionally substituted hydrocarbyl groups, or $R^{a1}$ and $R^{a2}$ or $R^{b1}$ and $R^{b2}$ may be optionally substituted cyclic form, L is a leaving group (e.g. halogen atom such as chlorine, bromine and iodine, etc, sulfonyloxy group such as p-toluenesulfonyloxy group, methanesulfonyloxy group and trifluoromethanesulfonyloxy group, and acyloxy group such as acetyloxy group and benzoyloxy group) and each of other symbols has a meaning defined above.

Compound (III) or a salt thereof can be prepared by alkylation of compound (II) or a salt thereof. An alkylation reagent is preferably alkyl halides [$R^{2a}$Hal] or alkyl sulfates [$(R^{2a}O)_2SO_2$].

In this reaction, 1 to 5 moles, preferably 1 to 3 moles of an alkylation reagent and 1 to 5 moles, preferably 1 to 3 moles of a base are employed per 1 mole of compound (II) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, ketones such as acetone, amides such as N,N-dimethylformamide and N,N-dimethylacetamide, and sulfoxides such as dimethylsulfoxide. These solvents may be used by mixing at an appropriate ratio.

While the reaction temperature may vary depending on compound (II) or a salt thereof employed as well as other reaction conditions, it is −20 to 200° C., preferably 0 to 150° C. The reaction time is 5 minutes to 48 hours, preferably 5 minutes to 24 hours.

The thus obtained Compound (III) can be isolated and purified by the known isolating and purifying methods, for example, concentration, concentration under reduced pressure, extraction with solvent, crystallization, recrystallization, transfer dissolution and chromatography.

Compound (IV) or a salt thereof can be prepared by halogenation of compound (III) or a salt thereof. Examples of the halogenation agent include chlorine, bromine, iodine, thionyl chloride, thionyl bromide, sulfuryl chloride, oxalyl chloride, phosphorus trichloride, phosphorous pentachloride, phosphorous oxychloride, N-chlorosuccinimide, N-bromosuccinimide, and N-iodosuccinimide, etc.

In this step, the halogenation agent is employed in an amount of 1 to 10 moles, preferably 1 to 3 moles per 1 mole of compound (III) or a salt thereof.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, acids such as acetic acid, amides such as N,N-dimethylformamide and N,N-dimethylacetamide, and sulfoxides such as dimethylsulfoxide. These solvents may be used by mixing at an appropriate ratio.

While the reaction temperature may vary depending on the reagent employed as well as other conditions, it is −20 to 200° C., preferably 20 to 100° C. The reaction time is 5 minutes to 48 hours, preferably 30 minutes to 24 hours.

The thus obtained compound (IV) can be isolated and purified by the known isolating and purifying methods, for example, concentration, concentration under reduced pressure, extraction with solvent, crystallization, recrystallization, transfer dissolution and chromatography.

When $W^1$ is bond in compound (V), compound (V) or a salt thereof can be prepared by reacting compound (IV) with a boronic acid $ArB(OH)_2$ or boronic acid esters or a salt thereof in the presence of a palladium catalyst, preferably tetrakis(triphenylphosphine)palladium(0) and a base according to the procedure of Suzuki coupling (Organic Synthesis via Boranes, vol. 3: Suzuki coupling, A. Suzuki and H. C. Brown, Aldrich, 2002) and the modified methods, or a trialkyl aryl tin such as aryl trimethyltin or aryl tributyltin, etc. or a salt thereof and optional additives according to the procedure of Stille coupling (Angew. Chem. Int. Ed. Engl., 25, 504 (1986)) and the modified methods.

When $W^1$ is NH in compound (V), compound (V) or a salt thereof can be also prepared by reacting compound (IV) or a salt thereof with $ArNH_2$ or a salt thereof in the presence of a palladium catalyst, preferably palladium(II) acetate and a catalytic amount of a phosphine ligand, preferably 2-(dicyclohexylphosphino)biphenyl, according to the procedure of Buchwald et al. (J. Am. Chem. Soc. 1998, 120, 9722) and the modified methods.

Compound (VI) or a salt thereof can be prepared by hydrogenation of compound (V) or a salt thereof in the presence of a hydrogenation catalyst, or prepared by a reduction reaction for compound (V) or a salt thereof.

As the catalyst, a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel, and Raney nickel are used.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, acids such as acetic acid, amides such as N,N-dimethylformamide and N,N-dimethylacetamide, and sulfoxides such as dimethylsulfoxide. These solvents may be used by mixing at an appropriate ratio.

The reaction temperature is 0° C. to 200° C., preferably 20° C. to 100° C. The reaction time is usually 0.5 to 48 hours, preferably 1 to 16 hours. While a reaction is usually performed at atmospheric pressure, it can be performed under pressure (3 to 10 atom) if necessary.

While the amount of a catalyst employed may vary depending on the type of the catalyst employed, it is usually 0.1 to 20% by weight based on an active intermediate or a salt thereof.

Compound (VI) or a salt thereof can be also prepared by reduction of compound (V) or a salt thereof. A reducing agent is preferably Fe, Zn, Sn or $SnCl_2$.

This reaction may be performed under acidic conditions. An acid employed in this reduction may for example be an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, acids such as acetic acid, amides such as N,N-dimethylformamide and N,N-dimethylacetamide, and sulfoxides such as dimethylsulfoxide. These solvents may be used by mixing at an appropriate ratio.

While the reaction temperature may vary depending on the substrate employed as well as other conditions, it is −20 to 200° C., preferably 0 to 100° C. The reaction time is usually 5 minutes to 24 hours, preferably 5 minutes to 10 hours.

The thus obtained compound (VI) can be isolated and purified by the known isolating and purifying methods, for example, concentration, concentration under reduced pressure, extraction with solvent, crystallization, recrystallization, transfer dissolution and chromatography.

Compound (Ia) or a salt thereof, which is encompassed within compound (I) of the invention, can be prepared from compound (VI) or a salt thereof and a carbonyl compound $R^{a1}R^{a2}C=O$ or $R^{b1}R^{b2}C=O$ by in situ production of an imine which is then reduced by an appropriate reducing agent or catalytic hydrogenation (reaction A). When $R^a$ is equal to $R^b$ in Compound (Ia), $R^{a1}R^{a2}C=O$ may be used in this step. When $R^a$ is not equal to $R^b$ in compound (Ia), the alkylation reactions may be performed stepwise by $R^{a1}R^{a2}C=O$ and $R^{b1}R^{b2}C=O$ in this step.

A reducing agent is preferably sodium borohydride, lithium borohydride, sodium cyanoborohydride and sodium triacetoxyborohydride.

In this reaction, 1 to 10 moles, preferably 1 to 3 moles of the carbonyl compound $R^{a1}R^{a2}C=O$, $R^{b1}R^{b2}C=O$ and 0.5 to 10 moles, preferably 0.5 to 3 moles of the reducing agent per 1 mole of compound (VI) or a salt thereof are used. The reaction solvent may for example be alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, acids such as acetic acid, and sulfoxides such as dimethylsulfoxide. These solvents may be used by mixing at an appropriate ratio.

When producing an imine, use of molecular sieves or addition of an acid serves to promote the reaction. An acid employed here is preferably acetic acid and trifluoroacetic acid, etc. While the reaction temperature in this imine production may vary depending on compound (VI) or a salt thereof as well as other conditions, it is 0 to 200° C., preferably 0 to 150° C. The reaction time is 30 minutes to 48 hours, preferably 1 hour to 24 hours.

The reaction temperature in the reducing reaction is −20 to 200° C., preferably 0 to 100° C. The reaction time is 30 minutes to 24 hours, preferably 30 minutes to 12 hours.

Compound (Ia) or a salt thereof can be also prepared by reacting compound (VI) or a salt thereof with $R^aL$ or $R^bL$ (reaction B). When $R^a$ is equal to $R^b$ in compound (Ia), $R^aL$ may be used in this step. When $R^a$ is not equal to $R^b$ in compound (Ia), the alkylation reactions may be performed stepwise by $R^aL$ and $R^bL$ in this step.

In this reaction, 1 to 10 moles, preferably 1 to 5 moles of a compound represented by $R^aL$ or $R^bL$ or a salt thereof and 1 to 10 moles, preferably 1 to 3 moles of a base are employed per 1 mole of compound (VI) or a salt thereof. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (VI) or a salt thereof employed as well as other reaction conditions, it is −20 to 200° C., preferably 0 to 150° C. The reaction time is 5 minutes to 48 hours, preferably 5 minutes to 24 hours.

Alkylation of Compound (VI) to prepare compound (Ia) may be performed by combined reactions of reactions A and B.

The thus obtained Compound (Ia) can be isolated and purified by the known isolating and purifying methods, for example, concentration, concentration under reduced pressure, extraction with solvent, crystallization, recrystallization, transfer dissolution and chromatography.

(Scheme 2)

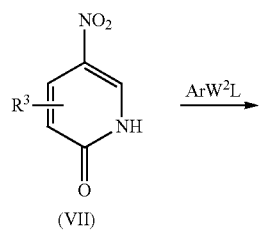

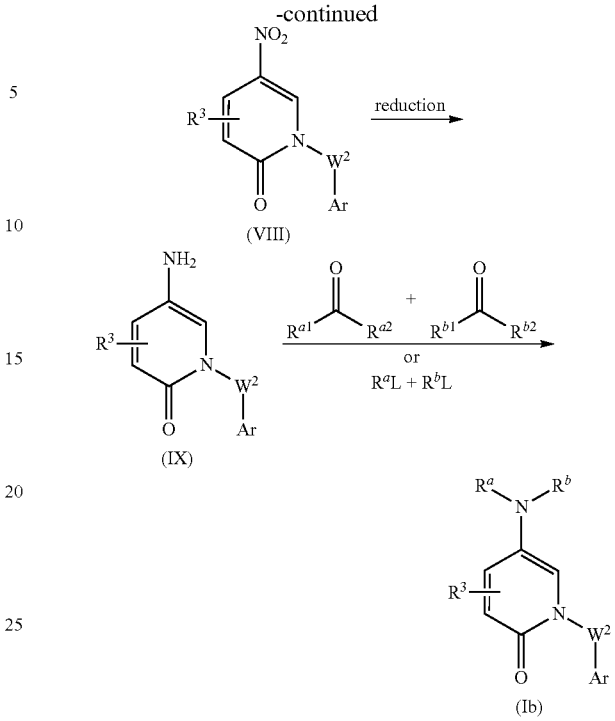

wherein $W^2$ is optionally substituted methylene and each of other symbols has a meaning defined above.

Compound (VIII) or salt thereof can be prepared by reaction of compound (VII) or salt thereof with $ArW^2L$.

In this step, 1 to 5 moles, preferably 1 to 3 moles of a compound represented by $ArW^2L$ or a salt thereof and 1 to 5 moles, preferably 1 to 3 moles of a base are employed per 1 mole of compound (VII) or a salt thereof. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (VII) or a salt thereof employed as well as other reaction conditions, it is −20 to 200° C., preferably 0 to 150° C. The reaction time is 5 minutes to 48 hours, preferably 5 minutes to 24 hours.

The thus obtained compound (VIII) can be isolated and purified by the known isolating and purifying methods, for example, concentration, concentration under reduced pressure, extraction with solvent, crystallization, recrystallization, transfer dissolution and chromatography.

Preparation of compound (IX) or a salt thereof from Compound (VIII) or a salt thereof can be carried out similar to preparation of compound (VI) in the scheme 1.

Preparation of compound (Ib) or a salt thereof, which is encompassed within compound (I) of the invention, from Compound (IX) or a salt thereof can be carried out similar to preparation of compound (Ia) in the scheme 1.

(Scheme 3)

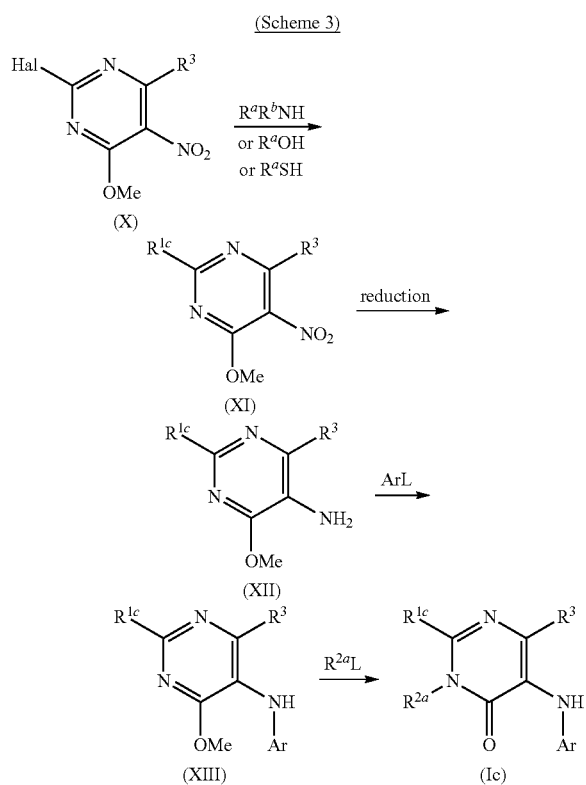

wherein $R^{1c}$ is substituted amino, optionally substituted cyclic amino, substituted hydroxy, substituted sulfanyl, optionally substituted sulfinyl, or optionally substituted sulfonyl and each of the other symbols has a meaning defined above.

Compound (XI) or a salt thereof can be prepared by reacting compound (X) with $R^aR^bNH$, $R^aOH$ or $R^aSH$.

In this step, 1 to 5 moles, preferably 1 to 3 moles of a compound represented by $R^aR^bNH$, $R^aOH$ or $R^aSH$ or a salt thereof and 0 to 5 moles, preferably 0 to 3 moles of a base are employed per 1 mole of compound (X) or a salt thereof. Examples of base are described above.

Examples of solvent having no adverse effect on the reaction include water, alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio or may not be used.

While the reaction temperature may vary depending on compound (X) or a salt thereof employed as well as other reaction conditions, it is −20 to 200° C., preferably 0 to 150° C. The reaction time is 5 minutes to 48 hours, preferably 5 minutes to 24 hours.

When $R^{1a}$ is substituted sulfanyl in compound (XI) or a salt thereof, oxidation of this compound can give compound (XI) or a salt thereof, wherein $R^{1a}$ is optionally substituted sulfinyl, or optionally substituted sulfonyl in compound (XI). A oxidation agent is preferably hydrogen peroxide, organic peroxides (e.g. 3-chloroperoxybenzoic acid, peroxyacetic acid, etc.), manganese(IV) oxide, sodium metaperiodate.

In this oxidation reaction, 1 to 10 moles, preferably 1 to 5 moles of oxidation agent are employed per 1 mole of compound (XI) or a salt thereof.

This reaction may be performed under acidic conditions. An acid employed in this oxidation may for example be an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

A reaction solvent may for example be water, alcohols such as methanol and ethanol, etc., ethers such as dioxane and tetrahydrofuran, etc., aromatic hydrocarbons such as benzene, toluene and xylene, etc., esters such as ethyl acetate, etc., halogenated hydrocarbons such as chloroform and dichloromethane, etc., nitriles such as acetonitrile, etc., amides such as N,N-dimethylformamide and N,N-dimethylacetamide, etc. and sulfoxides such as dimethylsulfoxide, etc. These solvents may be used by mixing at an appropriate ratio.

While the reaction temperature may vary depending on the substrate employed as well as other conditions, it is −20 to 200° C., preferably 0 to 100° C. The reaction time is usually 5 minutes to 24 hours, preferably 5 minutes to 10 hours.

The thus obtained compound (XI) can be isolated and purified by the known isolating and purifying methods, for example, concentration, concentration under reduced pressure, extraction with solvent, crystallization, recrystallization, transfer dissolution and chromatography.

Preparation of compound (XII) or a salt thereof from compound (XI) or a salt thereof can be carried out similar to preparation of compound (VI) in the scheme 1.

Compound (XIII) can be prepared by reacting compound (XII) with ArL or a salt thereof in the presence of a palladium catalyst, preferably palladium(II) acetate and a catalytic amount of a phosphine ligand, preferably 2-(dicyclohexylphosphino)biphenyl, according to the procedure of Buchwald et al. (J. Am. Chem. Soc. 1998, 120, 9722) and the modified methods.

Compound (Ic) or a salt thereof, which is encompassed within compound (I) of the invention, can be prepared by reacting compound (XIII) or a salt thereof with $R^{2a}L$.

In this reaction, 1 to 5 moles, preferably 1 to 3 moles of an $R^{2a}L$ are employed per 1 mole of compound (XIII) or a salt thereof.

This reaction may be performed under basic conditions. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XIII) or a salt thereof employed as well as other reaction conditions, it is −20 to 200° C., preferably 0 to 150° C. The reaction time is 5 minutes to 48 hours, preferably 5 minutes to 24 hours.

The thus obtained compound (Ic) can be isolated and purified by the known isolating and purifying methods, for example, concentration, concentration under reduced pressure, extraction with solvent, crystallization, recrystallization, transfer dissolution and chromatography.

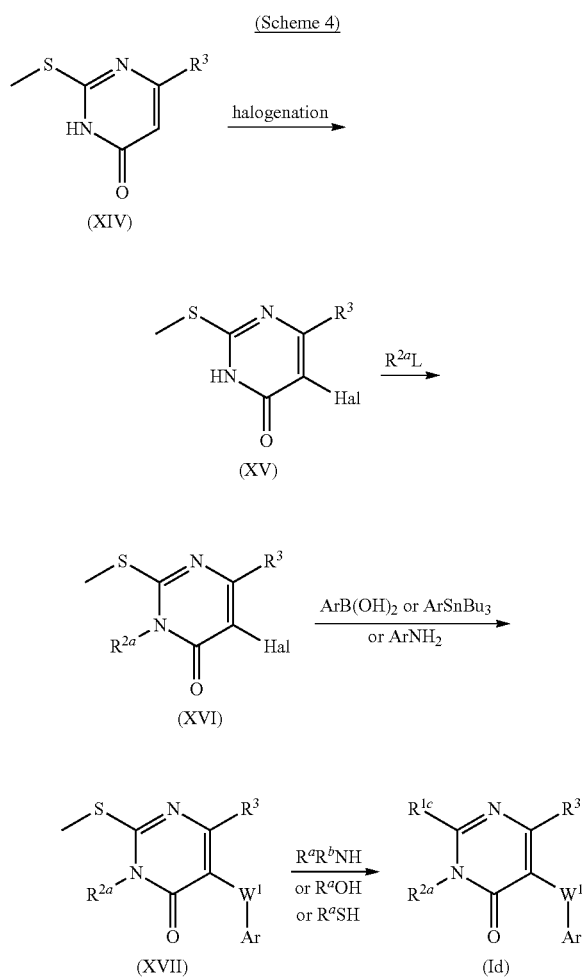

wherein each of the symbols has a meaning defined above.

Preparation of Compound (XV) or a salt thereof from compound (XIV) or a salt thereof can be carried out similar to preparation of Compound (IV) in the scheme 1.

Compound (XVI) or a salt thereof can be prepared by reacting compound (XV) with $R^{2a}L$.

In this reaction, 1 to 5 moles, preferably 1 to 3 moles of $R^{2a}L$ and 1 to 5 moles, preferably 1 to 3 moles of a base are employed per 1 mole of compound (XV) or a salt thereof. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XV) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XVI) can be isolated and purified by the known isolating and purifying methods, for example, concentration, concentration under reduced pressure, extraction with solvent, crystallization, recrystallization, transfer dissolution and chromatography.

Preparation of compound (XVII) or a salt thereof from compound (XVI) or a salt thereof can be carried out similar to preparation of compound (V) in the scheme 1.

Compound (Id) or a salt thereof, which is encompassed within compound (I) of the invention, can be prepared by reacting compound (XVII) with $R^aR^bNH$, $R^aOH$ or $R^aSH$.

In this step, 1 to 5 moles, preferably 1 to 3 moles of a compound represented by $R^aR^bNH$, $R^aOH$ or $R^aSH$ or a salt thereof are employed per 1 mole of compound (XVII) or a salt thereof.

This reaction may performed after oxidation of (XVII) to the correspond sulfone. A oxidation agent is preferably hydrogen peroxide, organic peroxides (e.g. 3-chloroperoxybenzoic acid, peroxyacetic acid, etc.), manganese(IV) oxide, sodium metaperiodate.

This reaction may be performed under basic conditions. Examples of base are described above.

Examples of solvent having no adverse effect on the reaction include water, alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide and N,N-dimethylacetamide, and sulfoxides such as dimethylsulfoxide. These solvents may be used by mixing at an appropriate ratio, or may not be used.

While the reaction temperature may vary depending on compound (XVII) or a salt thereof employed as well as other reaction conditions, it is −20 to 200° C., preferably 0 to 150° C. The reaction time is 5 minutes to 48 hours, preferably 5 minutes to 24 hours.

The thus obtained compound (Id) can be isolated and purified by the known isolating and purifying methods, for example, concentration, concentration under reduced pressure, extraction with solvent, crystallization, recrystallization, transfer dissolution and chromatography.

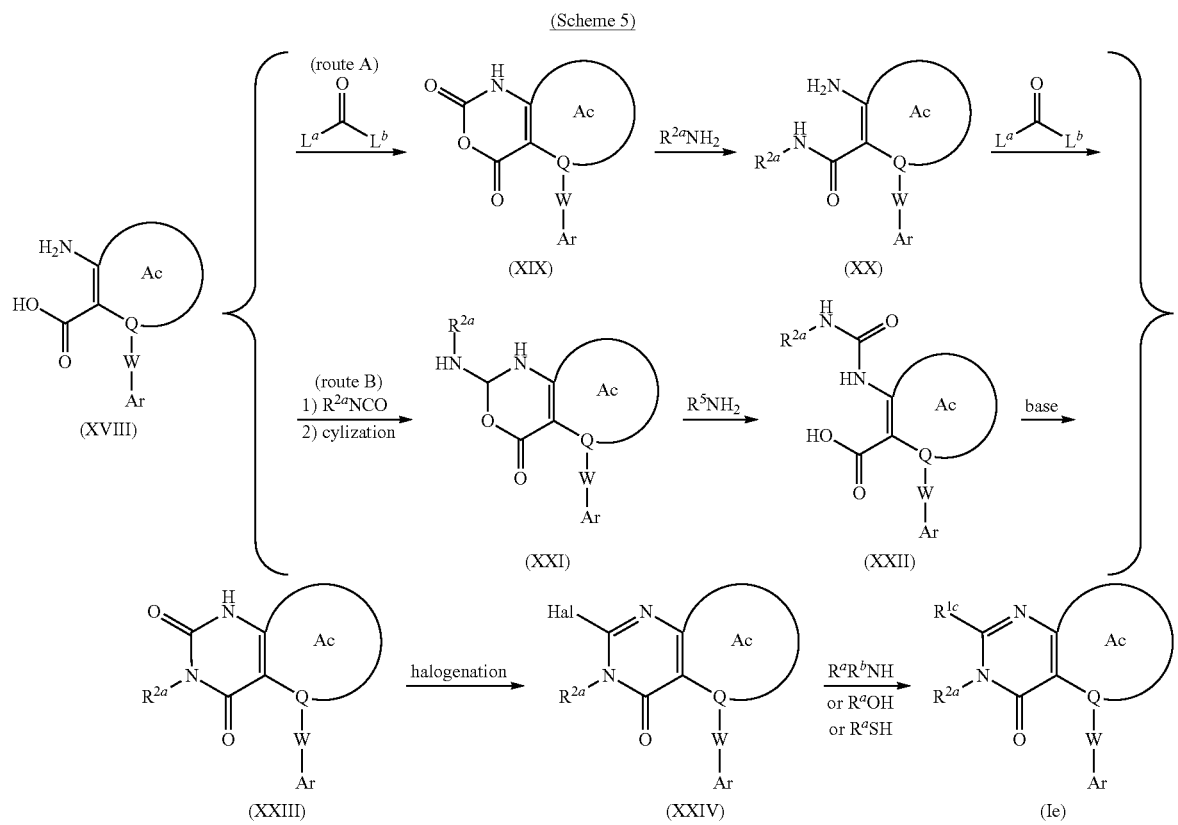

(Scheme 5)

wherein $L^a$ and $L^b$ are halogen atom such as chlorine, bromine and iodine, etc., or alkoxy group, $R^5$ is a lower alkyl group, and each of other symbols has a meaning defined above.

Compound (XXIII) can be prepared by route A or route B in scheme 5.

In route A, compound (XIX) or a salt thereof can be prepared by reacting compound (XVIII) or a salt thereof with $L^aCOL^b$.

In this step, 1 to 5 moles, preferably 1 to 3 moles of a compound represented by $L^aCOL^b$ such as phosgene, triphosgene and diethyl carbonate or a salt thereof are employed per 1 mole of compound (XVIII) or a salt thereof.

This reaction may be performed under basic conditions. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XVIII) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XIX) can be isolated and purified by the known isolating and purifying methods, for example, concentration, concentration under reduced pressure, extraction with solvent, crystallization, recrystallization, transfer dissolution and chromatography.

In route A, compound (XX) or a salt thereof can be prepared by reacting compound (XIX) or a salt thereof with $R^{2a}NH_2$.

In this step, 1 to 5 moles, preferably 1 to 3 moles of a compound represented by $R^{2a}NH_2$ or a salt thereof are employed per 1 mole of compound (XIX) or a salt thereof.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XIX) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XX) can be isolated and purified by the known isolating and purifying methods, for example, concentration, concentration under reduced pressure, extraction with solvent, crystallization, recrystallization, transfer dissolution and chromatography.

In route A, Compound (XXIII) or a salt thereof can be prepared by reacting compound (XX) or a salt thereof with L$^a$COL$^b$. This reaction can be carried out similar to preparation of Compound (XIX) in scheme 5.

In route B, compound (XXI) or a salt thereof can be prepared by reacting compound (XVIII) or a salt thereof with R$^{2a}$NCO followed by intramolecular cyclization, according to the procedure of Buchman et al. (Tetrahedron Letters 1998, 1487) and the modified methods.

In route B, compound (XXII) or a salt thereof can be prepared by reacting compound (XXI) or a salt thereof with R$^5$NH$_2$. This reaction can be carried out similar to preparation of Compound (XX) in scheme 5.

In route B, compound (XXIII) or a salt thereof can be prepared by cyclization of compound (XXII) or a salt thereof under basic conditions.

In this step, 1 to 5 moles, preferably 1 to 3 moles of a base are employed per 1 mole of compound (XXII) or a salt thereof. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XXII) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XXIII) can be isolated and purified by the known isolating and purifying methods, for example, concentration, concentration under reduced pressure, extraction with solvent, crystallization, recrystallization, transfer dissolution and chromatography.

Preparation of compound (XXIV) or a salt thereof from compound (XXIII) or a salt thereof can be carried out similar to preparation of compound (IV) in the scheme 1.

Preparation of compound (Ie) or a salt thereof, which is encompassed within compound (I) of the invention, from compound (XXIV) or a salt thereof can be carried out similar to preparation of compound (XI) in the scheme 3.

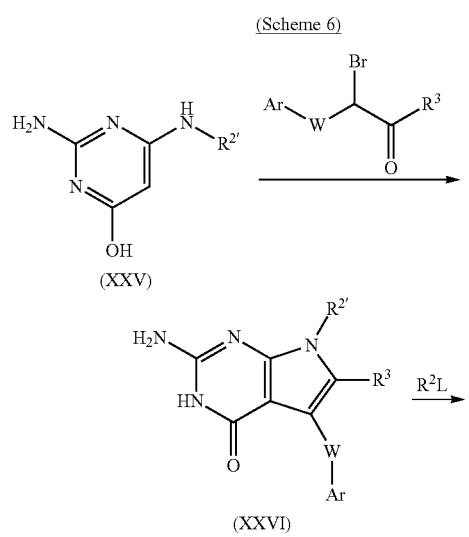

(Scheme 6)

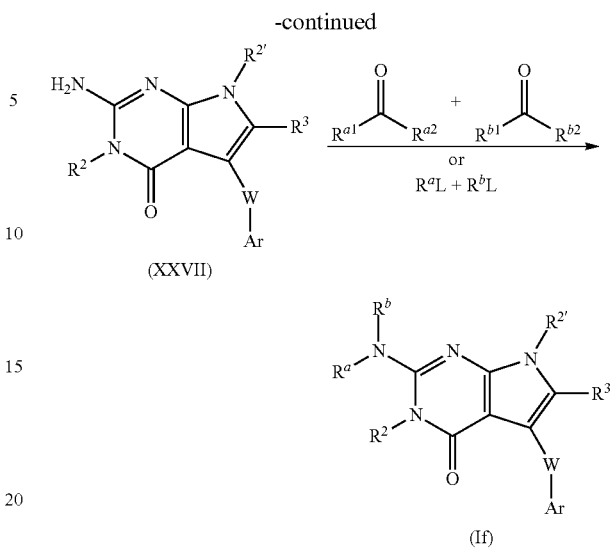

wherein each of symbols has a meaning defined above.

Compound (XXVI) or a salt thereof can be prepared by reacting compound (XXV) or a salt thereof with ArWCH(Br)COR$^3$.

In this step, 1 to 5 moles, preferably 1 to 3 moles of a compound represented by ArWCH(Br)COR$^3$ or a salt thereof are employed per 1 mole of compound (XXV) or a salt thereof.

This reaction may be performed under basic conditions or neutral conditions. Examples of base are described above Examples of solvent having no adverse effect on the reaction include water, alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XXV) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XXVI) can be isolated and purified by the known isolating and purifying methods, for example, concentration, concentration under reduced pressure, extraction with solvent, washing, crystallization, recrystallization, transfer dissolution and chromatography.

Compound (XXVII) or a salt thereof can be prepared by reacting compound (XXVI) or a salt thereof with R$^{2'}$L. This reaction can be carried out similar to preparation of compound (III) in scheme 1.

Preparation of compound (If) or a salt thereof, which is encompassed within compound (I) of the invention, from compound (XXVII) or a salt thereof can be carried out similar to preparation of compound (Ia) in scheme 1.

(Scheme 7)

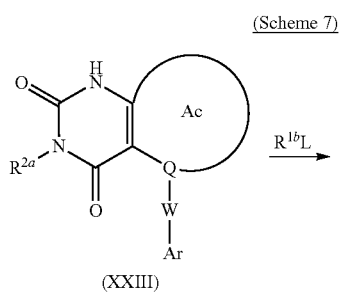

(XXIII)

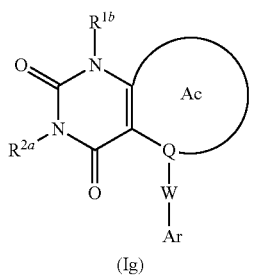

(Ig)

wherein each of symbols has a meaning defined above.

Preparation of compound (Ig) or a salt thereof, which is encompassed within compound (I) of the invention, from compound (XXIII) or a salt thereof can be carried out similar to preparation of compound (XVI) in the scheme 4.

(Scheme 8)

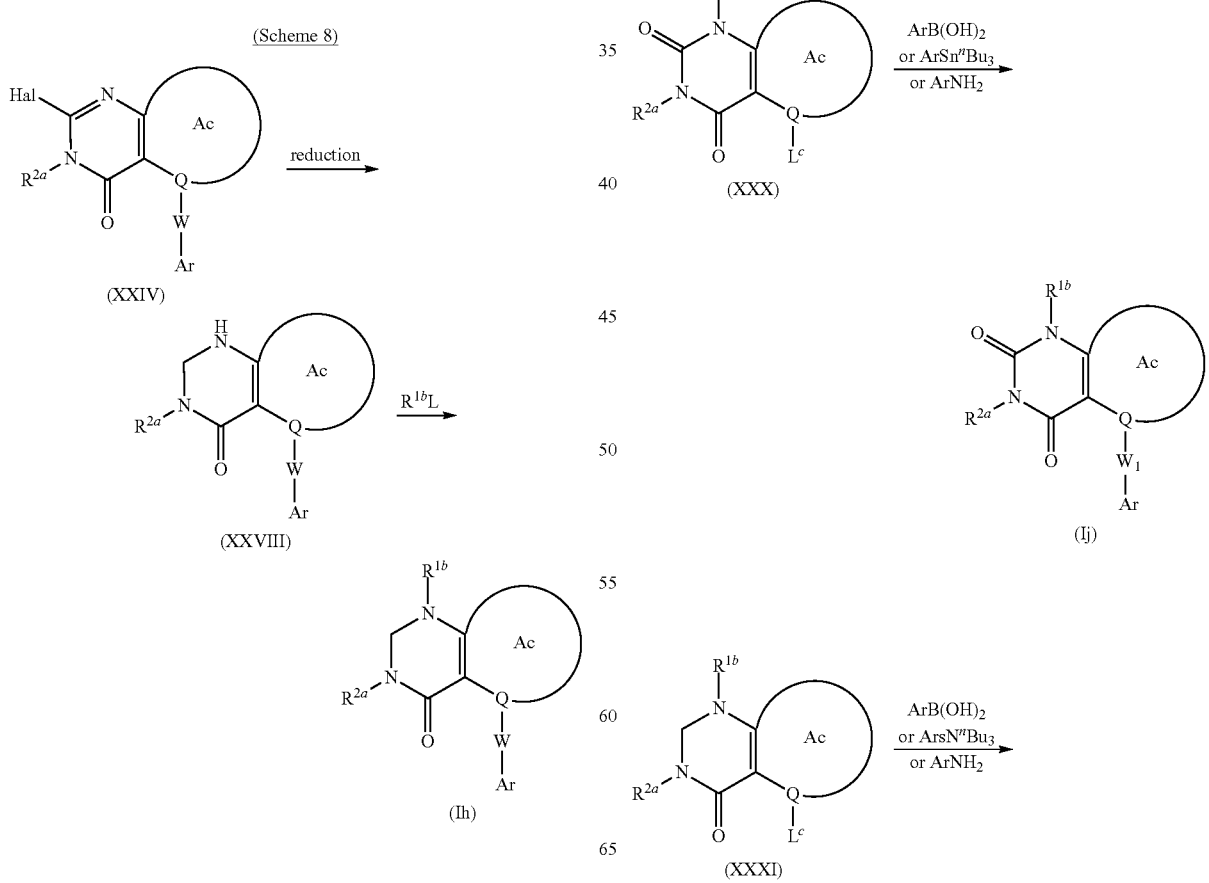

wherein each of symbols has a meaning defined above.

Preparation of compound (XXVIII) or a salt thereof from compound (XXIV) or a salt thereof can be carried out similar to preparation of compound (VI) in the scheme 1.

Preparation of compound (Ih) or a salt thereof, which is encompassed within compound (I) of the invention, from compound (XXVIII) or a salt thereof can be carried out similar to preparation of compound (XVI) in the scheme 4.

(Scheme 9)

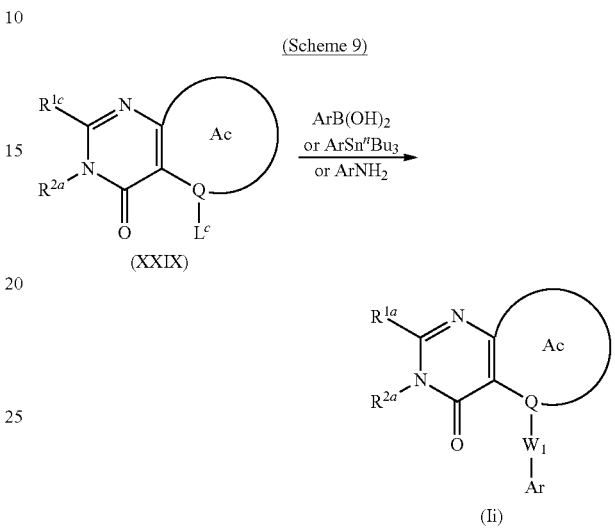

-continued

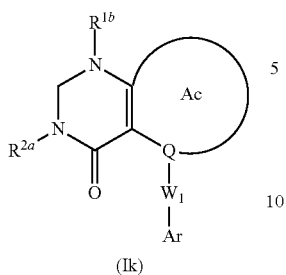

(Ik)

wherein $L^c$ is halogen atom such as chlorine, bromine and iodine, etc, sulfonyloxy group such as p-toluenesulfonyloxy group, methanesulfonyloxy group and trifluoromethanesulfonyloxy group, and each of other symbols has a meaning defined above.

Preparation of compounds (Ii), (Ij), or (Ik) or a salt thereof, which is encompassed within compound (I) of the invention, from compound (XXIX), (XXX), or (XXXI) or a salt thereof, respectively, can be carried out similar to preparation of compound (V) in the scheme 1.

(Scheme 10)

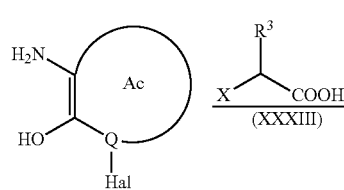

(XXXII)

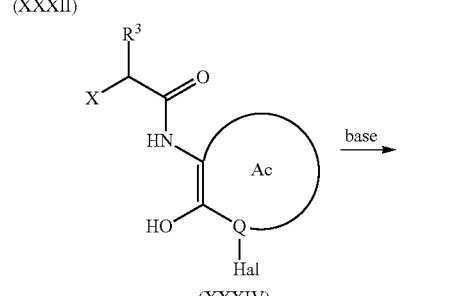

(XXXIV)

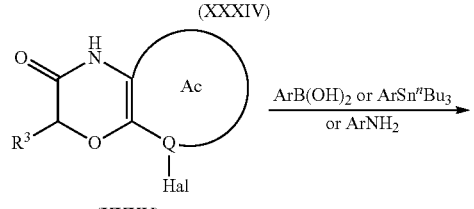

(XXXV)

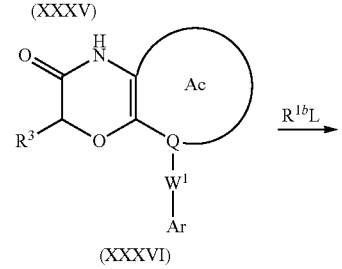

(XXXVI)

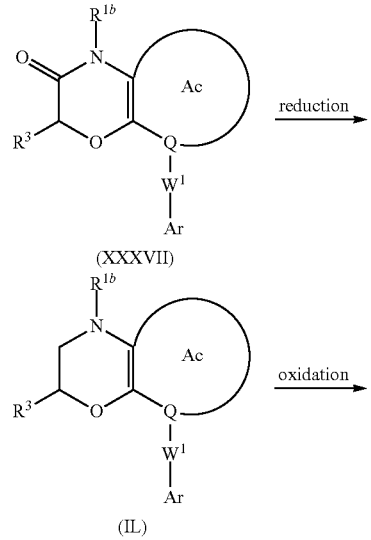

(XXXVII)

(IL)

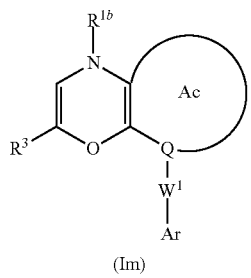

(Im)

wherein each of symbols has a meaning defined above.

Compound (XXXIV) is prepared by reacting a carboxylic acid (XXXIII) or a reactive derivative at a carboxyl group thereof and a salt thereof with compound (XXXII) or a reactive derivative at an amino group thereof or a salt thereof. Examples of the suitable reactive derivative at an amino group of compound (XXXII) include Schiff base type imine produced by reaction of compound (XXXII) with a carbonyl compound such as aldehyde, ketone and the like; silyl derivative produced by a reaction of compound (XXXII) and a silyl compound such as bis(trimethylsilyl)acetamide, mono(trimethylsilyl)acetamide, bis(trimethylsilyl)urea and the like; derivative produced by a reaction of compound (XXXII) with phosphorus trichloride or phosgene.

Specific examples of the suitable reactive derivative at a carboxyl group of compound (XXXIII) include acid halide, acid anhydride, activated amide, activated ester and the like. Examples of the suitable reactive derivative include: acid chloride; acid azide; mixed acid anhydride with an acid such as substituted phosphoric acid such as dialkylphosphoric acid, phenylphosphoric acid, diphenylphosphoric acid, dibenzylphosphoric acid, halogenated phosphoric acid and the like, dialkylphosphorous acid, sulfurous acid, thiosulfuric acid, sulfuric acid, sulfonic acid such as methanesulfonic acid and the like, aliphatic carboxylic acid such as acetic acid, propionic acid, butyric acid, isobutyric acid, pivalic acid, pentanoic acid, isopentanoic acid, trichloroacetic acid and the like or aromatic carboxylic acid such as benzoic acid and the like; symmetric acid anhydride; activated amide with imidazole; 4-substituted imidazole, dimethylpyrazole, triazole or tetrazole; activated ester such as cyanomethylester, methoxymethyl ester, dimethyliminoinethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxylmethyl thioester, pyranyl ester, pyridyl ester, piperidyl ester, 8-quinolyl thioester and the like, or esters with N-hydroxy compound such as N,N-dimethylhydroxyamine, 1-hydroxy-2-(1H)-pyridone, N-hydroxysuccinimide, N-hydroxyphthalimide, 1-hydroxy-1H-benzotriazole and the like. These reactive derivatives can be arbitrarily selected depending on a kind of compound (XXXII) to be used. Examples of the suitable reactive derivative of compound (XXXIII) include alkali metal salts such as sodium salt, potassium salt and the like, alkaline earth metal salts such as calcium salt, magnesium salt and the like, and basic salts such as organic base salts such as ammonium salt, trimethylamine salt, triethylamine salt, pyridine salt, picoline salt, dicyclohexylamine salt, N,N-dibenzylethylenediamine salt and the like. Although the reaction is usually carried out in the conventional solvent such as water, alcohols such as methanol, ethanol and the like, acetone, dioxane, acetonitrile, chloroform, dichloromethane, tetrahydrofuran, ethyl acetate, N,N-dimethylformamide and pyridine, the reaction may be carried out in any other organic solvents as long as they have no adverse effect on the reaction. These solvents may be used as a mixture with water.

When compound (XXXIII) is used as the form of a free acid or a salt thereof in this reaction, it is desirable that the reaction is carried out in the presence of the normally used condensing agent such as so-called Vilsmeier reagent and the like prepared by a reaction of N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide, N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; polyethyl phosphate; polyisopropyl phosphate; phosphorus oxychloride; diphenylphosphorylazide; thionyl chloride; oxalyl chloride; lower alkyl haloformate such as ethyl chloroformate; isopropyl chloroformate and the like; triphenylphosphine; 2-ethyl-7-hydroxybenzisooxazolium salt, 2-ethyl-5-(m-sulfopheny)isooxazoliumhydroxide internal salt; N-hydroxybenzotriazole; 1-(p-chlorobenzenesulfonyloxy)-6-chloro-1H-benzotriazole; N,N-dimethylformamide with thionyl chloride, phosgene, trichloromethyl chloroformate, phosphorus oxychloride or the like. Alternatively, the reaction may be carried out in the presence of an inorganic base or an organic base such as alkali metal bicarbonate salt, tri(lower)alkylamine, pyridine, N-(lower)alkylmorpholine, N,N-di(lower)alkylbenzylamine and the like. A reaction temperature is not particularly limited, but the reaction is carried out under cooling or under warming.

An amount of compound (XXXIII) to be used is 1 to 10 mole equivalent, preferably 1 to 3 equivalents relative to Compound (XXXII).

A reaction temperature is usually −30° C. to 100° C.

A reaction time is usually 0.5 to 20 hours.

In addition, when a mixed acid anhydride is used, compound (XXXIII) and chlorocarbonic ester (e.g. methyl chlorocarbonate, ethyl chlorocarbonate, isobutyl chlorocarbonate etc.) are reacted in the presence of a base (e.g. triethylamine, N-methylmorpholine, N,N-dimethylaniline, sodium bicarbonate, sodium carbonate, potassium carbonate etc.) and is further reacted with compound (XXXII).

An amount of compound (XXXIII) to be used is usually 1 to 10 mole equivalents, preferably 1 to 3 mole equivalents relative to compound (XXXII).

A reaction temperature is usually −30° C. to 100° C.

A reaction time is usually 0.5 to 20 hours.

The thus obtained compound (XXXIV) can be isolated and purified by the known isolating and purifying methods, for example, concentration, concentration under reduced pressure, extraction with solvent, crystallization, recrystallization, transfer dissolution and chromatography.

Compound (XXXV) or a salt thereof can be prepared by cyclization of compound (XXXIV) or a salt thereof under basic conditions.

In this step, 1 to 5 moles, preferably 1 to 3 moles of a base are employed per 1 mole of compound (XXXIV) or a salt thereof. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XXXIV) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XXXV) can be isolated and purified by the known isolating and purifying methods, for example, concentration, concentration under reduced pressure, extraction with solvent, crystallization, recrystallization, transfer dissolution and chromatography.

Preparation of compound (XXXVI) or a salt thereof from compound (XXXV) or a salt thereof can be carried out similar to preparation of compound (V) in the scheme 1.

Preparation of compound (XXXVII) or a salt thereof from compound (XXXVI) or a salt thereof can be carried out similar to preparation of compound (XVI) in the scheme 4.

Compound (IL) or a salt thereof, which is encompassed within compound (I) of the invention, can be prepared by reduction of compound (XXXVII) or a salt thereof. A reducing agent is preferably lithium aluminum hydride, sodium borohydride, lithium borohydride, sodium cyanoborohydride, sodium triacetoxyborohydride or borane.

This reaction may be performed under acidic conditions. An acid employed in this reduction may for example be an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

A reaction solvent may for example be alcohols such as methanol and ethanol, etc., ethers such as dioxane and tetrahydrofuran, etc., aromatic hydrocarbons such as benzene, toluene and xylene, etc., esters such as ethyl acetate, etc., halogenated hydrocarbons such as chloroform and dichloromethane, etc., nitriles such as acetonitrile, etc., amides such as N,N-dimethylformamide and N,N-dimethylacetamide, etc. and sulfoxides such as dimethylsulfoxide, etc. These solvents may be used by mixing at an appropriate ratio.

While the reaction temperature may vary depending on the substrate employed as well as other conditions, it is −20 to 200° C., preferably 0 to 100° C. The reaction time is usually 5 minutes to 24 hours, preferably 5 minutes to 10 hours.

The thus obtained compound (IL) can be isolated and purified by the known isolating and purifying methods, for example, concentration, concentration under reduced pressure, extraction with solvent, crystallization, recrystallization, transfer dissolution and chromatography.

Compound (Im) or a salt thereof, which is encompassed within compound (I) of the invention, can be prepared by oxidation of compound (IL) or a salt thereof. A oxidation agent is preferably hydrogen peroxide, organic peroxides (e.g. 3-chloroperoxybenzoic acid, peroxyacetic acid, etc.), manganese(IV) oxide, or sodium metaperiodate.

This reaction may be performed under basic conditions. Examples of base are described above.

Examples of solvent having no adverse effect on the reaction include water, alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (IL) or a salt thereof employed as well as other reaction conditions, it is −20 to 200° C., preferably 0 to 150° C. The reaction time is 5 minutes to 48 hours, preferably 5 minutes to 24 hours.

The thus obtained compound (Im) can be isolated and purified by the known isolating and purifying methods, for example, concentration, concentration under reduced pressure, extraction with solvent, crystallization, recrystallization, transfer dissolution and chromatography.

Preparation of compound (XXXIX) or a salt thereof from compound (XXXVIII) or a salt thereof can be carried out similar to preparation of compound (XXXIV) in the scheme 10.

Compound (XXXX) or a salt thereof can be prepared by reductive cyclization of compound (XXXVIII) or a salt thereof, according to the procedure of Roelen et al. (J. Med. Chem., 1991, 34, 1036) and the modified methods.

Preparation of compound (In) or a salt thereof, which is encompassed within compound (I) of the invention, from compound (XXXX) or a salt thereof can be carried out similar to preparation of compound (XVI) in the scheme 4.

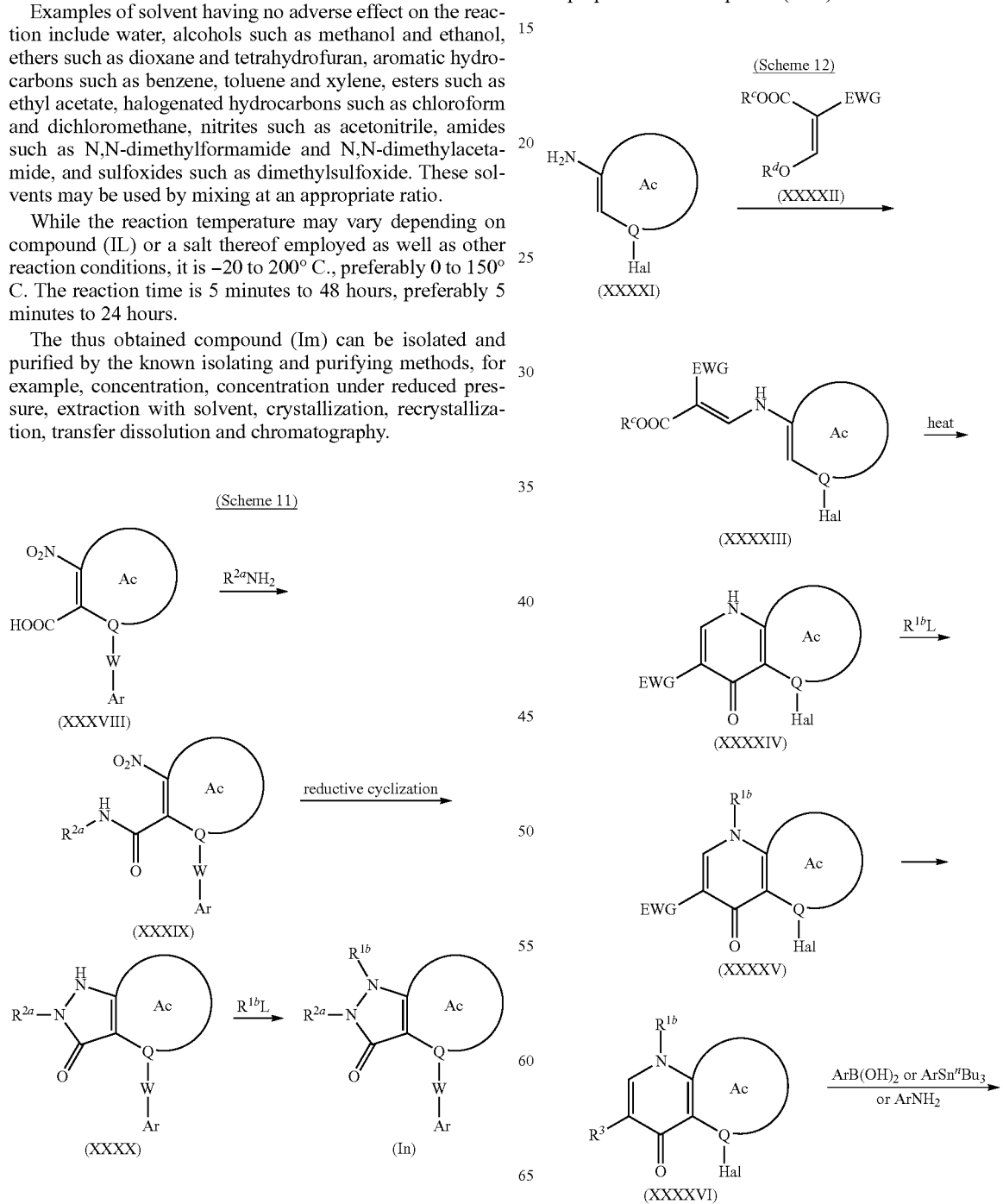

wherein each of symbols has a meaning defined above.

-continued

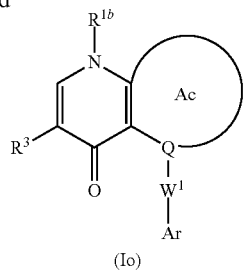

(Io)

wherein $R^c$ and $R^d$ are independently optionally substituted hydrocarbyl groups, EWG is electron withdrawing group (i.e. nitrile, ester, nitro, and aldehyde etc.) and each of other symbols has a meaning defined above.

Compound (XXXXIII) or a salt thereof can be prepared by reacting compound (XXXXI) or a salt thereof with compound (XXXXII) or a salt thereof.

In this step, 1 to 5 moles, preferably 1 to 3 moles of a compound (XXXXII) or a salt thereof are employed per 1 mole of compound (XXXXI) or a salt thereof.

This reaction may be performed under basic conditions. Examples of base are described above.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XXXXI) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XXXXIII) can be isolated and purified by the known isolating and purifying methods, for example, concentration, concentration under reduced pressure, extraction with solvent, crystallization, recrystallization, transfer dissolution and chromatography.

Compound (XXXXIV) or a salt thereof can be prepared by cyclization of compound (XXXXIII) or a salt thereof under heating conditions.

Examples of solvent having no adverse effect on the reaction include alcohols such as methanol and ethanol, ethers such as dioxane, tetrahydrofuran and diphenyl ether, aromatic hydrocarbons such as benzene, toluene, xylene, and biphenyl, esters such as ethyl acetate, halogenated hydrocarbons such as chloroform and dichloromethane, nitrites such as acetonitrile, amides such as N,N-dimethylformamide and N,N-dimethylacetamide, and sulfoxides such as dimethylsulfoxide, polyphosphate ester, and polyphosphoric acid. These solvents may be used by mixing at an appropriate ratio.

While the reaction temperature may vary depending on compound (XXXXIII) or a salt thereof employed as well as other reaction conditions, it is −20 to 300° C., preferably 50 to 250° C. The reaction time is 5 minutes to 48 hours, preferably 5 minutes to 24 hours.

The thus obtained compound (XXXXIV) can be isolated and purified by the known isolating and purifying methods, for example, concentration, concentration under reduced pressure, extraction with solvent, crystallization, recrystallization, transfer dissolution and chromatography.

Preparation of compound (XXXXV) or a salt thereof from compound (XXXXIV) or a salt thereof can be carried out similar to preparation of compound (XVI) in the scheme 4.

Compound (XXXXV) or a salt thereof can be converted to compound (XXXXVI) or a salt thereof by conventional organic reactions such as reduction, oxidation, halogenation, alkylation, etc. according to Organic Synthesis, Organic Reactions, etc.

Preparation of compound (Io) or a salt thereof, which is encompassed within compound (I) of the invention, from compound (XXXXVI) or a salt thereof can be carried out similar to preparation of compound (V) in the scheme 1.

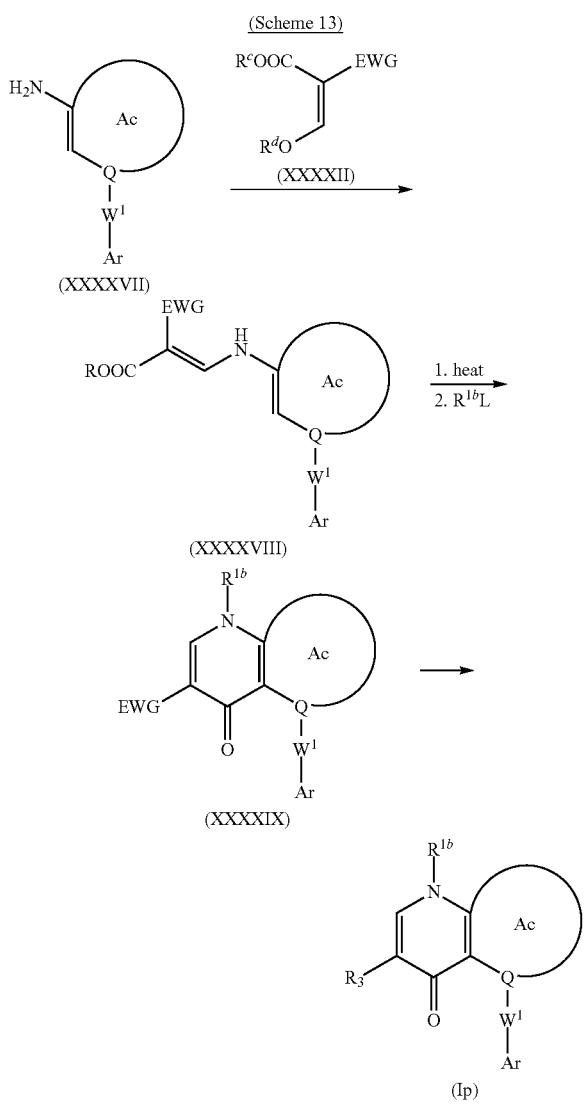

wherein each of other symbols has a meaning defined above.

Preparation of compound (XXXXVIII) or a salt thereof from compound (XXXXVII) or a salt thereof can be carried out similar to preparation of compound (XXXXIII) in scheme 12.

Preparation of compound (XXXXIX) or a salt thereof from compound (XXXXVIII) or a salt thereof can be carried out similar to preparation of compounds (XXXXIV and XXXXV) in scheme 12.

Preparation of compound (Ip) or a salt thereof, which is encompassed within compound (I) of the invention, from compound (XXXXIX) or a salt thereof can be carried out similar to preparation of compound (XXXXVI) in scheme 12.

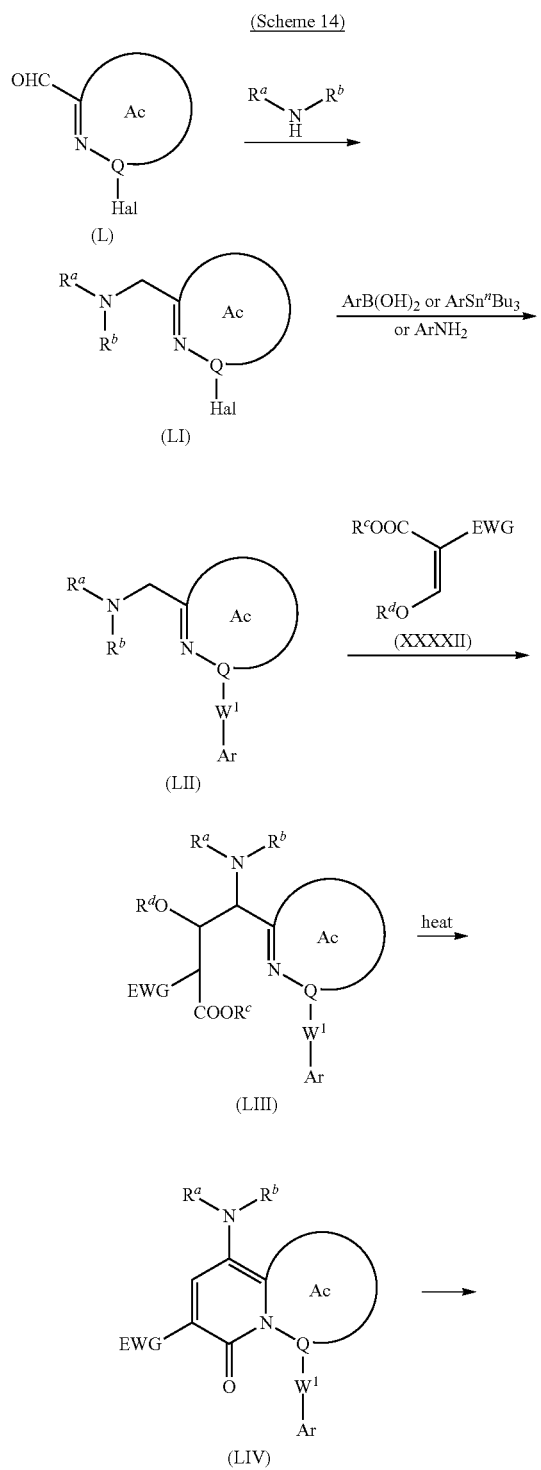

-continued

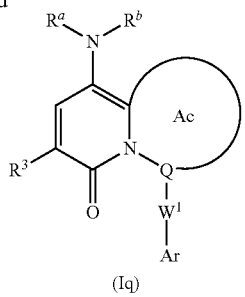

(Iq)

wherein each of symbols has a meaning defined above.

Compound (LI) or a salt thereof can be prepared from compound (L) or a salt thereof and an amino compound $R^aR^bNH$ by in situ production of an imine which is then reduced by an appropriate reducing agent.

A reducing agent is preferably sodium borohydride, lithium borohydride, sodium cyanoborohydride and sodium triacetoxyborohydride.

In this reaction, 1 to 10 moles, preferably 1 to 3 moles of the amino compound $R^aR^bNH$ and 0.5 to 10 moles, preferably 0.5 to 3 moles of the reducing agent per 1 mole of compound (L) or a salt thereof are used. The reaction solvent may for example be alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, acids such as acetic acid, and sulfoxides such as dimethylsulfoxide. These solvents may be used by mixing at an appropriate ratio.

When producing an imine, use of molecular sieves or addition of an acid serves to promote the reaction. An acid employed here is preferably acetic acid and trifluoroacetic acid, etc. While the reaction temperature in this imine production may vary depending on compound (L) or a salt thereof as well as other conditions, it is 0 to 200° C., preferably 0 to 150° C. The reaction time is 30 minutes to 48 hours, preferably 1 hour to 24 hours.

The reaction temperature in the reducing reaction is −20 to 200° C., preferably 0 to 100° C. The reaction time is 30 minutes to 24 hours, preferably 30 minutes to 12 hours.

The thus obtained compound (LI) can be isolated and purified by the known isolating and purifying methods, for example, concentration, concentration under reduced pressure, extraction with solvent, crystallization, recrystallization, transfer dissolution and chromatography.

Preparation of compound (LII) or a salt thereof from compound (LI) or a salt thereof can be carried out similar to preparation of compound (V) in the scheme 1.

Compound (LIII) or a salt thereof can be prepared by reacting compound (LII) or a salt thereof with compound (XXXXII) or a salt thereof.

In this reaction, 1 to 5 moles, preferably 1 to 3 moles of compound (XXXXII) and 1 to 5 moles, preferably 1 to 3 moles of a base are employed per 1 mole of compound (LII) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, lithium amide, alkyl lithium such as n-butyllithium, sec-buthillityhium and tert-butyllthium, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

Examples of solvent having no adverse effect on the reaction include alcohols such as methanol and ethanol, ethers such as dioxane and tetrahydrofuran, aromatic hydrocarbons example, concentration, concentration under reduced pressure, extraction with solvent, crystallization, recrystallization, transfer dissolution and chromatography.

Preparation of compound (LIV) or a salt thereof from compound (LIII) or a salt thereof can be carried out similar to preparation of compound (XXXXIV) in the scheme 12.

Preparation of compound (Iq) or a salt thereof, which is encompassed within compound (I) of the invention, from compound (LV) or a salt thereof can be carried out similar to preparation of compound (XXXXVI) in the scheme 12.

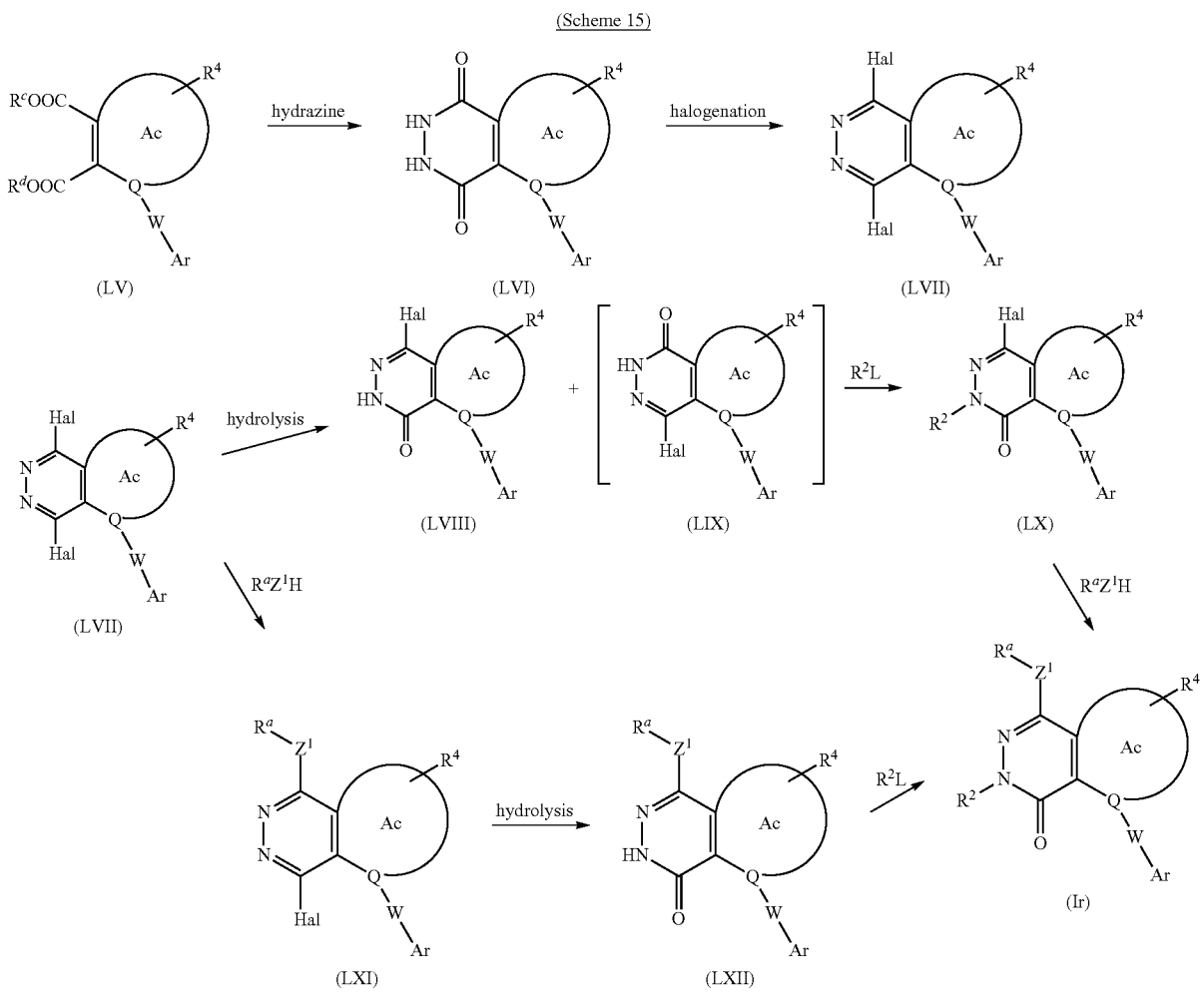

such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (LII) or a salt thereof employed as well as other reaction conditions, it is −100 to 100° C., preferably −100 to 50° C. The reaction time is 5 minutes to 48 hours, preferably 5 minutes to 24 hours.

The thus obtained compound (LIII) can be isolated and purified by the known isolating and purifying methods, for wherein $Z^1$ is oxygen, sulfur, —$NR^6$—, —SO—, —$SO_2$—, $R^6$ is same as $R^2$ defined above, and each of other symbols has meaning defined above.

Compound (LVI) or salt thereof can be prepared from compound (LV) or salt thereof with hydrazine.

In this reaction, 1 to 30 moles, preferably 3 to 10 moles of hydrazine are employed per 1 mole of compound (LV).

Examples of solvent having no adverse effect on the reaction include water, alcohols such as methanol, ethanol, aromatic hydrocarbons such as benzene, toluene and xylene, ethers such as dioxane and tetrahydrofuran, esters such as ethyl acetate, nitriles such as acetonitrile, halogenated hydrocarbon such as chloroform and dichloromethane, amides such as N,N-dimethlformamide and N,N-dimethylacetamide, and sulfoxides such as dimethylsulfoxide. These solvents may be used by mixing at an appropriate ratio.

While the reaction temperature may vary depending on compound (LV) or a salt thereof employed as well as other conditions, it is 20 to 200° C., preferably 20 to 100° C. The reaction time is 1 hour to 96 hours, preferably 1 hour to 48 hours.

The thus obtained compound (LVI) can be isolated and purified by the known isolating and purifying methods, for example, concentration under reduced pressure, extraction with solvent, crystallization, recrystallization, transfer dissolution and chromatography.

Compound (LVII) or a salt thereof can be prepared by alkylation of compound (LVI) or a salt thereof with a halogenation agent.

Examples of halogenation agent include phosphorous oxychloride, phosphorous trichloride, phosphorous pentachloride, chlorine, thionyl chloride. The halogenation agent is employed in an amount of 2 moles to excess per 1 mole of compound (LVI) or as a solvent.

Examples of solvent having no adverse effect on the reaction include aromatic hydrocarbons such as benzene, toluene and xylene, ethers such as dioxane and tetrahydrofuran, esters such as ethyl acetate, nitriles such as acetonitrile, halogenated hydrocarbon such as chloroform and dichloromethane, amides such as N,N-dimethlformamide and N,N-dimethylacetamide, and sulfoxides such as dimethylsulfoxide. These solvents may be used by mixing at an appropriate ratio.

While the reaction temperature may vary depending on compound (LVI) or a salt thereof employed as well as other conditions, it is 20 to 200° C., preferably 20 to 150° C. The reaction time is 10 minute to 12 hours, preferably 30 minutes to 6 hours.

The thus obtained compound (LVII) can be isolated and purified by the known isolating and purifying methods, for example, concentration under reduced pressure, extraction with solvent, crystallization, recrystallization, transfer dissolution and chromatography.

Compound (LVIII) or a salt thereof can be prepared by hydrolysis of compound (LVII) or a salt thereof.

In this reaction, 1 to 50 moles, preferably 1 to 30 moles of a base are employed per 1 mole of compound (LVII) or a salt thereof.

A base may for example be an alkaline metal hydroxide such as sodium hydroxide and potassium hydroxide, alkaline earth metal hydroxide such as magnesium hydroxide and calcium hydroxide, an alkaline metal carbonate such as sodium carbonate and potassium carbonate, an alkaline metal hydrogen carbonate such as sodium hydrogen carbonate and potassium hydrogen carbonate.

Examples of solvent having no adverse effect on the reaction include water, amides such as N,N-dimethlformamide and N,N-dimethylacetamide, and sulfoxides such as dimethylsulfoxide, ethers such as dioxane and tetrahydrofuran, aromatic hydrocarbons such as benzene, toluene and xylene. These solvents may be used by mixing at an appropriate ratio.

While the reaction temperature may vary depending on compound (LVII) or a salt thereof employed as well as other conditions, it is 20 to 200° C., preferably 20 to 150° C. The reaction time is 15 minutes to 12 hours, preferably 30 minutes to 6 hours.

The thus obtained compound (LVIII) can be isolated and purified by the known isolating and purifying methods, for example, concentration under reduced pressure, extraction with solvent, crystallization, recrystallization, transfer dissolution and chromatography.

Compound (LX) or a salt thereof can be prepared by alkylation of compound (LVIII) or a salt thereof with $R^2L$.

In this reaction, 1 to 10 moles, preferably 1 to 5 moles of $R^2L$ or a salt thereof and 1 to 5 mole, preferably 1 to 3 moles of a base, are employed per 1 mole of compound (LVIII) or a salt thereof.

A base may for example be an alkaline metal hydroxide such as sodium hydroxide and potassium hydroxide, alkaline earth metal hydroxide such as magnesium hydroxide and calcium hydroxide, an alkaline metal carbonate such as sodium carbonate and potassium carbonate, an alkaline metal hydrogen carbonate such as sodium hydrogen carbonate and potassium hydrogen carbonate.

Examples of solvent having no adverse effect on the reaction include amides such as N,N-dimethlformamide and N,N-dimethylacetamide, and sulfoxides such as dimethylsulfoxide, ethers such as dioxane and tetrahydrofuran, aromatic hydrocarbons such as benzene, toluene and xylene. These solvents may be used by mixing at an appropriate ratio.

While the reaction temperature may vary depending on compound (LVIII) or a salt thereof employed as well as other conditions, it is 20 to 200° C., preferably 20 to 150° C. The reaction time is 15 minute to 12 hours, preferably 30 minutes to 6 hours.

The thus obtained compound (LX) can be isolated and purified by the known isolating and purifying methods, for example, concentration under reduced pressure, extraction with solvent, crystallization, recrystallization, transfer dissolution and chromatography.

Compound (Ir) or a salt thereof, which is encompassed within compound (I) of the invention, can be prepared by reacting compound (LX) or a salt thereof with $R^aZ^1H$.

In this reaction, 1 to 5 moles, preferably 1 to 3 moles of a compound represented $R^aZ^1H$ or a salt thereof and 1 to 3 moles of a base are employed per 1 mole of compound (LX).

A base may for example be an alkaline metal hydroxide such as sodium hydroxide and potassium hydroxide, alkaline earth metal hydroxide such as magnesium hydroxide and calcium hydroxide, an alkaline metal carbonate such as sodium carbonate and potassium carbonate, an alkaline metal hydrogen carbonate such as sodium hydrogen carbonate and potassium hydrogen carbonate, an alkaline metal hydride such as sodium hydride, potassium hydride, etc., sodium amide, an alkoxide such as sodium methoxide, sodium ethoxide, sodium tert-butoxide and potassium tert-butoxide, etc., organic base such as trimethylamine, triethylamine, pyridine, N-methylmorpholine, etc.

Examples of solvent having no adverse effect on the reaction include water, amides such as N,N-dimethlformamide and N,N-dimethylacetamide, and sulfoxides such as dimethylsulfoxide, ethers such as dioxane and tetrahydrofuran, aromatic hydrocarbons such as benzene, toluene and xylene. These solvents may be used by mixing at an appropriate ratio or may not be used.

While the reaction temperature may vary depending on compound (LX) or a salt thereof employed as well as other conditions, it is 20 to 250° C., preferably 20 to 200° C. The reaction time is 15 minute to 24 hours, preferably 30 minutes to 12 hours.

The thus obtained compound (Ir) can be isolated and purified by the known isolating and purifying methods, for example, concentration under reduced pressure, extraction with solvent, crystallization, recrystallization, transfer dissolution and chromatography.

When $Z^1$ is —$NR^5$— in $R^aZ^1H$, compound (Ir) or a salt thereof can be also prepared by reacting compound (LX) or a salt thereof in $R^aZ^1H$ as a solvent with or without a base.

When $Z^1$ is —SO— or —SO2— in compound (Ir) or a salt thereof, which is encompassed within (I) in the invention, can be prepared by oxidation of compound (Ir) or a salt thereof. In this oxidation, 1 to 10 moles, preferably 1 to 5 moles of oxidation agent are employed per 1 mole of compound (Ir) or a salt thereof.

An oxidation agent is preferably hydrogen peroxide, organic peroxide such as 3-chloroperoxybezoic acid, peroxyacetic acid, etc., manganese(IV) oxide, or sodium metaperiocate.

This reaction may be performed under acidic conditions. An acid employed may for example be an inorganic acid such as hydrochloric acid, sulfuric acid and nitric acid, etc., and ordinally organic acid such as formic acid, acetic acid, trifluoroacetic acid and methanesulfonic acid, etc., as well as Lewis acid.

Examples of solvent having no adverse effect on the reaction include water, alcohols such as methanol and ethanol, ethers such as dioxane and tetrahydrofuran, halogenated hydrocarbon such as dichloromethane and chloroform, nitriles such as acetonitrile, amides such as N,N-dimethlformamide and N,N-dimethylacetamide, and sulfoxides such as dimethylsulfoxide, and aromatic hydrocarbons such as benzene, toluene and xylene. These solvents may be used by mixing at an appropriate ratio.

While the reaction temperature may vary depending an compound (Ir) or a salt thereof employed as well as other conditions, it is 0 to 200° C., preferably 20 to 100° C. The reaction time is 5 minutes to 24 hours, preferably 5 minutes to 12 hours.

The thus obtained compound (Ir) can be isolated and purified by the known isolating and purifying methods, for example, concentration under reduced pressure, extraction with solvent, crystallization, recrystallization, transfer dissolution and chromatography.

Preparation of compound (LXI) or a salt thereof from compound (LVII) or a salt thereof can be carried out similar to preparation of compound (Ir) described above.

Preparation of compound (LXII) or a salt thereof from compound (LXI) or a salt thereof can be carried out similar to preparation of compound (LVIII) described above.

Preparation of compound (Ir) or a salt thereof from compound (LXII) or a salt thereof can be carried out similar to preparation of compound (LX) described above.

(Scheme 16)

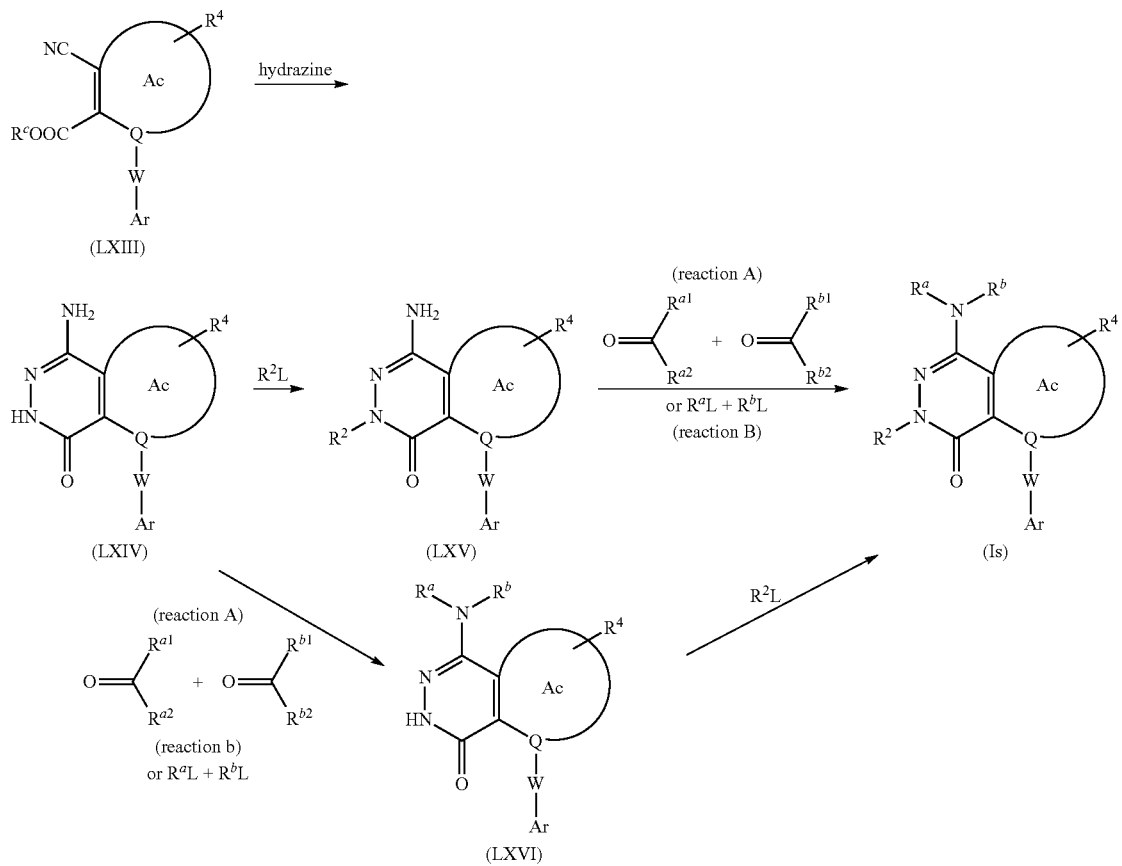

wherein each of other symbols has a meaning defined above.

Preparation of compound (LXIV) or a salt thereof from compound (LXIII) or a salt thereof can be carried out similar to preparation of compound (LVI) in scheme 15.

Preparation of compound (LXV) or a salt thereof from compound (LXIV) or a salt thereof can be carried out similar to preparation of compound (LX) in scheme 15.

Preparation of compound (Is) or a salt thereof, which is encompassed within compound (I) of the invention, from compound (LXV) or a salt thereof can be carried out similar to preparation of compound (Ia) in scheme 1.

Preparation of compound (LXVI) or a salt thereof from compound (LXIV) or a salt thereof can be carried out similar to preparation of compound (Ia) in scheme 1.

Preparation of compound (Is) or a salt thereof from compound (LXVI) or a salt thereof can be carried out similar to preparation of compound (LX) in scheme 15.

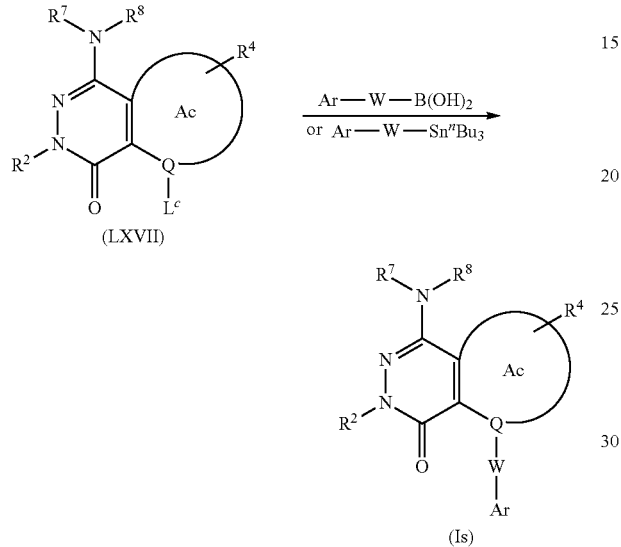

(Scheme 17)

wherein $R^7$, $R^8$ are hydrogen, or independently optionally substituted hydrocarbyl groups, or $R^7$ and $R^8$ may be optionally substituted cyclic form, and each of other symbols has a meaning defined above.

When Q is carbon in compound (LXVII), compound (Is) or a salt thereof can be prepared from compound (LXVII) or a salt thereof similar to preparation of compound (V) in scheme 1.

When Q is nitrogen in compound (LXVII), compound (Is) or a salt thereof can be prepared by reacting compound (LXVII) with a boronic acid ArWB(OH)$_2$ or boronic acid esters or a salt thereof in the presence of an equivalent or a catalytic amount of copper catalyst, preferably copper(II) diacetate and a base with or without an oxidant according to the reported procedure (Tetrahedron Lett., 42, 3415-3418 (2001)) and the modified methods.

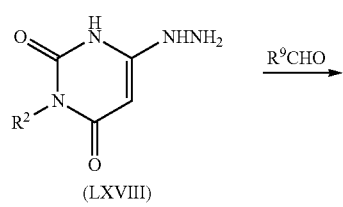

(Scheme 18)

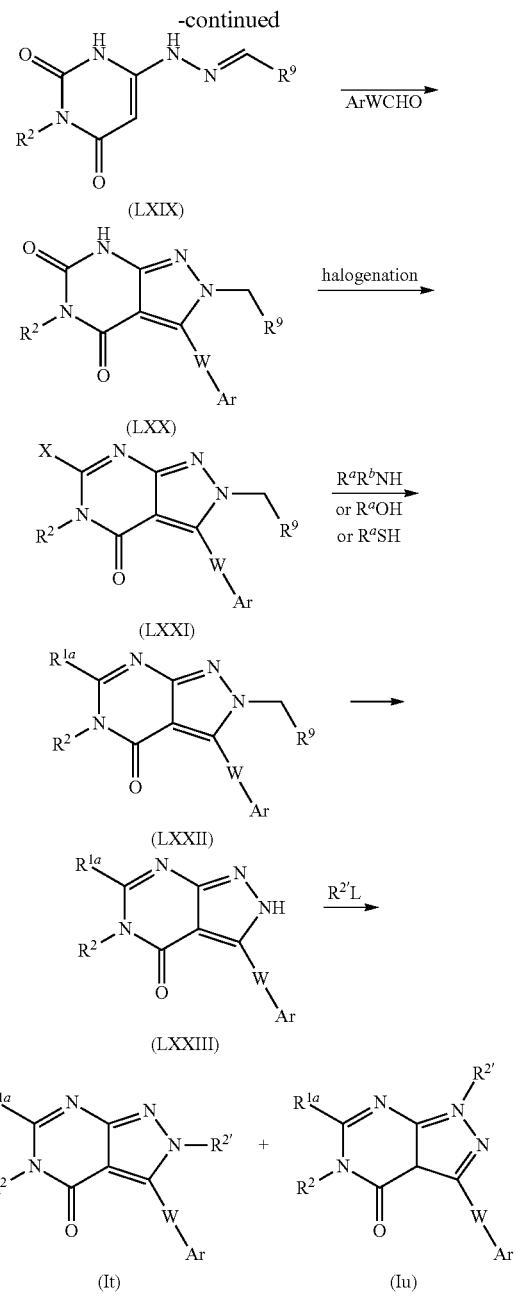

wherein $R^9$ is phenyl or optionally substituted phenyl, and each of the other symbols has a meaning defined above.

Compound (LXIX) can be prepared by reacting compound (LXVIII) or a salt thereof with $R^9$CHO.

In this step, 1 to 5 moles, preferably 1 to 3 moles of a compound represented by $R^9$CHO are employed per 1 mole of compound (LXVIII) or a salt thereof.

Examples of solvent having no adverse effect on the reaction include water, alcohols such as methanol, ethanol, aromatic hydrocarbons such as benzene, toluene and xylene, ethers such as dioxane and tetrahydrofuran, esters such as ethyl acetate, nitriles such as acetonitrile, halogenated hydrocarbon such as chloroform and dichloromethane, amides such as N,N-dimethlformamide and N,N-dimethylacetamide, and sulfoxides such as dimethylsulfoxide. These solvents may be used by mixing at an appropriate ratio.

While the reaction temperature may vary depending on compound (LXVIII) or a salt thereof, it is −20 to 200° C., preferably 0 to 100° C. The reaction time is 5 minutes to 48 hours, preferably 5 minutes to 24 hours.

The thus obtained compound (LXIX) can be isolated and purified by the known isolating and purifying methods, for example, concentration under reduced pressure, extraction with solvent, crystallization, recrystallization, transfer dissolution and chromatography.

Compound (LXX) or a salt thereof can be prepared by reacting compound (LXIX) or a salt thereof with ArWCHO.

In this step, 1 to 5 moles, preferably 1 to 3 moles of a compound represent by ArWCHO are employed per 1 mole of compound (LXIX) or a salt thereof.

This reaction may be performed under basic conditions. Examples of base are described above.

Examples of solvent having no adverse effect on the reaction include water, alcohols such as methanol, ethanol, aromatic hydrocarbons such as benzene, toluene and xylene, ethers such as dioxane and tetrahydrofuran, esters such as ethyl acetate, nitriles such as acetonitrile, halogenated hydrocarbon such as chloroform and dichloromethane, amides such as N,N-dimethlformamide and N,N-dimethylacetamide, and sulfoxides such as dimethylsulfoxide. These solvents may be used by mixing at an appropriate ratio.

While the reaction temperature may vary depending on compound (LXIX) or a salt thereof, it is −20 to 200° C., preferably 0 to 150° C. The reaction time is 5 minutes to 48 hours, preferably 5 minutes to 24 hours.

Compound (LXXI) or a salt thereof from compound (LXX) or a salt thereof can be carried out similar to preparation of compound (LVII) in scheme 15.

Preparation of compound (LXXII) or a salt thereof can be carried out similar to the preparation of compound (XI) in scheme 3.

Compound (LXXIII) or a salt thereof can be prepared by reacting a compound (LXXII) or a salt thereof under conditions for hydrogenolysis including phase transfer conditions, Pearlman's catalyst, etc.

In the present reaction, if needed, any solvents can be used as long as they do not inhibit the reaction. Inter alia, alcohols (e.g. $C_{1-3}$ alcohol such as methanol, ethanol, propanol and the like), ethers (diethyl ether, diisopropyl ether, ethylene glycol dimethyl ether, tetrahydrofuran, dioxane, etc.), or esters (ethyl acetate, etc.) are preferable. These solvents may be used by mixing at an appropriate ratio.

The reaction temperature is 0° C. to 200° C., preferably 20° C. to 100° C. The reaction time is usually 0.5 to 48 hours, preferably 1 to 16 hours. While a reaction is usually performed at atmospheric pressure, it can be performed under pressure (3 to 10 atom) if necessary.

While the amount of a catalyst employed may vary depending on the type of the catalyst employed, it is usually 0.1 to 20% by weight based on an active intermediate or a salt thereof.

Preparation of compounds (It) and (Iu) or a salt thereof, which is encompassed within compound (I) of the invention, from compound (LXXIII) can be carried out similar to preparation of compound (XXXXV) in scheme 12.

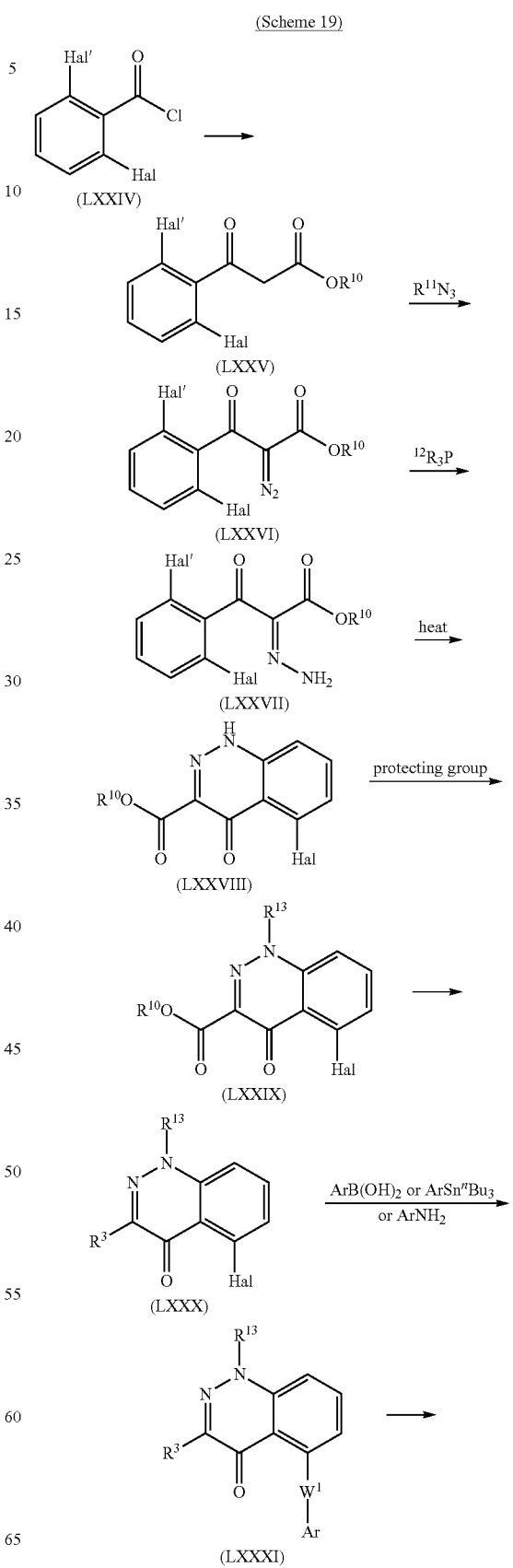

-continued

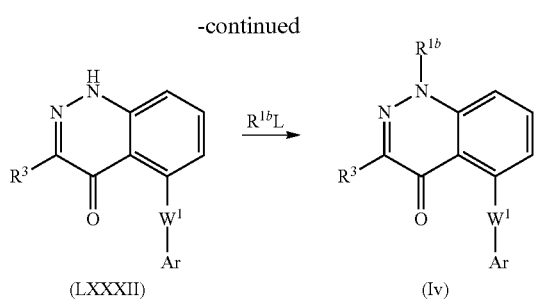

wherein Hal and Hal' is halogen, $R^{10}$ is optionally substituted hydrocarbyl, $R^{11}N_3$ is an organic or inorganic azide, $^{12}R_3P$ is a trialkyl- or triarylphosphine, $R^{13}$ is an amino protecting group. A protective group for an amino group may for example be an optionally substituted $C_{1-6}$ alkylcarbonyl (for example, formyl, methylcarbonyl and ethylcarbonyl, etc.), phenylcarbonyl, a $C_{1-6}$ alkyloxycarbonyl (for example, methoxycarbonyl and ethoxycarbonyl, etc.), phenyloxycarbonyl (for example, benzoxycarbonyl), $C_{7-10}$ aralkylcarbonyl (for example, benzyloxycarbonyl), trityl, phthaloyl, etc. A substituent on each of the groups listed above may be a halogen atom (for example, fluorine, chlorine, bromine and iodine, etc.), a $C_{1-6}$ alkylcarbonyl (for example, methylcarbonyl, ethylcarbonyl and butylcarbonyl, etc.). Each of the other symbols has meaning defined above.

Compound (LXXV) can be prepared by alkylation of compound (LXXIV) according to the procedure of Rathke et al. (J. Org. Chem. 1985, 50, 2622) and the modified methods.

Compound (LXXVI) can be prepared via diazotization of compound (LXXV). As a diazotizing agent, mesyl azide, tosyl azide, sodium azide, etc. are utilized.

Examples of solvent having no adverse effect on the reaction include water, nitriles such as acetonitrile, and halogenated hydrocarbon such as chloroform and dichloromethane. These solvents may be used by mixing at an appropriate ratio.

While the reaction temperature may vary depending on compound (LXXV), it is −20 to 100° C., preferably 0 to 50° C. The reaction time is 5 minutes to 48 hours, preferably 5 minutes to 24 hours.

Compound (LXXVII) can be prepared by reacting compound (LXXVI) with a trialkyl- or triarylphosphine according to the procedure of Miyamoto et al. (*Chem. Phar. Bull.* 1988, 36, 1321) and the modified methods. Examples of solvent having no adverse effect on the reaction include ethers such as dioxane, diisopropylether and tetrahydrofuran.

While the reaction temperature may vary depending on compound (LXXVI), it is −20 to 100° C., preferably 0 to 50° C. The reaction time is 5 minutes to 48 hours, preferably 5 minutes to 10 hours.

Compound (LXXIII) or a salt thereof can be prepared by cyclization of compound (LXXVII) under heating conditions.

Examples of solvent having no adverse effect on the reaction include alcohols such as methanol and ethanol, ethers such as dioxane, tetrahydrofuran, tri(ethylene glycol)dimethyl ether and diphenyl ether, aromatic hydrocarbons such as benzene, toluene, xylene, and biphenyl, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide, polyphosphate ester, and polyphosphoric acid. These solvents may be used by mixing at an appropriate ratio.

While the reaction temperature may vary depending on compound (LXXVII) employed as well as other reaction conditions, it is −20 to 300° C., preferably 50 to 250° C. The reaction time is 5 minutes to 72 hours, preferably 5 minutes to 48 hours.

The thus obtained compound (LXXVIII) can be isolated and purified by the known isolating and purifying methods, for example, concentration, concentration under reduced pressure, extraction with solvent, crystallization, recrystallization, transfer dissolution and chromatography.

Compound (LXXIX) or a salt thereof can be prepared by protecting the amino group utilizing standard organic chemistry as described by Greene et al. (Protective Groups in Organic Synthesis, 1991, Wiley Interscience).

Preparation of compound (LXXX) or a salt thereof from compound (LXXIX) or a salt thereof can be carried out similar to preparation of compound (XXXXVI) in scheme 12.

Compound (LXXXI) or a salt thereof can be carried out similar to the preparation of compound (V) in scheme 1.

Compound (LXXXII) can be prepared utilizing standard organic chemistry as described by Green et al. (Protective Groups in Organic Synthesis, 1991, Wiley Interscience).

Preparation of compound (Iv) or a salt thereof, which is encompassed within compound (I) of the invention, from compound (LXXXII) can be carried out similar to preparation of compound (XXXXV) in scheme 12.

The thus obtained compound (Iv) can be isolated and purified by the known isolating and purifying methods, for example, concentration, concentration under reduced pressure, extraction with solvent, crystallization, recrystallization, transfer dissolution and chromatography.

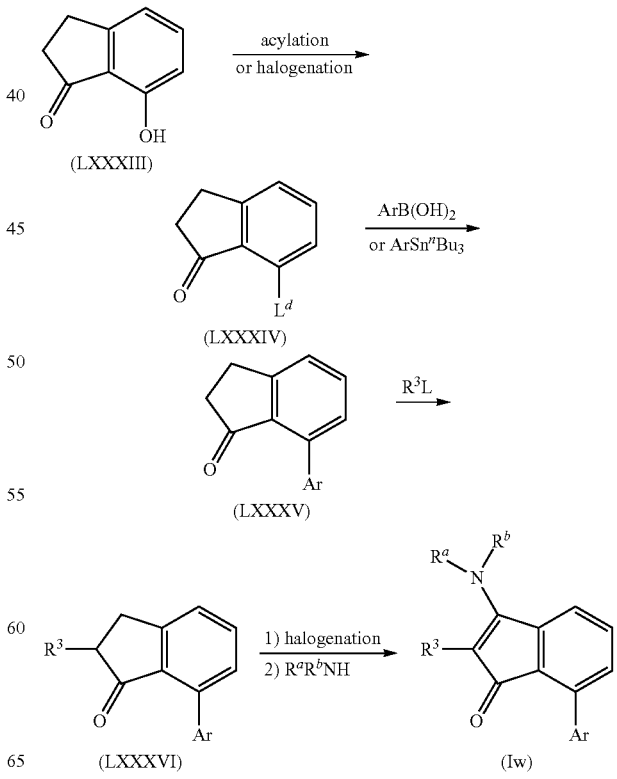

(Scheme 20)

wherein $L^d$ is a halogen atom such as chlorine, bromine and iodine, etc. and a sulfonyloxy group such as trifluoromethanesulfonyloxy group and each of other symbols has a meaning defined above.

Compound (LXXXIV) or a salt thereof can be prepared by acylation of compound (LXXXIII) or a salt thereof or conversion of the hydroxy group of compound (LXXXIII) or a salt thereof to a halogen.

An acylation reagent is preferably trifluoromethanesulfonic anhydride or trifluoromethanesulfonyl chloride.

In this reaction, 1 to 5 moles, preferably 1 to 3 moles of an acylation reagent and 1 to 10 moles, preferably 1 to 5 moles of a base are employed per 1 mole of compound (LXXXIII) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

Examples of solvents having no adverse effect on the reaction include water, alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, ketones such as acetone, amides such as N,N-dimethylformamide, N,N-dimethylacetamide and 1-methyl-2-pyrrolidinone and sulfoxides such as dimethylsulfoxide. These solvents may be used by mixing at an appropriate ratio.

While the reaction temperature may vary depending on compound (LXXXIII) or a salt thereof employed as well as other reaction conditions, it is −20 to 200° C., preferably −20 to 100° C. The reaction time is 5 minutes to 48 hours, preferably 5 minutes to 24 hours.

Examples of the halogenation agents include chlorine, bromine, iodine, thionyl chloride, thionyl bromide, sulfuryl chloride, oxalyl chloride, phosphorus trichloride, phosphorus tribromide, phosphorous pentachloride, phosphorous oxychloride, phosphorousoxy bromide, etc.

Examples of solvents having no adverse effect on the reaction include, alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, ketones such as acetone, amides such as N,N-dimethylformamide, N,N-dimethylacetamide and 1-methyl-2-pyrrolidinone and sulfoxides such as dimethylsulfoxide. These solvents may be used by mixing at an appropriate ratio.

While the reaction temperature may vary depending on compound (LXXXIII) or a salt thereof employed as well as other reaction conditions, it is −20 to 200° C., preferably 0 to 150° C. The reaction time is 5 minutes to 48 hours, preferably 5 minutes to 24 hours.

The thus obtained compound (LXXXIV) can be isolated and purified by the known isolating and purifying methods, for example, concentration, concentration under reduced pressure, extraction with solvent, crystallization, recrystallization, transfer dissolution and chromatography.

Preparation of compound (LXXXV) or a salt thereof, which is encompassed within compound (I) of the invention, from compound (LXXXIV) or a salt thereof can be carried out similar to preparation of compound (V) in scheme 1.

Compound (LXXXVI) or a salt thereof can be prepared by alkylation of compound (LXXXV) or a salt thereof with $R^3L$.

In this step, 1 to 20 moles, preferably 1 to 10 moles of $R^3L$ and 1 to 5 moles, preferably 1 to 3 moles of a base are employed per 1 mole of compound (LXXXV) or a salt thereof.

A base may for example be an alkaline metal hydroxide such as sodium hydroxide and potassium hydroxide, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide etc., an alkaline alkylsilazide such as lithium hexamethyldisilazide and sodium hexamethyldisilazide, etc.

Examples of solvents having no adverse effect on the reaction include ethers such as dioxane, tetrahydrofuran, diethyl ether and 1,2-dimethoxyethane, aromatic hydrocarbons such as benzene, toluene and xylene, halogenated hydrocarbons such as chloroform and dichloromethane, nitriles such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXV) or a salt thereof employed as well as other reaction conditions, it is −20 to 200° C., preferably −20 to 100° C. The reaction time is 5 minutes to 24 hours, preferably 5 minutes to 12 hours.

The thus obtained compound (LXXXVI) can be isolated and purified by the known isolating and purifying methods, for example, concentration, concentration under reduced pressure, extraction with solvent, crystallization, recrystallization, transfer dissolution and chromatography.

Compound (Iw) or a salt thereof, which is encompassed within compound (I) of the invention, can be prepared by halogenation of compound (LXXXVI) or a salt thereof with a halogenation reagent and animation of the halogenated compound or a salt thereof. Examples of the halogenation reagent include chlorine, bromine, iodine, N-chlorosuccinimide, N-bromosuccinimide, and N-iodosuccinimide, etc.

In the halogenation step, 1 to 10 moles, preferably 1 to 5 moles of a halogenation reagent, 1 to large excess of a base and 0.01 to 2 moles, preferably 0.1 to 0.5 moles of an additive are employed per 1 mole of compound (LXXXVI) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

An additive may for example be a peroxide such as benzoyl peroxide, etc., an acid such as hydrogen chloride, hydrogen bromide and acetic acid, etc.

Examples of solvents having no adverse effect on the reaction include alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as tetrachloromethane, chloroform and dichloromethane, nitriles such as acetonitrile, ketones such as acetone, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXVI) or a salt thereof employed as well as other reaction conditions, it is −20 to 200° C., preferably 0 to 150° C. The reaction time is 5 minutes to 24 hours, preferably 5 minutes to 12 hours.

In the animation step, 1 mole to large excess of an amine can be employed per 1 mole of compound (LXXXVI) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

Examples of solvents having no adverse effect on the reaction include water, alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitrites such as acetonitrile, ketones such as acetone, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXVI) or a salt thereof employed as well as other reaction conditions, it is 0 to 200° C., preferably 20 to 150° C. The reaction time is 5 minutes to 48 hours, preferably 5 minutes to 24 hours.

The thus obtained compound (Iw) can be isolated and purified by the known isolating and purifying methods, for example, concentration, concentration under reduced pressure, extraction with solvent, crystallization, recrystallization, transfer dissolution and chromatography.

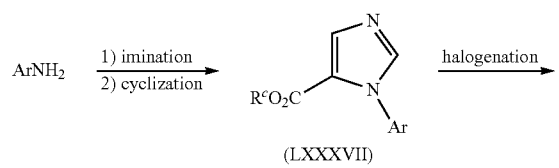

(Scheme 21)

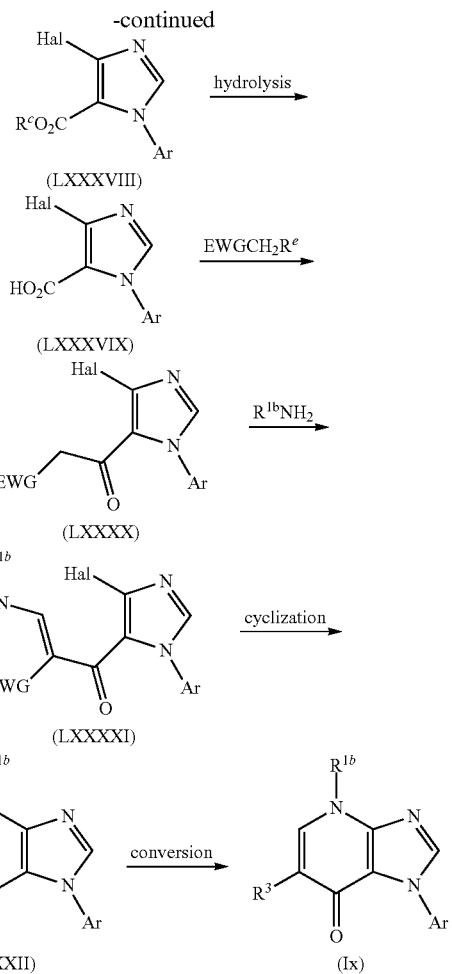

wherein $R^e$ is a hydrogen, an optionally substituted hydrocarbyl group, an optionally substituted acyl and each of other symbols has a meaning defined above.

Compound (LXXXVII) or a salt thereof can be prepared by imitation of an aromatic amine or a salt thereof and ring construction from the imino ester or a salt thereof.

In the imitation step, a reagent is preferably alkyl glyoxalate.

In this reaction, 1 to 20 moles, preferably 1 to 10 moles of alkyl glyoxalate are employed per 1 mole of an aromatic amine or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

Examples of solvents having no adverse effect on the reaction include alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXVII) or a salt thereof employed as well as other reaction conditions, it is 0 to 200° C., preferably 20 to 100° C. The reaction time is 5 minutes to 48 hours, preferably 5 minutes to 24 hours.

In the ring construction step, a reagent is preferably tosylmethylisocyanide.

In this reaction, 1 to 10 moles, preferably 1 to 5 moles of tosylmethylisocyanide are employed per 1 mole of the imino ester or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide etc., an amine such as trimethylamine, triethylamine and diisopropylethylamine, etc., a cyclic amine such as pyridine, etc.

Examples of solvents having no adverse effect on the reaction include, alcohols such as methanol and ethanol, ethers such as dioxane, tetrahydrofuran, diethyl ether and 1,2-dimethoxyethane, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, ketones such as acetone, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on the imino ester or a salt thereof employed as well as other reaction conditions, it is –20 to 200° C., preferably 0 to 150° C. The reaction time is 5 minutes to 24 hours, preferably 5 minutes to 12 hours.

The thus obtained compound (LXXXVII) can be isolated and purified by the known isolating and purifying methods, for example, concentration, concentration under reduced pressure, extraction with solvent, crystallization, recrystallization, transfer dissolution and chromatography.

Preparation of compound (LXXXVIII) or a salt thereof from compound (LXXXVII) or a salt thereof can be carried out similar to preparation of compound (IV) in scheme 1.

Compound (LXXXVIX) or a salt thereof can be prepared by hydrolysis of compound (LXXXVIII) or a salt thereof under base conditions or acidic conditions.

Examples of bases include alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc.

Examples of acids include an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

In this reaction, 1 to large excess of a base or an acid is employed per 1 mole of compound (LXXXVIII) or a salt thereof.

Examples of solvents having no adverse effect on the reaction include water, alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitrites such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXVIX) or a salt thereof employed as well as other reaction conditions, it is –20 to 200° C., preferably 0 to 100° C. The reaction time is 5 minutes to 24 hours, preferably 5 minutes to 12 hours.

The thus obtained compound (LXXXVIX) can be isolated and purified by the known isolating and purifying methods, for example, concentration, concentration under reduced pressure, extraction with solvent, crystallization, recrystallization, transfer dissolution and chromatography. Compound (LXXXX) or a salt thereof can be prepared by halogenation of compound (LXXXVIX) or a salt thereof.

Compound (LXXXX) or a salt thereof can be prepared by condensation of a suitable reactive derivative of compound (LXXXVIX) or a salt thereof with $EWGCH_2R^e$.

The suitable reactive derivative at a carboxyl group of compound (LXXXVIX) or the salt thereof may for example be an acid halide such as acid chloride, etc., an acid anhydride or a mixed acid anhydride with an acid such as substituted phosphoric acid such as dialkylphosphoric acid, phenylphosphoric acid, diphenylphosphoric acid, dibenzylphosphoric acid, halogenated phosphoric acid, etc., dialkylphosphorous acid, sulfurous acid, thiosulfuric acid, sulfuric acid, sulfonic acid such as methanesulfonic acid, etc., aliphatic carboxylic acid such as acetic acid, propionic acid, butyric acid, isobutyric acid, pivalic acid, pentanoic acid, isopentanoic acid, trichloroacetic acid, etc. or aromatic carboxylic acid such as benzoic acid, etc.; symmetric acid anhydride, activated amide with a heteroaryl compound such as 4-substituted imidazole, dimethylpyrazole, triazole, tetrazole, etc., an activated ester such as cyanomethylester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxylmethyl thioester, pyranyl ester, pyridyl ester, piperidyl ester, 8-quinolyl thioester, etc., an ester with N-hydroxy compound such as N,N-dimethylhydroxyamine, 1-hydroxy-2-(1H)-pyridone, N-hydroxysuccinimide, N-hydroxyphthalimide, 1-hydroxy-1H-benzotriazole, etc. These reactive derivatives can be arbitrarily selected depending on a kind of compound (LXXXVIX) to be used. Examples of the suitable reactive derivative of compound (LXXXVIX) include alkali metal salts such as sodium salt, potassium salt, etc., alkaline earth metal salts such as calcium salt, magnesium salt, etc., and basic salts such as organic base salts such as ammonium salt, trimethylamine salt, triethylamine salt, pyridine salt, picoline salt, dicyclohexylamine salt, N,N-dibenzylethylenediamine salt etc, and can be prepared by conventional conditions.

In this reaction, 1 to 20 moles, preferably 1 to 10 moles of $EWGCH_2R^e$ is employed per 1 mole of compound (LXXXVIX) or a salt thereof.

A base may for example be an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an alkyl lithium such as n-butyl lithium, sec-butyl lithium and tert-butyl lithium, etc., a Grinard reagent such as methylmagnesium chloride, methylmagnesium bromide and ethylmagnesium bromide, etc.

Examples of solvents having no adverse effect on the reaction include ethers such as dioxane, tetrahydrofuran, diethyl ether and 1,2-dimethoxyethane, aromatic hydrocarbons such as benzene, toluene and xylene, halogenated hydrocarbons such as chloroform and dichloromethane, nitriles such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXVIX) or a salt thereof employed as well as other reaction conditions, it is −80 to 100° C., preferably −80 to 50° C. The reaction time is 5 minutes to 24 hours, preferably 5 minutes to 12 hours.

The thus obtained compound (LXXXX) can be isolated and purified by the known isolating and purifying methods, for example, concentration, concentration under reduced pressure, extraction with solvent, crystallization, recrystallization, transfer dissolution and chromatography.

Compound (LXXXXI) or a salt thereof can be prepared by condensation of compound (LXXXX) or a salt thereof with trialkylorthoformate and amination of the alkoxymethylene compound or the salt thereof with $R^{1b}NH_2$.

Examples of trialkylorthoformate include trimethylorthoformate and triethylorthoformate, etc.

In the first reaction, an additive may for example be an inorganic acid such as hydrochloric acid, sulfuric acid and nitric acid, etc., an organic acid such as formic acid, acetic acid, trifluoroacetic acid, methanesulfonic acid, benzenesulfonic acid, toluenesulfonic acid, oxalic acid, fumaric acid, maleic acid and tartaric acid, etc., acid anhydride such as acetic anhydride, etc., as well as a Lewis acid.

In this reaction, 1 to large excess of trialkylorthoformate and catalytic amount to 5 moles of an additive are employed per 1 mole of compound (LXXXX) or a salt thereof.

Solvents having no adverse effect on the reaction may be employed. Examples of solvents may include alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXX) or a salt thereof employed as well as other reaction conditions, it is 0 to 200° C., preferably 0 to 150° C. The reaction time is 5 minutes to 24 hours, preferably 5 minutes to 12 hours.

In animation reaction, 1 to 10 moles, preferably 1 to 5 moles of $R^{1b}NH_2$ is employed per 1 mole of compound (LXXXX) or a salt thereof.

Solvents having no adverse effect on the reaction may be employed. Examples of solvents may include water, alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXX) or a salt thereof employed as well as other reaction conditions, it is −20 to 100° C., preferably 0 to 100° C. The reaction time is 5 minutes to 24 hours, preferably 5 minutes to 12 hours.

The thus obtained compound (LXXXXI) can be isolated and purified by the known isolating and purifying methods, for example, concentration, concentration under reduced pressure, extraction with solvent, crystallization, recrystallization, transfer dissolution and chromatography.

Compound (LXXXXII) or a salt thereof can be prepared by cyclization of compound (LXXXVI) or a salt thereof.

In this reaction, 1 to 10 moles, preferably 1 to 5 moles of a base is employed per 1 mole of compound (LXXXXI) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

Examples of solvents may include ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXXI) or a salt thereof employed as well as other reaction conditions, it is 0 to 250° C., preferably 20 to 200° C. The reaction time is 5 minutes to 24 hours, preferably 5 minutes to 12 hours.

The thus obtained compound (LXXXVII) can be isolated and purified by the known isolating and purifying methods, for example, concentration, concentration under reduced pressure, extraction with solvent, crystallization, recrystallization, transfer dissolution and chromatography.

Preparation of compound (Ix) or a salt thereof, which is encompassed within compound (I) of the invention, from compound (LXXXXII) or a salt thereof can be carried out similar to preparation of compound (XXXVI) in scheme 12.

(Scheme 22)

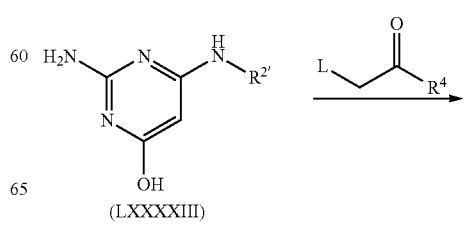

(LXXXXIII)

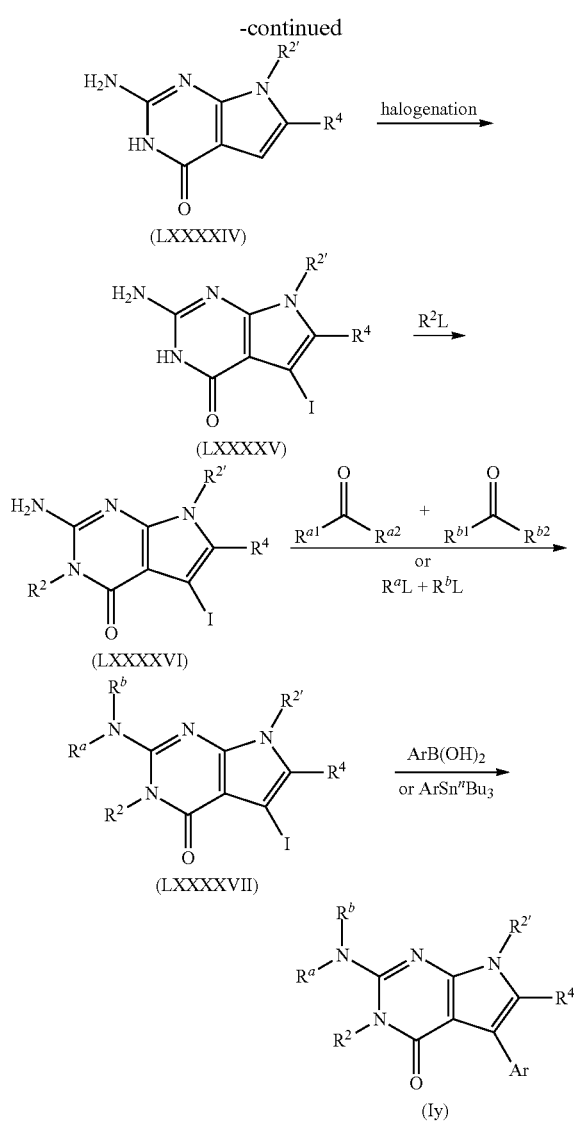

wherein each of symbols has a meaning defined above.

Compound (LXXXXIV) or a salt thereof can be prepared by cyclization of compound (LXXXXIII) or a salt thereof with $LCH_2COR^4$.

In this reaction, 1 to 10 moles, preferably 1 to 5 moles of $LCH_2COR^4$ are employed per 1 mole of compound (LXXXXIII) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkaline metal alkoxide such as sodium methoxide, sodium ethoxide, sodium tert-butoxide and potassium text-butoxide, etc., an amine such as trimethylamine, triethylamine and diisopropylethylamine, etc., a cyclic amine such as pyridine, etc.

Examples of solvents having no adverse effect on the reaction include water, alcohols such as methanol and ethanol, ethers such as dioxane, tetrahydrofuran, diethyl ether and 1,2-dimethoxyethane, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide, N,N-dimethylacetamide and 1-methyl-2-pyrrolidinone, and sulfoxides such as dimethylsulfoxide. These solvents may be used by mixing at an appropriate ratio.

While the reaction temperature may vary depending on compound (LXXXXIII) or a salt thereof employed as well as other reaction conditions, it is 0 to 200° C., preferably 20 to 150° C. The reaction time is 5 minutes to 48 hours, preferably 5 minutes to 24 hours.

The thus obtained compound (LXXXXIV) can be isolated and purified by the known isolating and purifying methods, for example, concentration, concentration under reduced pressure, extraction with solvent, crystallization, recrystallization, transfer dissolution and chromatography.

Compound (LXXXXV) or a salt thereof can be prepared from compound (LXXXXIV) according to the procedure described in J. Med. Chem., 35, 4450 (1992) or the modified methods.

Preparation of compound (LXXXXVI) or a salt thereof from compound (LXXXXV) or a salt thereof can be carried out similar to preparation of compound (XVI) in scheme 4.

Compound (LXXXXVII) or a salt thereof can be prepared from compound (LXXXXVI) or a salt thereof similar to preparation of compound (Ia) in scheme 1.

Preparation of compound (Iy) or a salt thereof, which is encompassed within compound (I) of the invention, from compound (LXXXXVII) or a salt thereof can be carried out similar to preparation of compound (V) in scheme 1.

A starting compound for compound (I) according to the invention may be in a form of a salt, including a salt with an inorganic acid (for example, hydrochloric acid, phosphoric acid, hydrobromic acid and sulfuric acid, etc.) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid and benzenesulfonic acid, etc.). When any of these compounds carries an acidic group such as —COOH, etc., a salt with an inorganic base (for example, an alkaline metal or an alkaline earth metal such as sodium, potassium, calcium and magnesium, ammonia, etc.) or with an organic base (for example, tri-$C_{1-3}$ alkylamine such as triethylamine, etc.) may be formed.

In each of the reactions described above, when a starting compound carries as a substituent an amino group, a carboxyl group or a hydroxyl group, then such group is derivatized with a protective group employed ordinarily in peptide chemistry, which is cleaved after a reaction if desired to yield an intended compound.

A protective group for an amino group may for example be an optionally substituted $C_{1-6}$ alkylcarbonyl (for example, formyl, methylcarbonyl and ethylcarbonyl, etc.), phenylcarbonyl, a $C_{1-6}$ alkyloxycarbonyl (for example, methoxycarbonyl and ethoxycarbonyl, etc.), phenyloxycarbonyl (for example, benzoxycarbonyl), $C_{7-10}$ aralkylcarbonyl (for example, benzyloxycarbonyl), trityl, phthaloyl, etc. A substituent on each of the groups listed above may be a halogen atom (for example, fluorine, chlorine, bromine and iodine, etc.), a $C_{1-6}$ alkylcarbonyl (for example, methylcarbonyl, ethylcarbonyl and butylcarbonyl, etc.) and a nitro group, which may occur 1 to about 3 times.

A protective group for a carboxyl group may for example be an optionally substituted $C_{1-6}$ alkyl (for example, methyl, ethyl, n-propyl, i-propyl, n-butyl and t-butyl, etc.), phenyl, trityl and silyl, etc. A substituent on each of the groups listed above may be a halogen atom (for example, fluorine, chlorine, bromine and iodine, etc.), a $C_{1-6}$ alkylcarbonyl (for example, formyl, methylcarbonyl, ethylcarbonyl and butylcarbonyl, etc.) and a nitro group, which may occur 1 to about 3 times.

A protective group for a hydroxyl group may for example be an optionally substituted $C_{1-6}$ alkyl (for example, methyl, ethyl, n-propyl, i-propyl, n-butyl and tert-butyl, etc.), phenyl, a $C_{7-10}$ aralkyl (for example, benzyl, etc.), a $C_{1-6}$ alkylcarbonyl (for example, formyl, methylcarbonyl and ethylcarbonyl, etc.), phenyloxycarbonyl (for example, benzoxycarbonyl, etc.), $C_{7-10}$ aralkylcarbonyl (for example, benzyloxycarbonyl, etc.), pyranyl, furanyl, silyl, etc. A substituent on each of the groups listed above may be a halogen atom (for example, fluorine, chlorine, bromine and iodine, etc.), a $C_{1-6}$ alkyl, phenyl, a $C_{7-10}$ aralkyl, nitro, etc., which may occur 1 to about 4 times.

A method for cleaving a protective group is a method known per se or an analogous method, such as a treatment for example with an acid, a base, a reduction, UV light, hydrazine, phenylhydrazine, sodium N-methyldithiocarbamate, tetrabutylammonium fluoride, palladium acetate, etc.

The pharmaceutical composition containing compound (I) of the present invention is expected to be useful in the treatment and prevention of diseases, in which CRF is involved, such as major depression, postpartum depression, suppression symptom, mania, anxiety, generalized anxiety disorder, panic disorder, phobia, obsessive-compulsive disorder, post psychic trauma stress disorder, Tourette's syndrome, autism, passion disorder, adjustment disorder, dysthymic disorder, sleep disorder, insomnia, bipolar disorder, circulatory disease, neurosis, schizophrenia, digestive ulcer, irritable bowl syndrome, ulcerative colitis, Crohn's disease, diarrhea, constipation, postoperative ileus, gastrointestine dysfunction and nervous vomiting associated with stress, Alzheimer's disease, Alzheimer's type senile dementia, nervous degenerated disease such as Parkinson's disease and Huntington's disease, multi-infarct dementia, senile dementia, nervous orexia inactivity, hyperphagia and other ingestion disorder, obesity, diabetes, alcohol dependency, pharmacophinia, drug withdrawal, migraine, stress headache, tension headache, ischemic nervous disorder, nervous disorder, cerebral paralysis, progressive supranuclear palsy, amyotrophic lateral sclerosis, multiple sclerosis, muscular convulsion, chronic fatigue syndrome, glaucoma, Meniere syndrome, autonomic imbalance, alopecia, hypertension, cardiovascular disorder, tachycardia, congestive heart attack, hyperplea, bronchial asthma, apnea, infant sudden death syndrome, inflammatory disorder, pain, allergic disorder, impotence, menopausal disorder, fertilization disorder, infertility, cancer, immune function abnormality at HIV infection, immune functional abnormality due to stress, cerebrospinal meningitis, acromegaly, incontinence or osteoporosis.

Compound (I) of the present invention can be formulated with a pharmaceutically acceptable carrier and can be orally or parenterally administered as solid formulations such as tablets, capsules, granules, powders, or the like; or liquid formulations such as syrups, injections, or the like. Also, there can be prepared formulations for transdermal administration such as patchings, cataplasms, ointments (including creams), plasters, tapes, lotions, liquids and solutions, suspensions, emulsions, sprays, and the like.

As for a pharmaceutically acceptable carrier, a variety of organic or inorganic carrier substances, which have been conventionally employed as formulation materials, is used and compounded as a bulking agent, a lubricant, a binding agent, and a disintegrator in solid formulations; a vehicle, a solubilizing agent, a suspending agent, an isotonicity agent, a buffering agent, and an analgesic in liquid formulations. If necessary, formulation excipients such as a preservative, an antioxidant, a stabilizer, a coloring agent, a sweetening agent, and the like can be used.

Preferred examples of the bulking agent include lactose, sucrose, D-mannitol, starch, crystalline cellulose, light anhydrous silicic acid, and the like. Preferred examples of the lubricant include magnesium stearate, potassium stearate, talc, colloidal silica, and the like. Preferred examples of the binding agent include crystalline cellulose, α-starch, sucrose, D-mannitol, dextrin, hydroxypropyl cellulose, hydroxypropylmethyl cellulose, polyvinyl pyrrolidone, and the like. Preferred examples of the disintegrator include starch, carboxymethyl cellulose, calcium carboxymethyl cellulose, croscarmellose sodium, sodium carboxymethyl starch, low-substituted hydroxypropyl cellulose, and the like. Preferred examples of the vehicle include water for injection, alcohol, propylene glycol, macrogol, sesame oil, corn oil, and the like.

If necessary, for the purpose of taste masking, enteric coating, or prolonged action, oral formulations can be prepared by coating by a per se known method. Examples of this coating agent include hydroxypropylmethyl cellulose, ethyl cellulose, hydroxymethyl cellulose, hydroxypropyl cellulose, polyoxyethylene glycol, Tween 80, Pluronic F68 [polyoxyethylene (160) polyoxypropylene (30) glycol], cellulose acetate phthalate, hydroxypropylmethyl cellulose phthalate, hydroxymethyl cellulose acetate phthalate, Eudragit (manufactured by Rohm Company, methacrylic acid-acrylic acid copolymer), and the like.

Preferred examples of the solubilizing agent include polyethylene glycol, propylene glycol, benzyl benzoate, ethanol, trisaminomethane, cholesterol, triethanolamine, sodium carbonate, sodium citrate, and the like. Preferred examples of the suspending agent include surface active agents such as stearyltriethanolamine, sodium lauryl sulfate, laurylaminopropionic acid, lecithin, benzalkonium chloride, benzethonium chloride, glycerin monostearate, and the like; hydrophilic, high molecular substances such as polyvinyl alcohol, polyvinyl pyrrolidone, sodium carboxymethyl cellulose, methyl cellulose, hydroxymethyl cellulose, hydroxyethyl cellulose, hydroxypropyl cellulose, and the like; and so on. Preferred examples of the isotonicity agent include sodium chloride, glycerin, D-mannitol, and the like. Preferred examples of the buffering agent include buffer solutions of a phosphate, an acetate, a carbonate, a citrate, or the like. Preferable examples of the analgesic include benzyl alcohol and the like. Preferred examples of the preservative include paraoxybenzoic acid esters, chlorobutanol, benzyl alcohol, phenethyl alcohol, dehydroacetic acid, sorbic acid, and the like. Preferred examples of the antioxidant include sulfites, ascorbic acid, and the like.

The following examples and experiments describe the manner and process of making and using the present invention and are illustrative rather than limiting. It is to be understood that there may be other embodiments which fall within the spirit and scope of the present invention as defined by the claims appended hereto.

Example 1

3-(2,4-Dimethylphenyl)-5-(dipropylamino)-1-methylpyridin-2(1H)-one

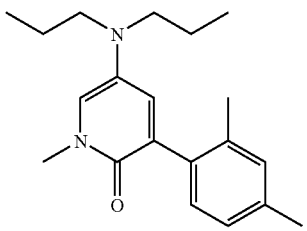

1-Methyl-5-nitropyridin-2(1H)-one

To a mixture containing 20.0 ml (211.40 mmol) of dimethyl sulfate and 45 ml of 3N sodium hydroxide was added 4.00 g (28.55 mmol) of 2-hydroxy-5-nitropyridine in portions over 15 min. After complete addition, the reaction was allowed to stir at 25° C. overnight. The reaction was acidified with 1N HCl and the solids filtered, washed with ethanol and dried to afford 1.31 g (29.77%) of product.

$^1$H NMR (CDCl$_3$) δ: 3.67 (s, 3H), 6.57 (d, J=10 Hz, 1H), 8.10 (d, J=10 Hz, 1H), 8.64 (s, 1H).

3-Bromo-1-methyl-5-nitropyridin-2(1H)-one

To a solution containing 0.55 g (3.57 mmol) of 1-methyl-5-nitropyridin-2(1H)-one in 10 ml of N,N-dimethylformamide under a nitrogen atm. was added 0.76 g (4.27 mmol) of N-bromosuccinimide. The reaction was allowed to stir at 25° C. overnight. The reaction was diluted with dichloromethane and washed with water. The organic phase was dried over magnesium sulfate. Filtration, removal of solvent and purification of the residue via biotage eluting with 70% ethyl acetate/hexanes gave 0.60 g (72.15%) of product as a white solid.

$^1$H NMR (CDCl$_3$) δ: 3.75 (s, 3H), 8.53 (d, J=2.8 Hz, 1H), 8.65 (d, J=2.8 Hz, 1H).

3-(2,4-Dimethylphenyl)-1-methyl-5-nitropyridin-2(1H)-one

A mixture containing 0.40 g (1.72 mmol) of 3-bromo-1-methyl-5-nitropyridin-2(1H)-one, 0.39 g (2.60 mmol) of 2,4-dimethylphenyl boronic acid, 0.70 g (5.06 mmol) of potassium carbonate, 0.31 ml (17.22 mmol) of water, and 0.99 g (0.86 mmol) of tetrakis(triphenylphosphine)palladium(0) in 80 ml of dioxane was heated to 90° C. under a nitrogen atm. overnight. The reaction was cooled to room temperature, diluted with ethyl acetate and washed with saturated sodium bicarbonate. The organic phase was dried over magnesium sulfate. Filtration, removal of solvent and purification of the residue via biotage eluting with 60% ethyl acetate/hexanes gave 0.37 g (82.55%) of product.

$^1$H NMR (CDCl$_3$) δ: 2.19 (s, 3H), 2.35 (s, 3H), 3.71 (s, 3H), 7.03-7.09 (m, 3H), 8.06 (d, J=3.2 Hz, 1H), 8.66 (d, J=3.2 Hz, 1H).

5-Amino-3-(2,4-dimethylphenyl)-1-methylpyridin-2(1H)-one

To a solution containing 0.17 g (0.66 mmol) of 3-(2,4-dimethylphenyl)-1-methyl-5-nitropyridin-2(1H)-one in 50 ml of ethanol was added 0.10 g of 10% palladium on carbon (Degussa type; 50% wet). The flask was fitted with a balloon of hydrogen and allowed to stir for 5 h. The reaction was filtered through GF/F paper and the filtrate concentrated under reduced pressure to afford 0.063 g (41.9%) of product.

$^1$H NMR (CDCl$_3$) δ: 2.20 (s, 3H), 2.33 (s, 3H), 3.54 (s, 3H), 6.81 (bd, J=2.4 Hz, 1H), 6.98-7.04 (m, 4H)

MS Calcd.: 228. Found: 229 (M+H).

3-(2,4-Dimethylphenyl)-5-(dipropylamino)-1-methylpyridin-2(1H)-one

To a solution containing 0.063 g (0.27 mmol) of 5-amino-3-(2,4-dimethylphenyl)-1-methylpyridin-2(1H)-one in 20 ml of dichloromethane was added 0.060 ml (0.83 mmol) of propionaldehyde followed by 0.20 g (0.94 mmol) of sodium triacetoxyborohydride under a nitrogen atmosphere. The reaction was allowed to stir at 25° C. overnight. The reaction was diluted with dichloromethane and washed with saturated sodium bicarbonate. The organic phase was dried over magnesium sulfate. Filtration, removal of solvent and purification of the residue via biotage eluting with ethyl acetate gave 0.088 g (100%) of product.

$^1$H NMR (CDCl$_3$) δ: 0.89 (t, J=7.6 Hz, 6H), 1.45-1.52 (m, 4H), 2.22 (s, 3H), 2.34 (s, 3H), 2.89-2.93 (m, 4H), 3.58 (s, 3H), 6.71 (d, J=3.2 Hz, 1H), 6.98-7.11 (m, 3H), 7.20 (d, J=3.2 Hz, 1H)

MS Calcd.: 312. Found: 313 (M+H).

Example 2

3-[(2,4-Dimethylphenyl)amino]-5-(dipropylamino)-1-methylpyridin-2(1H)-one

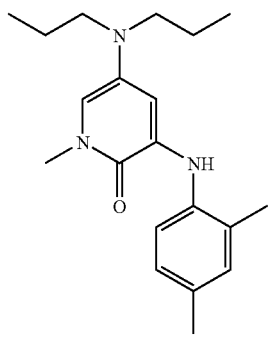

3-[(2,4-Dimethylphenyl)amino]-1-methyl-5-nitropyridin-2(1H)-one

To a solution containing 0.60 g (2.57 mmol) of 3-bromo-1-methyl-5-nitropyridin-2(1H)-one in 120 ml of toluene under a nitrogen atmosphere was added 0.64 ml (5.15 mmol) of 2,4-dimethylaniline, 1.61 g (2.57 mmol) of rac-2,2'-bis(diphenylphosphino)-1,1'-binaphthyl (racemic BINAP), 0.37 g (3.85 mmol) of sodium t-butoxide and 1.20 g (1.31 mmol) of tris(dibenzylideneacetone)dipalladium (0). The reaction was heated to 95° C. overnight. The reaction was cooled to room temperature, diluted with ethyl acetate and washed with saturated sodium bicarbonate. The organic phase was dried over magnesium sulfate. Filtration, removal of solvent and purification of the residue via biotage eluting with 60% ethyl acetate/hexanes gave the desired product with some starting aniline. The material was triturated with hexanes and the solids filtered and dried to afford 0.154 g (21.9%) of product.

$^1$H NMR (CDCl$_3$) δ: 2.22 (s, 3H), 2.35 (s, 3H), 3.74 (s, 3H), 6.72 (bs, 1H), 7.06-7.18 (m, 4H), 8.06 (d, J=2.8 Hz, 1H).

3-[(2,4-Dimethylphenyl)amino]-5-(dipropylamino)-1-methylpyridin-2(1H)-one

To a mixture containing 0.11 g (0.40 mmol) of 3-[(2,4-dimethylphenyl)amino]-1-methyl-5-nitropyridin-2(1H)-one in 50 ml of ethanol was added 0.062 ml (0.86 mmol) of propionaldehyde, 0.15 ml of glacial acetic acid and 0.15 g of 10% palladium on carbon (Degussa type, 50% wet). The flask was fitted with a balloon of hydrogen and allowed to stir at room temperature for 4 h. The reaction was filtered through GF/F paper and the filtrate concentrated under reduced pressure. The residue was purified via preparative HPLC to afford 5 mg (3.7%) of product.

$^1$H NMR (CDCl$_3$) δ: 0.85 (t, J=7.2 Hz, 6H), 1.40-1.47 (m, 4H), 2.29 (s, 3H), 2.30 (s, 3H), 2.82-2.86 (m, 4H), 3.58 (s, 3H), 6.12 (d, J=2.4 Hz, 1H), 6.55 (d, J=2.8 Hz, 1H), 6.98-7.02 (m, 1H), 7.04 (s, 1H), 7.16 (d, J=8 Hz, 1H)

MS Calcd.: 327. Found: 328 (M+H).

Example 3

2-(Dipropylamino)-5-(mesitylamino)-3,6-dimethylpyrimidin-4(3H)-one

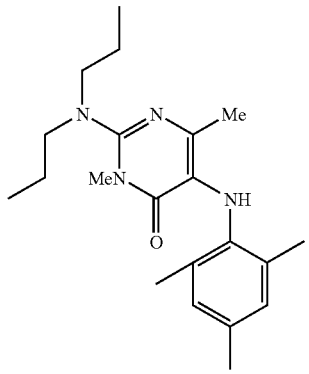

2-Chloro-4-methoxy-6-methyl-5-nitropyrimidine 2,4-Dichloro-6-methyl-5-nitropyrimidine (3.0 g, 14.4 mmol) was dissolved in methanol (30 mL). The solution was cooled to −10° C. and sodium methoxide (25% in methanol, 3.3 mL, 14.4 mmol) was added drop wise. After 10 minutes, the solution was quenched with acetic acid (5 mL) and concentrated. The residue was suspended in saturated sodium bicarbonate and extracted twice with ethyl acetate. The organic layer was dried over sodium sulfate, filtered and concentrated. Flash chromatography (5% ethyl acetate/hexanes) gave 1.91 g (65% yield) of the title compound as a white solid.

$^1$H NMR (CDCl$_3$) δ: 2.53 (s, 3H), 4.13 (s, 3H).
MS Calcd.: 203. Found: 174 [M−(OCH$_3$)+H].

4-Methoxy-6-methyl-5-nitro-N,N-dipropylpyrimidin-2-amine

2-Chloro-4-methoxy-6-methyl-5-nitrolpyrimidine (0.040 g, 0.20 mmol) was dissolved in N,N-dimethylformamide (1 mL). Dipropyl amine (67 μL, 0.49 mmol) was added at room temperature. After 15 minutes, the solution was flash chromatographed (5% ethyl acetate/hexanes) to give 0.048 g (91% yield) of the desired compound.

$^1$H NMR (CDCl$_3$) δ: 0.93 (t, J=7.2 Hz, 6H), 1.58-1.72 (m, 4H), 2.47 (s, 3H), 3.49-3.60 (m, 4H), 3.98 (s, 3H).
MS Calcd.: 268. Found: 269 (M+H).

4-Methoxy-6-methyl-N$^2$,N$^2$-dipropylpyrimidin-2,5-diamine

4-Methoxy-6-methyl-5-nitro-N,N-dipropylpyrimidin-2-amine (0.040 g, 0.15 mmol) was diluted with ethyl acetate (2 mL). 0.020 g of 10% Pd over charcoal was added. The solution was evacuated and filled with a hydrogen balloon. The reaction solution was stirred overnight. The solution was filtered and concentrated. Flash chromatography (40% ethyl acetate/hexanes) gave 0.025 g of a white solid (70% yield).

$^1$H NMR (CDCl$_3$) δ: 0.89 (t, J=7.2 Hz, 6H), 1.57-1.63 (m, 4H), 2.22 (s, 3H), 2.94 (bs, 2H), 3.45 (t, J=8.0 Hz, 4H), 3.91 (s, 3H).
MS Calcd.: 238. Found: 239 (M+H).

N$^5$-Mesityl-4-methoxy-6-methyl-N$^2$,N$^2$-dipropylpyrimidin-2,5-diamine

4-Methoxy-6-methyl-N$^2$,N$^2$-dipropylpyrimidin-2,5-diamine (0.022 g, 0.092 mmol) was charged with 2,4,-6-trimethylbromobenzene (16.7 μL, 0.11 mmol), rac-2,2'-bis(diphenylphosphino)-1,1'-binaphthyl (BINAP) (0.012 g, 0.018 mmol), sodium t-butoxide (0.012 g, 0.13 mmol) and tris(dibenzylideneacetone) dipalladium (0) (Pd$_2$(dba)$_3$) (0.017 g, 0.018 mmol). The reagents were diluted in 1 mL of toluene and heated at 115° C. for 1.5 h. The solution was cooled and flash chromatographed (5% ethyl acetate/hexanes) to give 0.019 g (58%) of the title compound as an oil.

$^1$H NMR (CDCl$_3$) δ: 0.89 (t, J=7.2 Hz, 6H), 1.59-1.65 (m, 4H), 1.93 (s, 3H), 2.04 (s, 6H), 2.21 (s, 3H), 3.48 (t, J=7.2 Hz, 4H), 3.86 (s, 3H), 4.37 (s, 1H), 6.74 (s, 2H).
MS Calcd.: 356. Found: 357 (M+H).

2-(Dipropylamino)-5-(mesitylamino)-3,6-dimethylpyrimidin-4(3H)-one

N$^5$-Mesityl-4-methoxy-6-methyl-N$^2$,N$^2$-dipropylpyrimidin-2,5-diamine (9.0 mg, 0.025 mmol) was dissolved in iodomethane (2 mL). The solution was heated in a sealed tube for 6 h at 140° C. The solution was cooled and concentrated. Flash chromatography (20% ethyl acetate/hexanes) gave 2.6 mg (29% yield) of the desired compound.

$^1$H NMR (CDCl$_3$) δ: 0.86 (t, J=7.6 Hz, 6H), 1.48-1.56 (m, 4H), 1.60 (s, 3H), 2.10 (s, 6H), 2.26 (s, 3H), 2.99 (t, J=7.6 Hz, 4H), 3.56 (s, 3H), 5.53 (s, 1H), 6.82 (s, 2H).
MS Calcd.: 356. Found: 357 (M+H).

Other analogues prepared in an analogous manner:

| Example | Structure | Name | Physical Data |
|---|---|---|---|
| 4 | 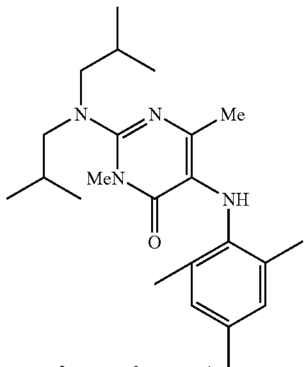 | 2-(diisobutylamino)-5-(mesitylamino)-3,6-dimethylpyrimidin-4(3H)-one | ¹HNMR (CDCl₃) δ: 0.85 (d, J=6.8 Hz, 12H), 1.59 (s, 3H), 1.86-1.90 (m, 2H), 2.10 (s, 6H), 2.26 (s, 3H), 2.90 (d, J=7.2 Hz, 4H), 3.57 (s, 3H), 5.49 (s, 1H), 6.82 (s, 2H). MS Calcd.: 384, Found: 385 (M + H). |
| 5 | 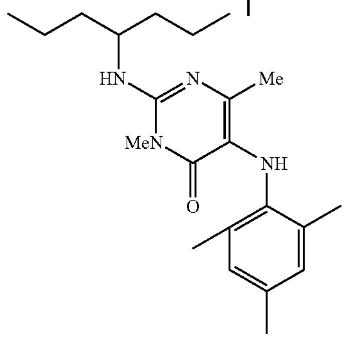 | 5-(mesitylamino)-3,6-dimethyl-2-[(1-propylbutyl)amino]pyrimidin-4(3H)-one | ¹HNMR (CDCl₃) δ: 0.86 (t, J=7.6 Hz, 6H), 1.32-1.61 (m, 8H), 1.60 (s, 3H), 2.21 (s, 6H), 2.24 (s, 3H), 3.42 (s, 3H), 3.82 (d, J=8.4 Hz, 1H), 4.10-4.14 (m, 1H), 4.99 (s, 1H), 6.79 (s, 2H). MS Calcd.: 370, Found: 371 (M + H). |
| 6 | 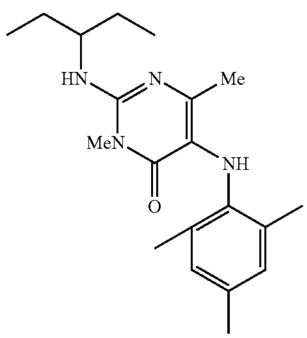 | 2-[(1-ethylpropyl)amino]-5-(mesitylamino)-3,6-dimethylpyrimidin-4(3H)-one | ¹HNMR (CDCl₃) δ: 0.86 (t, J=7.6 Hz, 6H), 1.45-1.70 (m, 4H), 1.68 (s, 3H), 2.21 (s, 6H), 2.23 (s, 3H), 3.42 (s, 3H), 3.85 (d, J=7.2 Hz, 1H), 3.95-3.97 (m, 1H), 5.00 (s, 1H), 6.79 (s, 2H). MS Calcd.: 342, Found: 343 (M + H). |

Example 7

2-Benzyl-3-(2,4-dimethylphenyl)-6-dipropylamino-5-methyl-2,5-dihydro-4H-pyrazolo[3,4-d]pyrimidin-4-one

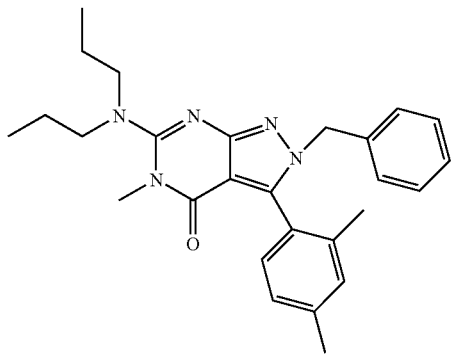

6-Hydrazino-3-methylpyrimidine-2,4(1H,3H)-dione

To a mixture containing 10.0 g (62.28 mmol) of 6-chloro-3-methyluracil in 200 ml of ethanol was added 13.70 ml (436.50 mmol) of hydrazine. The mixture was heated to 75° C. under a nitrogen atmosphere overnight. The solids were filtered, washed with ethanol and dried to afford 9.70 g (99.74%) of product as a pale yellow solid.

¹H NMR (CDCl₃) δ: 3.02 (s, 3H), 4.78 (s, 1H), 6.28 (bs, 4H)

MS Calcd.: 156. Found: 155 (M−H).

6-(N"-Benzylidenehydrazino)-3-methyl-1H-pyrimidine-2,4-dione

To a warm solution containing 1.0 g (6.40 mmol) of 6-hydrazino-3-methylpyrimidine-2,4(1H,3H)-dione in 60 ml of methanol was added benzaldehyde. The reaction was allowed to stir at rt for 2 h. The solids were filtered, washed with ethanol and dried to afford 0.772 g (49.35%) of product as a yellow solid.

$^1$H NMR (CDCl$_3$) δ: 3.10 (s, 3H), 4.95 (s, 1H), 7.40-7.42 (m, 3H), 7.88 (d, J=6.4 Hz, 2H), 7.99 (s, 1H), 10.95 (bs, 2H).

MS Calcd.: 244. Found: 245 (M+H).

2-Benzyl-3-(2,4-dimethylphenyl)-5-methyl-2H-pyrazolo[3,4-d]pyrimidine-4,6(5H,7H)-dione To a mixture containing 0.51 g (3.78 mmol) of 6-(N"-benzylidene-hydrazino)-3-methyl-1H-pyrimidine-2,4-dione in 30 ml of N,N-dimethylformamide and 16 ml of isopropanol was added 0.77 g (3.15 mmol) of 2,4-dimethyl benzaldehyde followed by 0.31 ml (3.15 mmol) of piperidine and 0.036 ml (0.63 mmol) of acetic acid. The reaction was heated to 120° C. under a nitrogen atmosphere overnight. The reaction was diluted with ethyl acetate and washed with water. The organic phase was dried over magnesium sulfate. Filtration, removal of solvent and purification of the residue via biotage eluting with 50% ethyl acetate/hexanes gave 0.68 g (57.21%) of product as a white solid.

$^1$H NMR (CDCl$_3$) δ: 2.02 (s, 3H), 2.39 (s, 3H), 3.31 (s, 3H), 5.15 (ABq, J=18.8 Hz, 2H), 7.03-7.14 (m, 5H), 7.23-7.27 (m, 3H), 9.83 (s, 1H).

MS Calcd.: 360. Found: 3.61 (M+H).

2-Benzyl-6-chloro-3-(2,4-dimethylphenyl)-5-methyl-2,5-dihydro-4H-pyrazolo[3,4-d]pyrimidin-4-one A mixture containing 0.11 g (0.31 mmol) of 2-benzyl-3-(2,4-dimethylphenyl)-5-diethyl-2,7-dihydropyrazolo[3,4-d]pyrimidine-4,6-dione and 1.40 ml (15.26 mmol) of phosphorus oxychloride was heated to 100° C. under a nitrogen atmosphere overnight. The reaction was concentrated under reduced pressure and the residue dissolved in dichloromethane and washed with saturated sodium bicarbonate. The organic phase was dried over magnesium sulfate. Filtration, removal of solvent and purification of the residue via biotage eluting with 40% ethyl acetate/hexanes gave 0.103 g (89.0%) of product as a white solid.

$^1$H NMR (CDCl$_3$) δ: 1.92 (s, 3H), 2.39 (s, 3H), 3.60 (s, 3H), 5.22 (ABq, J=14.4 Hz, 2H), 7.01-7.13 (m, 5H), 7.22-7.27 (m, 3H).

MS Calcd.: 378. Found: 379 (M+H).

2-Benzyl-3-(2,4-dimethylphenyl)-6-dipropylamino-5-methyl-2,5-dihydro-4H-pyrazolo[3,4-d]pyrimidin-4-one To a solution containing 0.089 g (0.23 mmol) of 2-benzyl-6-chloro-3-(2,4-dimethylphenyl)-5-methyl-2,5-dihydro-4H-pyrazolo[3,4-d]pyrimidin-4-one in 15 ml of dioxane was added 0.06 ml (0.47 mmol) of dipropyl amine. The mixture was heated to 100° C. under a nitrogen atmosphere for 48 h. The reaction was concentrated under reduced pressure. The residue was dissolved in dichloromethane and washed with saturated sodium bicarbonate. The organic phase was dried over magnesium sulfate. Filtration, removal of solvent and purification of the residue via biotage eluting with 40% ethyl acetate/hexanes gave 0.094 g (90.2%) of product.

$^1$H NMR (CDCl$_3$) δ: 0.89 (t, J=7.2 Hz, 6H), 1.59-1.65 (m, 4H), 1.99 (s, 3H), 2.38 (s, 3H), 3.08-3.23 (m, 4H), 3.43 (s, 3H), 5.12 (d, J=14.4 Hz, 1H), 5.26 (d, J=14.4 Hz, 1H), 7.03-7.20 (m, 5H), 7.21-7.24 (m, 3H).

MS Calcd.: 443. Found: 444 (M+H).

Example 8

3-(2,4-Dimethlyphenyl)-6-dipropylamino-5-methyl-2,5-dihydro-4H-pyrazolo[3,4-d]pyrmidin-4-one

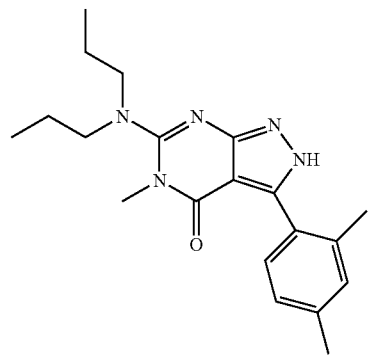

To a Parr flask was added 0.14 g (0.31 mmol) of 2-benzyl-3-(2,4-dimethylphenyl)-6-dipropylamino-5-methyl-2,5-dihydro-4H-pyrazolo[3,4-d]pyrimidin-4-one and 30 ml of ethanol, followed by 0.10 g of 20 palladium hydroxide. The flask was purged with hydrogen and pressurized to 50 psig hydrogen and shaken. After complete reaction, the mixture was filtered through GF/F paper and the filtrate concentrated under reduced pressure. The residue was purified via biotage eluting with 50% ethyl acetate/hexanes to afford 0.092 g (82.47%) of product.

$^1$H NMR (CDCl$_3$) δ: 0.93 (t, J=7.6 Hz, 6H), 1.62-1.69 (m, 4H), 2.38 (s, 3H), 2.39 (s, 3H), 3.23 (t, J=7.2 Hz, 4H), 3.50 (s, 3H), 7.08 (d, J=7.6 Hz, 1H), 7.11 (s, 1H), 7.42 (d, J=7.6 Hz, 1H).

MS Calcd.: 353. Found: 354 (M+H).

Example 9

3-(2,4-Dimethylphenyl)-6-dipropylamino-1,5-dimethyl-1,5-dihydro-4H-pyrazolo[3,4-d]pyrimidin-4-one (A) and 3-(2,4-dimethylphenyl)-6-dipropylamino-2,5-dimethyl-pyrazolo[3,4-d]pyrimidin-4-one (B)

(A)

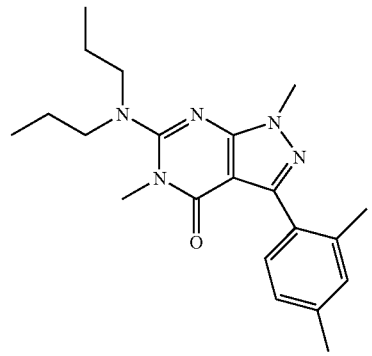

81

-continued (B)

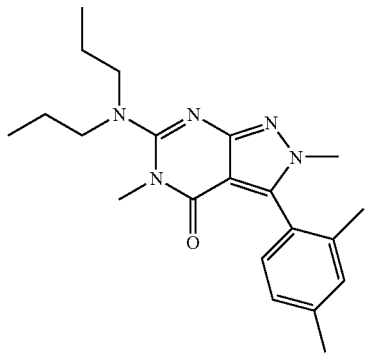

To a solution containing 0.09 g (0.25 mmol) of 3-(2,4-dimethlyphenyl)-6-dipropylamino-5-methyl-2,5-dihydro-4H-pyrazolo[3,4-d]pyrmidin-4-one in 6 ml of N,N-dimethylformamide under a nitrogen atmosphere was added 0.02 g (0.83 mmol) of sodium hydride followed by 0.063 ml (1.02 mmol) of methyl iodide. The reaction was allowed to stir at room temperature for 30 min., quenched with water and extracted with ethyl acetate. The organic phase was dried over magnesium sulfate. Filtration, removal of solvent and purification of the residue via biotage eluting with 50% ethyl acetate/hexanes gave 0.048 g (51.3%) of compound (A) and 0.02 g (21.4%) of compound (B).

Compound (A):

$^1$H NMR (CDCl$_3$) δ: 0.90 (t, J=7.2 Hz, 6H), 1.58-1.65 (m, 4H), 2.32 (s, 3H), 2.36 (s, 3H), 3.17 (t, J=7.2 Hz, 4H), 3.45 (s, 3H), 3.89 (s, 3H), 7.02 (d, J=7.6 Hz, 1H), 7.06 (s, 1H), 7.37 (d, J=7.6 Hz, 1H).

MS Calcd.: 367. Found: 368 (M+H).

Compound (B):

$^1$H NMR (CDCl$_3$) δ: 0.88 (t, J=7.2 Hz, 6H), 1.57-1.64 (m, 4H), 2.14 (s, 3H), 2.37 (s, 3H), 3.08-3.18 (m, 4H), 3.43 (s, 3H), 3.72 (s, 3H), 7.09 (bs, 2H), 7.14 (s, 1H).

MS Calcd.: 367. Found: 368 (M+H).

Example 10

8-(2,4-Dimethylphenyl)-2-methyl-2H-1,4-benzoxazin-3(4H)-one

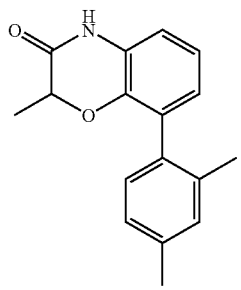

82

2-Amino-6 0bromophenol

A mixture of 2-bromo-6-nitrophenol (4.00 g, 18.4 mmol) and tin(II) chloride dihydrate (20.7 g, 91.7 mmol) in ethanol (80 ml) was heated at 70° C. for 1 h. The mixture was poured into ice and the pH was made slightly basic (pH 7-8) by addition of 1N sodium hydroxide solution in water. The aqueous solution was extracted with ethyl acetate. The extract was washed with brine, dried over magnesium sulfate and concentrated under vacuum to afford 2.74 g (79%) of the title compound.

$^1$H-NMR (CDCl$_3$) δ: 3.85 (m, 2H), 5.39 (m, 1H), 6.60-6.70 (m, 2H), 6.80-6.90 (m, 1H).

MS Calcd.: 187. Found: 188 (M+H), 190.

2-Bromo-N-(3-bromo-2-hydroxyphenyl)propionamide

2-Bromopropionyl chloride (1.47 ml, 14.6 mmol) was added dropwise to a vigorously stirred and ice-cooling mixture of 2-amino-6-bromophenol (2.74 g, 14.6 mmol) and sodium bicarbonate (3.06 g, 36.4 mmol) in ethyl acetate (50 ml)/water (15 ml). The mixture was stirred at 0° C. for 3 h and diluted with water. The aqueous layer was extracted with ethyl acetate. The extract was washed with brine, dried over magnesium sulfate and concentrated under vacuum. The residue used for the following step without further purification to afford 4.71 g (99%) of the title compound.

8-Bromo-2-methyl-2H-1,4-benzoxazin-3(4H)-one

A mixture of 2-bromo-N-(3-bromo-2-hydroxyphenyl)propionamide (4.70 g, 14.6 mmol) and potassium carbonate (2.01 g, 14.6 mmol) in N,N-dimethylformamide (100 ml) was stirred at room temperature for 15 h. The mixture was poured into water and extracted with ether. The extract was washed with brine, dried over magnesium sulfate and concentrated under vacuum. The residue was purified by column chromatography eluting with 20% ethyl acetate/n-hexane to afford 2.12 g (60%) of the title compound.

$^1$H-NMR (CDCl$_3$) δ: 1.63 (d, J=6.8 Hz, 3H), 4.77 (q, J=6.8 Hz, 1H), 6.76 (dd, J=8.0, 1.6 Hz, 1H), 6.85 (t, J=8.0 Hz, 1H), 7.22 (dd, J=8.0, 1.6 Hz, 1H).

8-(2,4-Dimethylphenyl)-2-methyl-2H-1,4-benzoxazin-3(4H)-one

To a solution of 8-bromo-2-methyl-2H-1,4-benzoxazin-3(4H)-one (1.20 g, 4.96 mmol) in 1,2-dimethoxyethane (50 ml) were added 2,4-dimethylphenylboronic acid (818 mg, 5.45 mmol), tetrakis(triphenylphosphine)palladium(0) (286 mg, 0.245 mmol) and 2M sodium carbonate solution (4.96 ml, 9.92 mmol). The mixture was refluxed for 16 h and diluted with water. The aqueous solution was extracted with ethyl acetate. The extract was washed with brine, dried over magnesium sulfate and concentrated under vacuum. The residue was purified by column chromatography eluting with 20% ethyl acetate/n-hexane to afford 1.20 g (91%) of the title compound.

$^1$H-NMR (CDCl$_3$) δ: 1.50 (dd, J=6.8 Hz, 1.2 Hz, 3H), 2.15 (s, 3H), 2.37 (s, 3H), 4.60-4.65 (m, 1H), 6.80-6.90 (m, 2H), 6.95-7.02 (m, 1H), 7.05-7.10 (m, 3H), 9.01 (s, 1H).

Example 11

8-(2,4-Dimethylphenyl)-2-methyl-4-(1-propylbutyl)-2H-1,4-benzoxazin-3(4H)-one

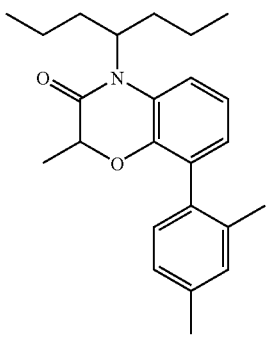

To a solution of 8-(2,4-dimethylphenyl)-2-methyl-2H-1,4-benzoxazin-3(4H)-one (300 mg, 1.12 mmol) in N,N-dimethylformamide (5 ml) was added sodium hydride (43 mg, 1.68 mmol). After the mixture was stirred at 80° C. for 30 min, 4-bromoheptane (804 mg, 4.49 mmol) was added. The mixture was stirred at 80° C. for 18 h and diluted with water. The aqueous solution was extracted with ethyl acetate. The extract was washed with brine, dried over magnesium sulfate and concentrated under vacuum. The residue was purified by column chromatography eluting with 5% ethyl acetate/n-hexane to afford 186 mg (30%) of the title compound.

$^1$H-NMR (CDCl$_3$) δ: 0.80-1.00 (m, 6H), 1.25-1.34 (m, 4H), 1.40 (d, J=7.2 Hz, 3H), 1.45-1.60 (m, 2H), 1.70-1.80 (m, 2H), 2.00-2.10 (m, 1H), 2.12 (s, 3H), 2.37 (s, 3H), 4.40-4.50 (m, 1H), 6.87 (d, J=7.6 Hz, 1H), 6.95-7.10 (m, 3H), 7.16 (d, J=7.6 Hz, 1H), 7.26 (s, 1H).

MS Calcd.: 365. Found: 366 (M+H).

Example 12

8-(2,4-Dimethylphenyl)-2-methyl-4-(1-propylbutyl)-3,4-dihydro-2H-1,4-benzoxazine

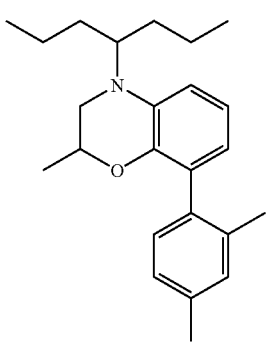

To a solution of 8-(2,4-dimethylphenyl)-2-methyl-4-(1-propylbutyl)-2H-1,4-benzoxazin-3(4H)-one (50 mg, 0.14 mmol) was added dropwise to borane-tetrahydrofuran complex (1M solution in tetrahydrofuran, 1.37 ml, 1.4 mmol) in tetrahydrofuran (2 ml) with ice-cooling. The mixture was refluxed for 24 h and then decomposed at room temperature by dropwise addition of 6N hydrochloric acid (2 ml). The mixture was stirred at 50° C. for 30 min. The acidic solution was made alkaline with excess ammonium hydroxide, and the basic mixture was extracted with ethyl acetate. The extract was washed with brine, dried over magnesium sulfate and concentrated under vacuum. The residue was purified by column chromatography eluting with 1% ethyl acetate/n-hexane to afford 15 mg (31%) of the title compound.

$^1$H-NMR (CDCl$_3$) δ: 0.86-0.95 (m, 6H), 1.26 (m, 3H), 1.27-1.60 (m, 8H), 2.16 (s, 3H), 2.35 (s, 3H), 2.79-2.85 (m, 1H), 3.16 (d, J=11.6 Hz, 1H), 3.80 (m, 1H), 4.09 (m, 1H), 6.42 (d, J=8.0 Hz, 1H), 6.74 (d, J=8.0 Hz, 1H), 6.81 (t, J=8.0 Hz, 1H), 7.01 (d, J=8.0 Hz, 1H), 7.09 (s, 1H), 7.10 (d, J=8.0 Hz, 1H).

MS Calcd.: 351. Found: 352 (M+H).

Example 13

5-(2,4-Dimethylphenyl)-2-(dipropylamino)-3-methylquinazolin-4(3H)-one

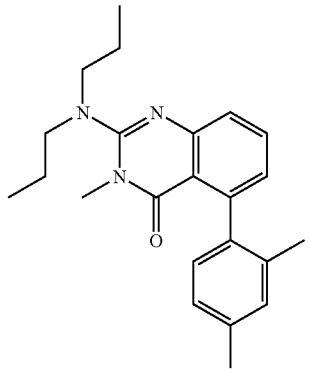

5-Methoxy-2-(methylamino)-4H-3,1-benzoxazin-4-one

A mixture of 2-amino-6-methoxybenzoic acid (2.00 g, 12.0 mmol) and methylisocyanate (1.00 g, 17.5 mmol) in dioxane (50 ml) was stirred at 80° C. for 2 h. After cooling to room temperature, 1-(3-dimethylaminopropyl)-3-ethylcarbodiimide hydrochloride (6.88 g, 36.0 mmol) and triethylamine (5.00 ml, 36.0 mmol) were added. The mixture was stirred at room temperature for 16 h, diluted with water and extracted with ethyl acetate. The extract was washed with brine, dried over magnesium sulfate and concentrated under vacuum. The residue was purified by column chromatography eluting with 20% ethyl acetate/n-hexane to afford 1.06 g (43%) of the title compound.

$^1$H-NMR (CDCl$_3$) δ: 3.03 (3H, d, J=3.6 Hz), 3.97 (3H, s), 4.89 (1H, m), 6.62 (1H, d, J=8.0 Hz), 6.87 (1H, d, J=8.0 Hz), 7.53 (1H, t, J=8.0 Hz).

MS Calcd.: 206. Found: 207 (M+H).

2-Methoxy-N-methyl-6-[[(methylamino)carbonyl]amino]benzamide

A mixture of 5-Methoxy-2-(methylamino)-4H-3,1-benzoxazin-4-one (1.05 g, 5.09 mmol) and methylamine (2.0 M solution in tetrahydrofuran; 12.7 ml, 25.5 mmol) in dimethylsulfoxide (2 ml) was heated in sealed tube for 15 h. After cooling, the mixture was diluted with water and extracted with ethyl acetate. The extract was washed with brine, dried over magnesium sulfate and concentrated under vacuum to afford 0.980 g (81%) of the title compound.

$^1$H-NMR (CDCl$_3$) δ: 2.61 (3H, s), 2.86 (3H, m), 3.91 (3H, s), 4.66 (1H, m), 6.56 (1H, d, J=8.4 Hz), 7.27 (1H, t, J=8.4 Hz), 7.87 (1H, m), 8.14 (1H, d, J=8.4 Hz), 11.46 (1H, s).

MS Calcd.: 237. Found: 238 (M+H).

5-Methoxy-3-methylquinazoline-2,4(1H,3H)-dione

A mixture of 2-Methoxy-N-methyl-6-[[(methylamino)carbonyl]amino]benzamide (200 mg, 0.843 mmol), 5% sodium hydroxide solution in water (8 ml) and ethanol (4 ml) was refluxed for 1 h. The solution was allowed to cool and then acidified with acetic acid. The aqueous solution was extracted with ethyl acetate. The extract was washed with brine, dried over magnesium sulfate, and concentrated under vacuum to afford 168 mg (97%) of the title compound.

$^1$H-NMR (CDCl$_3$) δ: 3.43 (3H, s), 3.98 (3H, s), 3.95-4.05 (2H, m), 6.63 (1H, d, J=8.4 Hz), 6.68 (1H, d, J=8.4 Hz), 7.49 (1H, t, J=8.4 Hz), 9.19 (1H, s).

MS Calcd.: 206. Found: 207 (M+H).

2-Chloro-5-methoxy-3-methylquinazolin-4(3H)-one

A mixture of 5-methoxy-3-methyl-1H-quinazoline-2,4-dione (165 mg, 0.800 mmol) and N,N-diisopropylethylamine (0.307 ml, 1.76 mmol) in phosphorus oxychloride (2.2 ml, 24.0 mmol) was refluxed for 18 h with stirring and concentrated to dryness under vacuum. The residue was diluted with water. The aqueous solution was extracted with dichloromethane. The extract was washed with water, dried over magnesium sulfate and concentrated under vacuum to afford 179 mg (99%) of the title compound. The residue was used for the next reaction without further purification.

$^1$H-NMR (CDCl$_3$) δ: 3.69 (3H, s), 3.99 (3H, s), 6.50 (1H, d, J=8.4 Hz), 7.18 (1H, d, J=8.4 Hz), 7.63 (1H, t, J=8.4 Hz).

MS Calcd.: 224. Found: 225 (M+H).

2-Dipropylamino-5-methoxy-3-methylquinazolin-4(3H)-one

A mixture of 2-chloro-5-methoxy-3-methylquinazolin-4(3H)-one (75 mg, 0.334 mmol) and dipropylamine (0.137 ml, 1.00 mmol) in tetrahydrofuran (1 ml) was stirred at 80° C. for 60 h and diluted with water. The aqueous solution was extracted with ethyl acetate. The extract was washed with brine, dried over magnesium sulfate and concentrated under vacuum. The residue was purified by column chromatography eluting with 50% ethyl acetate/n-hexane to afford 44 mg (45%) of the title compound.

$^1$H-NMR (CDCl$_3$) δ: 0.89 (6H, t, J=7.2 Hz), 1.55-1.64 (4H, m), 3.16 (4H, t, J=7.2 Hz), 3.50 (3H, s), 3.97 (3H, s), 6.70 (1H, d, J=8.4 Hz), 7.06 (1H, d, J=8.4 Hz), 7.50 (1H, d, J=8.4 Hz).

MS Calcd.: 289. Found: 290 (M+H).

2-Dipropylamino-5-hydroxy-3-methylquinazolin-4(3H)-one

To a solution of 2-dipropylamino-5-methoxy-3-methylquinazolin-4(3H)-one (130 mg, 0.449 mmol) in dichloroethane (2 ml) was added boron tribromide-methyl sulfide complex (1M solution in dichloromethane, 0.899 ml, 0.899 mmol) under nitrogen atmosphere. The mixture was refluxed for 2 h. The reaction was quenched with water and stirred for 10 min at room temperature. The aqueous phase was extracted with ether. The extract was washed with brine, dried over magnesium sulfate and concentrated under vacuum to afford 123 mg (99%) of the title compound. The residue was used for the next reaction without further purification.

$^1$H-NMR (CDCl$_3$) δ: 0.85-0.95 (6H, m), 1.55-1.68 (4H, m), 3.13-3.20 (4H, m), 3.54 (3H, s), 6.72 (1H, d, J=8.0 Hz), 6.96 (1H, m), 7.51 (1H, t, J=8.0 Hz), 11.67 (1H, s).

MS Calcd.: 275. Found: 276 (M+H).

2-Dipropylamino-3-methyl-4-oxo-3,4-dihydroquinazolin-5-yl-trifluoromethanesulfonate To a solution of 2-dipropylamino-5-hydroxy-3-methylquinazolin-4(3H)-one (67 mg, 0.24 mmol) in N,N-dimethylformamide (2 ml) was added sodium hydride (6.7 mg, 0.268 mmol). After the mixture was stirred at room temperature for 15 min, N-phenyltrifluoromethanesulfonimide (96 mg, 0.27 mmol) was added. The mixture was stirred for 18 h at room temperature. The reaction was quenched with water. The aqueous solution was extracted with ethyl acetate. The extract was washed with 5% citric acid solution in water and brine, dried over magnesium sulfate, and concentrated under vacuum. The residue was purified by column chromatography eluting with 5% ethyl acetate/n-hexane to afford 70 mg (71%) of the title compound.

$^1$H-NMR (CDCl$_3$) δ: 0.91 (6H, t, J=7.6 Hz), 1.55-1.70 (4H, m), 3.20 (4H, t, J=7.6 Hz), 3.55 (3H, s), 7.04 (1H, d, J=8.0 Hz), 7.49 (1H, d, J=8.0 Hz), 7.60 (1H, t, J=8.0 Hz).

MS Calcd.: 407. Found: 408 (M+H).

5-(2,4-Dimethylphenyl)-2-(dipropylamino)-3-methylquinazolin-4(3H)-one

To a mixture of 2-dipropylamino-3-methyl-4-oxo-3,4-dihydroquinazolin-5-yl-trifluoromethanesulfonate (87 mg, 0.21 mmol), 2,4-dimethylphenylboroic acid (64 mg, 0.427 mmol) and potassium carbonate (59 mg, 0.43 mmol) and toluene (2 ml) was added of tetrakis(triphenylphosphine)palladium(0) (47 mg, 0.0405 mmol). The mixture was stirred at 90° C. for 18 h and diluted with water. The aqueous solution was extracted with ethyl acetate. The extract was washed with saturated sodium bicarbonate solution in water, 10% citric acid solution in water and brine, dried over magnesium sulfate, and concentrated under vacuum. The residue was purified by column chromatography eluting with 5% ethyl acetate/n-hexane to afford 55 mg (71%) the title compound.

$^1$H-NMR (CDCl$_3$) δ: 0.85-0.92 (6H, m), 1.55-1.68 (4H, m), 2.01 (3H, s), 2-37 (3H, s), 3.13-3.20 (4H, m), 3.42 (3H, s), 6.95-7.10 (4H, m), 7.49 (1H, d, J=8.4 Hz), 7.55-7.62 (1H, m).

MS Calcd.: 363. Found: 364 (M+H).

Example 14

5-(2,4-Dimethylphenyl)-1-(2-ethylbutyl)-3-methylquinazoline-2,4(1H,3H)-dione

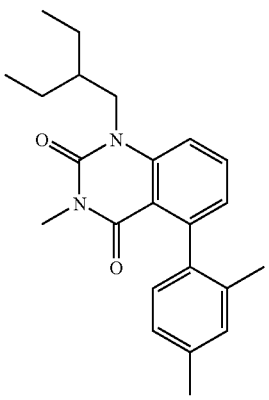

1-(2-Ethylbutyl)-5-hydroxy-3-methyl-2,4(1H,3H)-dione (A) and 5-(2-ethylbutoxy)-1-(2-ethylbutyl)-3-methylquinazoline-2,4(1H,3H)-dione (B)

To a solution of 5-methoxy-3-methylquinazoline-2,4(1H,3H)-dione (47 mg, 0.228 mmol) [example 5] in N,N-dimethylformamide (1 ml) was added sodium hydride (8.6 mg, 0.342 mmol). The mixture was stirred at 80° C. for 15 min and 1-bromo-2-ethylbutane (0.064 ml, 0.0753 mmol) was added. The resulting mixture was stirred at 80° C. for 18 h and diluted with water. The aqueous solution was extracted with ethyl acetate. The extract was washed with brine, dried over magnesium sulfate and concentrated under vacuum. The residue was purified by column chromatography eluting 50% ethyl acetate/n-hexane to afford 20 mg (32%) of 1-(2-ethylbutyl)-5-hydroxy-3-methyl-2,4(1H,3H)-dione (A) and 9 mg (11%) of 5-(2-ethylbutoxy)-1-(2-ethylbutyl)-3-methylquinazoline-2,4(1H,3H)-dione (B).

Compound (A):
$^1$H-NMR (CDCl$_3$) δ: 0.91-0.98 (6H, m), 1.35-1.43 (4H, m), 1.82-1.86 (1H, m), 3.46 (3H, s), 4.05 (2H, d, J=6.8 Hz), 6.61 (1H, d, J=8.0 Hz), 6.70 (1H, d, J=8.0 Hz), 7.49 (1H, t, J=8.0 Hz), 12.18 (1H, s).
MS Calcd.: 276. Found: 277 (M+H).

Compound (B):
$^1$H-NMR (CDCl$_3$) δ: 0.90-0.98 (12H, m), 1.33-1.43 (4H, m), 1.55-1.66 (4H, m), 1.78-1.85 (4H, m), 3.45 (3H, s), 3.98 (2H, d, J=6.0 Hz), 4.08 (2H, d, J=6.0 Hz), 6.72 (1H, d, J=8.0 Hz), 6.75 (1H, d, J=8.0 Hz), 7.50 (1H, t, J=8.0 Hz).
MS Calcd.: 360. Found: 361 (M+H).

[1-(2-Ethylbutyl)-3-methyl-2,4-dioxo-1,2,3,4-tetrahydroquinazolin-5-yl]trifluoromethanesulfonate To a solution of 1-(2-ethylbutyl)-5-hydroxy-3-methyl-2,4(1H,3H)-dione (20 mg, 0.072 mmol) in N,N-dimethylformamide (1 ml) was added sodium hydride (2.0 mg, 0.080 mmol). After the mixture was stirred at room temperature for 15 min, N-phenyltrifluoromethanesulfonimide (28 mg, 0.080 mmol) was added. The mixture was stirred for 18 h at room temperature. The reaction was quenched with water. The aqueous solution was extracted with ethyl acetate. The extract was washed with 5% citric acid solution in water and brine, dried over magnesium sulfate, and concentrated under vacuum to afford 29 mg (94%) of the title compound.
$^1$H-NMR (CDCl$_3$) δ: 0.92-0.98 (6H, m), 1.20-1.46 (4H, m), 1.75-1.80 (1H, m), 3.49 (3H, s), 4.10-4.22 (2H, m), 7.06 (1H, d, J=8.0 Hz), 7.18-7.29 (1H, m), 7.68 (1H, t, J=8.0 Hz).

5-(2,4-Dimethylphenyl)-1-(2-ethylbutyl)-3-methylquinazoline-2,4(1H,3H)-dione

To a mixture of [1-(2-ethylbutyl)-3-methyl-2,4-dioxo-1,2,3,4-tetrahydroquinazolin-5-yl]-trifluoromethanesulfonate (29 mg, 0.071 mmol), 2,4-dimethylphenylboroic acid (21 mg, 0.14 mmol) and potassium carbonate (20 mg, 0.14 mmol) and toluene (2 ml) was added of tetrakis(triphenylphosphine)palladium(0) (41 mg, 0.036 mmol). The mixture was stirred at 90° C. for 18 h and diluted with water. The aqueous solution was extracted with ethyl acetate. The extract was washed with saturated sodium bicarbonate solution in water, 10% citric acid solution in water and brine, dried over magnesium sulfate, and concentrated under vacuum. The residue was purified by column chromatography eluting with 5% ethyl acetate/n-hexane to afford 11 mg (41%) the title compound.
$^1$H-NMR (CDCl$_3$) δ: 0.94-1.00 (6H, m), 1.40-1.51 (4H, m), 1.85-1.95 (1H, m), 1.99 (3H, s), 2.38 (3H, s), 3.35 (3H, s), 4.08-4.20 (2H, m), 6.94 (1H, d, J=8.0 Hz), 6.96 (1H, d, J=8.0 Hz), 7.05 (1H, d, J=8.0 Hz), 7.08 (1H, s), 7.23 (1H, d, J=8.0 Hz), 7.62 (1H, t, J=8.0 Hz).
MS Calcd.: 364. Found: 365 (M+H).

Example 16

1-(2,4-Dimethylbenzyl)-5-(dipropylamino)-3-methylpyridin-2(1H)-one

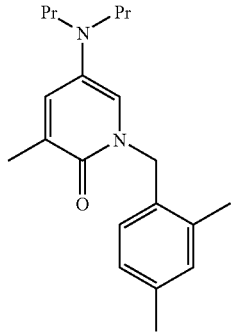

3-Methyl-5-nitropyridine-2(1H)-one

A solution of (3-methylpyridin-2-yl)amine (10 g, 90 mmol) in 50 ml of concentrated sulfuric acid was cooled to 5° C. in ice-salt bath. A mixture of 7 ml each of concentrated sulfuric acid and concentrated nitric acid was added slowly with stirring while maintaining the reaction temperature below 10° C. This mixture was then allowed to warm to 30° C. overnight. The solution was stirred rapidly while 7 ml of concentrated nitric acid was added at such a rate as to keep the temperature below 40° C. Approximately 10 ml of the solution was then poured into 20 ml of water and heated to 100° C.; large quantities of gas were evolved. When gas evolution ceased, the remainder of the nitrating mixture was added in 10 ml portions with heating. When the last of the nitrating mixture had been added, the solution was cooled rapidly by placing the flask in an ice bath and by adding ice directly to the solution. The light brown precipitate was filtered and dried to afford 5.0 g (35%) of the title compound.
$^1$H NMR (CDCl$_3$) δ: 2.14 (s, 3H), 8.11 (s, 1H), 8.49 (s, 1H).

1-(2,4-Dimethylbenzyl)-3-methyl-5-nitropyridin-2(1H)-one

To a solution containing 0.20 g (1.3 mmol) of 3-methyl-5-nitropyridine-2(1H)-one in 5 ml of N,N-dimethylformamide under a nitrogen atmosphere was added 0.037 g (1.6 mmol) of sodium hydride followed by 0.31 g (1.6 mmol) of 1-bromomethyl-2,4-dimethylbenzene. The reaction was allowed to stir at room temperature for 30 min., quenched with water and extracted with ethyl acetate. The organic phase was dried over magnesium sulfate. Filtration, removal of solvent and purification of the residue via biotage eluting with 25% ethyl acetate/hexanes gave 0.12 g (34%) of compound.

$^1$H NMR (CDCl$_3$) δ: 2.20 (s, 6H), 2.30 (s, 3H), 5.14 (s, 2H), 7.02 (s, 2H), 7.04 (s, 1H), 7.92 (s, 1H), 8.21 (d, J=2.9 Hz, 1H).

5-Amino-1-(2,4-dimethylbenzyl)-3-methylpyridin-2(1H)-one

To a solution containing 0.2 g (0.73 mmol) of 1-(2,4-dimethylbenzyl)-3-methyl-5-nitropyridin-2(1H)-one in 50 ml of methanol was added 0.017 g (0.073 mmol) of platinum (IV) oxide (Adam's catalyst). The flask was fitted with a balloon of hydrogen and allowed to stir for 1 h. The reaction was filtered through GF/F paper and the filtrate concentrated under reduced pressure to afford 0.11 g (62%) of product.

MS Calcd.: 242. Found: 243 (M+H).

1-(2,4-Dimethylbenzyl)-5-(dipropylamino)-3-methylpyridin-2(1H)-one

To a solution containing 0.04 g (0.165 mmol) of 5-amino-1-(2,4-dimethylbenzyl)-3-methylpyridin-2(1H)-one in 20 ml of methanol was added 0.1 ml (1.6 mol) of propionaldehyde followed by 0.026 g (0.41 mmol) of sodium cyanoborohydride under a nitrogen atmosphere. The reaction was allowed to stir at 25° C. overnight. The reaction was diluted with dichloromethane and washed with saturated sodium bicarbonate. The organic phase was dried over magnesium sulfate. Filtration, removal of solvent and purification of the residue via Biotage eluting with 20% ethyl acetate/hexanes gave 0.025 g (46%) of product.

$^1$H NMR (CDCl$_3$) δ: 0.79 (t, J=7.5 Hz, 6H), 1.29-1.38 (m, 4H), 2.18 (s, 3H), 2.23 (s, 3H), 2.29 (s, 3H), 2.76-2.80 (m, 4H), 5.08 (s, 2H), 6.33 (d, J=2.7 Hz, 1H), 6.93-7.01 (m, 3H), 7.11 (s, 1H).

MS Calcd.: 326. Found: 327 (M+H).

Example 17

5-(2,4-Dimethylphenyl)-3-methyl-2-(methylthio)pyrimidin-4(3H)-one

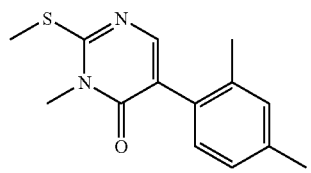

2-(Methylthio)pyrimidin-4(3H)-one

A mixture of 12.8 g (99.9 mmol) of 2-thiouracil and 4.3 g (108 mmol) of sodium hydroxide was placed in 500 ml Erlenmeyer flask, and dissolved on the oil bath with a minimum amount of water. Twice the volume of 99% ethanol was then added, the solution cooled to 30° C., and 6.3 ml (99.9 mmol) of methyl iodide added. The solution was heated to 60° C. for 20 min, then cooled to room temp. The precipitate was filtered off, and, after acidifying the filtrate with acetic acid, the excess solvent was removed in vacuo. The combined precipitates were thoroughly washed with water and recrystallized from ethanol to give 6.0 g (47%) of product.

$^1$H NMR (CDCl$_3$) δ: 2.59 (s, 3H), 6.23 (d, J=6.7 Hz, 1H), 7.89 (d, J=6.4 Hz, 1H).

5-Bromo-2-(methylthio)pyrimidin-4(3H)-one

To a solution containing 2.0 g (14 mmol) of 2-(methylthio)pyrimidin-4(3H)-one in 10 ml of acetic acid under a nitrogen atmosphere was added 1.04 ml (14 mmol) of bromine in 2 ml acetic acid. The reaction was allowed to stir at room temperature for 30 min. The precipitated product was filtered, washed with acetic acid and suspended in hot acetic acid. To this suspension was added 0.2 ml bromine in 1 ml acetic acid. The product was collected, washed with acetic acid and recrystallized from ethanol to yield 1.4 g (45%) of product.

$^1$H NMR (CD$_3$OD) δ: 2.61 (s, 3H), 8.29 (s, 1H).

5-Bromo-3-methyl-2-(methylthio)pyrimidin-4(3H)-one

To a mixture containing 0.70 g (5.5 mmol) of dimethyl sulfate and 0.25 g (4.5 mmol) of potassium hydroxide in 10 ml of tetrahydrofuran was added 0.5 g (2.25 mmol) of 5-Bromo-2-(methylthio)pyrimidin-4(3H)-one in portions over 15 min. After complete addition, the mixture was stirred overnight then diluted with ethyl acetate and washed with water. The organic phase was dried over magnesium sulfate. Filtration, removal of solvent and purification of the residue via Biotage chromatography eluting with 20% ethyl acetate/dichloromethane gave 0.5 g (94%) of product.

$^1$H NMR (CDCl$_3$) δ: 2.58 (s, 3H), 3.58 (s, 3H), 8.06 (s, 1H).

5-(2,4-Dimethylphenyl)-3-methyl-2-(methylthio)pyrimidin-4(3H)-one

A mixture containing 0.2 g (0.84 mmol) of 5-bromo-3-methyl-2-(methylthio)pyrimidin-4(3H)-one, 0.19 g (1.3 mmol) of 2,4-dimethylphenyl boronic acid, 0.35 g (2.5 mmol) of potassium carbonate, 0.15 ml (8.4 mmol) of water, and 0.25 g (0.21 mmol) of tetrakis(triphenylphosphine)palladium(0) in 10 ml of dioxane was heated to 90° C. under a nitrogen atmosphere overnight. The reaction was cooled to room temperature, diluted with ethyl acetate and washed with saturated sodium bicarbonate. The organic phase was dried over magnesium sulfate. Filtration, removal of solvent and purification of the residue via biotage eluting with 30% ethyl acetate/hexanes gave 0.18 g (86%) of product.

MS Calcd.: 260. Found: 261 (M+H).

Example 18

5-(2,4-Dimethylphenyl)-3-methyl-2-propylaminopyrimidin-4(3H)-one

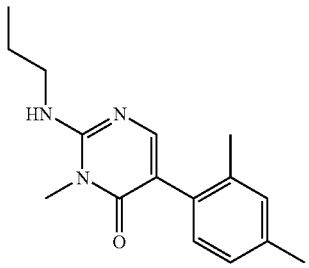

To a sealed tube was added 0.15 g (0.57 mmol) of 5-(2,4-dimethyl-phenyl)-3-methyl-2-(methylthio)pyrimidin-4 (3H)-one and 3 ml (50 mmol) of propyl amine. The mixture was heated to 100° C. for 48 h. The reaction was concentrated under reduced pressure. The residue was dissolved in ethyl acetate and washed with saturated sodium bicarbonate. The organic phase was dried over magnesium sulfate. Filtration, removal of solvent and purification of the residue via biotage eluting with 50% ethyl acetate/hexanes gave 0.1 g (67%) of product.

MS Calcd.: 271. Found: 272 (M+H).

Example 19

5-(2,4-Dimethylphenyl)-2-(dipropylamino)-3-methylpyrimidin-4(3H)-one

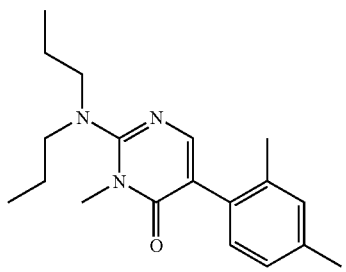

To a solution containing 0.2 g (0.74 mmol) of 5-(2,4-dimethylphenyl)-3-methyl-2-propylaminopyrimidin-4(3H)-one in 5 ml of tetrahydrofuran under a nitrogen atmosphere was added 0.12 g (2.2 mmol) of potassium hydroxide followed by 0.38 g (2.2 mmol) of 1-iodopropane. The reaction was allowed to stir at room temperature for 12 h, diluted with ethyl acetate and washed with saturated sodium bicarbonate. The organic phase was dried over magnesium sulfate. Filtration, removal of solvent and purification of the residue via Biotage chromatography eluting with 30% ethyl acetate/dichloromethane gave 0.15 g (65%) of product.

$^1$H NMR (CDCl$_3$) δ: 0.91 (t, J=7.5 Hz, 6H), 1.57-1.66 (m, 4H), 2.21 (s, 3H), 2.33 (s, 3H), 3.15-3.21 (m, 4H), 3.53 (s, 3H), 6.95-7.09 (m, 3H), 7.69 (s, 1H).

MS Calcd.: 313. Found: 314 (M+H).

Example 21

4-(2,4-Dimethylphenyl)-1-(1-ethylpropyl)-2-methyl-1,2-dihydro-3H-indazol-3-one

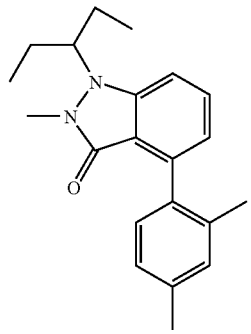

Methyl 2-chloro-6-nitrobenzoate

To a suspension containing 3.0 g (15 mmol) of 2-chloro-6-nitrobenzoic acid in 150 ml of dichloromethane was added 2.8 g (22 mmol) of oxalyl chloride followed by 0.055 ml (0.75 mmol) of N,N-dimethylformamide. The reaction was allowed to stir at room temperature for 2 h, quenched with 50 ml of methanol and concentrated under reduced pressure. The residue was dissolved in ethyl acetate and washed with saturated sodium bicarbonate. The organic phase was dried over magnesium sulfate. Filtration, removal of solvent and purification of the residue via biotage eluting with 10% ethyl acetate/hexanes gave 3.1 g (9-7%) of product.

$^1$H NMR (CDCl$_3$) δ: 4.02 (s, 3H), 7.55 (t, J=8.2 Hz, 1H), 7.75 (d, J=8.2 Hz, 1H), 8.13 (d, J=8.2 Hz, 1H).

Methyl 2-(2,4-dimethylphenyl)-6-nitrobenzoate

A mixture containing 0.5 g (2.3 mmol) of methyl 2-chloro-6-nitrobenzoate, 0.76 g (3.5 mmol) of 2,4-dimethylphenyl boronic acid, 0.7 g (4.6 mmol) of cesium fluoride, and 0.27 g (0.23 mmol) of tetrakis(triphenylphosphine)palladium(0) in 10 ml of 1,2-dimethoxyethane was heated to 100° C. under a nitrogen atmosphere overnight. The reaction was cooled to room temperature, diluted with ethyl acetate and washed with saturated sodium bicarbonate. The organic phase was dried over magnesium sulfate. Filtration, removal of solvent and purification of the residue via biotage eluting with 20% ethyl acetate/hexanes gave 0.312 g (47%) of product.

$^1$H NMR (CDCl$_3$) δ: 2.08 (s, 3H), 2.35 (s, 3H), 3.61 (s, 3H), 7.01 (s, 2H), 7.07 (s, 1H), 7.54-7.62 (m, 2H), 8.16 (d, J=8.1 Hz, 1H).

2-(2,4-Dimethylphenyl)-N-methyl-6-nitrobenzamide

To a mixture containing 0.32 g (1.12 mmol) of methyl 2-(2,4-dimethylphenyl)-6-nitrobenzoate in methanol (2.2 ml), tetrahydrofuran (3.5 ml) and water (3.5 ml) was added 0.18 g (4.5 mmol) of sodium hydroxide. The reaction was allowed to stir at 65° C. for 12 h. The solution was cooled, diluted with ethyl acetate (10 mL) and water (10 mL) and shaken vigorously. The aqueous layer was separated, acidified to pH=3 and extracted with ethyl acetate (3×). The combined ethyl acetate layers were washed with brine, dried (Na$_2$SO$_4$), filtered and concentrated. The residue was then dissolved in tetrahydrofuran (10 mL) and methylamine (0.14 g, 2.2 mmol), O-(benzotriazol-1-yl)-N,N,N',N'-tetramethyluronium hexafluorophosphate (HBTU) (0.62 g, 1.66 mmol), and diisopropylethylamine (0.28 mL, 2.2 mmol) were added. The reaction was allowed to stir at room temperature for 12 h. The reaction was diluted with ethyl acetate and washed with saturated sodium bicarbonate. The organic phase was dried over magnesium sulfate. Filtration, removal of solvent and purification of the residue via biotage eluting with 30% ethyl acetate/hexanes gave 0.095 g (30%) of product.

MS Calcd.: 284. Found: 285 (M+H).

4-(2,4-Dimethylphenyl)-2-methyl-1,2-dihydro-3H-indazol-3-one

A solution of sodium hydroxide (0.035 g, 0.88 mmol) in water (2 ml) was added to a solution containing 0.095 g (0.33 mmol) of 2-(2,4-dimethylphenyl)-N-methyl-6-nitrobenzamide in methanol (1.5 ml). Zinc powder (0.03 g, 0.44 mmol) was then added to the mixture, which was heated under reflux for 24 h. After cooling, the zinc residue was separated by filtration and the methanol was partially evaporated. The residual solution was then adjusted to pH 7 with aqueous hydrochloric acid. The mixture was diluted with ethyl acetate and washed with saturated sodium bicarbonate. The organic phase was dried over magnesium sulfate. Filtration, removal of solvent and purification of the residue via biotage eluting with 40% ethyl acetate/hexanes gave 0.01 g (22%) of product.

$^1$H NMR (CDCl$_3$) δ: 2.13 (s, 3H), 2.34 (s, 3H), 3.35 (s, 3H), 6.97-7.12 (m, 5H), 7.17 (br, s, 1H), 7.48 (t, J=8.1 Hz, 1H).

MS Calcd.: 252. Found: 253 (M+H).

4-(2,4-Dimethylphenyl)-1-(1-ethylpropyl)-2-methyl-1,2-dihydro-3H-indazol-3-one

To a solution containing 0.008 g (0.03 mmol) of 4-(2,4-dimethylphenyl)-2-methyl-1,2-dihydro-3H-indazol-3-one in 2 ml of N,N-dimethylformamide under a nitrogen atmosphere was added 0.001 g (0.038 mmol) of sodium hydride followed by 0.007 g (0.048 mmol) of 3-bromopentane. The reaction was allowed to stir at room temperature for 48 h, quenched with water and extracted with ethyl acetate. The organic phase was dried over magnesium sulfate. Filtration, removal of solvent and purification of the residue via biotage eluting with 25% ethyl acetate/dichloromethane gave 0.003 g (30%) of compound.

$^1$H NMR (CDCl$_3$) δ: 0.90-0.95 (m, 6H), 1.68-1.82 (m, 4H), 2.13 (s, 3H), 2.36 (s, 3H), 3.39 (s, 3H), 3.64-3.71 (m, 1H), 6.89 (d, J=7.2 Hz, 1H), 7.03-7.15 (m, 4H), 7.46 (t, J=8.3 Hz, 1H).

MS Calcd.: 322. Found: 323 (M+H).

Example 22

5-(2,4-Dimethylphenyl)-1-(1-propylbutyl)quinolin-4(1H)-one

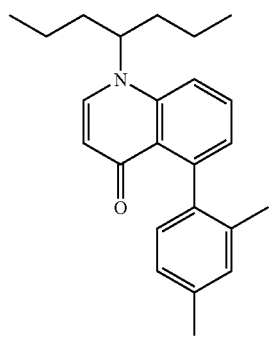

Diethyl [[(3-bromophenyl)amino]methylene]malonate

3-Bromoaniline (10.0 g, 47 mmol) was dissolved in abs. ethanol (100 mL). Diethyl ethoxymethylenemalonate (10.2 g, 47 mmol) was added. The solution stirred at 80° C. overnight. The solution was slowly cooled and a precipitant formed. The product was filtered and dried to give 12.6 g (70%) of the title compound.

$^1$H NMR (CDCl$_3$) δ: 1.34 (t, J=7.6 Hz, 3H), 1.38 (t, J=7.6 Hz, 3H), 4.60 (q, J=7.2, 14.0 Hz, 2H), 4.31 (q, J=7.2, 14.4 Hz, 2H), 7.05 (d, J=7.6 Hz, 1H), 7.20-7.30 (m, 3H), 8.44 (d, J=13.2 Hz, 1H), 10.98 (d, J=13.6 Hz, 1H).

Ethyl 5-bromo-4-oxo-1-(1-propylbutyl)-1,4-dihydroquinoline-3-carboxylate

Diethyl [[3-bromophenyl)amino]methylene]malonate (18.0 g, 53 mmol) was stirred in 100 mL of polyphosphate ester (PPE). The solution was heated for 3 h at 100° C. The solution was cooled to room temperature and water was carefully added to form a precipitant. The solution was filtered and the solid was washed with water. The precipitant was dried to give 24 g of the crude mixture of isomers.

MS Calcd.: 295. Found: 296 (M+H) and 298 (M+3H).

MS Calcd.: 296. Found: 296 (M) and 298 (M+2).

A portion of the crude solid (3.0 g) was dissolved in 15 mL of 4-bromoheptane followed by addition of 2.1 g of potassium carbonate. The suspension was heated in a sealed tube at 160° C. overnight. The brown solution was cooled and diluted with water. The material was extracted with ethyl acetate (3 times), dried over sodium sulfate and concentrated. Flash chromatography (50% ethyl acetate/hexanes) provided 0.48 g (12% yield) of the two isomers, the tile compound and ethyl 7-bromo-4-oxo-1-(1-propylbutyl)-1,4-dihydroquinoline-3-carboxylate, as a mixture. A small amount of ester (B) was purified from the mixture using preparative TLC (50% ethyl acetate/hexane) for characterization purposes.

$^1$H NMR (CDCl$_3$) δ: 0.90 (t, J=7.2 Hz, 6H), 1.22-1.31 (m, 4H), 1.42 (t, J=6.8 Hz, 3H), 1.88-1.85 (m, 2H), 4.42 (q, J=7.2, 14.4 Hz, 4H), 4.60-4.64 (m, 1H), 7.39 (t, J=8.0 Hz, 1H), 7.55 (d, J=8.4 Hz, 1H), 7.66 (d, J=7.6 Hz, 1H), 8.44 (s, 1H).

MS Calcd. for (B): 393. Found: 394 (M+H) 396 (M+3H).

5-Bromo-1-(1-propylbutyl)quinolin-4(1H)-one

Ethyl 5-bromo-4-oxo-1-(1-propylbutyl)-1,4-dihydroquinoline-3-carboxylate, 0.977 g (2.48 mmol) of the isomeric mixture, and 7-bromo-4-oxo-1-(1-propylbutyl)-1,4-dihydroquinoline-3-carboxylic acid ethyl ester was dissolved in 6 mL of 48% hydrobromic acid. The solution was heated at 90° C. for 36 h. The solution was cooled and neutralized with saturated sodium carbonate. The solution was extracted using ethyl acetate (3 times), dried over magnesium sulfate and concentrated to give 0.700 g of a yellow solid. The crude acid was dissolved in dimethyl sulfoxide (10 mL) and potassium cyanide (2.48 g, 38 mmol) was added. The reaction was heated to 115° C. for 9 h. The solution was cooled and diluted with ethyl acetate. The mixture was washed with water and brine. The organic phase was dried over sodium sulfate and concentrated. Flash chromatography (75% ethyl acetate/hexanes) gave 0.203 g (25% yield) of the title compound as an off white solid.

MS Calcd.: 321. Found: 322 (M+H) 324 (M+3H).

5-(2,4-Dimethylphenyl)-1-(1-propylbutyl)quinolin-4(1H)-one

A mixture of 5-Bromo-1-(1-propylbutyl)quinolin-4(1H)-one (0.096 g, 0.30 mmol), 2,4-dimethylbenzeneboronic acid (0.067 g, 0.45 mmol), potassium carbonate (0.124 g, 0.89 mmol) and tetrakis(triphenylphosphine)palladium(0) (0.17 g, 0.15 mmol) were put under nitrogen gas. Dioxane (4 mL) was added followed by water (27 μL 1.5 mmol). The reaction was heated at 90° C. overnight. The solution was cooled and concentrated. Flash chromatography (60% ethyl acetate/hexanes) gave 0.088 g (85% yield) of the desired product.

$^1$H NMR (CDCl$_3$) δ: 0.85-0.97 (m, 6H), 1.20-1.40 (m, 4H), 1.73-1.92 (m, 4H), 1.99 (s, 3H), 2.36 (s, 3H), 4.65-4.75 (m, 1H), 6.15 (d, J=8.0 Hz, 1H), 6.95-7.03 (m, 3H), 7.30-7.40 (m, 1H), 7.47-7.59 (m, 3H).

MS Calcd.: 347. Found: 348 (M+H).

Example 23

3-Bromo-5-(2,4-dimethylphenyl)-1-(1 propylbutyl)quinolin-4(1H)-one

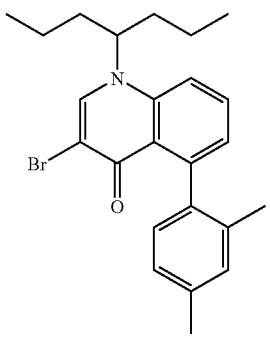

5-(2,4-Dimethylphenyl)-1-(1-propylbutyl)quinolin-4(1H)-one, (0.21 g, 0.61 mmol), was dissolved in N,N-dimethylformamide (10 mL). The solution was cooled to 0° C. and N-bromosuccinimide (0.11 g, 0.62 mmol) was added. After 10 minutes, the solution was diluted with water, extracted with ethyl acetate, dried (Na$_2$SO$_4$), and concentrated. Flash chromatography (20% ethyl acetate/hexanes) gave 0.136 g (53% yield) of the title compound as a white solid.

(MS Calcd.: 425. Found 426 (M+H) 428 (M+3H)).

Example 24

5-(2,4-Dimethylphenyl)-3-methyl-1-(1-propylbutyl)quinolin-4(1H)-one

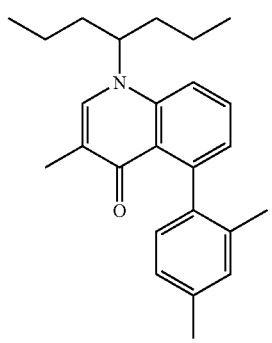

3 Bromo-5-(2,4-dimethylphenyl)-1-(1-propylbutyl)quinolin-4(1H)-one was then charged with methylboronic acid (0.19 g, 3.2 mmol), potassium carbonate (0.22 g, 1.6 mmol), tetrakis(triphenylphosphine)palladium(0) (0.18 g, 0.16 mmol) and diluted with dioxane (8 mL) under nitrogen gas. Water (29 μL, 1.6 mmol) was added last. The reaction was stirred at 90° C. overnight. The solution was cooled and concentrated. Flash chromatography (40% ethyl acetate/hexanes) gave 0.049 g (43% yield) of the title compound as a white solid.

$^1$H NMR (CDCl$_3$) δ: 0.85-0.97 (m, 6H), 1.20-1.36 (m, 4H), 1.81-1.90 (m, 4H), 1.96 (s, 3H), 2.02 (s, 3H), 2.36 (s, 3H), 4.65-4.70 (m, 1H), 6.96-7.04 (m, 4H), 7.47 (s, 1H), 7.52-7.59 (m, 2H).

MS Calcd.: 361. Found: 362.

| Example | Structure | Name | Physical Data |
|---|---|---|---|
| 25 | 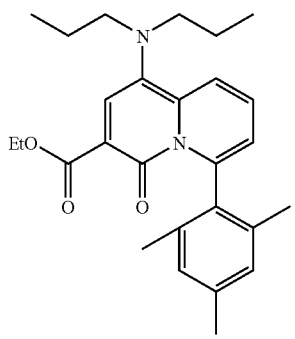 | 5-(2,4-Dimethyl-phenyl)-1-(2-ethylbutyl)-3-methyl-quinolin-4(1H)-one | $^1$H NMR (CDCl$_3$) δ: 0.94-1.00 (m, 6H), 1.37-1.45 (m, 4H), 1.96 (s, 3H), 1.95-2.00 (m, 1H), 2.00 (s, 3H), 2.37 (s, 3H), 3.91-4.01 (m, 2H), 6.96-7.04 (m, 4H), 7.38-7.40 (m, 2H), 7.55-7.60 (m, 1H). MS Calcd.: 347, Found: 348. |

Example 26

Ethyl 1-(dipropylamino)-6-mesityl-4-oxo-4H-quino-lizine-3-carboxylate

N-[(6-Bromopyridin-2-yl)methyl]-N-propylpropan-1-amine

Dipropylamine (7.4 mL, 54 mmol) and 6-bromopyridine-2-carbaldehyde (5.0 g, 27 mmol) were dissolved in 1,2-dichloroethane (50 mL). 2 drops of glacial acetic acid was added followed by sodium triacetoxyborohydride (11.4 g, 54 mmol). The reaction was stirred at 50° C. for 1 h. The reaction was cooled and quenched with water. The solution was diluted with saturated sodium bicarbonate and extracted with ethyl acetate (3 times). The organic layers were dried over magnesium sulfate, filtered and concentrated. Flash chromatography gave 5.34 g (73% yield) of product.

MS Calcd.: 270. Found: 271 (M+H) 273 (M+3H).

N-[(6-mesitylpyridin-2-yl)methyl]-N-propylpropan-1-amine

N-[(6-Bromopyridin-2-yl)methyl]-N-propylpropan-1-amine (7.0 g, 26 mmol) was dissolved in 1,2-dimethoxy-ethane (100 mL). Tetrakis(triphenylphosphine)palladium(0) (1.49 g, 1.29 mmol) was added and the solution was heated to 50° C. for 15 minutes. The solution was cooled and 2,4,6-trimethylbenzeneboronic acid (4.44 g, 27.1 mmol) in 30 mL 1,2 dimethoxyethane was added followed by potassium tert-butoxide (5.79 g, 51.6 mmol) in 30 mL of tBuOH. The reaction was heated at 90° C. for 0.5 h. The solution was filtered through filter paper and concentrated. Flash chromatography gave 3.83 g of the title compound (48% yield).

$^1$H NMR (CDCl$_3$) δ: 0.87 (t, J=7.2 Hz, 6H), 1.47-1.53 (m, 4H), 2.00 (s, 6H), 2.30 (s, 3H), 2.46 (t, J=6.4 Hz, 4H), 3.77 (s, 2H), 6.91 (s, 2H), 7.05 (d, J=7.6 Hz, 1H), 7.47 (d, J=8.8 Hz, 1H), 7.69 (t, J=6.8 Hz, 1H).

MS Calcd.: 310. Found: 311.

Diethyl [2-(dipropylamino)-1-ethoxy-2-(6-mesi-tylpyridin-2-yl)ethyl]malonate N-[(6-mesitylpyridin-2-yl)methyl]-N-propylpropan-1-amine (0.71 g, 2.29 mmol), was dissolved in tetrahydrofuran (15 mL). The solution was cooled to −78° C. and n-butyl-lithium (2.5M, 1.0 mL, 2.51 mmol) was added drop wise. After 0.5 h, diethyl ethoxymethylene malonate (0.48 mL, 2.40 mmol) was added. The reaction was removed from the dry ice bath and allowed to warm to room temperature. The mixture was quenched with water, extracted with ether, dried over sodium sulfate, filtered and concentrated. Flash chromatography gave 0.65 g (59% yield) of an isomeric mixture of the title compound.

MS Calcd.: 526. Found: 527 (M+H). Two peaks observed.

Ethyl 1-(dipropylamino)-6-mesityl-4-oxo-4H-quino-lizine-3-carboxylate

Diethyl [2-(dipropylamino)-1-ethoxy-2-(6-mesitylpyri-din-2-yl)ethyl]malonate (0.65 g, 1.35 mmol), was dissolved in 5 mL of Dowtherm A (1:2 biphenyl:phenyl ether). The solution was placed in a pre-heated oil bath at 220° C. The reaction stirred at this temperature for 20 minutes. The solution was cooled and flash chromatographed (15%-35% ethyl acetate/hexanes) to give 0.28 g (48% yield) of an orange solid.

$^1$H NMR (CDCl$_3$) δ: 0.88 (t, J=7.2 Hz, 6H), 1.37 (t, J=7.2 Hz, 3H), 1.35-1.47 (m, 4H), 1.97 (s, 6H), 2.30 (s, 3H), 2.89 (t, J=6.0 Hz, 4H), 4.30 (q, J=7.2, 14.4 Hz, 2H), 6.68 (d, J=5.6 Hz, 1H), 6.85 (s, 2H), 7.39-7.43 (m, 1H), 8.26 (s, 1H), 8.34 (d, J=7.2 Hz, 1H).

MS Calcd.: 434. Found: 434 (M+H).

Example 27

1-(Dipropylamino)-3-(hydroxymethyl)-6-mesityl-4H-quinolizin-4-one

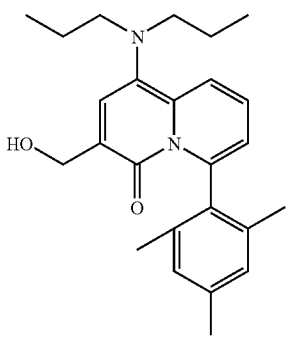

Ethyl 1-(dipropylamino)-6-mesityl-4-oxo-4H-quinolizine-3-carboxylate, (0.020 g, 0.046 mmol), in tetrahydrofuran (1 mL) was cooled to −40° C. Diisobutylaluminum hydride (1.5M, 92 mL, 0.14 mmol) was added rapidly and the solution was warmed to room temperature. The reaction was quenched with methanol and stirred with saturated Rochelle's salt for 1 h. The solution was extracted with ethyl acetate, dried over sodium sulfate, filtered and concentrated. Flash chromatography (25% ethyl acetate/hexanes) gave 0.0107 g (59% yield) of the title compound as a yellow solid.

$^1$H NMR (CDCl$_3$) δ: 0.88 (t, 7.2 Hz, 6H), 1.25-1.41 (m, 4H), 1.99 (s, 6H), 2.33 (s, 3H), 2.87 (t, J=6.0 Hz, 4H), 4.30 (t, J=6.8 Hz, 1H), 4.57 (d, J=6.0 Hz, 2H), 6.53 (d, J=6.4 Hz, 1H), 6.88 (s, 2H), 7.11-7.15 (m, 1H), 7.61 (s, 1H), 8.27 (d, J=7.6 Hz, 1H).

MS Calcd.: 392. Found: 393 (M+H).

Example 28

1-(Dipropylamino)-6-mesityl-3-methyl-4H-quinolizin-4-one

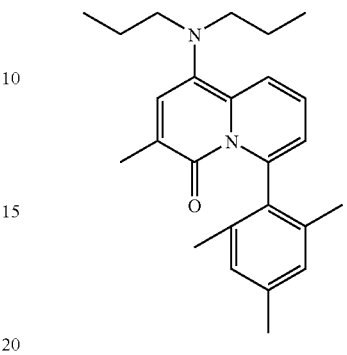

1-(Dipropylamino)-3-(hydroxymethyl)-6-mesityl-4H-quinolizin-4-one, (0.067 g, 0.17 mmol), was dissolved in 2 mL of dichloromethane. The solution was cooled to −20° C. and triethylamine (0.12 mL, 0.85 mmol) was added. Methanesulfonylchloride (0.039 μL, 0.51 mmol) was added dropwise and the reaction stirred for 0.5 h. The solution was quenched with water and warmed to room temperature. The solution was extracted with ethyl acetate, dried over magnesium sulfate, filtered, and concentrated to give the crude mesylate. The mesylate was dissolved in tetrahydrofuran (3 mL) and solid lithium aluminum hydride (0.010 g, 0.25 mmol) was added in one portion. The reaction stirred for 0.5 hr at room temperature. Glauber's salt was added and the solution was filtered and concentrated. Flash chromatography (15% ethyl acetate/hexanes) gave 0.0094 g (15% yield) of the title compound.

$^1$H NMR (CDCl$_3$) δ: 0.90 (t, J=7.2 Hz, 6H), 1.28-1.40 (m, 4H), 1.98 (s, 6H), 2.17 (s, 3H), 2.30 (s, 3H), 2.86 (t, J=6.8 Hz, 4H), 6.43 (d, J=6.4 Hz, 1H), 6.85 (s, 2H), 6.98-7.02 (m, 1H), 7.52 (s, 1H), 8.17 (d, J=9.2 Hz, 1H).

MS Calcd.: 376. Found: 377 (M+H).

Example 29 was prepared with ethyl(ethoxymethylene)cyanoacetate as opposed to diethyl(ethoxymethylene)malonate. The coupled product was then cyclized according to the conditions used for Example 26.

| Example | Structure | Name | Physical Data |
| --- | --- | --- | --- |
| 29 | 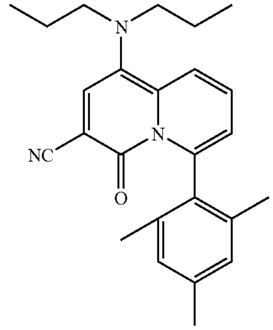 | 1-(dipropylamino)-6-mesityl-4-oxo-4H-quinolizine-3-carbonitrile | $^1$H NMR (CDCl$_3$) δ: 0.89 (t, J=7.2 Hz, 6H), 1.38-1.44 (m, 4H), 1.96 (s, 6H), 2.32 (s, 3H), 2.87 (bs, 4H), 6.82 (d, J=6.8 Hz, 1H), 6.88 (s, 2H), 7.52-7.56 (m, 1H), 7.80 (s, 1H), 8.42 (d, J=7.2 Hz, 1H). MS Calcd.: 387, Found: 388 (M + H). |

Example 30

1-(Dipropylamino)-6-mesityl-4H-quinolizin-4-one

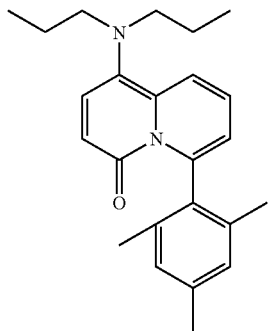

Ethyl 1-(dipropylamino)-6-mesityl-4-oxo-4H-quinolizine-3-carboxylate (0.0145 g, 0.033 mmol) was dissolved in ethanol (0.3 mL). Potassium hydroxide (6M in ethanol, 94 µL, 0.57 mmol) was added. The solution was heated at 60° C. for 1 h. The solution was extracted using ethyl acetate, dried over magnesium sulfate and concentrated to give 0.010 g (83% yield) of the title compound.

$^1$H NMR (CDCl$_3$) δ: 0.86-0.90 (m, 6H), 1.38-1.44 (m, 4H), 1.96 (s, 6H), 2.35 (s, 3H), 2.95 (t, J=6.4 Hz, 4H), 6.91 (s, 2H), 6.91-6.93 (m, 2H), 7.60-7.64 (m, 1H), 8.55-8.59 (m, 2H).

MS Calcd.: 362. Found: 363.

Example 31

1-(Dipropylamino)-6-mesityl-4-oxo-4H-quinolizine-3-carbaldehyde

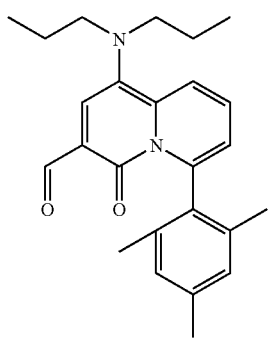

1-(Dipropylamino)-3-(hydroxymethyl)-6-mesityl-4H-quinolizin-4-one (0.60 g, 1.53 mmol) was dissolved in dichloromethane (20 mL) and acetonitrile (4 mL). 0.5 g of crushed sieves (4 angstroms) was added followed by N-methylmorpholine N-oxide (NMO) (0.27 g, 2.3 mmol). Tetrapropylammonium perruthenate (TPAP) (0.081 g, 0.23 mmol) was added last. The reaction stirred for 0.5 h. The solution was filtered and concentrated. Flash chromatography (20% ethyl acetate/hexanes) gave 0.436 g (73% yield) of the title compound as a red solid.

$^1$H NMR (CDCl$_3$) δ: 0.87 (t, J=7.2 Hz, 6H), 1.37-1.43 (m, 4H), 1.99 (s, 6H), 2.34 (s, 3H), 2.89 (t, J=7.6 Hz, 4H), 6.83 (d, J=7.2 Hz, 1H), 6.92 (s, 2H), 7.59 (t, J=6.8 Hz, 1H), 8.15 (s, 1H), 8.49 (d, J=8.8 Hz, 1H), 10.2 (s, 1H).

MS Calcd.: 390. Found: 391 (M+H).

Example 32

1-(Dipropylamino)-6-mesityl-3-vinyl-4H-quinolizin-4-one

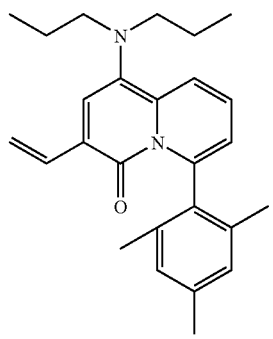

Methyltriphenylphosphonium bromide (0.46 g, 1.28 mmol) was suspended in tetrahydrofuran (10 mL). The solution was cooled to −78° C. n-Butyllithium (1.6M, 0.80 µL, 1.28 mmol) was added. After 0.5 h, the solution was warmed to 0° C. and stirred for an addition 0.5 h. The solution was cooled again to −78° C. and 1-(dipropylamino)-6-mesityl-4-oxo-4H-quinolizine-3-carbaldehyde (A) (0.050 g, 0.128 mmol) was added dropwise as a solution in tetrahydrofuran (0.5 mL). The reaction was warmed to −30° C. for 0.5 h. The reaction was quenched with water, extracted with ethyl acetate, dried, and concentrated. Flash chromatography (15% ethyl acetate/hexanes) gave the desired alkene (0.022 g, 45% yield) as a red oil.

$^1$H NMR (CDCl$_3$) δ: 0.88 (t, J=7.6 Hz, 6H), 1.37-1.43 (m, 4H), 1.98 (s, 6H), 2.31 (s, 3H), 2.89 (t, J=7.2 Hz, 4H), 5.15 (d, J=11.2 Hz, 1H), 5.72 (d, J=18.0 Hz, 1H), 6.52 (d, J=6.4 Hz, 1H), 6.86 (s, 2H), 6.96-7.04 (m, 1H), 7.13 (t, J=6.8 Hz, 1H), 7.81 (s, 1H), 8.26 (d, J=9.6 Hz, 1H).

MS Calcd.: 388. Found: 389 (M+H).

Example 33

1-(Dipropylamino)-3-ethyl-6-mesityl-4H-quinolizin-4-one

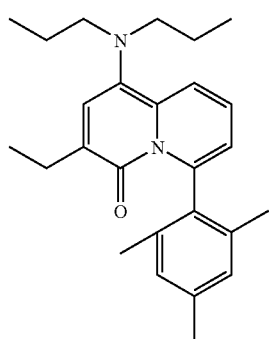

1-(Dipropylamino)-6-mesityl-3-vinyl-4H-quinolizine-4-one (9.4 mg, 0.024 mmol) was dissolved in methanol (1 mL) 10 mg of 10% Pd/C was added. The solution was evacuated and filled with a hydrogen balloon at room temperature. After 1 h, the solution was filtered and concentrated. Flash chromatography (5% ethyl acetate/hexanes) gave 9.4 mg (100% yield) of the title compound.

¹H NMR (CDCl₃) δ: 0.88 (t, J=7.6 Hz, 6H), 1.12 (t, J=7.2 Hz, 3H), 1.35-1.43 (m, 4H), 1.98 (s, 6H), 2.30 (s, 3H), 2.58 (q, J=7.2, 14.8 Hz, 2H), 2.86 (t, J=7.2 Hz, 4H), 6.42 (d, J=6.4 Hz, 1H), 6.84 (s, 2H), 6.99 (t, J=8.8 Hz, 1H), 7.51 (s, 1H), 8.15 (d, J=9.2 Hz, 1H).

MS Calcd.: 390. Found: 391 (M+H).

Example 34

Ethyl 1-((dipropylamino)methyl)-6-mesityl-4-oxo-4H-quinolizine-3-carboxylate

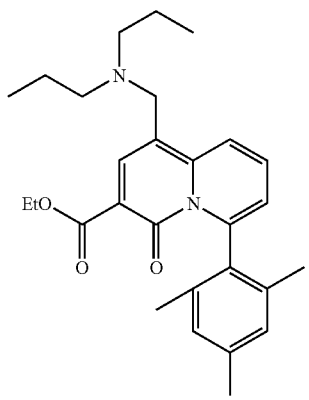

2-Bromo-6-mesitylpyridine 2,6-Dibromopyridine (9.47 g, 40 mmol) was dissolved in 80 mL of 1,2-dimethoxyethane (1,2-dimethoxyethane). Tetrakis(triphenylphosphine)palladium(0) (2.31 g, 2.00 mmol) was added and the mixture was heated at 50° C. for 15 min. The solution was cooled and 2,4,6-trimethylbenzeneboronic acid (6.56 g, 40 mmol) dissolved in 40 mL of 1,2 dimethoxyethane was added. Finally, potassium t-butoxide (8.97 g, 80 mmol) was added as a solution in 40 mL of t-butanol. The reaction was heated for 0.5 h at 90° C. The solution was cooled and filtered through celite. Flash chromatography (2% ethyl acetate/hexanes) gave 7.48 g (68% yield) of the title compound.

¹H NMR (CDCl₃) δ: 2.03 (s, 6H), 2.30 (s, 3H), 6.91 (s, 2H), 7.17 (d, J=7.2 Hz, 1H), 7.44 (d, 1H), 7.59 (t, J=7.2 Hz, 1H).

MS Calcd.: 275. Found: 276 (M+H) 278 (M+3H).

(6-Mesitylpyridin-2-yl)acetonitrile n-Butyllithium (2.5M, 19.1 mL, 47.8 mmol) was added to tetrahydrofuran (135 mL) and the solution was cooled to −78° C. Acetonitrile (2.5 mL, 47.8 mmol) was then added dropwise and the reaction stirred for 45 min. 2-Bromo-6-mesitylpyridine (2.00 g, 7.24 mmol) was added as a solution in 10 mL of tetrahydrofuran. The reaction continued to stir at −78° C. for 0.5 hr and was then warmed to room temperature for 1 h. The reaction was quenched with water and extracted with ethyl acetate, dried, and concentrated. Flash chromatography (20% ethyl acetate/hexanes) gave 0.70 g (41% yield) of the desired product as an orange oil.

¹H NMR (CDCl₃) δ: 2.01 (s, 6H), 2.31 (s, 3H), 3.97 (s, 2H), 6.94 (s, 2H), 7.21 (d, J=7.2 Hz, 1H), 7.42 (d, J=8.0 Hz, 1H), 7.79 (t, J=7.6 Hz, 1H).

MS Calcd.: 236. Found: 237 (M+H).

Ethyl 1-cyano-6-mesityl-4-oxo-4H-quinolizine-3-carboxylate

Diisopropylamine (1.6 mL, 11.6 mmol) in tetrahydrofuran (15 mL) was charged with n-butyllithium (2.5M, 4.6 mL, 11.6 mmol) at 0° C. The reaction stirred for 0.5 h. The solution was cooled to −20° C. and (6-mesitylpyridin-2-yl)acetonitrile (2.49 g, 10.5 mmol) was added drop wise (as a solution in 5 mL tetrahydrofuran). After 0.5 h, the solution was cooled to −78° C. and diethyl ethoxymethylenemalonate (2.1 mL, 10.5 mmol) was added. The reaction stirred for 0.5 h and was then cooled to room temperature. The reaction was quenched with water and extracted with ethyl acetate. The organic layer was dried over magnesium sulfate, filtered and concentrated to give an orange residue. The material was dissolved in acetic acid (20 mL) and heated at 100° C. for 4 h. The solution was cooled and poured into an Erlenmeyer flask and washed with water. The solution was neutralized with saturated sodium bicarbonate. The solution was extracted with ethyl acetate (3 times), dried, and concentrated. Flash chromatography (25% ethyl acetate/hexanes) gave 3.19 g (84% yield) of the title compound as a yellow solid.

¹H NMR (CDCl₃) δ: 1.31 (t, J=7.6 Hz, 3H), 1.94 (s, 6H), 2.31 (s, 3H), 4.30 (q, J=6.8, 14.0 Hz, 2H), 6.88 (s, 2H), 6.96 (dd, J=1.6, 7.2 Hz, 1H), 7.83 (t, J=8.0 Hz, 1H), 8.00 (dd, J=2.0, 8.8 Hz, 1H), 8.51 (a, 1H).

MS Calcd.: 360. Found: 361 (M+H).

Ethyl 1-((dipropylamino)methyl)-6-mesityl-4-oxo-4H-quinolizine-3-carboxylate

Ethyl 1-cyano-6-mesityl-4-oxo-4H-quinolizine-3-carboxylate (0.110 g, 0.30 mmol) was dissolved in 20 mL ethanol and HCl (0.15 mL) and treated with 20% Pd(OH)₂ over charcoal (0.050 g). The solution was evacuated and filled with a hydrogen balloon. After 5 h, the solution was filtered and concentrated to give a yellow solid. The hydrochloride salt was then dissolved in 1,2-dichloroethane (5 mL) and propionaldehyde (0.078 mL, 1.1 mmol) was added followed by sodium triacetoxyborohydride (0.23 g, 1.1 mmol). The reaction was heated to 40° C. overnight. The solution was cooled, quenched with water. Extraction with ethyl acetate was followed by drying the organic layer, concentration, and flash chromatography (ethyl acetate) to give 0.059 g (42% yield) of the title compound.

¹H NMR (CDCl₃) δ: 0.84 (t, J=7.2 Hz, 6H), 1.31 (t, J=7.2 Hz, 3H), 1.47-1.52 (m, 4H), 1.95 (s, 6H), 2.30 (s, 3H), 2.41 (t, J=7.2H, 4H), 3.68 (s, 2H), 4.29 (q, J=7.2, 14.0 Hz, 2H), 6.73 (d, J=6.0 Hz, 1H), 6.85 (s, 2H), 7.47 (t, J=7.2 Hz, 1H), 8.09 (d, J=9.2 Hz, 1H), 8.17 (s, 1H).

Example 35

1-((Dipropylamino)methyl)-3-(hydroxymethyl)-6-mesityl-4H-quinolizin-4-one

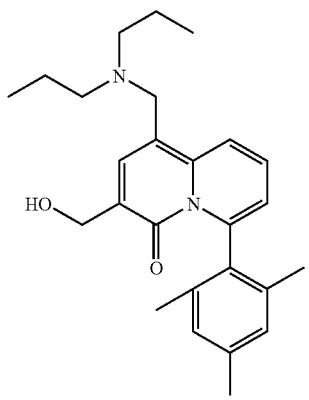

Ethyl 1-((dipropylamino)methyl)-6-mesityl-4-oxo-4H-quinolizine-3-carboxylate (0.228 g, 0.51 mmol) was dissolved in tetrahydrofuran (3.5 mL). The solution was cooled to −40° C. and diisobutylaluminum hydride (DIBAL-H) (1M, 1.5 mL, 1.5 mmol) was added rapidly. The reaction stirred for 1 h and was warmed to room temperature. Methanol and Rochelle's salt were added and the mixture stirred at room temperature for 3 h. The organic layer was separated and the aqueous layer was extracted with dichloromethane. The combined organic layers were dried, concentrated, and flash chromatographed (2% methanol/ethyl acetate) to give 0.096 g (46% yield) of the desired product.

MS Calcd.: 406. Found: 389 (M−OH).

Example 36

1-((Dipropylamino)methyl)-6-mesityl-3-methyl-4H-quinolizin-4-one

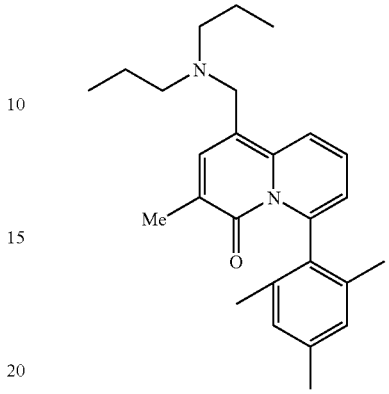

1-((Dipropylamino)methyl)-3-(hydroxymethyl)-6-mesityl-4H-quinolizin-4-one (0.050 g, 0.12 mmol) was dissolved in 2 mL of dichloromethane. The solution was cooled to −20° C. Triethylamine (86 μL, 0.61 mmol) and methanesulfonyl chloride (29 μL, 0.37 mmol) were added. The reaction was allowed to stir for 0.5 h. The solution was quenched with water and warmed to room temperature. The mixture was extracted with ethyl acetate, dried over magnesium sulfate, filtered, and concentrated to give the crude mesylate. The mesylate was redissolved in tetrahydrofuran (3 mL). Lithium aluminum hydride (0.010 g, 0.27 mmol) was added and the reaction stirred at room temperature for 1 h. Glauber's salt was added and the solution was filtered and concentrated. Flash chromatography (ethyl acetate) gave 0.017 g (35% yield) of the title compound as a yellow solid.

$^1$H NMR (CDCl$_3$) δ: 0.829 (t, J=7.2 Hz, 6H), 1.48 (q, J=7.2, 14.8 Hz, 4H), 1.96 (s, 6H), 2.16 (s, 3H), 2.30 (s, 3H), 2.39 (t, J=7.6H, 4H), 3.64 (s, 2H), 6.48 (dd, J=1.6, 6.8 Hz, 1H), 6.85 (s, 2H), 7.09 (dd, J=6.8, 8.8 Hz, 1H), 7.44 (s, 1H), 7.87 (dd, J=1.6, 9.6 Hz, 1H).

MS Calcd.: 390. Found: 391.

Example 37 was prepared by substituting acetaldehyde from propionaldehyde.

| Example | Structure | Name | Physical Data |
|---|---|---|---|
| 37 | 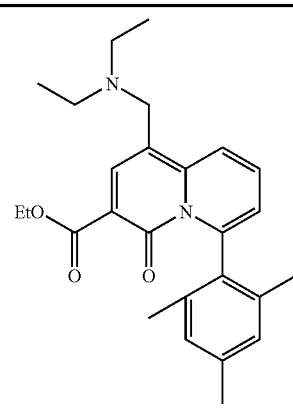 | Ethyl 1-((diethylamino)methyl)-6-mesityl-4-oxo-4H-quinolizine-3-carboxylate | MS Calcd.: 420, Found: 421 (M + H). |

Example 38

Ethyl 1-butyryl-6-mesityl-4-oxo-4H-quinolizine-3-carboxylate

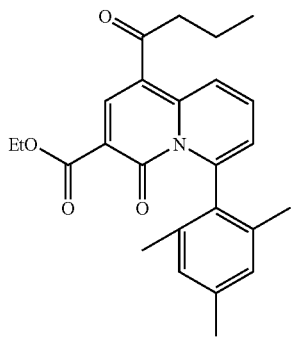

1-(6-Bromopyridin-2-yl)pentan-2-ol

Diisopropyl amine (4.3 mL, 30.5 mmol) in 40 mL of tetrahydrofuran was cooled to 0° C. n-Butyllithium (2.5M, 12.2 mL, 30.5 mmol) was added and the reaction stirred for 0.5 h. The reaction was cooled to −20° C. and 2-bromo-6-methylpyridine was added as a solution in tetrahydrofuran (20 mL). The reaction continued to stir for 0.5 h and was then cooled to −78° C. Freshly distilled butyraldehyde (3.14 mL, 35 mmol) was added dropwise. The reaction was warmed to room temperature. The solution was quenched with saturated sodium bicarbonate. Extraction with ethyl acetate was followed by drying and concentrating. Flash chromatography (25% ethyl acetate/hexanes) gave 2.93 g (41% yield) of the product as an oil.

MS Calcd.: 243. Found: 244 (M+H) 246 (M+3H).

1-(6-Mesitylpyridin-2-yl)pentan-2-ol 1-(6-Bromopyridin-2-yl)pentan-2-ol (3.23 g, 13.2 mmol) was dissolved in 30 mL of 1,2-dimethoxyethane. Tetrakis(triphenylphosphine)palladium(0) (0.76 g, 0.66 mmol) was added and the solution was heated to 50° C. for 15 min. After cooling the solution, 2,4,6-trimethylbenzeneboronic acid (2.60 g, 15.9 mmol) in 15 mL 1,2-dimethoxyethane was added to parent solution. Potassium t-butoxide (2.96 g, 26.5 mmol) in 15 mL t-butanol was added last. The reaction was heated at 90° C. for 0.5 h. After cooling, the solution was filtered and concentrated. Flash chromatography (20% ethyl acetate/hexanes) gave the title compound (2.91 g, 77% yield).

$^1$H NMR (CDCl$_3$) δ: 0.93 (t, J=7.2 Hz, 3H), 1.37-1.58 (m, 4H), 2.01 (s, 6H), 2.31 (s, 3H), 2.85-3.00 (m, 2H), 4.04-4.10 (m, 1H), 5.05 (s, 1H), 6.91 (s, 2H), 7.08 (d, J=7.6 Hz, 2H), 7.67 (t, 1H).

MS Calcd.: 283. Found: 284 (M+H).

1-(6-Mesitylpyridin-2-yl)pentan-2-one 1-(6-Mesitylpyridin-2-yl)pentan-2-ol (2.91 g, 10.3 mmol) in 100 mL of dichloromethane and 20 mL of acetonitrile was combined with 4 angstrom crushed molecular sieves (2.5 g) and N-methylmorpholine-N-oxide (1.80 g, 15.4 mmol). Tetrapropylammonium perruthenate (0.54 g, 1.54 mmol) was added last. The reaction stirred at room temperature for 1 h. The reaction was filtered and concentrated. Flash chromatography (10% ethyl acetate/hexanes) gave 0.87 g (30%) of the title compound as an yellow oil.

MS Calcd.: 281. Found: 282 (M+H).

Diethyl [1-ethoxy-2-(6-mesitylpyridin-2-yl)-3-oxohexyl]malonate

Diisopropyl amine (0.16 mL, 1.13 mmol) was dissolved in tetrahydrofuran (2 mL). n-Butyllithium (2.5M, 0.45 mL, 1.13 mmol) was added at 0° C. and the reaction stirred for 0.5 h. The solution was cooled to −78° C. and 1-(6-mesityl-pyridin-2-yl)-pentan-2-one (0.29 g, 1.0 mmol) was added. After 0.5 h, ethyl ethoxymethylene malonate (0.21 mL, 1.0 mmol) was added and the reaction was warmed to room temperature. The solution was quenched with water, extracted with ethyl acetate, dried, and concentrated. Flash chromatography (10%-20% ethyl acetate/hexanes) gave the title compound as a mixture of two isomers.

MS Calcd.: 497. Found: 498 (M+H). Two peaks observed.

Ethyl 1-butyryl-6-mesityl-4-oxo-4H-quinolizine-3-carboxylate

Diethyl [1-ethoxy-2-(6-mesitylpyridin-2-yl)-3-oxohexyl]malonate (0.045 g, 0.10 mmol) was dissolved in acetic acid (3 mL). The reaction was heated at 100° C. for 20 minutes. Acetic acid was stripped off via rotavap. Saturated sodium bicarbonate was added and the solution was extracted with ethyl acetate. The organics were dried, concentrated, and flash chromatographed (20% ethyl acetate/hexanes) to give 0.015 g (37% yield) of the title compound.

$^1$H NMR (CDCl$_3$) δ: 0.88 (t, J=7.6 Hz, 3H), 1.36 (t, J=7.2 Hz, 3H), 1.70-1.76 (m, 2H), 2.04 (s, 6H), 2.33 (s, 3H), 2.76 (t, J=7.6 Hz, 2H), 4.36 (q, J=7.2, 14.4 Hz, 2H), 6.95 (s, 2H), 7.23-7.33 (m, 2H), 7.85 (t, J=8.0 Hz, 1H), 8.43 (s, 1H).

MS Calcd.: 405. Found: 406 (M+H).

Example 39

Ethyl 1-butyryl-6-mesityl-4-oxo-3,4-dihydro-2H-quinolizine-3-carboxylate

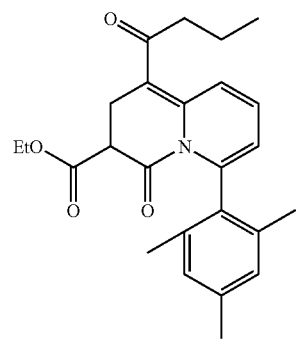

Ethyl 1-butyryl-6-mesityl-4-oxo-4H-quinolizine-3-carboxylate (0.034 g, 0.084 mmol) was dissolved in tetrahydrofuran (1 mL). Lithium aluminum hydride (0.007 g, 0.17 mmol) was added at 0° C. After 15 minutes, the reaction was quenched with Glauber's salt. The solution was filtered, concentrated, and flash chromatographed (15% ethyl acetate/hexanes) to give the title compound (0.014 g, 41% yield).

$^1$H NMR (CDCl$_3$) δ: 0.84 (t, J=7.6 Hz, 3H), 1.28 (t, J=7.2 Hz, 3H), 1.54-1.61 (m, 2H), 2.02 (s, 6H), 2.32 (s, 3H), 2.32-

2.48 (m, 2H), 3.04-3.20 (m, 2H), 3.70 (dd, J=6.8, 9.2 Hz, 1H), 4.25 (q, J=7.6, 14.4 Hz, 2H), 6.93 (s, 2H), 7.12 (d, J=7.6 Hz, 1H), 7.20 (d, H=7.6 Hz, 1H), 7.74 (t, J=8.0 Hz, 1H).
MS Calcd.: 407. Found: 408 (M+H).

Example 40

Ethyl 6-mesityl-4-oxo-1-propoxy-4H-quinolizine-3-carboxylate

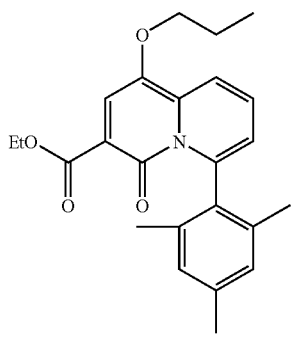

(6-Bromopyridin-2-yl)-methanol n-BuLi (2.5M, 20.0 mL, 50.0 mmol) in tetrahydrofuran (40 mL) was cooled to −78° C. 2,6-Dibromopyridine (11.85 g, 50.0 mmol) in 70 mL tetrahydrofuran was added dropwise while keeping the internal temperature of the reaction below −70° C. The resulting dark green solution stirred for 15 min at this temperature upon which N,N-dimethylformamide (6.0 mL, 78 mmol) was added over a period of 30 seconds. The reaction stirred at −78° C. for 15 min and methanol (50 mL) and acetic acid (3.2 mL) were added. Sodium borohydride (1.89 g, 50.0 mmol) was added last. The reaction was allowed to warm to room temperature. The solution was carefully quenched with sat. ammonium chloride and then extracted with ethyl acetate (2 times). The organic layers were combined and washed with brine, dried over sodium sulfate, filtered, and concentrated. Flash chromatography (25% ethyl acetate/hexanes) gave 2.57 g (27% yield) of the alcohol as a pale yellow oil.
$^1$H NMR (CDCl$_3$) δ: 3.02 (t, J=5.2 Hz, 1H), 4.75 (d, J=6.0 Hz, 2H), 7.28 (d, J=7.6 Hz, 1H), 7.40 (d, J=8.0 Hz, 1H), 7.56 (t, J=8.0 Hz, 1H).
MS Calcd.: 187. Found: 188 (M+H) 190 (M+3H).

(6-Mesitylpyridin-2-yl)methanol (6-Bromopyridin-2-yl)-methanol (4.23 g, 22.5 mmol) was dissolved in 1,2-dimethoxyethane. Tetrakis(triphenylphosphine)palladium(0) (1.30 g, 1.12 mmol) was added and the reaction stirred for 15 minutes at 50° C. Upon cooling, 2,4,6-trimethylbenzeneboronic acid (3.69 g, 22.5 mmol) in 20 mL 1,2-dimethoxyethane was added to the reaction followed by potassium t-butoxide (5.05 g, 50.0 mmol) in 20 mL of t-butanol. The reaction was heated at 90° C. for 0.5 hr. The solution was cooled and filtered through paper. Flash chromatography (30% ethyl acetate/hexanes) gave the desired product as a white solid (3.50 g, 68% yield).
$^1$H NMR (CDCl$_3$) δ: 2.02 (s, 6H), 2.34 (s, 3H), 3.92 (s, 1H), 4.79 (d, J=4.8 Hz, 2H), 6.96 (s, 2H), 7.15 (dd, J=7.6, 14.8 Hz, 2H), 7.74 (t, J=8.0 Hz, 1H)
MS Calcd.: 227. Found: 228 (M+H).

6-Mesityl-2-propoxymethylpyridine (6-Mesitylpyridin-2-yl)methanol (1.03 g, 4.54 mmol) was dissolved in N,N-dimethylformamide (5 mL) and the solution was charged with sodium hydride (60% dispersion in mineral oil, 0.23 g, 5.7 mmol). The reaction stirred for 0.5 h at room temperature. Bromopropane (0.52 mL, 5.7 mmol) was added last. The reaction ran for 2.5 h. The solution was quenched with water, extracted with ether, dried, and concentrated. Flash chromatography (15% ethyl acetate/hexanes) gave 0.65 g (53% yield) of the desired product.
MS Calcd.: 269. Found: 270 (M+H).

Diethyl [2-(6-mesitylpyridin-2-yl)-2-propoxyethylidene]-malonate

6-Mesityl-2-propoxymethylpyridine (0.65 g, 2.41 mmol) in tetrahydrofuran (15 mL) was cooled to −78° C. n-Butyllithium (2.5M, 1.0 mL, 2.65 mmol) was added in dropwise fashion. The solution continued to stir at −78° C. for 0.5 h. Diethyl ethoxymethylene malonate (0.50 mL, 2.5 mmol) was added and the reaction was warmed to room temperature. The reaction was quenched with water, extracted with ether, dried, and concentrated. Flash chromatography (10% ethyl acetate/hexanes) gave 0.36 g (34% yield) of the product as a red-orange oil.
MS Calcd.: 439. Found: 440 (M+H).

Ethyl 6-mesityl-4-oxo-1-propoxy-4H-quinolizine-3-carboxylate

Diethyl 2[2-propoxy-2-(6-mesitylpyridin-2-yl)-ethylidene]-malonate (0.189 g, 0.43 mmol) was dissolved in 4 mL of Dowtherm A (phenyl ether: biphenyl 2:1 ratio). The solution was placed in a pre-heated oil bath set at 220° C. The reaction stirred at this temperature for 15 minutes. The solution was cooled and flash chromatographed (20-50% ethyl acetate/hexanes) to give 0.012 g (7% yield) of the title compound.
MS Calcd.: 393. Found: 394 (M+H).

Example 41

2-(Dipropylamino)-5-mesityl-3,7-dimethyl-3,7-dihydro-4H-pyrrolo[2,3-d]pyrimidin-4-one

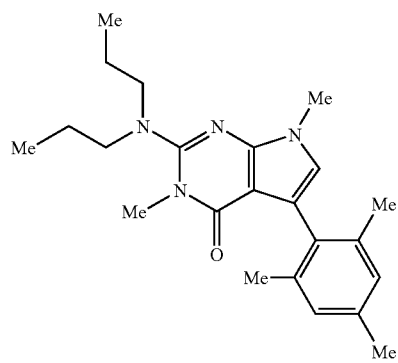

2-Amino-5-mesityl-7-methyl-3,7-dihydro-4H-pyrrolo[2,3-d]pyrimidin-4-one

A solution of dimethylsulfoxide (468 mg, 6.00 mmol) and acetonitrile (8 ml) was added to a mixture of mesitylacetoaldehyde (904 mg, 5.57 mmol), bromotrimethylsilane (919 mg, 6.00 mmol) and acetonitrile (8 ml) at 0° C. After stirring at room temperature for 0.5 hour, the mixture was diluted with water (70 ml) and extracted with ethyl acetate (100 ml×2). The extracts were combined, washed with brine, dried over sodium sulfate and concentrated in vacuo. A mixture of the residue, 2-amino-6-(methylamino)pyrimidin-4-ol (1.69 g, 6.00 mmol), potassium carbonate (50 mg) and dimethylsulfoxide (3 ml) was heated at 100° C. for 1 hour. After cooling, the mixture was diluted with water (100 ml) and extracted with ethyl acetate (100 ml×2). The extracts were combined, washed with saturated aqueous sodium hydrogen carbonate and brine, dried over sodium sulfate and concentrated in vacuo. The residue was purified by silica gel chromatography eluting with hexane/ethyl acetate (1:1) to give 1.07 g (68%) of the title compound.
mp 184-186° C.
$^1$H NMR (CDCl$_3$) δ: 2.07 (6H, s), 2.38 (3H, s), 3.60 (3H, s), 4.74 (2H, s, br), 6.21 (1H, s), 6.92 (2H, s), 10.50 (1H, s).

2-Amino-5-mesityl-3,7-dimethyl-3,7-dihydro-4H-pyrrolo[2,3-d]pyrimidin-4-one

To a solution of 2-amino-5-mesityl-7-methyl-3,7-dihydro-4H-pyrrolo[2,3-d]pyrimidin-4-one (847 mg, 3.00 mmol) and N,N-dimethylformamide (30 ml) was added sodium hydride (60% in oil, 120 mg, 3.00 mmol) at 0° C. and stirred for 0.5 hour. After stirring at room temperature for 0.5 hour, to the mixture was added a solution of MeI (426 mg, 3.0 mmol) and N,N-dimethylformamide (5 ml) at 0° C. and stirred for 0.5 hour. After stirring at room temperature for 1 hour, the mixture was diluted with water (20 ml) and extracted with ethyl acetate (50 ml×3). The extracts were combined, washed with brine, dried over sodium sulfate and concentrated in vacuo. The residue was purified by silica gel chromatography eluting with hexane/ethyl acetate (3:1) to give 553 mg (62%) of the title compound.
mp 229-231° C.
$^1$H NMR (CDCl$_3$) δ: 2.09 (6H, s), 2.29 (3H, s), 3.41 (3H, s), 3.65 (3H, s), 4.67 (2H, brs), 6.32 (1H, s), 6.90 (2H, s).

2-(Dipropylamino)-5-mesityl-3,7-dimethyl-3,7-dihydro-4H-pyrrolo[2,3-d]pyrimidin-4-one To a solution of 2-amino-5-mesityl-3,7-dimethyl-3,7-dihydro-4H-pyrrolo[2,3-d]pyrimidin-4-one (81 mg, 0.27 mmol) and N,N-dimethylformamide (3 ml) was added sodium hydride (60% in oil, 24 mg, 0.60 mmol) at 0° C. and stirred for 0.5 hour. After stirring at room temperature for 0.5 hour, to the mixture was added a solution of n-PrI (102 mg, 0.60 mmol) and N,N-dimethylformamide (1 ml) at 0° C. and stirred for 0.5 hour. After stirring at room temperature for 1 hour, the mixture was diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (4:1) to give 91 mg (87%) of the title compound.
mp 100-102° C.
$^1$H NMR (CDCl$_3$) δ: 0.90 (6H, t, J=7.5 Hz), 1.61 (4H, m), 2.11 (6H, s), 2.29 (3H, s), 3.11 (4H, t, J=7.5 Hz), 3.47 (3H, s), 3.70 (3H, s), 6.43 (1H, s), 6.90 (2H, s).

Example 42

2-(Dimethylamino)-5-mesityl-3,7-dimethyl-3,7-dihydro-4H-pyrrolo[2,3-d]pyrimidin-4-one

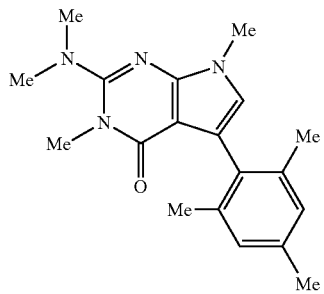

To a solution of 2-amino-5-mesityl-7-methyl-3,7-dihydro-4H-pyrrolo[2,3-d]pyrimidin-4-one (115 mg, 0.41 mmol) and N,N-dimethylformamide (3 ml) was added sodium hydride (60% in oil, 52 mg, 1.30 mmol) at 0° C. and stirred for 0.5 hour. After stirring at room temperature for 0.5 hour, to the mixture was added a solution of MeI (213 mg, 1.50 mmol) and N,N-dimethylformamide (1 ml) at 0° C. and stirred for 0.5 hour. After stirring at room temperature for 1 hour, the mixture was diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (4:1) to give 110 mg (83%) of the title compound.
mp 127-128° C.
$^1$H NMR (CDCl$_3$) δ: 2.10 (6H, s), 2.29 (3H, s), 2.85 (6H, s), 3.47 (3H, s), 3.72 (3H, s), 6.42 (1H, s), 6.90 (2H, s).

Example 43

2-(Dibutylamino)-5-mesityl-3,7-dimethyl-3,7-dihydro-4H-pyrrolo[2,3-d]pyrimidin-4-one

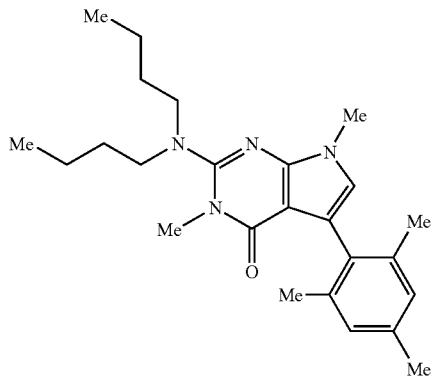

To a solution of 2-amino-5-mesityl-3,7-dimethyl-3,7-dihydro-4H-pyrrolo[2,3-d]pyrimidin-4-one (100 mg, 0.34 mmol) and N,N-dimethylformamide (2 ml) was added sodium hydride (60% in oil, 27 mg, 0.66 mmol) at 0° C. and stirred for 0.5 hour. After stirring at room temperature for 0.5 hour, to the mixture was added a solution of n-BuI (184 mg, 1.00 mmol) and N,N-dimethylformamide (1 ml) at 0° C. and stirred for 0.5 hour. After stirring at room temperature for 1 hour, the mixture was diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (4:1) to give 85 mg (62%) of the title compound as an oil.

$^1$H NMR (CDCl$_3$) δ: 0.93 (6H, t, J=7.5 Hz), 1.31 (8H, m), 2.11 (6H, s), 2.29 (3H, s), 3.12 (4H, t, J=7.5 Hz), 3.45 (3H, s), 3.70 (3H, s), 6.42 (1H, s), 6.89 (2H, s).

Example 44

5-Mesityl-2-[(2-methoxyethyl)amino]-3,7-dimethyl-3,7-dihydro-4H-pyrrolo[2,3-d]pyrimidin-4-one

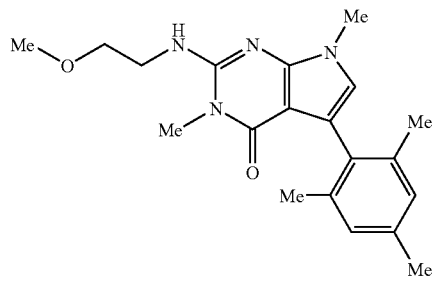

To a solution of 2-amino-5-mesityl-3,7-dimethyl-3,7-dihydro-4H-pyrrolo[2,3-d]pyrimidin-4-one (55 mg, 0.18 mmol) and N,N-dimethylformamide (2 ml) was added sodium hydride (60% in oil, 24 mg, 0.60 mmol) at 0° C. and stirred for 0.5 hour. After stirring at room temperature for 0.5 hour, to the mixture was added a solution of 2-methoxyethylbromide (232 mg, 0.60 mmol) and N,N-dimethylformamide (1 ml) at 0° C. and stirred for 0.5 hour. After stirring at room temperature for 2 hours and heating under reflux for 2 hours, the mixture was diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (9:1) to give 15 mg (23%) of the title compound as an oil.

$^1$H NMR (CDCl$_3$) δ: 2.10 (6H, s), 2.28 (3H, s), 3.36 (3H, s), 3.42 (3H, s), 3.65 (7H, m), 4.86 (1H, br), 6.31 (1H, s), 6.89 (2H, s).

Example 45

2-(Dipropylamino)-3-ethyl-5-mesityl-7-methyl-3,7-dihydro-4H-pyrrolo[2,3-d]pyrimidin-4-one

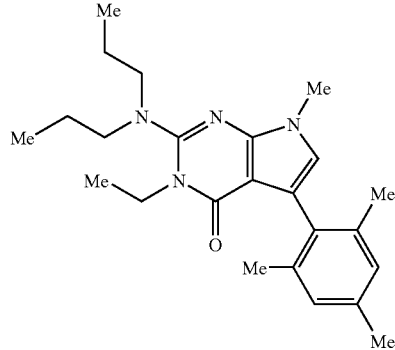

2-Amino-3-ethyl-5-mesityl-7-methyl-3,7-dihydro-4H-pyrrolo[2,3-d]pyrimidin-4-one

To a solution of 2-amino-5-mesityl-7-methyl-3,7-dihydro-4H-pyrrolo[2,3-d]pyrimidin-4-one (88 mg, 0.31 mmol) and N,N-dimethylformamide (3 ml) was added sodium hydride (60% in oil, 16 mg, 0.40 mmol) at 0° C. and stirred for 0.5 hour. After stirring at room temperature for 0.5 hour, to the mixture was added a solution of ethyl iodide (62 mg, 0.40 mmol) and N,N-dimethylformamide (1 ml) at 0° C. and stirred for 0.5 hour. After stirring at room temperature for 3 hours, the mixture was diluted with water (20 ml) and extracted with ethyl acetate (50 ml×3). The extracts were combined, washed with brine, dried over sodium sulfate and concentrated in vacuo. The residue was purified by silica gel chromatography eluting with hexane/ethyl acetate (3:1) to give 53 mg (55%) of the title compound.

$^1$H NMR (CDCl$_3$) δ: 1.11 (3H, t, J=7.2 Hz), 2.07 (6H, s), 2.32 (3H, s), 3.70 (3H, s), 4.27 (2H, q, J=7.2 Hz), 4.68 (2H, br), 6.42 (1H, s), 6.90 (2H, s).

2-(Dipropylamino)-3-ethyl-5-mesityl-7-methyl-3,7-dihydro-4H-pyrrolo[2,3-d]pyrimidin-4-one To a solution of 2-amino-3-ethyl-5-mesityl-7-methyl-3,7-dihydro-4H-pyrrolo[2,3-d]pyrimidin-4-one (80 mg, 0.26 mmol) and N,N-dimethylformamide (3 ml) was added sodium hydride (60% in oil, 40 mg, 1.0 mmol) at 0° C. and stirred for 0.5 hour. After stirring at room temperature for 0.5 hour, to the mixture was added a solution of n-PrI (170 mg, 1.0 mmol) and N,N-dimethylformamide (2 ml) at 0° C. and stirred for 0.5 hour. After stirring at 90° C. for 3 hours, the mixture was cooled and diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (20:1) to give 49 mg (54%) of the title compound.

$^1$H NMR (CDCl$_3$) δ: 1.00 (6H, t, J=7.5 Hz), 1.14 (3H, t, J=7.5 Hz), 1.68 (4H, sext, J=7.5 Hz), 2.00 (6H, s), 2.31 (3H, s), 3.55 (4H, t, J=7.5 Hz), 3.67 (3H, s), 4.28 (2H, q, J=7.5 Hz), 6.34 (1H, s), 6.89 (2H, s).

Example 46

3-Ethyl-5-mesityl-7-methyl-2-(propylamino)-3,7-dihydro-4H-pyrrolo[2,3-d]pyrimidin-4-one

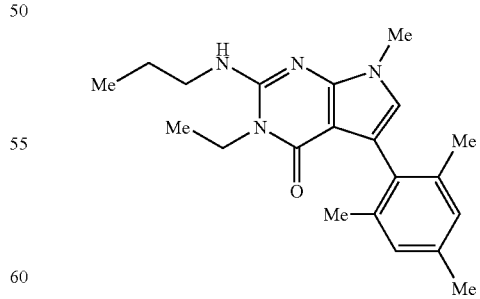

To a solution of 2-amino-3-ethyl-5-mesityl-7-methyl-3,7-dihydro-4H-pyrrolo[2,3-d]pyrimidin-4-one (80 mg, 0.26 mmol) and N,N-dimethylformamide (3 ml) was added sodium hydride (60% in oil, 40 mg, 1.0 mmol) at 0° C. and stirred for 0.5 hour. After stirring at room temperature for 0.5 hour, to the mixture was added a solution of n-PrI (170 mg, 1.0 mmol) and N,N-dimethylformamide (2 ml) at 0° C. and stirred for 0.5 hour. After stirring at 50° C. for 3 hours, the mixture was cooled and diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (20:1) to give 25 mg (25%) of the title compound.

$^1$H NMR (CDCl$_3$) δ: 0.94 (3H, t, J=7.5 Hz), 1.14 (3H, t, J=7.5 Hz), 1.65 (2H, m), 2.07 (6H, s), 2.31 (3H, s), 3.42 (2H, q, J=7.5 Hz), 3.69 (3H, s), 4.28 (2H, q, J=7.5 Hz), 4.76 (1H, br), 6.34 (1H, s), 6.89 (2H, s).

Example 47

2-(Dipropylamino)-3-isopropyl-5-mesityl-7-methyl-3,7-dihydro-4H-pyrrolo[2,3-d]pyrimidin-4-one

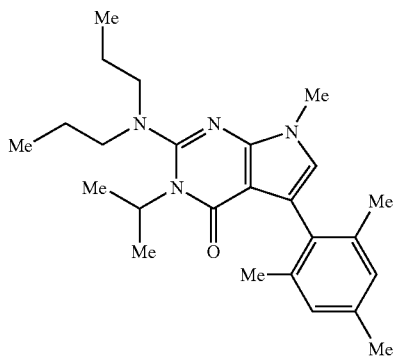

2-Amino-3-isopropyl-5-mesityl-7-methyl-3,7-dihydro-4H-pyrrolo[2,3-d]pyrimidin-4-one To a solution of 2-amino-5-mesityl-7-methyl-3,7-dihydro-4H-pyrrolo[2,3-d]pyrimidin-4-one (156 mg, 0.55 mmol) and N,N-dimethylformamide (5 ml) was added sodium hydride (60% in oil, 24 mg, 0.60 mmol) at 0° C. and stirred for 0.5 hour. After stirring at room temperature for 0.5 hour, to the mixture was added a solution of 2-iodopropane (102 mg, 0.60 mmol) and N,N-dimethylformamide (2 ml) at 0° C. and stirred for 0.5 hour. After stirring at room temperature for 3 hours, the mixture was diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (3:1) to give 88 mg (49%) of the title compound.

$^1$H NMR (CDCl$_3$) δ: 1.07 (6H, d, J=6.3 Hz), 2.05 (6H, s), 2.31 (3H, s), 3.69 (3H, s), 4.67 (2H, s), 5.24 (1H, sept, J=6.3 Hz), 6.40 (1H, s), 6.88 (2H, s).

2-(Dipropylamino)-3-isopropyl-5-mesityl-7-methyl-3,7-dihydro-4H-pyrrolo[2,3-d]pyrimidin-4-one To a solution of 2-amino-3-isopropyl-5-mesityl-7-methyl-3,7-dihydro-4H-pyrrolo[2,3-d]pyrimidin-4-one (100 mg, 0.31 mmol) and N,N-dimethylformamide (3 ml) was added sodium hydride (60% in oil, 40 mg, 1.0 mmol) at 0° C. and stirred for 0.5 hour. After stirring at room temperature for 0.5 hour, to the mixture was added a solution of n-PrI (170 mg, 1.0 mmol) and N,N-dimethylformamide (2 ml) at 0° C. and stirred for 0.5 hour. After stirring at 90° C. for 3 hours, the mixture was cooled and diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (20:1) to give 51 mg (41%) of the title compound.

$^1$H NMR (CDCl$_3$) δ: 0.94 (6H, t, J=7.5 Hz), 1.11 (6H, d, J=6.3 Hz), 1.69 (4H, sext, J=7.5 Hz), 2.07 (6H, s), 2.31 (3H, s), 3.54 (4H, t, J=7.5 Hz), 3.67 (3H, s), 5.21 (2H, sept, J=6.3 Hz), 6.32 (1H, s), 6.87 (2H, s).

Example 48

3-Isopropyl-5-mesityl-7-methyl-2-(propylamino)-3,7-dihydro-4H-pyrrolo[2,3-d]pyrimidin-4-one

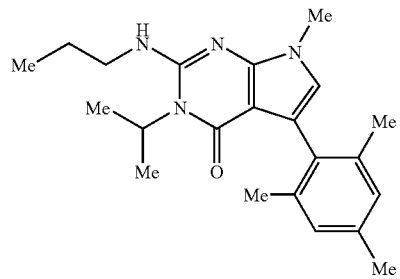

To a solution of 2-amino-3-isopropyl-5-mesityl-7-methyl-3,7-dihydro-4H-pyrrolo[2,3-d]pyrimidin-4-one (100 mg, 0.31 mmol) and N,N-dimethylformamide (3 ml) was added sodium hydride (60% in oil, 40 mg, 1.0 mmol) at 0° C. and stirred for 0.5 hour. After stirring at room temperature for 0.5 hour, to the mixture was added a solution of n-PrI (170 mg, 1.0 mmol) and N,N-dimethylformamide (2 ml) at 0° C. and stirred for 0.5 hour. After stirring at 50° C. for 3 hours, the mixture was cooled and diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (20:1) to give 68 mg (60%) of the title compound.

$^1$H NMR (CDCl$_3$) δ: 1.00 (3H, t, J=7.5 Hz), 1.08 (6H, d, J=6.3 Hz), 1.65 (2H, sext, J=7.5 Hz), 2.05 (6H, s), 2.31 (3H, s), 3.41 (4H, q, J=7.5 Hz), 3.68 (3H, s), 4.75 (1H, t, J=7.5 Hz), 5.24 (2H, sept, J=6.3 Hz), 6.45 (1H, s), 6.87 (2H, s).

Example 49

5-Mesityl-3,7-dimethyl-2-piperidin-1-yl-3,7-dihydro-4H-pyrrolo[2,3-d]pyrimidin-4-one

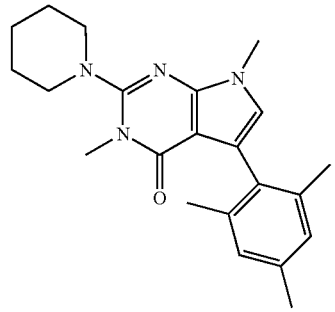

117

To a solution of 2-amino-5-mesityl-3,7-dimethyl-3,7-dihydro-4H-pyrrolo[2,3-d]pyrimidin-4-one (0.063 g, 0.212 mmol) in N,N-dimethylformamide (1 mL) was added 1,5-dibromopentane (0.029 mL, 0.212 mmol) and sodium hydride (66% in oil, 0.015 g, 0.426 mmol) at 0° C., and the mixture was allowed to stir at room temperature for 1 hour. The reaction mixture was diluted with ice-cold water and extracted with ethyl acetate. The organic layer was washed with water and brine, dried over sodium sulfate and concentrated in vacuo. The residue was purified by silica gel column chromatography eluting with hexane/ethyl acetate (10:1-3:1). The oil obtained was crystallized from diisopropyl ether-hexane to give 0.052 g (67%) of the title compound.

mp 210-212° C.

$^1$H NMR (CDCl$_3$) δ: 1.64-1.73 (m, 6H), 2.10 (s, 6H), 2.29 (s, 3H), 3.10-3.14 (m, 4H), 3.48 (s, 3H), 3.73 (s, 3H), 6.44 (s, 1H), 6.91 (s, 2H).

Example 50

2-(Dipropionylamino)-5-mesityl-3,7-dimethyl-3,7-dihydro-4H-pyrrolo[2,3-c]pyrimidin-4-one

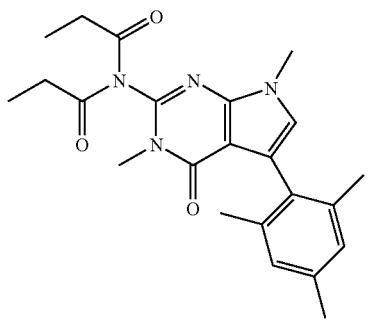

To a solution of 2-amino-5-mesityl-3,7-dimethyl-3,7-dihydro-4H-pyrrolo[2,3-d]pyrimidin-4-one (0.075 g, 0.252 mmol) in N,N-dimethylacetamide (1.5 mL) was added propionyl chloride (0.048 mL, 0.548 mmol), and the mixture was allowed to stir at 60° C. for 17 hour. After cooling, the reaction mixture was diluted with saturated aqueous sodium hydrogen carbonate and extracted with ethyl acetate. The organic layer was washed with water and brine, dried over sodium sulfate and concentrated in vacuo. The residual crystals were recrystallized from ethanol-diethyl ether to give 0.040 g (39%) of the title compound.

mp 215-217° C.

$^1$H NMR (CDCl$_3$) δ: 1.19 (t, J=7.29 Hz, 6H), 2.09 (s, 6H), 2.31 (s, 3H), 2.54 (dq, J=18.05, 7.32 Hz, 2H), 2.83 (dq, J=18.05, 7.32 Hz, 2H), 3.36 (s, 3H), 3.79 (s, 3H), 6.66 (s, 1H), 6.93 (s, 2H).

118

Example 51

2-[(1-Ethylpropyl)amino]-5-mesityl-3,7-dimethyl-3,7-dihydro-4H-pyrrolo[2,3-d]pyrimidin-4-one

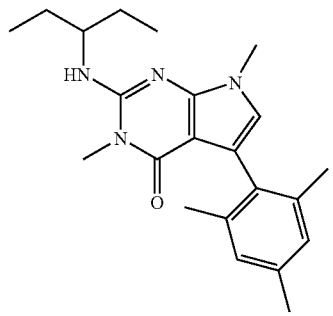

To a solution of 2-amino-5-mesityl-3,7-dimethyl-3,7-dihydro-4H-pyrrolo[2,3-d]pyrimidin-4-one (0.062 g, 0.209 mmol) in N,N-dimethylformamide (0.5 mL) was added sodium hydride (66% in oil, 0.016 g, 0.439 mmol), and the mixture was allowed to stir at room temperature for 25 minutes. 3-Bromopentane (0.055 mL, 0.439 mmol) twice at room temperature and sodium hydride (66% in oil, 0.016 g, 0.439 mmol) at 0° C. was added during the reaction, stirring at room temperature for 15 hours and at 60° C. for 52 hours. After cooling, the reaction mixture was diluted with ice-cold water and extracted with ethyl acetate. The organic layer was washed with water and brine, dried over sodium sulfate and concentrated in vacuo. The residue was purified by silica gel column chromatography eluting with hexane/ethyl acetate (4:1-2:1). The desired fractions were concentrated in vacuo. The residual crystals were washed with diisopropyl ether-hexane to give 0.019 g (25%) of the title compound.

mp 174-176° C.

$^1$H NMR (CDCl$_3$) δ: 0.98 (t, J=7.5 Hz, 6H), 1.50-1.77 (m, 4H), 2.11 (s, 6H), 2.28 (s, 3H), 3.37 (s, 3H), 3.65 (s, 3H), 4.03-4.14 (m, 2H), 6.30 (s, 1H), 6.90 (s, 2H).

Example 52

2-(Diallylamino)-5-mesityl-3,7-dimethyl-3,7-dihydro-4H-pyrrolo[2,3-d]pyrimidin-4-one trifluoroacetate

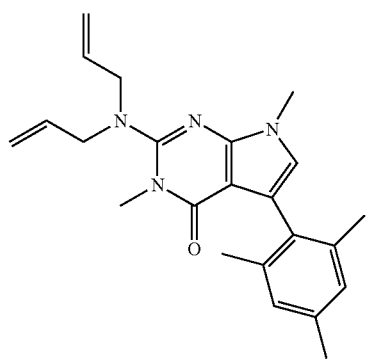

To a solution of 2-amino-5-mesityl-3,7-dimethyl-3,7-dihydro-4H-pyrrolo[2,3-d]pyrimidin-4-one (0.040 g, 0.109 mmol) in N,N-dimethylformamide (0.5 mL) was added allyl bromide (0.035 mL, 0.327 mmol) and sodium hydride (66% in oil, 0.012 g, 0.327 mmol), and the mixture was allowed to stir at 60° C. for 20 hour. The reaction mixture was diluted with dichloromethane, and the organic layer was washed with water and brine, separated with a filter tube (made by Wattmann) and concentrated in vacuo. The residue was dissolved in dimethylsulfoxide (1 mL) and purified by HPLC to give 0.018 mg (43%) of the title compound.

LC-MS analysis: purity 99% (retention time: 2.42 min)

MS (ESI+): 491 (M+H).

Abbreviations mean as described below.

LC-MS: liquid chromatography—mass chromatography

ESI: electron spray ionization

LC-MS analysis was carried out under a condition described below.

Equipment: Waters LC-MS system

A part of HPLC: Agilent HP1100

A part of MS: Micromass ZMD

Column: Shiseidou CAPCELL PAK C18UG120, S-3 µM, 1.5×35 mm

Solvent: A; 0.05% aqueous trifluoroacetic acid, B; 0.04% trifluoroacetic acid in acetonitrile Gradient cycle: 0.00 min (A/B=90/10), 2.00 min (A/B=5/95), 2.75 min (A/B=5/95), 2.76 min (A/B=90/10), 3.60 min (A/B=90/10)

Injection volume: 2 µL

Flow rate: 0.5 mL/min

Detection: UV 220 nm

MS condition (ionization method): ESI

Preparative HPLC was carried out under a condition described below.

Equipment: Gilson high through put purification system

Column: YMC CombiPrep ODS-A S-5 µm, 50×20 mm

Solvent: A; 0.1% aqueous trifluoroacetic acid, B; 0.1% trifluoroacetic acid in acetonitrile Gradient cycle: 0.00 min (A/B=95/5), 1.00 min (A/B=95/5), 5.20 min (A/B=5/95), 6.40 min (A/B=5/95), 6.50 min (A/B=95/5), 6.60 min (A/B=95/5)

Flow rate: 20 mL/min

Detection: UV 220 nm

Examples 53-90

Examples 53-90 in Table 1 were prepared with 30 types of commercially available alkyl halides illustrated below in the same procedure described in Example 52.

Alkyl Halide

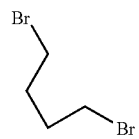
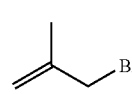
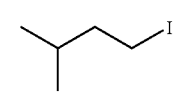

-continued

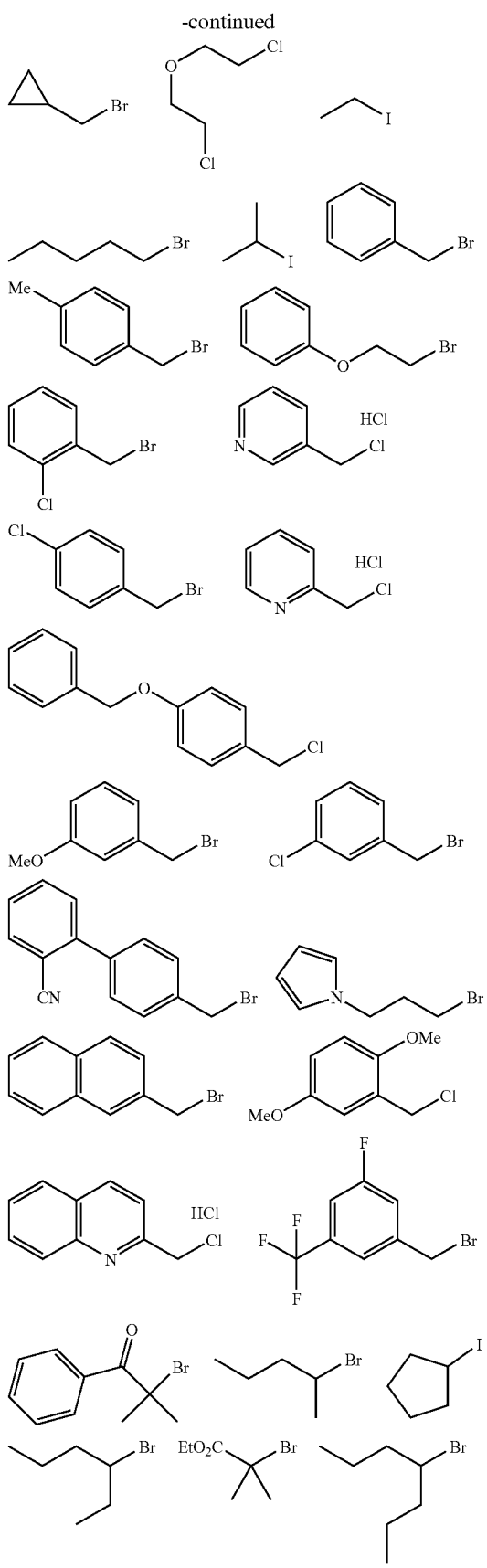

TABLE 1

| Example | Structure | additive | Name | MS (ESI+; M + H) |
|---|---|---|---|---|
| 53 | 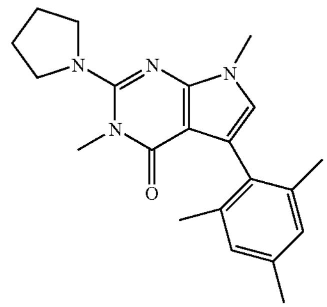 | CF$_3$COOH | 5-mesityl-3,7-dimethyl-2-pyrrolidin-1-yl-3,7-dihydro-4H-pyrrolo[2,3-d]pyrimidin-4-one | 351 |
| 54 | 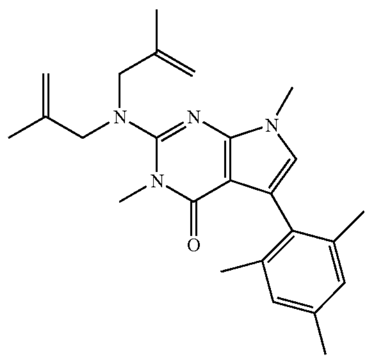 | CF$_3$COOH | 2-[bis (2-methylprop-2-enyl)amino]-5-mesityl-3,7-dimethyl-3,7-dihydro-4H-pyrrolo[2,3-d]pyrimidin-4-one | 405 |
| 55 | 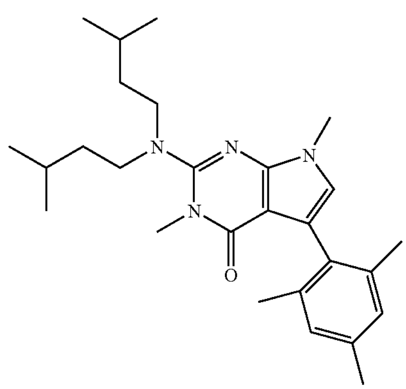 | CF$_3$COOH | 2-[bis(3-methylbutyl)amino]-5-mesityl-3,7-dimethyl-3,7-dihydro-4H-pyrrolo[2,3-d]pyrimidin-4-one | 437 |
| 56 | 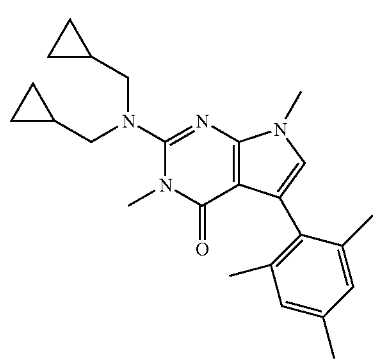 | CF$_3$COOH | 2-[bis(cyclopropylmethyl)amino]-5-mesityl-3,7-dimethyl-3,7-dihydro-4H-pyrrolo[2,3-d]pyrimidin-4-one | 405 |

TABLE 1-continued

| Example | Structure | additive | Name | MS (ESI+; M + H) |
|---|---|---|---|---|
| 57 | 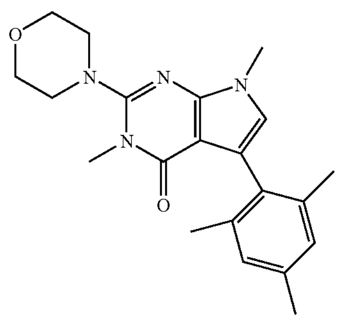 | CF₃COOH | 5-mesityl-3,7-dimethyl-2-morpholin-4-yl-3,7-dihydro-4H-pyrrolo[2,3-d]pyrimidin-4-one | 367 |
| 58 | 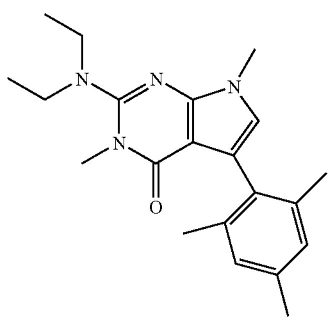 | CF₃COOH | 2-(diethylamino)-5-mesityl-3,7-dimethyl-3,7-dihydro-4H-pyrrolo[2,3-d]pyrimidin-4-one | 353 |
| 59 | 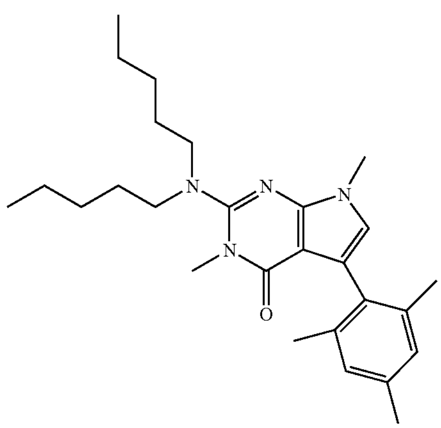 | CF₃COOH | 2-(dipentylamino)-5-mesityl-3,7-dimethyl-3,7-dihydro-4H-pyrrolo[2,3-d]pyrimidin-4-one | 437 |
| 60 | 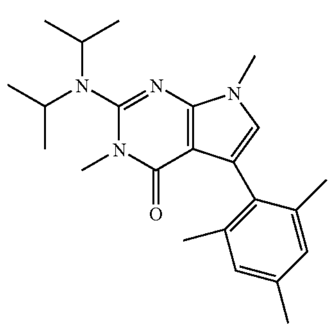 | CF₃COOH | 2-(diisopropylamino)-5-mesityl-3,7-dimethyl-3,7-dihydro-4H-pyrrolo[2,3-d]pyrimidin-4-one | 381 |

TABLE 1-continued

| Example | Structure | additive | Name | MS (ESI+; M + H) |
|---|---|---|---|---|
| 61 | 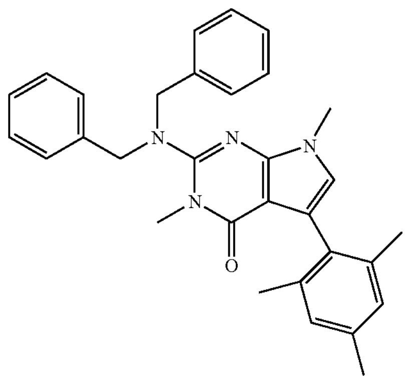 | CF$_3$COOH | 2-(dibenzylamino)-5-mesityl-3,7-dimethyl-3,7-dihydro-4H-pyrrolo[2,3-d]pyrimidin-4-one | 477 |
| 62 | 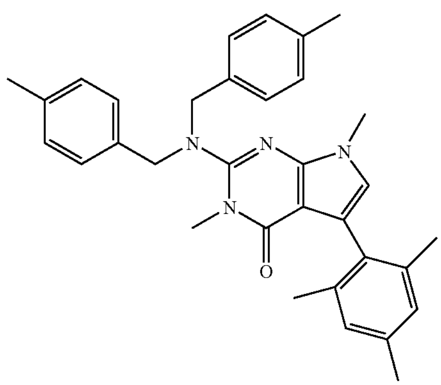 | CF$_3$COOH | 2-[bis(4-methylbenzyl)amino]-5-mesityl-3,7-dimethyl-3,7-dihydro-4H-pyrrolo[2,3-d]pyrimidin-4-one | 505 |
| 63 | 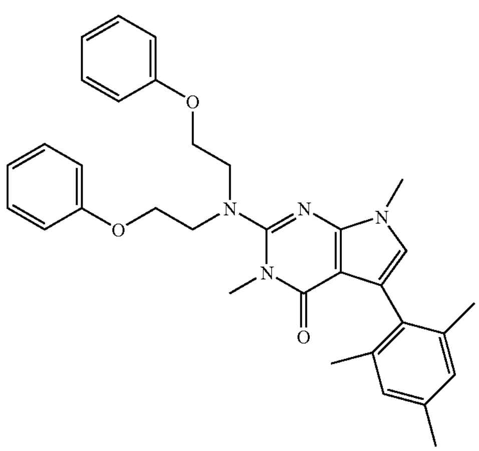 | CF$_3$COOH | 2-[bis(2-phenoxyethyl)amino]-5-mesityl-3,7-dimethyl-3,7-dihydro-4H-pyrrolo[2,3-d]pyrimidin-4-one | 537 |

TABLE 1-continued

| Example | Structure | additive | Name | MS (ESI+; M + H) |
|---|---|---|---|---|
| 64 | 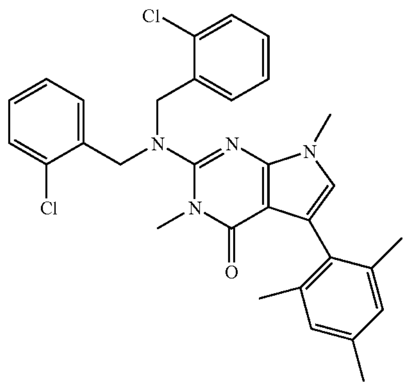 | CF$_3$COOH | 2-[bis(2-chlorobenzyl)amino]-5-mesityl-3,7-dimethyl-3,7-dihydro-4H-pyrrolo[2,3-d]pyrimidin-4-one | 545 |
| 65 | 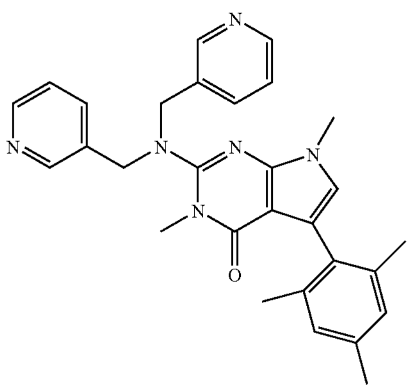 | CF$_3$COOH | 2-[bis(pyridin-3-ylmethyl)amino]-5-mesityl-3,7-dimethyl-3,7-dihydro-4H-pyrrolo[2,3-d]pyrimidin-4-one | 479 |
| 66 | 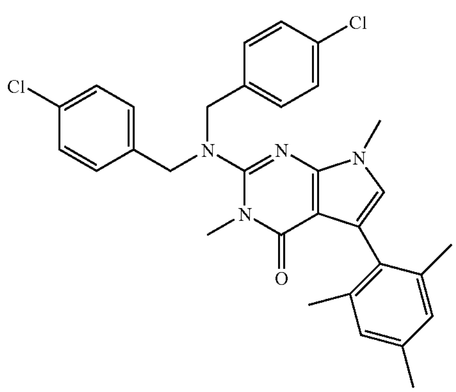 | CF$_3$COOH | 2-[bis(4-chlorobenzyl)amino]-5-mesityl-3,7-dimethyl-3,7-dihydro-4H-pyrrolo[2,3-d]pyrimidin-4-one | 545 |
| 67 | 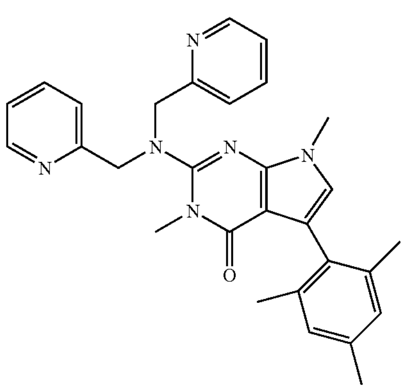 | CF$_3$COOH | 2-[bis(pyridin-2-ylmethyl)amino]-5-mesityl-3,7-dimethyl-3,7-dihydro-4H-pyrrolo[2,3-d]pyrimidin-4-one | 479 |

TABLE 1-continued

| Example | Structure | additive | Name | MS (ESI+; M + H) |
|---|---|---|---|---|
| 68 | 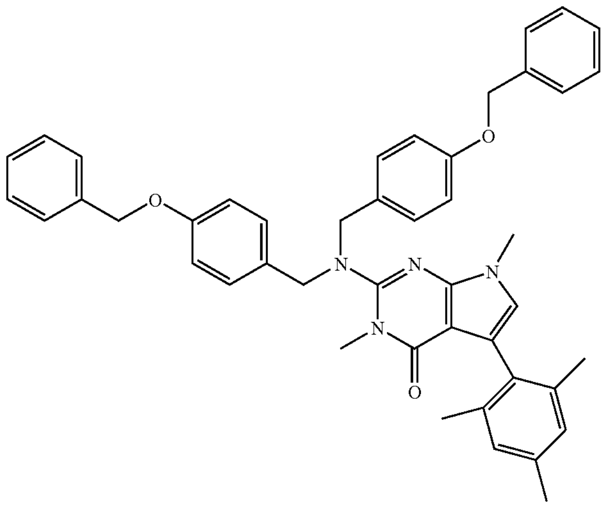 | CF$_3$COOH | 2-{bis[4-(benzyloxy)benzyl]amino}-5-mesityl-3,7-dimethyl-3,7-dihydro-4H-pyrrolo[2,3-d]pyrimidin-4-one | 689 |
| 69 | 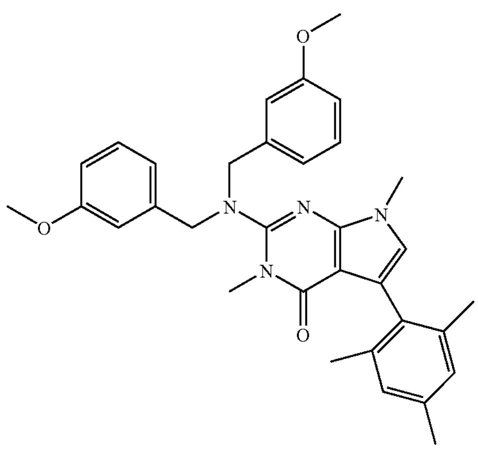 | CF$_3$COOH | 2-[bis(3-methoxybenzyl)amino]-5-mesityl-3,7-dimethyl-3,7-dihydro-4H-pyrrolo[2,3-d]pyrimidin-4-one | 537 |
| 70 | 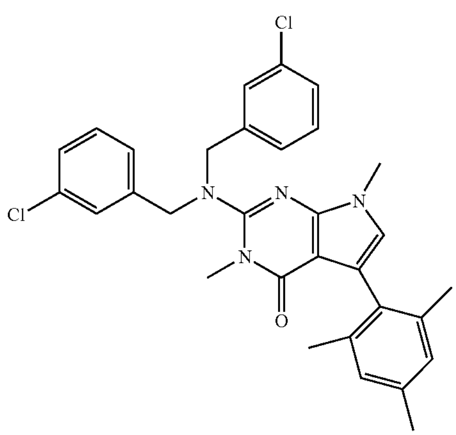 | CF$_3$COOH | 2-[bis(3-chlorobenzyl)amino]-5-mesityl-3,7-dimethyl-3,7-dihydro-4H-pyrrolo[2,3-d]pyrimidin-4-one | 545 |

TABLE 1-continued

| Example | Structure | additive | Name | MS (ESI+; M + H) |
|---|---|---|---|---|
| 71 | 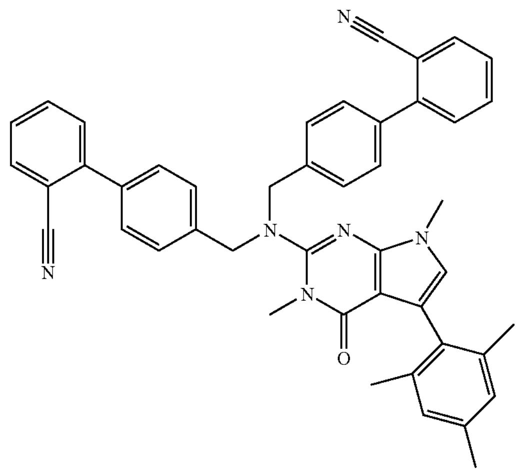 | CF₃COOH | 4',4''-[[(5-mesityl-3,7-dimethyl-4-oxo-4,7-dihydro-3H-pyrrolo[2,3-d]pyrimidin-2-yl)imino]bis(methylene)]dibiphenyl-2-carbonitrile | 679 |
| 72 | 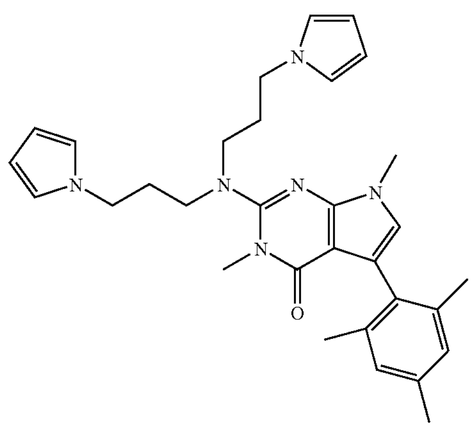 | CF₃COOH | 2-{bis[3-(1H-pyrrol-1-yl)propyl]amino}-5-mesityl-3,7-dimethyl-3,7-dihydro-4H-pyrrolo[2,3-d]pyrimidin-4-one | 511 |
| 73 | 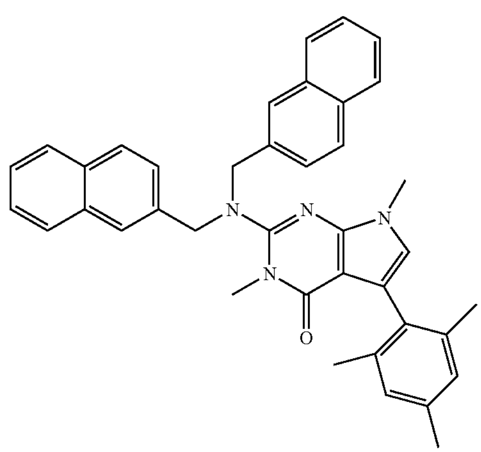 | CF₃COOH | 2-[bis(2-naphthylmethyl)amino]-5-mesityl-3,7-dimethyl-3,7-dihydro-4H-pyrrolo[2,3-d]pyrimidin-4-one | 577 |

TABLE 1-continued

| Example | Structure | additive | Name | MS (ESI+; M + H) |
|---|---|---|---|---|
| 74 | 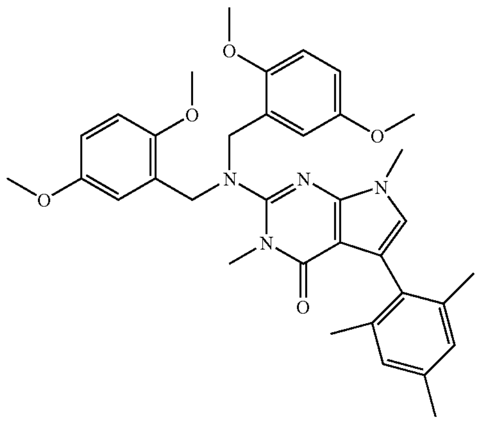 | CF₃COOH | 2-[bis(2,5-dimethoxybenzyl)amino]-5-mesityl-3,7-dimethyl-3,7-dihydro-4H-pyrrolo[2,3-d]pyrimidin-4-one | 597 |
| 75 | 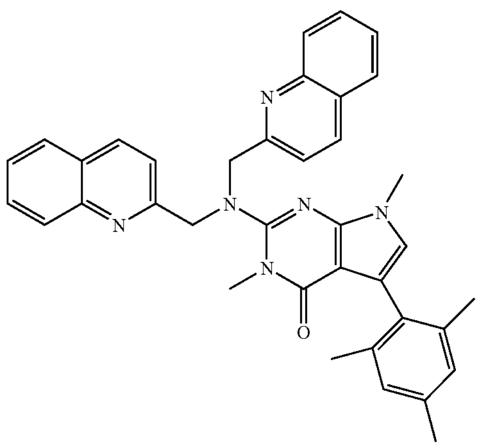 | CF₃COOH | 2-[bis(quinolin-2-ylmethyl)amino]-5-mesityl-3,7-dimethyl-3,7-dihydro-4H-pyrrolo[2,3-d]pyrimidin-4-one | 579 |
| 76 | 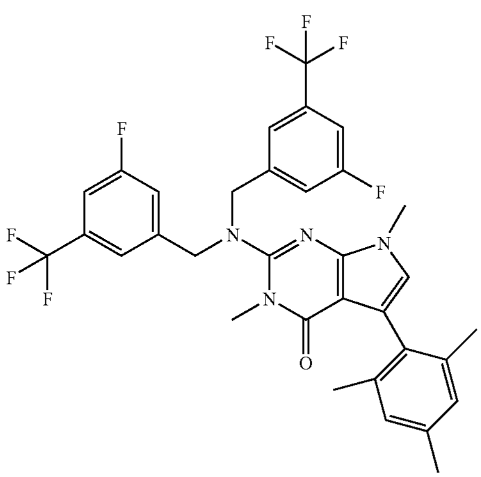 | CF₃COOH | 2-{bis[3-fluoro-5-(trifluoromethyl)benzyl]amino}-5-mesityl-3,7-dimethyl-3,7-dihydro-4H-pyrrolo[2,3-d]pyrinidin-4-one | 649 |

TABLE 1-continued

| Example | Structure | additive | Name | MS (ESI+; M + H) |
|---|---|---|---|---|
| 77 | 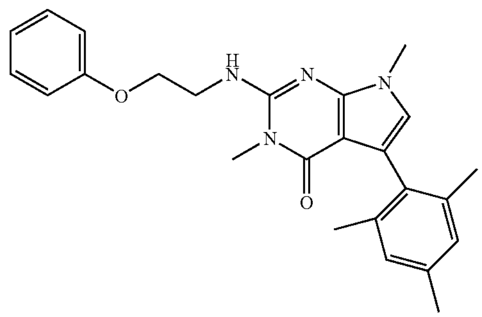 | CF₃COOH | 5-mesityl-3,7-dimethyl-2-[(2-phenoxyethyl)amino]-3,7-dihydro-4H-pyrrolo[2,3-d]pyrimidin-4-one | 417 |
| 78 | 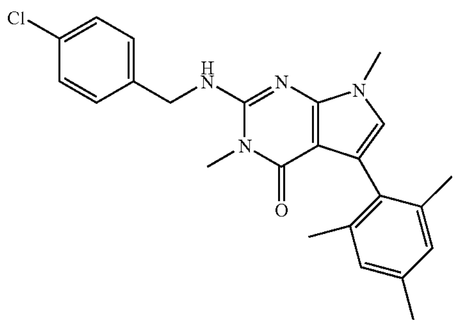 | CF₃COOH | 2-[(4-chlorobenzyl)amino]-5-mesityl-3,7-dimethyl-3,7-dihydro-4H-pyrrolo[2,3-d]pyrimidin-4-one | 421 |
| 79 | 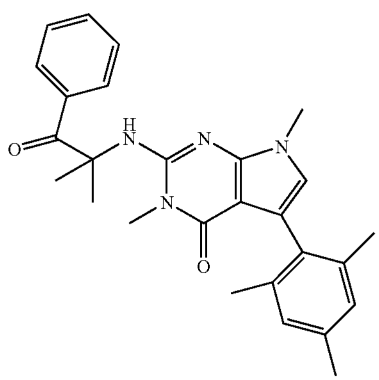 | CF₃COOH | 2-[(1,1-dimethyl-2-oxo-2-phenylethyl)amino]-5-mesityl-3,7-dimethyl-3,7-dihydro-4H-pyrrolo[2,3-d]pyrimidin-4-one | 443 |
| 80 | 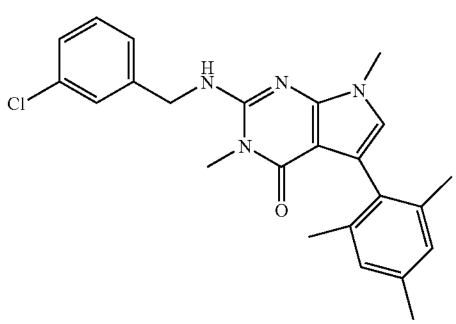 | CF₃COOH | 2-[(3-chlorobenzyl)amino]-5-mesityl-3,7-dimethyl-3,7-dihydro-4H-pyrrolo[2,3-d]pyrimidin-4-one | 421 |

TABLE 1-continued

| Example | additive | Name | MS (ESI+; M + H) |
|---|---|---|---|
| 81 | CF₃COOH | 4'-{[(5-mesityl-3,7-dimethyl-4-oxo-4,7-dihydro-3H-pyrrolo[2,3-d]pyrimidin-2-yl)amino]methyl}-1,1'-biphenyl-2-carbonitrile | 488 |
| 82 | CF₃COOH | 5-mesityl-3,7-dimethyl-2-[(2-naphthylmethyl)amino]-3,7-dihydro-4H-pyrrolo[2,3-d]pyrimidin-4-one | 437 |
| 83 | CF₃COOH | 2-{[3-fluoro-5-(trifluoromethyl)benzyl]amino}-5-mesityl-3,7-dimethyl-3,7-dihydro-4H-pyrrolo[2,3-d]pyrimidin-4-one | 473 |
| 84 | CF₃COOH | 5-mesityl-3,7-dimethyl-2-[(1-methylbutyl)amino]-3,7-dihydro-4H-pyrrolo[2,3-d]pyrimidin-4-one | 367 |

TABLE 1-continued

| Example | Structure | additive | Name | MS (ESI+; M + H) |
|---|---|---|---|---|
| 85 | 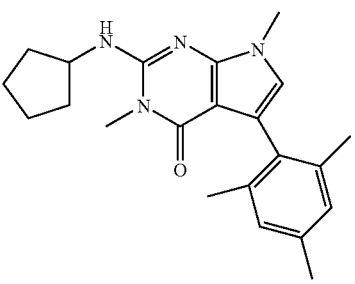 | CF₃COOH | 2-(cyclopentylamino)-5-mesityl-3,7-dimethyl-3,7-dihydro-4H-pyrrolo[2,3-d]pyrimidin-4-one | 365 |
| 86 | 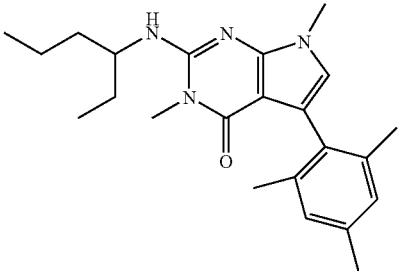 | CF₃COOH | 2-[(1-ethylbutyl)amino]-5-mesityl-3,7-dimethyl-3,7-dihydro-4H-pyrrolo[2,3-d]pyrimidin-4-one | 381 |
| 87 | 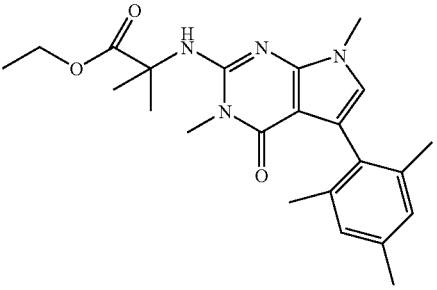 | CF₃COOH | ethyl N-(5-mesityl-3,7-dimethyl-4-oxo-4,7-dihydro-3H-pyrrolo[2,3-d]pyrimidin-2-yl)-2-methylalaninate | 411 |
| 88 | 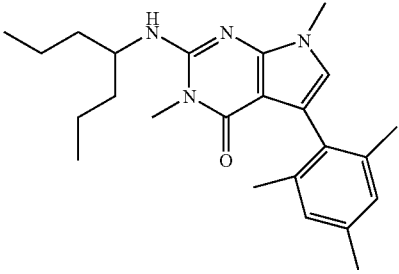 | CF₃COOH | 5-mesityl-3,7-dimethyl-2-[(1-propylbutyl)amino]-3,7-dihydro-4H-pyrrolo[2,3-d]pyrimidin-4-one | 395 |
| 89 | 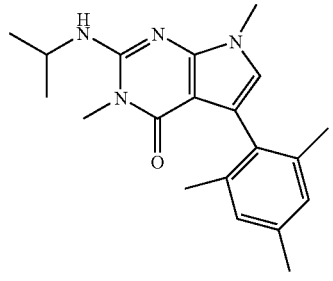 | CF₃COOH | 2-(isopropylamino)-5-mesityl-3,7-dimethyl-3,7-dihydro-4H-pyrrolo[2,3-d]pyrimidin-4-one | 339 |

TABLE 1-continued

| Example | Structure | additive | Name | MS (ESI+; M + H) |
|---|---|---|---|---|
| 90 | 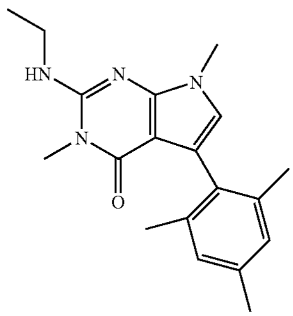 | CF$_3$COOH | 2-(ethylamino)-5-mesityl-3,7-dimethyl-3,7-dihydro-4H-pyrrolo[2,3-d]pyrimidin-4-one | 325 |

Example 91

2-[(1-Ethylpropyl)(methyl)amino]-5-mesityl-3,7-dimethyl-3,7-dihydro-4H-pyrrolo[2,3-d]pyrimidin-4-one hydrochloride To a solution of 2-[(1-Ethylpropyl)amino]-5-mesityl-3,7-dimethyl-3,7-dihydro-4H-pyrrolo[2,3-d]pyrimidin-4-one (0.073 g, 0.199 mmol) in N,N-dimethylformamide (1 mL) was added sodium hydride (66% in oil, 0.008 g, 0.219 mmol), and the mixture was allowed to stir at room temperature for 20 minutes. Iodomethane (0.014 mL, 0.219 mmol) was added to the mixture, followed by stirring at 0° C. for 1.5 hours. The reaction mixture was diluted with ice-cold water and extracted with ethyl acetate. The organic layer was washed with water and brine, dried over sodium sulfate and concentrated in vacuo. The residue was purified by silica gel column chromatography eluting with hexane/ethyl acetate (4:1-2:1). The desired fractions were concentrated in vacuo. The residual oil was dissolved in ethyl acetate, and 4N solution of hydrochloride in ethyl acetate (0.063 mL) was added. The solution was concentrated in vacuo, and the residue was crystallized from diethyl ether-hexane to give 0.014 g (17%) of the title compound.

mp 135-137° C.

$^1$H NMR (DMSO-d$_6$) δ: ppm 0.91 (t, J=7.3 Hz, 6H), 1.53-1.74 (m, 4H), 1.99 (s, 6H), 2.23 (s, 3H), 2.70 (s, 3H), 3.32 (s, 3H), 3.30-3.34 (m, 1H), 3.61 (s, 3H), 6.64 (s, 1H), 6.82 (s, 2H).

Example 92

N'-(5-Mesityl-3,7-dimethyl-4-oxo-4,7-dihydro-3H-pyrrolo[2,3-d]pyrimidin-2-yl)-N,N-dimethylurea To a solution of 2-amino-5-mesityl-3,7-dimethyl-3,7-dihydro-4H-pyrrolo[2,3-d]pyrimidin-4-one (0.040 g, 0.135 mmol) in tetrahydrofuran (1 mL) were added p-nitrophenyl chloroformate (0.073 g, 0.361 mmol) and triethylamine (0.050 mL, 0.361 mmol), and the mixture was allowed to stir at 60° C. for 2 hours. A 2M solution of dimethylamine in tetrahydrofuran (0.4 mL) was added to the mixture, followed by stirring at 60° C. for 15 hours. After cooling, the reaction mixture was diluted with ice-cold water and extracted with ethyl acetate. The organic layer was washed with water and brine, dried over sodium sulfate and concentrated in vacuo. The residue was purified by silica gel column chromatography eluting with hexane/ethyl acetate (4:1-1:2). The desired fractions were concentrated in vacuo, and the residual crystals were washed with diisopropyl ether-diethyl ether to give 0.012 g (24%) of the title compound.

mp 221-223° C.

$^1$H NMR (CDCl$_3$) δ: ppm 2.11 (s, 6H), 2.28 (s, 3H), 3.12 (s, 3H), 3.19 (s, 3H), 3.55 (s, 3H), 3.70 (s, 3H), 6.39 (s, 1H), 6.90 (s, 2H), 8.53 (s, 1H).

Example 93

2-(Dipropylamino)-5-mesityl-7-methyl-3,7-dihydro-4H-pyrrolo[2,3-d]pyrimidin-4-one

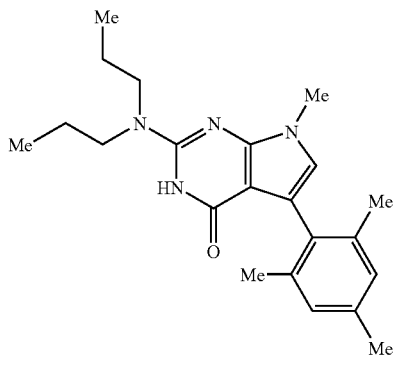

4-Chloro-5-mesityl-7-methyl-N,N-dipropyl-7H-pyrrolo[2,3-d]-pyrimidin-2-amine

A mixture of 2-amino-5-mesityl-7-methyl-3,7-dihydro-4H-pyrrolo[2,3-d]pyrimidin-4-one (142 mg, 0.50 mmol), N,N-diethylaniline (68 mg, 0.50 mmol), and phosphorus oxychloride (10 ml) was heated at 80° C. with stirring for 4 hours. The dark orange solution was allowed to cool to room temperature and concentrated in vacuo. Water (10 ml) was then added to the residue at 0° C. with vigorous stirring. Concentrated aqueous ammonium hydroxide was added and extracted with ethyl acetate (100 ml×2). The extracts were combined, washed with brine, dried over sodium sulfate and concentrated in vacuo. To a mixture of the residue and dimethylformamide (5 ml) was added sodium hydride (60% in oil, 50 mg, 1.25 mmol) at 0° C. and stirred for 0.5 hour. After stirring at room temperature for 0.5 hour, to the mixture was added a solution of n-PrI (213 mg, 1.25 mmol) and dimethylformamide (2 ml) at 0° C. and stirred for 0.5 hour. After stirring at room temperature for 1 hour, the mixture was diluted with water (20 ml) and extracted with ethyl acetate (50 ml×2). The extracts were combined, washed with brine, dried over sodium sulfate and concentrated in vacuo. The residue was purified by silica gel chromatography eluting with hexane/ethyl acetate (20:1) to give 59 mg (31%) of the title compound.

$^1$H NMR (CDCl$_3$) δ: 0.95 (6H, t, J=7.5 Hz), 1.66 (4H, m), 2.06 (6H, s), 2.32 (3H, s), 3.57 (4H, t, J=7.5 Hz), 3.69 (3H, s), 6.48 (1H, s), 6.91 (2H, s).

2-(Dipropylamino)-5-mesityl-7-methyl-3,7-dihydro-4H-pyrrolo[2,3-d]pyrimidin-4-one 4-Chloro-5-mesityl-7-methyl-N,N-dipropyl-7H-pyrrolo[2,3-d]pyrimidin-2-amine (50 mg, 0.13 mmol) in aqueous sodium hydroxide (2M, 10 ml) was heated at reflux for 6 hours. The solution was cooled to room temperature and neutralized with acetic acid. The mixture was diluted with water (20 ml) and extracted with ethyl acetate (50 ml×3). The extracts were combined, washed with brine, dried over sodium sulfate and concentrated in vacuo. The residue was purified by silica gel chromatography eluting with hexane/ethyl acetate (4:1) to give 39 mg (81%) of the title compound.

$^1$H NMR (CDCl$_3$) δ: 0.94 (6H, t, J=7.5 Hz), 1.67 (4H, m), 2.06 (6H, s), 2.30 (3H, s), 3.57 (4H, t, J=7.5 Hz), 3.69 (3H, s), 6.16 (1H, s), 6.48 (1H, s), 6.90 (2H, s).

Example 94

3-Benzyl-2-(dipropylamino)-5-mesityl-7-methyl-3,7-dihydro-4H-pyrrolo[2,3-d]pyrimidin-4-one

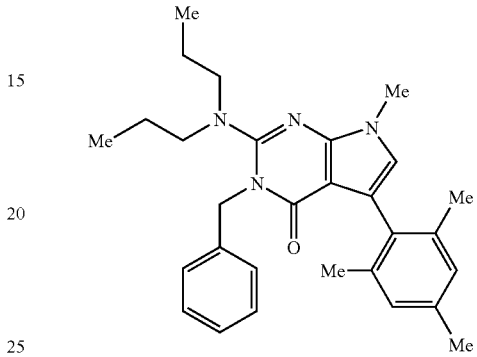

To a solution of 2-(dipropylamino)-5-mesityl-7-methyl-3,7-dihydro-4H-pyrrolo[2,3-d]pyrimidin-4-one (50 mg, 0.14 mmol) and dimethylformamide (3 ml) was added sodium hydride (60% in oil, 10 mg, 0.25 mmol) at 0° C. and stirred for 0.5 hour. After stirring at room temperature for 0.5 hour, to the mixture was added a solution of benzylchloride (64 mg, 0.50 mmol) and dimethylformamide (2 ml) at 0° C. and stirred for 0.5 hour. After stirring at room temperature for 1 hour, the mixture was heated at 80° C. After cooling to room temperature, the mixture was diluted with water (20 ml) and extracted with ethyl acetate (50 ml×3). The extracts were combined, washed with brine, dried over sodium sulfate and concentrated in vacuo. The residue was purified by silica gel chromatography eluting with hexane/ethyl acetate (20:1) to give 11 mg (17%) of the title compound.

$^1$H NMR (CDCl$_3$) δ: 0.90 (6H, t, J=7.5 Hz), 1.61 (4H, m), 2.11 (6H, s), 2.29 (3H, s), 3.11 (4H, t, J=7.5 Hz), 3.47 (3H, s), 3.61 (2H, s), 6.43 (1H, s), 6.90 (2H, s), 7.20 (5H, m).

Example 95

2-(Dipropylamino)-5-mesityl-7-methyl-3-propyn-2-yl-3,7-dihydro-4H-pyrrolo[2,3-d]pyrimidin-4-one

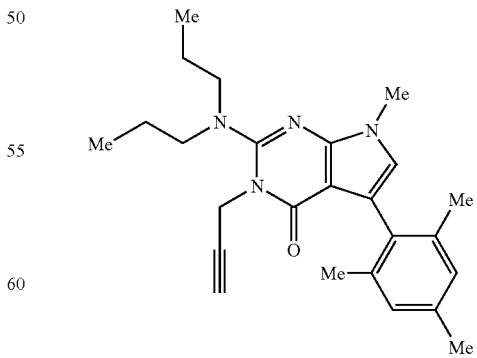

To a solution of 2-(dipropylamino)-5-mesityl-7-methyl-3,7-dihydro-4H-pyrrolo[2,3-d]pyrimidin-4-one (50 mg, 0.14 mmol) and dimethylformamide (3 ml) was added sodium hydride (60% in oil, 10 mg, 0.25 mmol) at 0° C. and stirred for 0.5 hour. After stirring at room temperature for 0.5 hour, to the mixture was added a solution of propargylbromide (54 mg, 0.50 mmol) and dimethylformamide (2 ml) at 0° C. and stirred for 0.5 hour. After stirring at room temperature for 1 hour, the mixture was heated at 80° C. After cooling to room temperature, the mixture was diluted with water (20 ml) and extracted with ethyl acetate (50 ml×3). The extracts were combined, washed with brine, dried over sodium sulfate and concentrated in vacuo. The residue was purified by silica gel chromatography eluting with hexane/ethyl acetate (20:1) to give 8 mg (14%) of the title compound.

$^1$H NMR (CDCl$_3$) δ: 0.91 (6H, t, J=7.5 Hz), 1.61 (4H, m), 2.11 (6H, s), 2.28 (3H, s), 3.02 (1H, t, J=2.4 Hz), 3.11 (4H, t, J=7.5 Hz), 3.46 (3H, s), 4.41 (2H, d, J=2.4 Hz), 6.43 (1H, s), 6.90 (2H, s).

Example 96

1-(2,4-Dimethylphenyl)-4-(1-ethylpropoxy)-6-methyl-1,6-dihydro-7H-pyrrolo[2,3-d]pyridazin-7-one

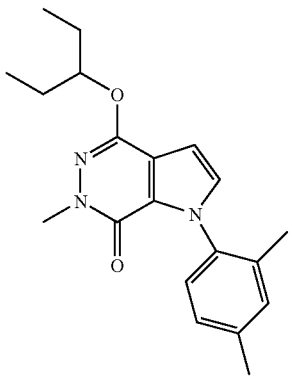

Diethyl 1-(2,4-Dimethylphenyl)-1H-pyrrole-2,3-dicarboxylate (Method A)

A mixture of diethyl 1H-pyrrole-2,3-dicarboxylate (4.21 g, 19.9 mmol), 2,4-dimethylphenylboronic acid (5.98 g, 39.9 mmol), Cu(OAc)$_2$ (5.43 g, 29.9 mmol), pyridine (3.22 ml, 39.9 mmol) and dichloromethane (60 ml) was stirred at room temperature for 62 hours. The mixture was diluted with water (100 ml) and extracted with ethyl acetate (100 ml×2). The extracts were combined, washed with 1N hydrochloric acid and saturated aqueous sodium bicarbonate, dried over magnesium sulfate and concentrated in vacuo. The residue was purified by silica gel chromatography eluting with hexane/ethyl acetate (10:1-5:1) to give 0.98 g (16%) of the title compound. The starting material (3.5 g) was recovered.

$^1$H NMR (CDCl$_3$) δ: 1.08 (3H, t, J=7.2 Hz), 1.35 (3H, t, J=7.2 Hz), 2.03 (3H, s), 2.36 (3H, s), 4.11 (2H, q, J=7.2 Hz), 4.32 (2H, q, J=7.2 Hz), 6.65 (2H, s), 7.00-7.15 (3H, m).

(Method B)

(i) Ethyl 3-cyano-1-(2,4-dimethylphenyl)-1H-pyrrole-2-carboxylate

A mixture of diethyl 3,6-dicyano-2,7-hydroxyccta-2,4,6-trienedioate (3.83 g, 12.5 mmol), 2,4-dimethylanilne (3.09 ml, 25.0 mmol) and toluene (50 ml) was heated under reflux for 2 hours. The mixture was cooled and purified by silica gel chromatography eluting with hexane/AcOEt (5:1) to give 3.10 g (92%) of the title compound as an oil.

$^1$H NMR (CDCl$_3$) δ: 1.28 (3H, t, J=7.2 Hz), 1.96 (3H, s), 2.38 (3H, s), 4.24 (2H, q, J=7.2 Hz), 6.65 (1H, d, J=2.8 Hz), 6.79 (1H, d, J=2.8 Hz), 7.00-7.15 (3H, m).

(ii) 1-(2,4-Dimethylphenyl)-1H-pyrrole-2,3-dicarboxylic Acid

A mixture of ethyl 3-cyano-1-(2,4-dimethylphenyl)-1H-pyrrole-2-carboxylate (3.0 g, 11.2 mmol) and 2.5N aqueous sodium hydroxide (18.5 ml, 44.7 mmol) was heated under reflux for 15 hours. After cooling, the insoluble material was removed through celite, acidified with 5N hydrochloric acid and extracted with ethyl acetate. The extract was washed with brine, dried over magnesium sulfate and concentrated in vacuo.

The residue was crystallized from hexane-ethyl acetate to give 2.26 g (74%) of the title compound.

$^1$H NMR (CDCl$_3$-DMSO-d$_6$ (1 drop)) δ: 1.95 (3H, s), 2.37 (3H, s), 6.77 (1H, d, J=2.8 Hz), 6.92 (1H, d, J=2.8 Hz), 6.98-7.20 (3H, m).

(iii) Diethyl 1-(2,4-Dimethylphenyl)-1H-pyrrole-2,3-dicarboxylate

To a solution of 1-(2,4-dimethylphenyl)-1H-pyrrole-2,3-dicarboxylic acid (2.2 g, 8.05 mmol) in DMF (20 ml) was added ethyl iodide (3.30 ml, 32.2 mmol) and potassium carbonate (4.45 g, 32.3 mmol) and the mixture was stirred at room temperature for 13 hours. The mixture was diluted with water (50 ml) and extracted with ethyl acetate (100 ml×2). The extracts were combined, washed with water, dried over magnesium sulfate and concentrated in vacuo. The residue was purified by silica gel chromatography eluting with hexane/ethyl acetate (10:1) to give 2.35 g (93%) of the title compound as an oil.

$^1$H NMR (CDCl$_3$) δ: 1.08 (3H, t, J=7.2 Hz), 1.35 (3H, t, J=7.2 Hz), 2.03 (3H, s), 2.36 (3H, s), 4.11 (2H, q, J=7.2 Hz), 4.32 (2H, q, J=7.2 Hz), 6.65 (2H, s), 7.00-7.15 (3H, m).

1-(2,4-Dimethylphenyl)-5,6-dihydro-1H-pyrrolo[2,3-d]pyridazine-4,7-dione

To a solution of diethyl 1-(2,4-dimethylphenyl)-1H-pyrrole-2,3-dicarboxylate (0.5 g, 1.59 mmol) in ethanol (5 ml) was added hydrazine monohydrate (0.38 ml, 7.93 mmol) and the mixture was heated under reflux for 14 hours. During the reaction, additional hydrazine monohydrate (0.2 ml×3) was added to the mixture. The solvent was removed in vacuo and the residue was treated with 2N hydrochloric acid at 80° C. for 20 min. After cooling, crystals were collected by filtration, washed with water and dried to give 0.36 g (89%) of the title compound.

LC/MS: 256 (MH$^+$).

4,7-Dichloro-1-(2,4-dimethylphenyl)-1H-pyrrolo[2,3-d]pyridazine

A mixture of 1-(2,4-dimethylphenyl)-5,6-dihydro-1H-pyrrolo[2,3-d]pyridazine-4,7-dione (0.255 g, 1.0 mmol) and phosphorous oxychloride (3 ml) was heated at 100° C. for 1 hour. The mixture was concentrated in vacuo, neutralized with saturated aqueous hydrogen bicarbonate and extracted with ethyl acetate (50 ml×2). The extracts were combined, washed with water, dried over magnesium sulfate and concentrated in vacuo. The residue was purified by silica gel chromatography eluting with dichloromethane/ethyl acetate (20:1) to give 0.26 g (88%) of the title compound.

mp 148-149° C.

$^1$H NMR (CDCl$_3$) δ: 1.55 (3H, s), 1.88 (3H, s), 6.83 (1H, d, J=2.8 Hz), 7.05-7.20 (3H, m), 7.31 (1H, d, J=2.8 Hz).

4-Chloro-1-(2,4-dimethylphenyl)-1,6-dihydro-7H-pyrrolo[2,3-d]pyridazin-7-one (A) and 7-chloro-1-(2,4-dimethylphenyl)-1,5-dihydro-4H-pyrrolo[2,3-d]pyridazin-4-one (B)

A mixture of 4,7-dichloro-1-(2,4-dimethylphenyl)-1H-pyrrolo[2,3-d]pyridazine (0.5 g, 1.71 mmol), sodium hydroxide (1.37 g, 34.2 mmol), water (5 ml) and dioxane (10 ml) was heated under reflux for 16 hours. The mixture was cooled, acidified with 5N hydrochloric acid and extracted with ethyl acetate (100 ml×2). The extracts were combined, washed with saturated aqueous sodium bicarbonate, dried over magnesium sulfate and concentrated in vacuo. The residue was purified by silica gel chromatography eluting with dichloromethane/ethyl acetate (50:1-10:1-2:1) to give 0.16 g (34%) of compound (A) as a first fraction and 0.26 g (56%) of compound (B) as a second fraction.

Compound (A):
mp 236-237° C.
$^1$H NMR (CDCl$_3$) δ: 2.03 (3H, s), 2.40 (3H, s), 6.65 (1H, d, J=3.0 Hz), 7.05-7.22 (4H, m), 9.93 (1H, brs).

Compound (B):
mp 270-273° C.
$^1$H NMR (CDCl$_3$) δ: 1.96 (3H, s), 2.43 (3H, s), 7.00-7.20 (5H, m), 9.96 (1H, brs).

4-Chloro-1-(2,4-dimethylphenyl)-6-methyl-1,6-dihydro-7H-pyrrolo[2,3-d]pyridazin-7-one A mixture of 4-chloro-1-(2,4-dimethylphenyl)-1,6-dihydro-7H-pyrrolo[2,3-d]pyridazin-7-one (0.30 g, 1.10 mmol), MeI (0.075 ml, 1.21 mmol), potassium carbonate (0.30 g, 2.2 mmol) and DMF (5 ml) was stirred at room temperature for 13 hours. The mixture was diluted with water (50 ml) and extracted with ethyl acetate (50 ml×2). The extracts were combined, washed with water, dried over magnesium sulfate and concentrated in vacuo. The residue was purified by silica gel chromatography eluting with hexane/ethyl acetate (5:1) to give 0.31 g (98%) of the title compound as crystals.

mp 119-120° C.
$^1$H NMR (CDCl$_3$) δ: 2.00 (3H, s), 2.39 (3H, s), 3.74 (3H, s), 6.61 (1H, d, J=3.0 Hz), 7.05-7.20 (4H, m).

1-(2,4-Dimethylphenyl)-4-(1-ethylpropoxy)-6-methyl-1,6-dihydro-7H-pyrrolo[2,3-d]pyridazin-7-one To a solution 3-pentanol (0.064 ml, 0.60 mmol) in DMF (1 ml) was added sodium hydride (60% in oil, 24 mg, 0.60 mmol). The mixture was stirred for 10 min before addition of 4-chloro-1-(2,4-dimethylphenyl)-6-methyl-1,6-dihydro-7H-pyrrolo[2,3-d]pyridazin-7-one (43.2 mg, 0.15 mmol). The mixture was stirred at 60° C. for 3 hours, then dilated with water (30 ml) and extracted with ethyl acetate (50 ml). The extract was washed with water, dried over magnesium sulfate and concentrated in vacuo. The residue was purified by silica gel chromatography eluting with hexane/ethyl acetate (5:1) to give 48 mg (94%) of the title compound as an oil.

LC/MS: 340 (MH$^+$).
$^1$H NMR (CDCl$_3$) δ: 0.95-1.10 (6H, m), 1.70-1.90 (4H, m), 2.02 (3H, s), 2.37 (3H, s), 3.61 (3H, s), 4.85-4.95 (1H, m), 6.56 (1H, d, J=2.7 Hz), 7.02 (1H, d, J=2.7 Hz), 7.05-7.20 (3H, m).

Example 97

1-(2,4-Dimethylphenyl)-6-methyl-4-(neopentyloxy)-1,6-dihydro-7H-pyrrolo[2,3-d]pyridazin-7-one

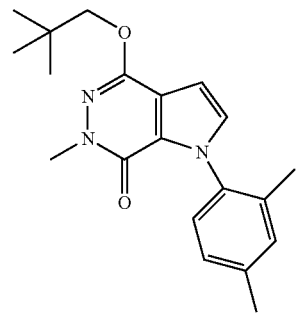

To a solution of neopentyl alcohol (39.7 mg, 0.45 mmol) in DMF (1 ml) was added sodium hydride (60% in oil, 18 mg, 0.45 mmol). The mixture was stirred for 10 min before addition of 4-chloro-1-(2,4-dimethylphenyl)-6-methyl-1,6-dihydro-7H-pyrrolo[2,3-d]pyridazin-7-one (43.2 mg, 0.15 mmol). The mixture was stirred at 60° C. for 2 hours, then diluted with water (30 ml) and extracted with ethyl acetate (30 ml). The extract was washed with water, dried over magnesium sulfate and concentrated in vacuo. The residue was purified by silica gel chromatography eluting with hexane/ethyl acetate (10:1) to give 32 mg (63%) of the title compounds as crystals.

mp 146-147° C.
$^1$H NMR (CDCl$_3$) δ: 1.08 (9H, s), 2.01 (3H, s), 2.38 (3H, s), 3.64 (3H, s), 3.94 (2H, s), 6.59 (1H, d, J=3.0 Hz), 7.05 (1H, d, J=3.0 Hz), 7.05-7.20 (3H, m).

Example 98

4-(2,3-Dihydro-1H-inden-1-yloxy)-1-(2,4-dimethylphenyl)-6-methyl-1,6-dihydro-7H-pyrrolo[2,3-d]-pyridazin-7-one

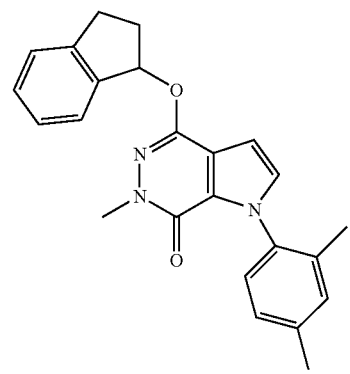

To a solution of 1-indanol (60 mg, 0.45 mmol) in DMF (1 ml) was added sodium hydride (60% in oil, 18 mg, 0.45 mmol). The mixture was stirred for 10 min before addition of 4-chloro-1-(2,4-dimethylphenyl)-6-methyl-1,6-dihydro-7H-pyrrolo[2,3-d]pyridazin-7-one (43.2 mg, 0.15 mmol). The mixture was stirred at 60° C. for 3 hours, then diluted with water (30 ml) and extracted with ethyl acetate (30 ml×2). The extract were combined, washed with water, dried over magnesium sulfate and concentrated in vacuo. The residue was purified by silica gel chromatography eluting with hexane/ethyl acetate (10:1) to give 28 mg (48%) of the title compounds as an oil.

$^1$H NMR (CDCl$_3$) δ: 2.01 (3H, s), 2.20-2.45 (1H, m), 2.38 (3H, s), 2.60-2.80 (1H, m), 2.85-3.05 (1H, m), 3.10-3.30 (1H, m), 3.71 (3H, s), 6.35-6.50 (1H, m), 6.53 (1H, d, J=2.8 Hz), 7.02 (1H, d, J=2.8 Hz), 7.05-7.20 (3H, m), 7.20-7.40 (3H, m), 7.55-7.70 (1H, m).

Example 99

1-(2,4-Dimethylphenyl)-6-ethyl-4-(1-ethylpropoxy)-1,6-dihydro-7H-pyrrolo[2,3-d]pyridazin-7-one

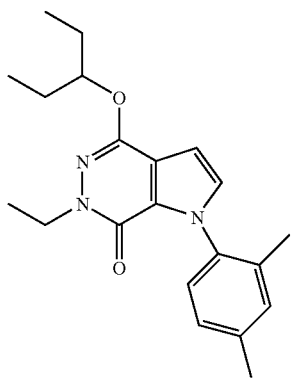

(1) 4-Chloro-1-(2,4-dimethylphenyl)-6-ethyl-1,6-dihydro-7H-pyrrolo[2,3-d]pyridazin-7-one A mixture of 4-chloro-1-(2,4-dimethylphenyl)-1,6-dihydro-7H-pyrrolo[2,3-d]pyridazin-7-one (100 mg, 0.365 mmol), ethyl iodide (0.032 ml, 0.40 mmol), potassium carbonate (100 mg, 0.73 mmol) and DMF (1 ml) was stirred at room temperature for 7 hours. The mixture was diluted with water (50 ml) and extracted with ethyl acetate (50 ml). The extract was washed with water, dried over magnesium sulfate and concentrated in vacuo. The residue was purified by silica gel chromatography eluting with hexane/ethyl acetate (5:1) to give 102 mg (93%) of the title compound as crystals.

mp 94-95° C.

$^1$H NMR (CDCl$_3$) δ: 1.33 (3H, t, J=7.2H z), 2.01 (3H, s), 2.39 (3H, s), 4.18 (2H, q, J=7.2 Hz), 6.60 (1H, d, J=3.0 Hz), 7.02 (1H, d, J=3.0 Hz), 7.05-7.20 (3H, m).

1-(2,4-Dimethylphenyl)-6-ethyl-4-(1-ethylpropoxy)-1,6-dihydro-7H-pyrrolo(2,3-d]pyridazin-7-one To a solution of 3-pentanol (0.079 ml, 0.73 mmol) in DMF (1 ml) was added sodium hydride (60% in oil, 29 mg, 0.73 mmol). The mixture was stirred for 10 min before addition of 4-chloro-1-(2,4-dimethylphenyl)-6-ethyl-1,6-dihydro-7H-pyrrolo[2,3-d]pyridazin-7-one (55 mg, 0.18 mmol). The mixture was stirred at 60° C. for 4 hours, then diluted with water (30 ml) and extracted with ethyl acetate (50 ml). The extract were combined, washed with water, dried over magnesium sulfate and concentrated in vacuo. The residue was purified by silica gel chromatography eluting with hexane/ethyl acetate (10:1) to give 48 mg (48%) of the title compound as an oil.

$^1$H NMR (CDCl$_3$) δ: 0.95-1.05 (6H, m), 1.28 (3H, t, J=7.5 Hz), 1.70-1.85 (4H, m), 2.02 (3H, s), 2.37 (3H, s), 4.00-4.17 (2H, m), 4.85-4.50 (1H, m), 6.57 (1H, d, J=3.0 Hz), 7.02 (1H, d, J=3.0 Hz), 7.05-7.20 (3H, m).

Example 100

4-(1-Ethylpropoxy)-1-mesityl-6-methyl-1,6-dihydro-7H-pyrrolo[2,3-d]pyridazin-7-one

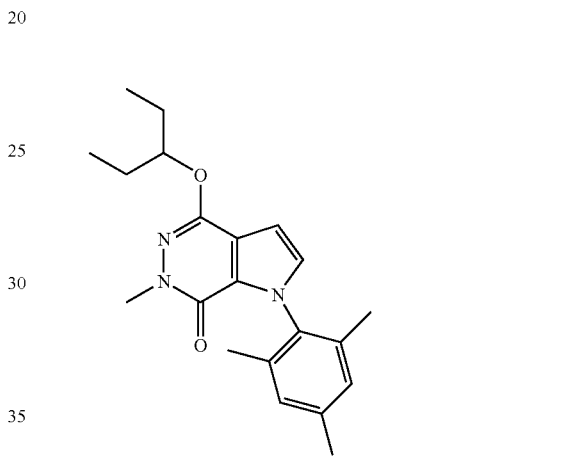

Ethyl 3-cyano-1-mesityl-1H-pyrrole-2-carboxylate

A mixture of diethyl 3,6-dicyano-2,7-hydroxyocta-2,4,6-trienedioate (10 g, 32.7 mmol), 2,4,6-trimethylaniline (9.10 ml, 65.3 mmol) and toluene (50 ml) was heated under reflux for 5 hours. After cooling, the mixture was purified by silica gel chromatography eluting with hexane/ethyl acetate (10:1) to give 3.10 g (92%) of the title compound as an oil.

LC/MS: 283 (MH$^+$).

$^1$H NMR (CDCl$_3$) δ: 1.27 (3H, t, J=7.2 Hz), 1.91 (6H, s), 2.33 (3H, s), 4.23 (2H, q, J=7.2 Hz), 6.70-6.80 (2H, m), 6.95 (2H, s).

1-Mesityl-1H-pyrrole-2,3-dicarboxylic acid

A mixture of ethyl 3-cyano-1-mesityl-1H-pyrrole-2-carboxylate (4.2 g, 14.9 mmol), 2.5N aqueous sodium hydroxide (23.8 ml, 59.5 mmol) was heated under reflux for 48 hours. After cooling, insoluble materials were removed through celite, the solution was acidified by 5N hydrochloric acid and extracted with ethyl acetate (50 ml×2). The extracts were combined, washed with water, dried over magnesium sulfate and concentrated in vacuo. The residue was crystallized form hexane-diethylether to give 2.56 g (63%) of the title compound.

mp 235-240° C. (dec.)
$^1$H NMR (CDCl$_3$) δ: 1.89 (6H, s), 2.32 (3H, s), 6.69 (1H, d, J=3.0 Hz), 6.93 (2H, s), 6.98 (1H, d, J=3.0 Hz).

Diethyl 1-mesityl-1H-pyrrole-2,3-dicarboxylate

A mixture of 1-mesityl-1H-pyrrole-2,3-dicarboxylic acid (3.23 g, 11.8 mmol), ethyl iodide (3.78 ml, 47.3 mmol), potassium carbonate (6.56 g, 47.3 mmol) and DMF (20 ml) was stirred at room temperature for 24 hours. The mixture was diluted with water (150 ml) and extracted with ethyl acetate (150 ml). The extract was washed with water, dried over magnesium sulfate and concentrated in vacuo. The residue was purified by silica gel chromatography eluting with hexane/ethyl acetate (5:1) to give 2.35 g (93%) of the title compound as an oil.
$^1$H NMR (CDCl$_3$) δ: 1.06 (3H, t, J=7.0 Hz), 1.36 (3H, t, J=7.0 Hz), 1.96 (6H, s), 2.31 (3H, s), 4.10 (2H, q, J=7.0 Hz), 4.31 (2H, q, J=7.0 Hz), 6.65 (1H, d, J=2.7 Hz), 6.70 (1H, d, J=2.7 Hz), 6.90 (2H, s).

1-Mesityl-5,6-dihydro-1H-pyrrolo[2,3-d]pyridazine-4,7-dione

A mixture of diethyl 1-mesityl-1H-pyrrole-2,3-dicarboxylate (3.4 g, 10.3 mmol), hydrazine monohydrate (2.0 ml, 41.3 mmol) and ethanol (20 ml) was heated under reflux for 48 hours. The mixture was acidified by addition of 5N hydrochloric acid and stirred at 80° C. for 20 min. After cooling, the crystals were collected by filtration to give 2.60 g (94%) of the title compound.
mp >300° C.

4,7-Dichloro-1-mesityl-1H-pyrrolo[2,3-d]pyridazine

A mixture of 1-Mesityl-5,6-dihydro-1H-pyrrolo[2,3-d]pyridazine-4,7-dione (2.50 g, 9.28 mmol) and phosphorous oxychloride (15 ml) was heated at 80° C. for 2 hours. The mixture was concentrated in vacuo, neutralized with saturated aqueous hydrogen bicarbonate and extracted with ethyl acetate (100 ml). The extract was washed with water, dried over magnesium sulfate and concentrated in vacuo. The residue was purified by silica gel chromatography eluting with dichloromethane/ethyl acetate (10:1) to give 2.82 g (99%) of the title compound.
mp 169-170° C.
$^1$H NMR (CDCl$_3$) δ: 1.87 (6H, s), 2.39 (3H, s), 6.91 (1H, d, J=3.0 Hz), 7.01 (2H, s), 7.28 (1H, d, J=3.0 Hz).

4-Chloro-1-mesityl-1,6-dihydro-7H-pyrrolo[2,3-d]pyridazin-7-one (A) and 7-chloro-1-mesityl-1,5-dihydro-4H-pyrrolo[2,3-d]pyridazin-4-one (B)

A mixture of 4,7-dichloro-1-mesityl-1H-pyrrolo[2,3-d]pyridazine (2.6 g, 8.5 mmol), 8N aqueous sodium hydroxide (21.2 ml, 170 mmol), dioxane (10 ml) and dimethyl sulfoxide (20 ml) was heated under reflux for 5 hours. The mixture was cooled, diluted with water (200 ml) and extracted with ethyl acetate (200 ml). The extract was washed with saturated aqueous sodium bicarbonate, dried over magnesium sulfate and concentrated in vacuo. The residue was purified by silica gel chromatography eluting with dichloromethane/ethyl acetate (10:1-1:1) to give 0.68 g (28%) of compound (A) as a first fraction and 1.97 g (53%) of compound (B) as a second fraction.

Compound (A):
mp 219-223° C.
$^1$H NMR (CDCl$_3$) δ: 1.93 (6H, s), 2.35 (3H, s), 6.68 (1H, d, J=3.0 Hz), 6.97 (2H, s), 7.07 (1H, d, J=3.0 Hz), 9.99 (1H, brs).

Compound (B):
mp 269-271° C.
$^1$H NMR (CDCl$_3$) δ: 1.92 (6H, s), 2.37 (3H, s), 6.98 (2H, s), 7.01 (1H, d, J=3.0 Hz), 7.10 (1H, d, J=3.0 Hz), 10.51 (1H, brs).

4-Chloro-1-mesityl-6-methyl-1,6-dihydro-7H-pyrrolo[2,3-d]pyridazin-7-one

A mixture of 4-chloro-1-mesityl-1,6-dihydro-7H-pyrrolo[2,3-d]pyridazin-7-one (0.43 g, 1.5 mmol), MeI (0.103 ml, 1.65 mmol), potassium carbonate (0.41 g, 3.0 mmol) and DMF (5 ml) was stirred at room temperature for 19 hours. The mixture was diluted with water (50 ml) and extracted with ethyl acetate (50 ml). The extract was washed with water, dried over magnesium sulfate and concentrated in vacuo. The residue was purified by silica gel chromatography eluting with hexane/ethyl acetate (3:1) to give 0.38 g (98%) of the title compound as crystals.
mp 170-171° C.
$^1$H NMR (CDCl$_3$) δ: 1.92 (6H, s), 2.34 (3H, s), 3.73 (3H, s), 6.64 (1H, d, J=3.0 Hz), 6.97 (2H, s), 7.05 (1H, d, J=3.0 Hz).

4-(1-Ethylpropoxy)-1-mesityl-6-methyl-1,6-dihydro-7H-pyrrolo[2,3-d]pyridazin-7-one To a solution of 3-pentanol (0.093 ml, 0.86 mmol) in DMF (2 ml) was added sodium hydride (60% in oil, 34 mg, 0.86 mmol). The mixture was stirred for 10 min before addition of 4-chloro-1-mesityl-6-methyl-1,6-dihydro-7H-pyrrolo[2,3-d]pyridazin-7-one (64.8 mg, 0.20 mmol). The mixture was stirred at 60° C. for 1.5 hours, then diluted with water (50 ml) and extracted with ethyl acetate (50 ml). The extract was washed with water, dried over magnesium sulfate and concentrated in vacuo. The residue was purified by silica gel chromatography eluting with hexane/ethyl acetate (10:1) to give 52 mg (69%) of the title compound as crystals.
mp 87-88° C.
$^1$H NMR (CDCl$_3$) δ: 1.00 (6H, t, J=7.2 Hz), 1.70-1.85 (4H, m), 1.93 (6H, s), 2.33 (3H, s), 3.61 (3H, s), 4.80-4.95 (1H, m), 6.60 (1H, d, J=3.0 Hz), 6.94 (1H, d, J=3.0 Hz), 6.94 (2H, s).

Example 101

4-Isopropoxy-1-mesityl-6-methyl-1,6-dihydro-7H-pyrrolo[2,3-d]pyridazin-7-one

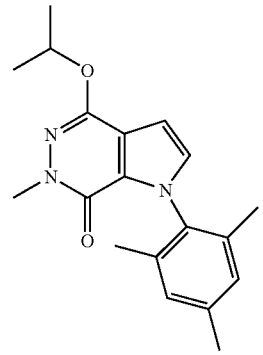

To a solution of 2-propanol (0.026 ml, 0.60 mmol) in DMF (1 ml) was added sodium hydride (60% in oil, 24 mg, 0.60 mmol). The mixture was stirred for 10 min before addition of 4-chloro-1-mesityl-6-methyl-1,6-dihydro-7H-pyrrolo[2,3-d]pyridazin-7-one (45.3 mg, 0.15 mmol). The mixture was stirred at 60° C. for 1 hour, then diluted with water (30 ml) and extracted with ethyl acetate (50 ml). The extract was washed with water, dried over magnesium sulfate and concentrated in vacuo. The residue was purified by silica gel chromatography eluting with hexane/ethyl acetate (5:1) to give 28.3 mg (58%) of the title compound as crystals.

mp 108-111° C.

$^1$H NMR (CDCl$_3$) δ: 1.42 (6H, d, J=6.0 Hz), 1.92 (6H, s), 2.33 (3H, s), 3.62 (3H, s), 5.10-5.25 (1H, m), 6.59 (1H, d, J=3.0 Hz), 6.94 (1H, d, J=3.0 Hz), 6.94 (2H, s).

Example 102

1-Mesityl-6-methyl-4-(1-phenylpropoxy)-1,6-dihydro-7H-pyrrolo[2,3-d]pyridazin-7-one

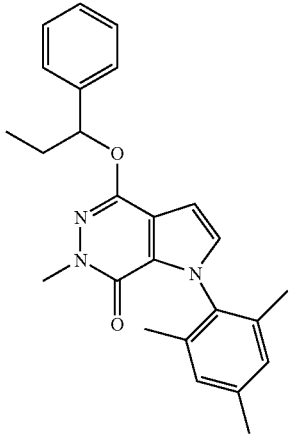

To a solution of 1-phenyl-1-propanol (0.061 ml, 0.45 mmol) in DMF (1 ml) was added sodium hydride (60% in oil, 18 mg, 0.45 mmol). The mixture was stirred for 10 min before addition of 4-chloro-1-mesityl-6-methyl-1,6-dihydro-7H-pyrrolo[2,3-d]pyridazin-7-one (45.3 mg, 0.15 mmol). The mixture was stirred at 60° C. for 1 hour, then diluted with water (30 ml) and extracted with ethyl acetate (50 ml). The extract was washed with water, dried over magnesium sulfate and concentrated in vacuo. The residue was purified by silica gel chromatography eluting with hexane/ethyl acetate (5:1) to give 49.4 mg (82%) of the title compound as an oil.

$^1$H NMR (CDCl$_3$) δ: 1.00 (3H, d, J=7.4 Hz), 1.88 (3H, s), 1.92 (3H, s), 1.95-2.20 (2H, m), 2.31 (3H, s), 3.53 (3H, s), 5.80 (1H, t, J=6.9 Hz), 6.67 (1H, d, J=3.0 Hz), 6.93 (2H, s), 6.95 (1H, d, J=3.0 Hz), 7.20-7.40 (3H, m), 7.40-7.50 (2H, m).

Example 103

1-Mesityl-6-methyl-4-[[4-(trifluoromethyl)benzyl]oxy]-1,6-dihydro-7H-pyrrolo[2,3-d]pyridazin-7-one

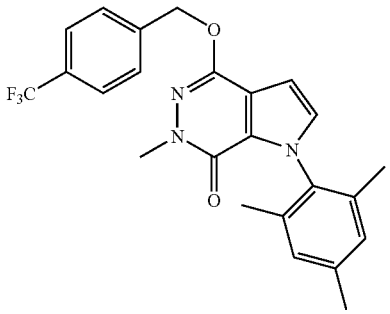

To a solution of 4-(trifluoromethyl)benzyl alcohol (0.062 ml, 0.45 mmol) in DMF (1 ml) was added sodium hydride (60% in oil, 18 mg, 0.45 mmol). The mixture was stirred for 10 min before addition of 4-chloro-1-mesityl-6-methyl-1,6-dihydro-7H-pyrrolo[2,3-d]pyridazin-7-one (45.3 mg, 0.15 mmol). The mixture was stirred at 60° C. for 1 hour, then diluted with water (30 ml) and extracted with ethyl acetate (50 ml). The extract was washed with water, dried over magnesium sulfate and concentrated in vacuo. The residue was purified by silica gel chromatography eluting with hexane/ethyl acetate (5:1) to give 16 mg (24%) of the title compound as crystals.

mp 178-180° C.

$^1$H NMR (CDCl$_3$) δ: 1.92 (6H, s), 2.33 (3H, s), 3.64 (3H, s), 5.40 (2H, s), 6.64 (1H, d, J=2.7 Hz), 6.95 (2H, s), 6.98 (1H, d, J=2.7 Hz), 7.60-7.75 (4H, m).

Example 104

1-Mesityl-4-(propylamino)-1,6-dihydro-7H-pyrrolo[2,3-d]pyridazin-7-one

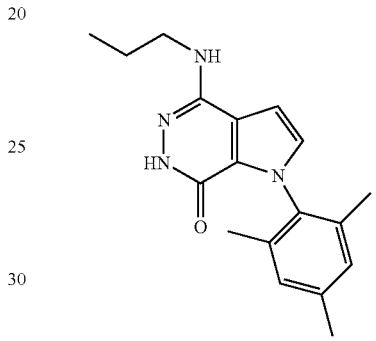

4-Amino-1-mesityl-1,6-dihydro-7H-pyrrolo[2,3-d]pyridazin-7-one

A mixture of ethyl 3-cyano-1-mesityl-1H-pyrrole-2-carboxylate (0.5 g, 1.77 mmol), hydrazine monohydrate (0.86 ml, 17.7 mmol) and ethanol (20 ml) was heated under reflux for 2 days. During the reaction, additional hydrazine monohydrate (0.86 ml×2) was added. The mixture was diluted with water (50 ml) and extracted with ethyl acetate (50 ml×2). The extracts were combined, washed with water, dried over magnesium sulfate and concentrated in vacuo. The residue was purified by silica gel chromatography eluting with dichloromethane/ethyl acetate (3:1-1:1) to give 297 mg (63%) of the title compound as crystals.

mp 290-292° C.

$^1$H NMR (CDCl$_3$) δ: 1.94 (6H, s), 2.34 (3H, s), 4.40-4.60 (2H, br), 6.51 (1H, d, J=3.0 Hz), 6.95 (2H, s), 6.99 (1H, d, J=3.0 Hz), 9.40-9.70 (1H, br).

1-Mesityl-4-(propylamino)-1,6-dihydro-7H-pyrrolo[2,3-d]pyridazin-7-one

A mixture of 4-amino-1-mesityl-1,6-dihydro-7H-pyrrolo[2,3-d]pyridazin-7-one (50 mg, 0.19 mmol), propionaldehyde (0.034 ml, 0.47 mmol), AcOH (0.013 ml, 0.224 mmol) and dichloromethane (10 ml) was stirred for 30 min before addition of NaBH(OAc)$_3$ (99 mg, 0-47 mmol). The mixture was stirred for 3 hours, then washed with saturated sodium bicarbonate (20 ml), dried over magnesium sulfate and concentrated in vacuo. The residue was purified by silica gel chromatography eluting with hexane/ethyl acetate (1:1-1:2) to give 19.4 mg (34%) of the title compound as crystals.

mp >300° C. (dec.).

$^1$H NMR (CDCl$_3$) δ: 1.04 (3H, t, J=7.2 Hz), 1.65-1.80 (2H, m), 1.93 (6H, s), 2.33 (3H, s), 3.30-3.40 (2H, m), 4.10-4.20 (1H, br), 6.47 (1H, d, J=3.0 Hz), 6.95 (2H, s), 6.97 (1H, d, J=3.0 Hz), 8.80 (1H, brs).

Example 105

1-Mesityl-6-methyl-4-[methyl(propyl)amino]-1,6-dihydro-7H-pyrrolo[2,3-d]pyridazin-7-one

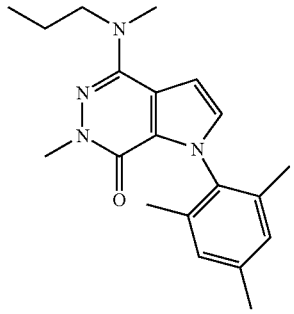

A mixture of 1-mesityl-4-(propylamino)-1,6-dihydro-7H-pyrrolo[2,3-d]pyridazin-7-one (29.8 mg, 0.092 mmol), methyl iodide (0.011 ml, 0.18 mmol), potassium carbonate (25.4 mg, 0.18 mmol) and DMF (1 ml) was stirred at 60° C. for 4 hours. The mixture was diluted with water (30 ml) and extracted with ethyl acetate (30 ml). The extract was washed with water, dried over magnesium sulfate and concentrated in vacuo. A mixture of the residue, methyl iodide (0.1 ml), sodium hydride (60% in oil, 8 mg, 0.2 mmol) and DMF (2 ml) was stirred room temperature for 3 hours. The mixture was diluted with water (30 ml) and extracted with ethyl acetate (30 ml). The extract was washed with water, dried over magnesium sulfate and concentrated in vacuo. The residue was purified by silica gel chromatography eluting with hexane/ethyl acetate (10:1-5:1) to give 6.5 mg (20%) of the title compound as crystals.

mp 105-108° C.

$^1$H NMR (CDCl$_3$) δ: 0.99 (3H, t, J=7.4 Hz), 1.70-1.85 (2H, m), 1.92 (6H, s), 2.32 (3H, s), 3.02 (3H, s), 3.39 (2H, t, J=7.4 Hz), 3.63 (3H, s), 6.58 (1H, d, J=3.0 Hz), 6.94 (2H, s), 6.95 (1H, d, J=3.0 Hz).

Example 106

4-Dipropylamino-1-mesityl-6-methyl-1,6-dihydro-7H-pyrrolo[2,3-d]pyridazin-7-one (A) and 1-mesityl-6-methyl-4-propylamino-1,6-dihydro-7H-pyrrolo[2,3-d]pyridazin-7-one (B)

(A)

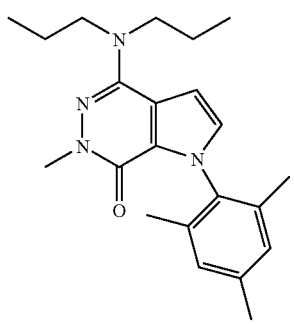

-continued (B)

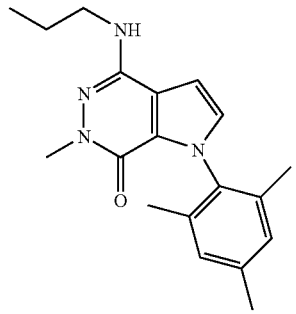

4-Amino-1-mesityl-6-methyl-1,6-dihydro-7H-pyrrolo[2,3-d]pyridazin-7-one

To an ice-cooled solution of 4-amino-1-mesityl-1,6-dihydro-7H-pyrrolo[2,3-d]pyridazin-7-one (268 mg, 1.0 mmol) in DMF (3 ml) was added sodium hydride (60% in oil, 44 mg, 1.1 mmol) and the mixture was stirred for 10 minutes. Methyl iodide (0.081 ml, 1.3 mmol) added and the mixture was stirred at room temperature for 1 hour. Additional sodium hydride (60% in oil, 44 mg, 1.1 mmol) and methyl iodide (0.081 ml, 1.3 mmol) were added and the mixture was stirred for 1 hour. The resulting mixture was diluted with water (30 ml) and extracted with ethyl acetate (30 ml×2). The extracts were combined, washed with water, dried over magnesium sulfate and concentrated in vacuo. The residue was subjected to silica gel column chromatography eluting with hexane/ethyl acetate (1:1-2:3) to give 140 mg (50%) of the title compound as crystals.

mp 254-256° C.

$^1$H-NMR (CDCl$_3$) δ: 1.93 (6H, s), 2.33 (3H, s), 3.61 (3H, s), 4.20 (2H, brs), 6.47 (1H, d, J=3.0 Hz), 6.95 (2H, s), 6.98 (1H, d, J=3.0 Hz).

4-Dipropylamino-1-mesityl-6-methyl-1,6-dihydro-7H-pyrrolo[2,3-d]pyridazin-7-one (A) and 1-mesityl-6-methyl-4-propylamino-1,6-dihydro-7H-pyrrolo[2,3-d]pyridazin-7-one (B)

To a solution of 4-amino-1-mesityl-6-methyl-1,6-dihydro-7H-pyrrolo[2,3-d]pyridazin-7-one (56.5 mg, 0.20 mmol) in DMF (1 ml) were added sodium hydride (24 mg, 60% in oil, 0.60 mmol) and 1-iodopropane (0.059 ml, 0.60 mmol). The mixture was stirred at 80° C. for 15 hours, then diluted with water (30 ml) and extracted with ethyl acetate (50 ml). The extract was washed with water, dried over magnesium sulfate and concentrated in vacuo. The residue was purified by silica gel column chromatography eluting with hexane/ethyl acetate (5:1-3:2) to give firstly, 12.8 mg (17%) of the compound (A) as an oil. From the second fraction, 44.5 mg (69%) of compound (B) was obtained as crystals.

Compound (A):

LC/MS: 367 (MH$^+$).

$^1$H-NMR (CDCl$_3$) δ: 0.96 (6H, t, J=7.5 Hz), 1.60-1.80 (4H, m), 1.93 (6H, s), 2.32 (3H, s), 3.30-3.45 (4H, m), 3.60 (3H, s), 6.53 (1H, d, J=3.0 Hz), 6.93 (1H, d, J=3.0 Hz), 6.94 (2H, s).

Compound (B):

LC/MS: 325 (MH$^+$).

mp 197-199° C.

$^1$H-NMR (CDCl$_3$) δ: 1.05 (6H, t, J=7.5 Hz), 1.65-1.80 (2H, m), 1.92 (6H, s), 2.32 (3H, s), 3.30-3.40 (2H, m), 3.62 (3H, s), 4.06 (1H, brs), 6.42 (1H, d, J=3.0 Hz), 6.94 (2H, s), 6.94 (1H, d, J=3.0 Hz).

Example 107

1-Mesityl-4-(3-pentylamino)-1,6-dihydro-7H-pyrrolo[2,3-d]pyridazin-7-one

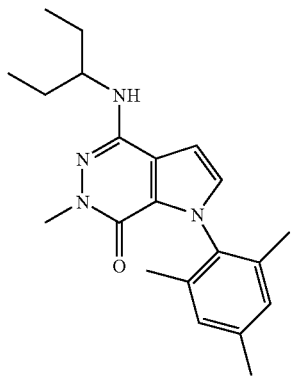

To a solution of 4-amino-1-mesityl-6-methyl-1,6-dihydro-7H-pyrrolo[2,3-d]pyridazin-7-one (113 mg, 0.40 mmol) in DMF (1 ml) were added sodium hydride (60% in oil, 48 mg, 1.20 mmol) and 3-bromopentane (0.15 ml, 1.20 mmol). The mixture was stirred at 80° C. for 15 hours, then diluted with water (30 ml) and extracted with ethyl acetate (50 ml). The extract was washed with water, dried over magnesium sulfate and concentrated in vacuo. The residue was purified by silica gel column chromatography eluting with hexane/ethyl acetate (5:1) to give 35 mg (25%) of the title compound as crystals.

mp 183-185° C.
$^1$H NMR (CDCl$_3$) δ: 0.99 (6H, t, J=7.4 Hz), 1.50-1.80 (4H, m), 1.93 (6H, s), 2.32 (3H, s), 3.60 (3H, s), 3.75-3.90 (2H, m), 6.42 (1H, d, J=3.0 Hz), 6.93 (1H, d, J=3.0 Hz), 6.94 (2H, brs).

Example 108

1-Benzyl-5-(2,4-dimethylphenyl)-3-methylcinnolin-4(1H)-one

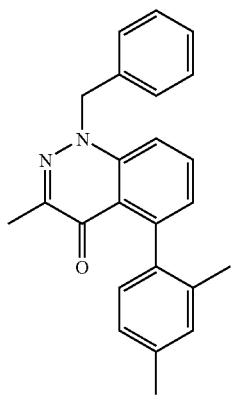

Methyl 3-(2-chloro-6-fluorophenyl)-3-oxopropionate

To 7.4 g (77.7 mmol) of magnesium chloride and 9.02 g (116.1 mmol) of methyl acetoacetate was added 30 mL acetonitrile. The mixture was cooled in an ice bath and 12.6 mL (155.4 mmol) of pyridine was slowly added while keeping the temperature below 5° C. The reaction was removed from the ice bath and was stirred for 30 min. at room temperature. A solution of 15.0 g (77.7 mmol) 2-chloro-6-fluorobenzoyl chloride in 20 mL toluene was added to the reaction and the mixture was subsequently refluxed for four hours. The reaction was then cooled to room temperature and carefully treated with 6.5 mL (98.1 mmol) of concentrated sulfuric acid. The reaction was diluted with water and the layers were separated. The aqueous layer was extracted with dichloromethane and the combined organic layers were dried over sodium sulfate and concentrated to a residue. The residue was purified by flash chromatography eluting with 15% ethyl acetate/hexanes mixture to give 14.0 g (78%) of the title compound as a reddish-pink oil.

$^1$H NMR (CDCl$_3$) δ: 3.74 (s, 2.0H), 3.82 (s, 1.0H), 3.92 (s, 1.4H), 5.32 (s, 0.3H), 7.04-7.09 (m, 1H), 7.23-7.33 (m, 1H), 7.34-7.39 (m, 1H), 12.21 (s, 0.3H).

Methyl 3-(2-chloro-6-fluorophenyl)-2-diazo-3-oxopropionate

To a solution of 5.80 g (25.1 mmol) of methyl 3-(2-chloro-6-fluorophenyl)-3-oxopropionate in 60 mL acetonitrile was added 3.9 mL (28 mmol) of triethylamine followed by 3.05 g (25.2 mmol) of methanesulfonyl azide. The mixture was stirred at room temperature for 18 h and concentrated by rotary evaporation. The resulting solid mass was washed with ethyl acetate/hexanes and the washings were filtered through a plug of silica gel. The filtrate was concentrated to give 4.90 g (76%) of the title compound as a light yellow solid.

$^1$H NMR (CDCl$_3$) δ: 3.75 (s, 3H), 7.04 (t, J=8.6 Hz, 1H), 7.21-7.26 (m, 1H), 7.32-7.38 (m, 1H). $^{19}$F NMR (CDCl$_3$) δ: −114.31 (s, 1F).

Methyl 3-(2-chloro-6-fluorophenyl)-2-hydrazono-3-oxopropionate

To 4.90 g (19.1 m=ol) of methyl 3-(2-chloro-6-fluorophenyl)-2-diazo-3-oxopropionate in 100 mL of diisopropyl ether was added 5.2 mL (21 mmol) of tributylphosphine. The bright yellow phosphazine adduct that precipitated from solution after 30 min. was collected, dissolved in dichloromethane and concentrated onto silica gel. The hydrazone product was eluted with a 75% hexanes/ethyl acetate mixture to give 3.14 g of the title compound as an off-white solid. The filtrate from the adduct formation was similarly loaded onto silica gel and eluted to give an additional 1.04 g of the title compound. An overall isolated yield of 4.18 g (85%) of the title compound as a 10:1 mixture of hydrazone isomers was obtained.

$^1$H NMR (DMSO-d$_6$) δ: 3.82 (s, 3H), 7.24-7.31 (m, 1H), 7.33-7.41 (m, 1H), 7.43-7.48 (m, 1H), 10.65 (br s, 1H), 10.83 (br s, 1H).

$^{19}$F NMR (CDCl$_3$) δ: −115.64 (t, J=97 Hz, 1F).

Methyl 5-chloro-4-oxo-1,4-dihydrocinnoline-3-carboxylate

A mixture of 4.2 g (16 mmol) of methyl 3-(2-chloro-6-fluorophenyl)-2-hydrazono-3-oxopropionate in 12 mL of triglyme was heated to 140° C. for 48 h. The slurry was then cooled to room temperature and the precipitate was collected by filtration. The precipitate was washed with diisopropyl ether and dried in vacuo to give 2.55 g (66%) of the title compound as a tan powder.

$^1$H NMR (DMSO-d$_6$) δ: 3.83 (s, 3H), 7.47-7.50 (m, 1H), 7.57-7.61 (m, 1H), 7.72-7.78 (m, 1H), 13.87 (s, 1H).

Methyl 1 benzyl-5-chloro-4oxo-1,4-dihydrocinnoline-3-carboxylate

To 1.00 g (4.2 mmol) of methyl 5-chloro-4-oxo-1,4-dihydrocinnoline-3-carboxylate and 0.86 g (5.0 mmol) of benzyl bromide in 30 mL of dimethylformamide was added 0.20 g (5.0 mmol) of sodium hydride (60% dispersion in mineral oil). The mixture was stirred for 4 h at room temperature and quenched with water. The mixture was extracted with ethyl acetate and the combined organic layers were washed with brine, dried over sodium sulfate, filtered and concentrated onto silica gel. The crude material was purified by flash chromatography eluting with a 33-50% ethyl acetate/hexanes gradient mixture to give 0.86 g (62%) of the title compound as a light yellow solid.

$^1$H NMR (CDCl$_3$) δ: 3.99 (s, 3H), 5.64 (s, 2H), 7.22 (d, J=7.4 Hz, 2H), 7.28-7.37 (m, 5H), 7.44-7.49 (m, 1H).

MS Calcd.: 328. Found: 329 (M+H).

1-Benzyl-5-chloro-3-hydroxymethylcinnolin-4(1H)-one

To 0.80 g (2.4 mmol) of methyl 1-benzyl-5-chloro-4-oxo-1,4-dihydrocinnoline-3-carboxylate in 50 mL of tetrahydrofuran at −78° C. was added 7.3 mL (7.3 mmol) of DIBAL (1M in tetrahydrofuran). The mixture was allowed to warm to room temperature and stirred for 6 h. The reaction was quenched with 1N HCl and concentrated to a slurry. The slurry was dissolved in dichloromethane and was concentrated onto silica gel. The crude material was purified by flash chromatography eluting with a 4% methanol/dichloromethane mixture to give 0.44 g (60%) of the title compound as a light yellow powder.

$^1$H NMR (CDCl$_3$) δ: 3.43 (t, J=6.3 Hz, 1H), 4.82 (d, J=6.5 Hz, 2H), 5.60 (s, 2H), 7.20 (d, J=7.5 Hz, 1H), 7.27 (d, J=8.6 Hz, 1H), 7.37-7.37 (m, 5H), 7.46 (t, J=7.8 Hz, 1H).

1-Benzyl-5-chloro-3-chloromethylcinnolin-4(1H)-one

To 0.42 g (1.4 mmol) of 1-benzyl-5-chloro-3-hydroxymethylcinnolin-4(1H)-one in 25 mL of dichloromethane at 0° C. was added 0.97 mL (7.0 mmol) of triethylamine and 0.33 mL (4.2 mmol) of methanesulfonyl chloride. The reaction was allowed to warm to room temperature and stirred for 5 h. The reaction was concentrated by rotary evaporation and was subsequently dissolved in dichloromethane and concentrated onto silica gel. The crude material was purified by flash chromatography eluting with a 33-50% ethyl acetate/hexanes gradient mixture to give 0.26 g (59%) of the title compound as an off-white solid.

$^1$H NMR (DMSO-d$_6$) δ: 4.74 (s, 2H), 5.73 (s, 2H), 7.27-7.37 (m, 5H), 7.47-7.50 (m, 1H), 7.67-7.72 (m, 2H).

MS Calcd.: 300. Found: 301 (M+H).

1-Benzyl-5-chloro-3-methylcinnolin-4(1H)-one

To 0.170 g (0.53 mmol) of 1-benzyl-5-chloro-3-chloromethylcinnolin-4(1H)-one in 6 mL of dimethylsulfoxide was added 0.050 g (1.3 mmol) of sodium borohydride. The reaction was stirred at room temperature for 3 h and diluted with water. The resulting precipitate was collected and dried to give 0.140 g (92%) of the title compound as a fluffy cream colored solid.

$^1$H NMR (DMSO-d$_6$) δ: 2.29 (s, 3H), 5.66 (s, 2H), 7.24-7.38 (m, 6H), 7.56-7.64 (m, 2H).

MS Calcd.: 284. Found: 285 (M+H).

1-Benzyl-5-(2,4-dimethylphenyl)-3-methylcinnolin-4(1H)-one

To 0.115 g (0.40 mmol) of 1-benzyl-5-chloro-3-methylcinnolin-4(1H)-one, 0.12 g (0.81 mmol) of cesium fluoride and 0.093 g (0.08 mmol) of tetrakis(triphenylphosphine)palladium(0) was added 4 mL of dimethoxyethane. The dark brown mixture was stirred at room temperature for 15 min. then 0.079 g (0.53 mmol) of 2,4-dimethylphenylboronic acid was added. This mixture was then heated to reflux for 5 h, cooled to room temperature, diluted with ethyl acetate and filtered through a plug of silica gel. The resulting filtrate was concentrated and the residue was purified by flash chromatography eluting with a 17% ethyl acetate/hexanes mixture to give 0.102 g (71%) of the title compound as a light yellow solid.

$^1$H NMR (DMSO-d$_6$) δ: 1.96 (s, 3H), 2.32 (s, 3H), 2.38 (s, 3H), 5.60 (s, 2H), 6.93-7.07 (m, 4H), 7.26-7.38 (m, 4H), 7.54 (d, J=8.2 Hz, 1H).

MS Calcd.: 354. Found: 355 (M+H).

Example 110

5-(2,4-Dimethylphenyl)-3-methyl-1-(1-propylbutyl)cinnolin-4(1H)-one

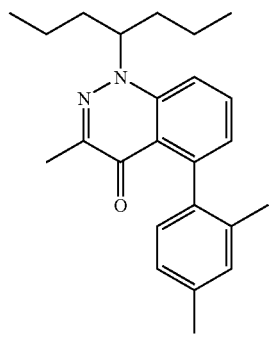

5-(2,4-Dimethylphenyl)-3-methylcinnolin-4(1H)-one

To 0.122 g (0.34 mmol) of 1-benzyl-5-(2,4-dimethylphenyl)-3-methylcinnolin-4(1H)-one and 0.14 g (0.10 mmol Pd) of 10% Pearlman's catalyst was added 4 mL of ethanol and two drops of concentrated HCl. The reaction vessel was charged with hydrogen via a balloon and stirred at room temperature for 3 h. The catalyst was removed by filtration, the filtrate was concentrated and the residue was purified by flash chromatography eluting with a 33% ethyl acetate/hexanes mixture to give 0.047 g (52%) of product as a white solid.

$^1$H NMR (DMSO-d$_6$) δ: 1.85 (s, 3H), 2.11 (s, 3H), 2.32 (s, 3H), 6.84-6.98 (m, 4H), 7.52 (d, J=8.6 Hz, 1H), 7.71 (t, J=8.6 Hz, 1H), 13.09 (s, 1H).

MS Calcd.: 264. Found: 265 (M+H).

5-(2,4-Dimethylphenyl)-3-methyl-1-(1-propylbutyl)cinnolin-4(1H)-one

To 0.041 g (0.16 mmol) of 5-(2,4-dimethylphenyl)-3-methylcinnolin-4(1H)-one in 0.5 mL of N-methylpyrrolidine was added 0.069 mL of 4-bromoheptane and 0.012 g (0.31 mmol) of sodium hydride (60% dispersion in mineral oil). The mixture was stirred for 75 min. at room temperature and quenched with water. The mixture was extracted with ethyl acetate and the combined organics were washed with water and brine, dried over sodium sulfate, filtered and concentrated. The residue was purified by flash chromatography eluting with a 8% ethyl acetate/hexanes mixture to give 0.042 g (75%) of the title compound as a light green-yellow semisolid.

$^1$H NMR (DMSO-d$_6$) δ: 0.83 (t, J=7.3 Hz, 6H), 1.07-1.09 (m, 2H), 1.16-1.24 (m, 2H), 1.72-1.73 (m, 2H), 1.83 (s, 3H), 1.93-1.96 (m, 2H), 2.14 (s, 3H), 2.32 (s, 3H), 5.01 (br s, 1H), 6.84 (d, J=7.6 Hz, 1H), 6.93-6.98 (m, 3H), 7.75 (t, J=8.4 Hz, 1H), 8.00 (d, J=8.8 Hz, 1H).

MS Calcd.: 362. Found: 363 (M+H).

Example 111

5-(2,4-Dimethylphenyl)-3-ethyl-1-(1-propylbutyl)cinnolin-4(1H)-one

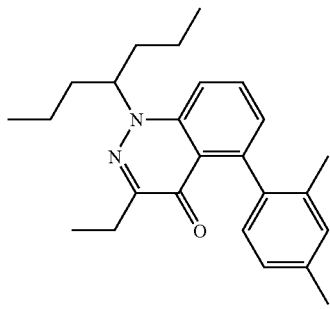

1-Benzyl-5-(2,4-dimethylphenyl)-4-oxo-1,4-dihydrocinnoline-3-carbaldehyde

To 0.20 g (0.54 mmol) of 1-benzyl-5-(2,4-dimethylphenyl)-3-(hydroxymethyl)cinnolin-4(1H)-one in 10 mL of dichloromethane was added 0.28 g (0.65 mmol) of Dess-Martin periodinane. The reaction was stirred at room temperature for 90 min before being diluted with sodium bicarbonate solution and extracted with dichloromethane. The combined organic layers were washed with brine, dried over sodium sulfate, filtered, concentrated in vacuo and purified by flash chromatography eluting with a 33% ethyl acetate/hexanes mixture to give 0.17 g (85%) of the title compound as a yellow powder.

$^1$H NMR (CDCl$_3$) δ: 1.98 (3H, s), 2.39 (3H, s), 5.78 (2H, s), 6.93 (1H, d, J=7.4 Hz), 7.05 (1H, d, J=7.8 Hz), 7.09 (1H, s), 7.19 (1H, d, J=7.2 Hz), 7.30-7.41 (5H, m), 7.53 (1H, d, J=8.6 Hz), 7.67 (1H, t, J=8.4 Hz), 10.33 (1H, s).

MS Calcd.: 368. Found: 369 (M+H).

1-Benzyl-5-(2,4-dimethylphenyl)-3-vinylcinnolin-4(1H)-one

To a slurry of 0.081 g (0.72 mmol) of potassium tert-butoxide in 10 mL of ether was added 0.22 g (0.60 mmol) of methyl triphenylphosphonium bromide. The resulting ylide solution was stirred for 30 min then 0.11 g (0.30 mmol) of 1-benzyl-5-(2,4-dimethylphenyl)-4-oxo-1,4-dihydrocinnoline-3-carbaldehyde was added. The reaction mixture was stirred for 3 h, diluted with water and extracted with ethyl acetate. The combined organic layers were washed with brine, dried over sodium sulfate, filtered, concentrated in vacuo and purified by flash chromatography eluting with a 9% ethyl acetate/hexanes mixture to give 0.035 g (32%) of the title compound as a light yellow solid.

$^1$H NMR (CDCl$_3$) δ: 1.97 (3H, s), 2.38 (3H, s), 5.40 (1H, dd, J=1.8, 11.3 Hz), 5.66 (2H, s), 6.32 (1H, dd, J=1.8, 17.8 Hz), 6.94 (1H, d, J=7.6 Hz), 7.01-7.12 (4H, m), 7.28-7.39 (6H, m), 7.55 (1H, t, J=8.8 Hz).

5-(2,4-Dimethylphenyl)-3-ethylcinnolin-4(1H)-one

Prepared from 1-benzyl-5-(2,4-dimethylphenyl)-3-vinylcinnolin-4(1H)-one according to the method described in Example 108 in 100% isolated yield.

$^1$H NMR (CDCl$_3$) δ: 1.18 (3H, t, J=7.2 Hz), 1.99 (3H, s), 2.27 (3H, s), 2.67-2.83 (2H, m), 6.97-7.03 (4H, m), 7.22 (1H, d, J=8.4 Hz), 7.58 (1H, t, J=7.6 Hz), 10.99 (1H, br s).

5-(2,4-Dimethylphenyl)-3-ethyl-1-(1-propylbutyl)cinnolin-4(1H)-one

Prepared from 5-(2,4-dimethylphenyl)-3-ethylcinnolin-4(1H)-one according to the method described in Example 109 in 38% isolated yield.

$^1$H NMR (CDCl$_3$) δ: 0.84-0.93 (6H, m), 1.16-1.34 (7H, m), 1.72-1.83 (2H, m), 1.96 (3H, s), 2.04-2.16 (2H, m), 2.37 (3H, s), 2.74 (2H, q, J=7.6 Hz), 4.69-4.75 (1H, m), 6.96-7.06 (4H, m), 7.54-7.64 (2H, m).

MS Calcd.: 376. Found: 377 (M+H).

Example 112

5-Mesityl-3-methyl-1-(1-propylbutyl)cinnolin-4(1H)-one

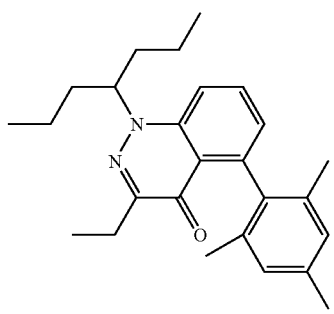

1-Benzyl-3-(hydroxymethyl)-5-mesitylcinnolin-4(1H)-one

A mixture of 0.144 g (0.479 mmol) of 1-benzyl-5-chloro-3-(hydroxymethyl)cinnolin-4(1H)-one, 0.126 g (0.766 mmol) of mesityl boronic acid, 0.111 g (0.096 mmol) of tetrakis and 0.254 g (1.20 mmol) of potassium phosphate in 8 mL of DMF was heated to 100° C. for 16 h. The reaction mixture was quenched with water and extracted with ethyl acetate containing 5% hexanes. The combined organic layers were washed with brine, dried over sodium sulfate, filtered through a plug of silica gel and concentrated in vacuo onto silica gel. The crude material was purified by flash chromatography eluting with a 25% ethyl acetate/hexanes mixture to give 0.087 g (47%) of the title compound as a tan solid.

MS Calcd.: 384. Found: 385 (M+H).

1-Benzyl-3-(chloromethyl)-5-mesitylcinnolin-4(1H)-one

Prepared from 1-benzyl-3-(hydroxymethyl)-5-mesitylcinnolin-4 (1H)-one according to the method described in Example 108 in 57% isolated yield.

$^1$H NMR (CDCl$_3$) δ: 1.85 (6H, s), 2.34 (3H, s), 4.66 (2H, s), 5.64 (2H, s), 6.93 (2H, s), 7.03 (1H, d, J=7.0 Hz), 7.30-7.40 (6H, m), 7.62 (1H, t, J=7.6 Hz).

MS Calcd.: 402. Found: 403 (M+H).

1-Benzyl-5-mesityl-3-methylcinnolin-4(1H)-one

Prepared from 1-benzyl-3-(chloromethyl)-5-mesitylcinnolin-4(1H)-one according to the method described in Example 108 in 77% isolated yield.

MS Calcd.: 368. Found: 369 (M+H).

5-Mesityl-3-methylcinnolin-4(1H)-one

Prepared from 1-benzyl-5-mesityl-3-methylcinnolin-4 (1H)-one according to the method described in Example 108 in 91% isolated yield.

$^1$H NMR (CDCl$_3$) δ: 1.88 (6H, s), 2.27 (3H, s), 2.33 (3H, s), 6.93 (2H, s), 6.98 (1H, d, J=7.2 Hz), 7.28 (1H, s), 7.67 (1H, t, J=8.2 Hz), 9.78 (1H, br s).

MS Calcd.: 278. Found: 279 (M+H).

5-Mesityl-3-methyl-1-(1-propylbutyl)cinnolin-4(1H)-one

Prepared from 5-mesityl-3-methylcinnolin-4(1H)-one according to the method described in Example 109 in 34% isolated yield.

$^1$H NMR (DMSO-d$_6$) δ: 0.83 (6H, t, J=7.2 Hz), 1.02-1.16 (2H, m), 1.18-1.30 (2H, m), 1.72 (8H, br s), 1.90-2.00 (2H, m), 2.14 (3H, s), 2.27 (3H, s), 5.01 (1H, br s), 6.82 (2H, s), 6.87 (1H, d, J=7.0 Hz), 7.78 (1H, t, J=8.8 Hz), 7.99 (1H, d, J=8.8 Hz). MS Calcd.: 376. Found: 377 (M+H).

The following compounds were prepared in an analogous manner.

| Example | Structure | Name | Physical Data |
|---|---|---|---|
| 113 | 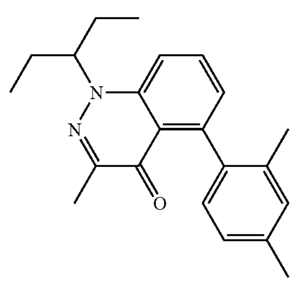 | 5-(2,4-dimethylphenyl)-1-(1-ethylpropyl)-3-methylcinnolin-4(1H)-one | $^1$H NMR (DMSO-d$_6$) δ: 0.75 (6H, t, J=7.2 Hz), 1.83 (3H, s), 1.89-2.03 (2H, m), 2.15 (3H, s), 2.32 (3H, s), 4.87 (1H, br s), 6.85 (1H, d, J=7.4 Hz), 6.94-6.98 (3H, m), 7.75 (1H, t, J=8.8 Hz), 8.00 (1H, d, J=9.0 Hz). MS Calcd.: 334; Found: 335 (M + H). |
| 114 | 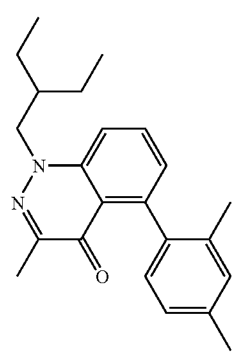 | 5-(2,4-dimethylphenyl)-1-(2-ethylbutyl)-3-methylcinnolin-4(1H)-one | $^1$H NMR (DMSO-d$_6$) δ: 0.86-0.89 (6H, m), 1.27-1.36 (4H, m), 1.83 (3H, s), 1.94-2.01 (1H, m), 2.12 (3H, s), 2.32 (3H, s), 4.28-4.40 (2H, m), 6.84 (1H, d, J=7.6 Hz), 6.94-6.98 (3H, m), 7.71-7.81 (2H, m). MS Calcd.: 348; Found: 349 (M + H). |

| Example | Structure | Name | Physical Data |
|---|---|---|---|
| 115 | 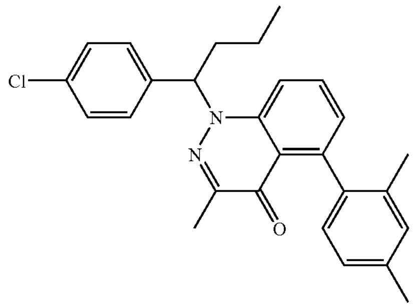 | 1-[1-(4-chlorophenyl)butyl]-5-(2,4-dimethylphenyl)-3-methylcinnolin-4(1H)-one | $^1$H NMR (DMSO-$d_6$) δ: 0.97 (3H, q, J=7.4 Hz), 1.26 (3H, s), 1.91 (1H, s), 1.97 (1H, s), 2.13-2.20 (1H, m), 2.33 (3H, s), 2.37 (3H, s), 2.50-2.61 (1H, m), 5.59 (1H, br s), 6.87-6.94 (1H, m), 7.00-7.06 (3H, m), 7.30-7.37 (4H, m), 7.47 (1H, t, J=9.2 Hz), 7.52-7.60 (1H, m). MS Calcd.: 430; Found: 431 (M + H). |
| 116 | 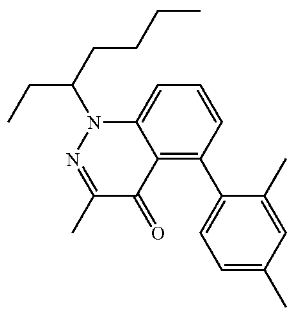 | 5-(2,4-dimethylphenyl)-1-(1-ethylpentyl)-3-methylcinnolin-4(1H)-one | MS Calcd.: 362; Found: 363 (M + H). |
| 117 | 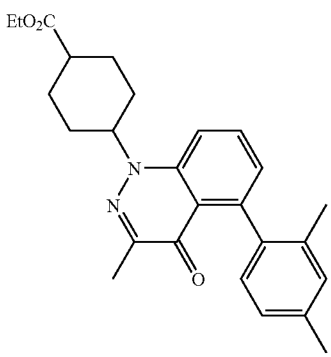 | ethyl 4-[5-(2,4-dimethylphenyl)-3-methyl-4-oxocinnolin-1(4H)-yl]cyclohexanecarboxylate | $^1$H NMR (DMSO-$d_6$) δ: 1.19-1.23 (5H, m), 1.67-2.10 (6H, m), 1.83 (3H, s), 2.12 (3H, s), 2.32 (3H, s), 2.42 (1H, t, J=11.9 Hz), 4.10 (2H, q, J=7.0 Hz), 4.84 (1H, br s), 6.82 (1H, d, J=7.6 Hz), 6.93-6.98 (3H, m), 7.77 (1H, t, J=8.8 Hz), 7.97 (1H, d, J=9.2 Hz). MS Calcd.: 418; Found: 419 (M + H). |

Example 118

1-(2,4-Dimethylphenyl)-4-(heptan-4-yl)-7-oxo-4,7-dihydro-1H-imidazo[4,5-b]pyridine-6-carboxylic acid

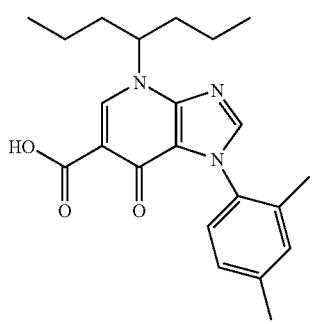

Ethyl 1-(2,4-dimethylphenyl)-1H-imidazole-5-carboxylate

To 10 g (83 mmol) of 2,4-dimethylaniline in 200 mL of methanol was added 80 mL (50% solution in toluene, 410 mmol) of ethyl gyloxalate. The mixture was heated to 70° C. for 7 h and then allowed to stand at room temperature overnight. The reaction was concentrated in vacuo, dissolved in dichloromethane and concentrated onto silica gel. The product was eluted with a 93-100% ethyl acetate/hexanes gradient mixture to give 8.0 g (47%) of ethyl 2-(2,4-dimethylphenylimino)acetate as an oil containing approximately 20% starting aniline by LCMS analysis. This material was used without further purification. MS Calcd.: 205. Found: 206 (M+H). To 7.2 g (35 mmol) of ethyl 2-(2,4-dimethylphenylimino)acetate, 11 g (56 mmol) of tosylmethylisocyanide and 9.7 g (70 mmol) of potassium carbonate was added 200 mL of a 2:1 ethanol:1,2-dimethoxyethane mixture. The resulting slurry was heated to 90° C. for 1 h. The cooled mixture was diluted with 300 mL of ethyl acetate and filtered through GFF paper. The resulting filter cake was washed with an additional 500 mL of ethyl acetate and the resulting filtrate was added to the previous filtrate. The combined filtrates were then concentrated in vacuo to give a brown semisolid. The crude material thus obtained was then purified by flash chromatography eluting with a 45% ethyl acetate/hexanes mixture to give 4.3 g (62%) of the title compound as a tan solid.

$^1$H NMR (CDCl$_3$) δ: 1.22 (3H, q, J=7.2 Hz), 2.00 (3H, s), 2.39 (3H, s), 4.18 (2H, q, J=7.2 Hz), 7.05-7.10 (2H, m), 7.14 (1H, s), 7.56 (1H, s), 7.86 (1H, s).

Ethyl 4-bromo-1-(2,4-dimethylphenyl)-1H-imidazole-5-carboxylate

To 5.0 g (21 mmol) of ethyl 1-(2,4-dimethylphenyl)-1H-imidazole-5-carboxylate in 40 mL of DMF was added 7.3 g (41 mmol) of N-bromosuccinimide and the resulting solution was heated to 75° C. for 75 min. The reaction was cooled to room temperature, diluted with 400 mL of water and extracted with ethyl acetate. The combined extracts were washed with water and brine, dried over sodium sulfate, filtered and the resulting filtrate was concentrated to an oil. The oil was purified by flash chromatography eluting with a 17-20% ethyl acetate/hexanes gradient mixture to give 1.89 g (29%) of the title compound as a light yellow solid.

$^1$H NMR (CDCl$_3$) δ: 1.16 (3H, q, J=7.2 Hz), 2.02 (3H, s), 2.39 (3H, s), 4.17 (2H, q, J=7.0 Hz), 7.06 (2H, q, J=7.8 Hz), 7.13 (1H, s), 7.45 (1H, s) MS Calcd.: 322. Found: 323 (M+H).

4-Bromo-1-(2,4-dimethylphenyl)-1H-imidazole-5-carboxylic acid

To 1.88 g (5.8 mmol) of ethyl 4-bromo-1-(2,4-dimethylphenyl)-1H-imidazole-5-carboxylate in 30 mL of ethanol was added 3.0 mL (18 mmol) of 6N KOH and the resulting mixture was stirred for 3 h at room temperature. Volatiles were removed in vacuo, the residue was diluted with water, washed with ether and acidified with 1N HCl. The resulting precipitate was collected by filtration and dried to give 1.54 g (90%) of the title compound as a white powder.

$^1$H NMR (DMSO-d$_6$) δ: 1.95 (3H, s), 2.34 (3H, s), 7.10 (1H, d, J=7.8 Hz), 7.16 (1H, s), 7.18 (1H, s), 7.91 (1H, d, J=1.4 Hz), 13.04 (br s, 1H).

4-Bromo-1-(2,4-dimethylphenyl)-1H-imidazole-5-carbonyl chloride hydrochloride

To 8 mL of thionyl chloride was added 1.2 g (3.9 mmol) of 4-bromo-1-(2,4-dimethylphenyl)-1H-imidazole-5-carboxylic acid and 2 drops of DMF. The solution was heated to 75° C. for 4 h. The resulting slurry was cooled to room temperature and the white precipitate was collected by filtration. The precipitate was then slurried in ethyl acetate, collected by filtration and dried to give 0.81 g of the title compound as a white solid. The original filtrate was also concentrated and slurried in ethyl acetate to give an additional 0.21 g of the title compound. The overall yield of the title compound was 1.02 g (74%).

$^1$H NMR (DMSO-d$_6$) δ: 1.95 (3H, s), 2.34 (3H, s), 7.10 (1H, d, J=8.0 Hz), 7.16 (1H, s), 7.18 (1H, s), 7.92 (1H, s).

Ethyl 3-[4-bromo-1-(2,4-dimethylphenyl)-1H-imidazol-5-yl]-3-oxopropanoate

To 1.6 mL (14 mmol) of mono-ethyl malonate in 35 mL of THF at 0° C. was added 9.3 mL (28 mmol) of 3.0 M methyl magnesium bromide (ether solution). The dianion solution was stirred for 30 min before adding 1.2 g (3.5 mmol) of 4-bromo-1-(2,4-dimethylphenyl)-1H-imidazole-5-carbonyl chloride hydrochloride in 50 mL of THF dropwise. The cooling bath was then removed and the mixture was allowed to stir at room temperature for 3 h. The reaction was quenched by pouring onto ice and was extracted with ethyl acetate after neutralizing to pH 7 with saturated ammonium chloride. The combined extracts were washed with brine, dried over sodium sulfate, filtered and the resulting filtrate was concentrated to an oil. The oil was purified by flash chromatography eluting with a 25% ethyl acetate/hexanes mixture to give 1.2 g (94%) of the title compound as a viscous golden oil.

MS Calcd.: 364. Found: 335 (M−OEt).

Ethyl 2-[4-bromo-1-(2,4-dimethylphenyl)-1H-imidazole-5-carbonyl]-3-(heptan-4-ylamino)acrylate To 1.20 g (3.3 mmol) of ethyl 3-[4-bromo-1-(2,4-dimethylphenyl)-1H-imidazol-5-yl]-3-oxopropanoate in 1.5 mL of triethylorthoformate was added 0.68 mL (7.2 mmol) of acetic anhydride. The solution was heated to 120° C. for 90 min, cooled to room temperature and concentrated in vacuo. The crude ethoxymethylene oxobutanoate was then dissolved in 35 mL of ethanol, cooled to 0° C., treated with 0.59 mL (3.9 mmol) of 4-aminoheptane and stirred at 0° C. for 1 h. The reaction mixture was concentrated in vacuo to a thick golden oil. The crude oil was purified by flash chromatography eluting with a 25-33% ethyl acetate/hexanes gradient mixture to give 0.62 g of the title compound as a white semisolid. Dirty fractions were combined, concentrated and purified to give an additional 0.20 g of the title compound. The overall yield of the title compound was 0.82 g (36%) which was found to be 70% pure by LCMS analysis. This material was used without further purification in the next step.

MS Calcd.: 489. Found: 490 (M+H).

1-(2,4-Dimethylphenyl)-4-(heptan-4-yl)-7-oxo-4,7-dihydro-1H-imidazo[4,5-b]pyridine-6-carboxylic acid To 0.60 g (1.2 mmol) of ethyl 2-[4-bromo-1-(2,4-dimethylphenyl)-1H-imidazole-5-carbonyl]-3-(heptan-4-ylamino)acrylate in 10 mL of NMP was added 0.15 g (3.7 mmol) of sodium hydride (60% dispersion in mineral oil). The mixture was stirred at room temperature for 1 h and subsequently heated to 140° C. for 25 min. The reaction mixture was cooled to room temperature, quenched with 2 mL of saturated ammonium bicarbonate, diluted with ten volumes of water and extracted with ethyl acetate. The combined extracts were washed with water and brine, dried over sodium sulfate, filtered and the resulting filtrate was concentrated to an oil. The oil was purified by flash chromatography eluting with a 3% methanol/dichloromethane mixture to give 0.12 g of the title compound as a light yellow solid. Dirty fractions were combined, concentrated and purified to give an additional 0.15 g of the title compound. The overall yield of the title compound was 0.27 g (57%).

$^1$H NMR (DMSO-d$_6$) δ: 0.86 (6H, t, J=7.4 Hz), 1.07-1.23 (4H, m), 1.86-1.94 (2H, m), 2.00 (3H, s), 2.14-2.18 (2H, m), 2.50 (3H, s), 5.04 (1H, br s), 7.16 (1H, d, J=7.8 Hz), 7.24 (1H, s), 7.35 (1H, d, J=7.8 Hz), 8.50 (1H, s), 8.75 (1H, s).

MS Calcd.: 381. Found: 382 (M+H).

Example 119

1-(2,4-Dimetylphenyl)-4-(heptan-4-yl)-6-(hydroxymethyl)-1H-imidazo[4,5-b]pyridin-7(4H)-one

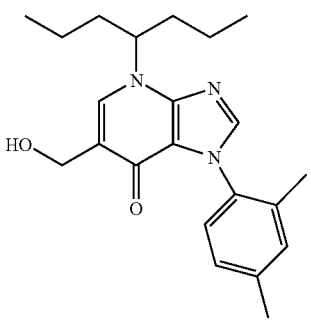

To 0.14 g (0.29 mmol) of 1-(2,4-dimethylphenyl)-4-(heptan-4-yl)-7-oxo-4,7-dihydro-1H-imidazo[4,5-b]pyridine-6-carboxylic acid in 5 mL of THF was added 0.15 mL (1.1 mmol) of triethylamine and 0.10 mL (1.0 mmol) of ethyl chloroformate. The resulting yellow slurry was stirred at room temperature for 40 min. The crude carbonate solution was then added to 0.135 g (3.6 mmol) of sodium borohydride in 5 mL of ethanol at room temperature and the resulting mixture was stirred for 30 min. The reaction was concentrated in vacuo, diluted with water and extracted with chloroform. The combined extracts were washed with brine, dried over sodium sulfate, filtered and the resulting filtrate was concentrated in vacuo. The crude material thus obtained was purified by flash chromatography eluting with a 3% methanol/dichloromethane mixture to give 45 mg of the title compound as a white solid. Dirty fractions were combined, concentrated and purified to give an additional 23 mg of the title compound. The overall yield of the title compound was 68 mg (65%).

$^1$H NMR (DMSO-$d_6$) δ: 0.85 (6H, t, J=7.0 Hz), 1.05-1.23 (4H, m), 1.76-1.84 (2H, m), 1.97 (5H, s), 2.36 (3H, s), 4.33 (2H, d, J=5.5 Hz), 4.81-4.84 (2H, m), 7.10 (1H, d, J=7.8 Hz), 7.17 (1H, s), 7.21 (1H, d, J=7.8 Hz), 7.72 (1H, s), 8.07 (1H, d, J=1.4 Hz).

MS Calcd.: 367. Found: 368 (M+H).

Example 120

1-(2,4-Dimethylphenyl)-4-(heptan-4-yl)-6-methyl-1H-imidazo[4,5-b]pyridin-7(4H)-one To 45 mg (0.12 mmol) of 1-(2,4-dimethylphenyl)-4-(heptan-4-yl)-6-(hydroxymethyl)-1H-imidazo[4,5-b]pyridin-7(4H)-one in 10 mL of dichloromethane was added 0.14 mL (0.98 mmol) of triethylamine and 0.047 mL (0.61 mmol) of methane sulfonyl chloride. The resulting mixture was stirred at room temperature for 24 h, concentrated in vacuo, diluted with water and extracted with ethyl acetate. The combined extracts were washed with brine, dried over sodium sulfate, filtered and the resulting filtrate was concentrated in vacuo. The crude mesylate thus obtained was dissolved in 5 mL of THF, treated with 40 mg (0.18 mmol) of lithium borohydride and heated to 50° C. for 2 h. The reaction was quenched with saturated ammonium chloride, diluted with water and extracted with ethyl acetate. The combined extracts were washed with brine, dried over sodium sulfate, filtered and the resulting filtrate was concentrated in vacuo. The crude material thus obtained was purified by preparative thin layer chromatography eluting with a 5% methanol/dichloromethane mixture to give 11 mg (26%) of the title compound as a light yellow solid.

$^1$H NMR (CDCl$_3$) δ: 0.92 (6H, t, J=7.2 Hz), 1.16-1.43 (4H, m), 1.77-1.96 (4H, m), 2.09 (3H, s), 2.10 (3H, s), 2.38 (3H, s), 4.89 (1H, br s), 7.08 (1H, d, J=8.0 Hz), 7.13 (1H, s), 7.18 (1H, d, J=7.8 Hz), 7.30 (1H, s), 7.59 (1H, d, J=1.4 Hz).

MS Calcd.: 351. Found: 352 (M+H).

Example 121

7-(2,4-dichlorophenyl)-3-(dipropylamino)-2-ethyl-1H-inden-1-one

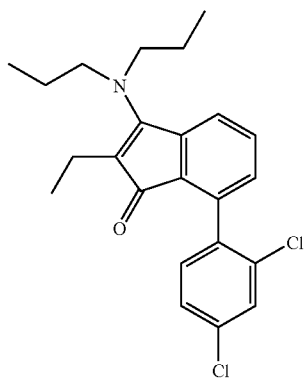

3-oxo-2,3-dihydro-1H-inden-4-yl trifluoromethanesulfonate

A solution of 7-hydroxy-2,3-dihydroinden-1-one (0.50 g 3.4 mmol; prepared as reported by Antkowiak, W. *Tetrahedron*, 1990, 46, 2445-2452) in dichloromethane (10 ml) was cooled to 0° C. Diisopropyethyl amine (1.8 mL, 10.1 mmol) and triflouroacetic anhydride (0.85 mL, 5.1 mmol) were added. The reaction stirred at 0° C. for 20 minutes. The solution was quenched with water, extracted with Ethyl acetate, dried (Na$_2$SO$_4$), and concentrated. Flash chromatography gave the desired product as a brown solid (0.776 g, 82%).

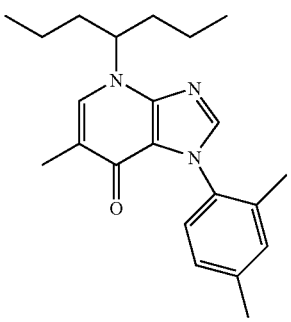

¹H NMR (CDCl₃) δ: 2.77 (t, J=6.4 Hz, 2H), 3.20 (t, J=6.0 Hz, 2H), 7.19, (d, J=8.0 Hz, 1H), 7.51 (d, J=8.0 Hz, 1H), 7.66 (t, J=8.0 Hz, 1H).

MS Calcd.: 280. Found: 281 (M+H).

7-(2,4-dichlorophenyl)-2,3-dihydroinden-1-one

A solution containing 3-oxo-2,3-dihydro-1H-inden-4-yl trifluoromethanesulfonate (0.666 g, 2.38 mmol), 2,4-dichlorobenzeneboronic acid (0.907 g, 4.75 mmol), and potassium carbonate (0.657 g, 4.75 mmol) in toluene (10 mL) stirred at room temperature for 15 minutes. Pd(PPh₃)₄ (1.37 g, 1.19 mmol) was added and the mixture was stirred at 90° C. for 2 hours. The catalyst was removed by filtration and concentrated. Flash chromatography gave the desired product as a brown solid (0.572 g, 87%).

¹H NMR (CDCl₃) δ: 2.65-2.70 (m, 2H), 3.15-3.20 (m, 2H), 7.15-7.17, (m, 2H), 7.28 (dd, J=2.0, 8.0 Hz, 1H), 7.47 (d, 1H), 7.52 (d, J=8.0 Hz, 1H), 7.62 (t, J=7.6 Hz, 1H).

7-(2,4-dichlorophenyl)-2-ethyl-2,3-dihydroinden-1-one 7-(2,4-dichlorophenyl)-2,3-dihydroinden-1-one (0.70 g, 2.53 mmol) was dissolved in 10 mL THF. NaHMDS (2.78 mL, 2.78 mmol, 1M in THF) was added dropwise at 0° C. After stirring for 0.5 hr, iodoethane (1.0 mL, 12.6 mmol) was added. The reaction stirred for 15 minutes and was quenched with water, extracted from Ethyl acetate, dried, and concentrated. Flash chromatography (5% Ethyl acetate/hexanes) gave two UV active compounds. The second eluting compound was the desired mono-alkylated product (0.113 g, 15%).

¹H NMR (CDCl₃) δ: 0.99 (t, J=7.6 Hz, 3H), 1.42-1.62 (m, 2H), 2.52-2.68, (m, 1H), 2.80-2.92 (m, 1H), 3.28-3.40 (m, 1H), 7.12-7.20 (m, 2H), 7.27-7.32 (m, 1H), 7.47 (s, 1H), 7.50 (d, J=7.6 Hz, 1H), 7.62 (t, J=7.6 Hz, 1H).

7-(2,4-dichlorophenyl)-3-(dipropylamino)-2-ethyl-1H-inden-1-one 7-(2,4-dichlorophenyl)-2-ethyl-2,3-dihydroinden-1-one (0.052 g, 0.17 mmol) was dissolved in CCl₄ (4 mL). N-bromosuccinimide (0.064 g, 0.36 mmol) and benzoyl peroxide (0.0083, 0.034) were added. The solution was stirred at 90° C. for 1 hr. The solution was cooled to RT and Et₃N (0.5 mL) was added. The solution stirred for 0.5 hr. and was concentrated. Flash chromatography gave the alkenyl bromide intermediate. This intermediate was re-dissolved in EtOH (4 mL) and dipropylamine was added (0.5 mL). The reaction mixture was stirred at 60° C. for 1.5 hr. The solution was cooled and concentrated. Flash chromatography gave a red oil (0.015 g, 22%).

¹H NMR (CDCl₃) δ: 0.953 (t, J=6.8 Hz, 6H), 1.01 (t, J=7.6 Hz, 3H), 1.68-1.74 (m, 4H), 2.29 (q, J=7.2, 14.4 Hz, 2H), 3.52 (t, J=7.2 Hz, 4H), 7.02 (d, J=7.2 Hz, 1H), 7.21-7.29 (m, 4H), 7.48 (s, 1H). MS Calcd.: 402. Found: 403 (M+H).

Compounds of Examples 122-145 were prepared in a manner similar to that described in Examples 7 and 8.

| Example | Structure | Name | Physical Data |
| --- | --- | --- | --- |
| 122 | 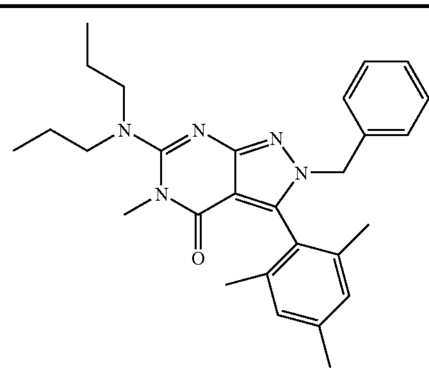 | 2-benzyl-6-(dipropylamino)-3-mesityl-5-methyl-2H-pyrazolo[3,4-d]pyrimidin-4(5H)-one | ¹H NMR (CDCl₃) δ: 0.88 (6H, t, J=7.3 Hz), 1.59-1.64 (4H, m), 1.83 (6H, s), 2.33 (3H, s), 3.13 (4H, t, J=7.6 Hz), 3.40 (3H, s), 5.02 (2H, s), 6.92 (2H, s), 7.08 (2H, d, J=3.4 Hz), 7.19-7.20 (3M, m). MS Calcd.: 357; Found: 358 (M + H). |
| 123 | 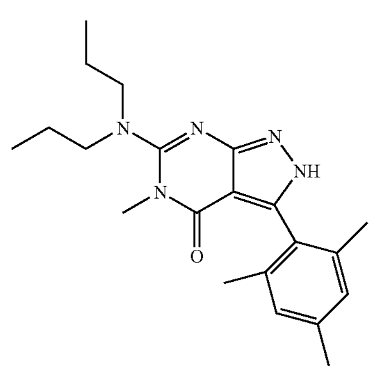 | 6-(dipropylamino)-3-mesityl-5-methyl-2H-pyrazolo[3,4-d]pyrimidin-4(5H)-one | ¹H NMR (CDCl₃) δ: 0.90 (6H, t, J=7.4 Hz), 1.59-1.66 (4H, m), 2.08 (6H, s), 2.29 (3H, s), 3.18 (4H, t, J=7.4 Hz), 3.44 (3H, s), 6.88 (2H, s). MS Calcd.: 367; Found: 368 (M + H). |

| Example | Structure | Name | Physical Data |
|---|---|---|---|
| 124 | 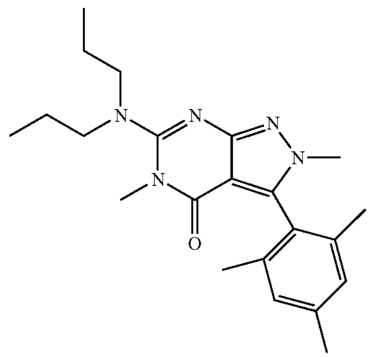 | 6-(dipropylamino)-3-mesityl-2,5-dimethyl-2,5-dihydro-4H-pyrazolo[3,4-d]pyrimidin-4-one | $^1$H NMR (CDCl$_3$) δ: 0.91 (6H, t, J=7.4 Hz), 1.64-1.70 (4H, m), 1.99 (6H, s), 2.32 (3H, s), 3.31 (4H, t, J=7.2 Hz), 3.42 (3H, s), 3.66 (3H, s), 6.96 (2H, s). MS Calcd.: 381; Found: 382 (M + H). |
| 125 | 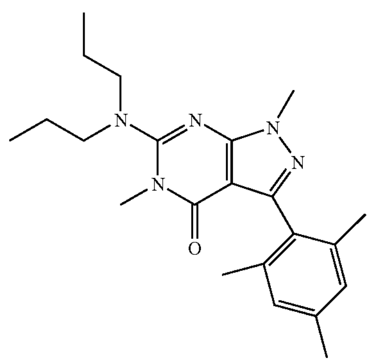 | 6-(dipropylamino)-3-mesityl-1,5-dimethyl-1,5-dihydro-4H-pyrazolo[3,4-d]pyrimidin-4-one | $^1$H NMR (CDCl$_3$) δ: 0.90 (6H, t, J=7.2 Hz), 1.60-1.65 (4H, m), 2.09 (6H, s), 2.29 (3H, s), 3.15-3.18 (4H, m), 3.42 (3H, s), 3.90 (3H, s), 6.89 (2H, s). MS Calcd.: 381; Found: 382 (M + H). |
| 126 | 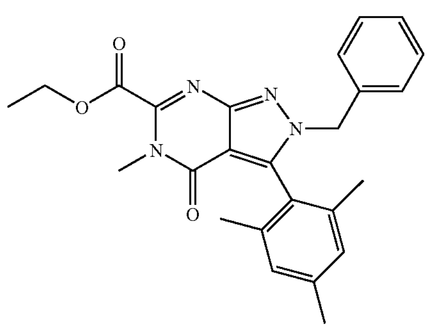 | ethyl 1-(2-benzyl-3-mesityl-5-methyl-4-oxo-4,5-dihydro-2H-pyrazolo[3,4-d]pyrimidin-6-yl)-1,2,3,6-tetrahydropyridine-4-carboxylate | $^1$H NMR (CDCl$_3$) δ: 1.30 (3H, t, J=7.2 Hz), 1.82 (6H, s), 2.33 (3H, s), 2.59 (2H, br s), 3.27 (2H, t, J = 5.4 Hz), 3.42 (3H, s), 4.01 (2H, s), 4.19-4.23 (2H, m), 5.02 (2H, s), 6.93 (2H, s), 7.01 (1H, br s), 7.07-7.08 (2H, m), 7.19-7.24 (3H, m). MS Calcd.: 511; Found: 512 (M + H). |
| 127 | 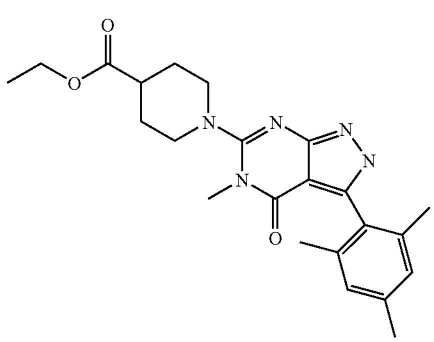 | ethyl 1-(3-mesityl-5-methyl-4-oxo-4,5-dihydro-2H-pyrazolo[3,4-d]pyrimidin-6-yl)piperidine-4-carboxylate | MS Calcd.: 423; Found: 424 (M + H). |

| Example | Structure | Name | Physical Data |
|---|---|---|---|
| 128 | 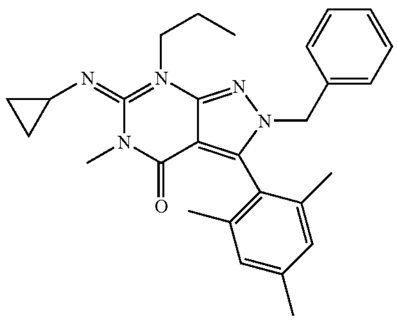 | (6Z)-2-benzyl-6-(cyclopropylimino)-3-mesityl-5-methyl-7-propyl-2,5,6,7-tetrahydro-4H-pyrazolo[3,4-d]pyrimidin-4-one | $^1$H NMR (CDCl$_3$) δ: 0.55 (2H, br s), 0.72-0.74 (2H, m), 0.93 (3H, t, J=7.4 Hz), 1.68-1.73 (2H, m), 1.84 (6H, s), 2.33 (3H, s), 2.83 (1H, br s), 3.27 (2H, t, J=7.4 Hz), 3.43 (3H, s), 5.00 (2H, s), 6.92 (2H, s), 7.09-7.10 (2H, m), 7.19-7.20 (3H, m). MS Calcd.: 455; Found: 456 (M + H). |
| 129 | 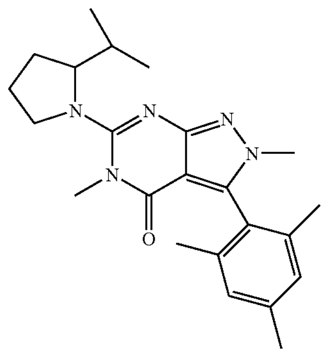 | 6-(2-isopropylpyrrolidin-1-yl)-3-mesityl-2,5-dimethyl-2,5-dihydro-4H-pyrazolo[3,4-d]pyrimidin-4-one | $^1$H NMR (CDCl$_3$) δ: 0.84 (3H, d, J=6.8 Hz), 0.94 (3H, d, J=6.8 Hz), 1.64-1.81 (2H, m), 1.90-1.97 (1H, m), 1.98-2.02 (7H, m), 2.04-2.21 (1H, m), 2.33 (3H, s), 3.20 (1H, t, J=8.4 Hz), 3.41 (3H, s), 3.43-3.50 (1H, m), 3.63 (3H, s), 4.50-4.56 (1H, m), 6.96 (2H, s). MS Calcd.: 393; Found: 394 (M + H). |
| 130 | 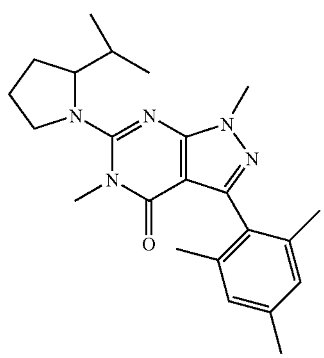 | 6-(2-isopropylpyrrolidin-1-yl)-3-mesityl-1,5-dimethyl-1,5-dihydro-4H-pyrazolo[3,4-d]pyrimidin-4-one | $^1$H NMR (CDCl$_3$) δ: 0.85-0.88 (3H, m), 0.97 (3H, d, J=7.0 Hz), 1.69-1.82 (2H, m), 2.11 (6H, s), 2.17-2.22 (1H, m), 2.28 (3H, s), 3.23-3.28 (1H, m), 3.41 (3H, s), 3.49-3.56 (1H, m), 3.88 (3H, s), 4.44-4.49 (1H, m), 6.88 (2H, s). MS Calcd.: 393; Found: 394 (M + H). |
| 131 | 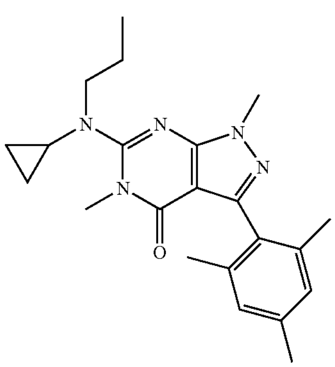 | 6-[cyclopropyl(propyl)amino]-3-mesityl-1,5-dimethyl-1,5-dihydro-4H-pyrazolo[3,4-d]pyrimidin-4-one | $^1$H NMR (CDCl$_3$) δ: 0.58 (2H, br s), 0.77-0.32 (2H, m), 0.97 (3H, t, J = 7.2 Hz), 1.69-1.76 (2H, m), 2.11 (6H, s), 2.29 (3H, s), 2.86-2.88 (1H, m), 3.33 (2H, t, J= 7.4 Hz), 3.48 (3H, s), 3.89 (3H, s), 6.89 (2H, s). MS Calcd.: 379; Found: 380 (M + H). |

-continued

| Example | Structure | Name | Physical Data |
|---|---|---|---|
| 132 | 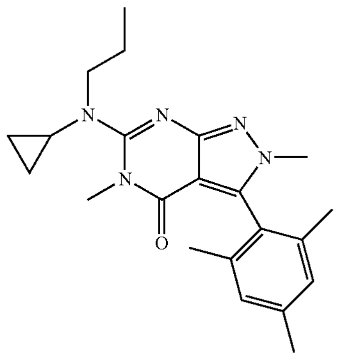 | 6-[cyclopropyl(propyl)amino]-3-mesityl-2,5-dimethyl-2,5-dihydro-4H-pyrazolo[3,4-d]pyrimidin-4-one | $^1$H NMR (CDCl$_3$) δ: 0.56 (2H, br s), 0.73-0.77 (2H, m), 0.94 (3H, t, J=7.4 Hz), 1.69-1.75 (2H, m), 2.01 (6H, s), 2.33 (3H, s), 3.28 (2H, t, J= 7.6 Hz), 3.46 (3H, s), 3.64 (3H, s), 6.96 (2H, s). MS Calcd.: 379; Found: 380 (M + H). |
| 133 | 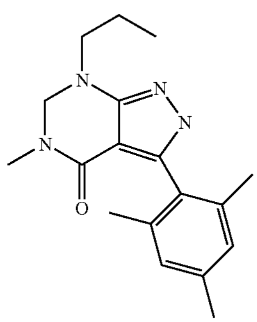 | 3-mesityl-5-methyl-7-propyl-2,5,6,7-tetrahydro-4H-pyrazolo[3,4-d]pyrimidin-4-one | $^1$H NMR (CDCl$_3$) δ: 1.02 (3H, t, J=7.4 Hz), 1.70-1.77 (2H, m), 2.11 (6H, s), 2.28 (3H, s), 2.96 (3H, s), 3.26 (2H, t, J= 7.6 Hz), 4.45 (2H, s), 6.90 (2H, s), 8.93 (1H, br s). MS Calcd.: 312; Found: 313 (M + H). |
| 134 | 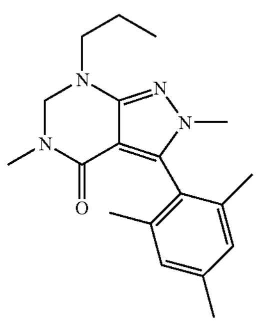 | 3-mesityl-2,5-dimethyl-7-propyl-2,5,6,7-tetrahydro-4H-pyrazolo[3,4-d]pyrimidin-4-one | $^1$H NMR (CDCl$_3$) δ: 1.02 (3H, t, J=7.2 Hz), 1.69-1.76 (2H, m), 2.04 (6H, s), 2.30 (3H, s), 2.94 (3H, s), 3.22-3.26 (2H, m), 3.42 (3H, s), 4.39 (2H, s), 6.92 (2H, s). MS Calcd.: 326; Found: 327 (M + H). |
| 135 | 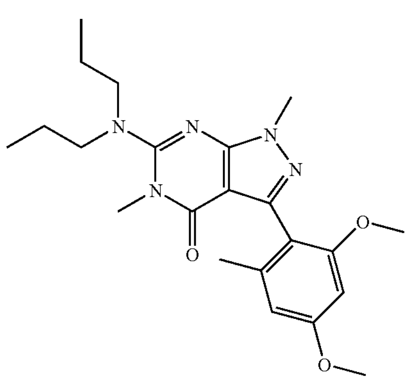 | 3-(2,4-dimethoxy-6-methylphenyl)-6-(dipropylamino)-1,5-dimethyl-1,5-dihydro-4H-pyrazolo[3,4-d]pyrimidin-4-one | $^1$H NMR (CDCl$_3$) δ: 0.89-0.93 (6H, m), 1.62-1.68 (4H, m), 2.16 (3H, s), 3.17 (4H, br s), 3.44 (3H, s), 3.72 (3H, s), 3.82 (3H, s), 3.91 (3H, s), 6.39 (1H, s), 6.42 (1H, s). MS Calcd.: 413; Found: 414 (M + H). |

-continued

| Example | Structure | Name | Physical Data |
|---|---|---|---|
| 136 | 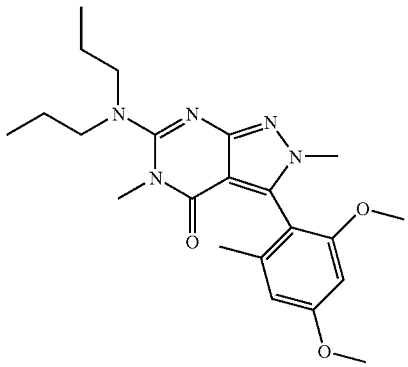 | 3-(2,4-dimethoxy-6-methylphenyl)-6-(dipropylamino)-2,5-dimethyl-2,5-dihydro-4H-pyrazolo[3,4-d]pyrimidin-4-one | $^1$H NMR (CDCl$_3$) δ: 0.89 (6H, t, J=7.2 Hz), 1.58-1.67 (4H, m), 2.13 (3H, s), 3.06-3.20 (4H, m), 3.45 (3H, s), 3.68 (3H, s), 3.71 (3H, s), 3.85 (3H, s), 6.39 (1H, s), 6.48 (1H, s). MS Calcd.: 413; Found: 414 (M + H). |
| 137 | 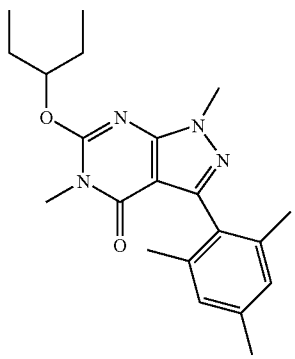 | 6-(1-ethylpropoxy)-3-mesityl-1,5-dimethyl-1,5-dihydro-4H-pyrazolo[3,4-d]pyrimidin-4-one | $^1$H NMR (CDCl$_3$) δ: 1.00 (6H, t, J=7.4 Hz), 1.77-1.84 (4H, m), 2.10 (6H, s), 2.29 (3H, s), 3.38 (3H, d, J=1.2 Hz), 3.90 (3H, d, J=1.2 Hz), 5.20-5.23 (1H, m), 6.89 (2H, s). MS Calcd.: 298; Found: 299 (M + H). |
| 138 | 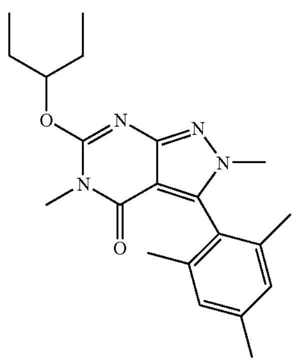 | 6-(1-ethylpropoxy)-3-mesityl-2,5-dimethyl-2,5-dihydro-4H-pyrazolo[3,4-d]pyrimidin-4-one | $^1$H NMR (CDCl$_3$) δ: 0.98 (6H, t, J=7.4 Hz), 1.75-1.82 (4H, m), 2.01 (6H, s), 2.33 (3H, s), 3.37 (3H, s), 3.64 (3H, s), 5.27-5.30 (1H, m), 6.97 (2H, s). MS Calcd.: 298; Found: 299 (M + H). |
| 139 | 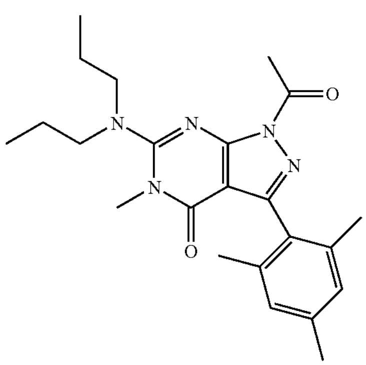 | 1-acetyl-6-(dipropylamino)-3-mesityl-5-methyl-1,5-dihydro-4H-pyrazolo[3,4-d]pyrimidin-4-one | $^1$H NMR (CDCl$_3$) δ: 0.94 (6H, t, J=7.4 Hz), 1.65-1.74 (4H, m), 2.12 (6H, s), 2.30 (3H, s), 2.79 (3H, s), 3.26-3.30 (4H, m), 3.45 (3H, s), 6.91 (2H, s). MS Calcd.: 409; Found: 410 (M + H). |

| Example | Structure | Name | Physical Data |
|---|---|---|---|
| 140 | 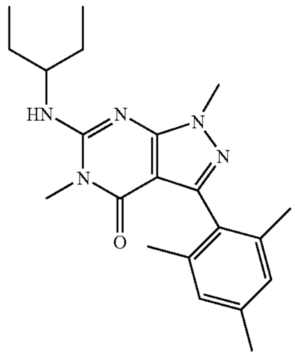 | 6-((1-ethylpropyl)amino)-3-mesityl-1,5-dimethyl-1,5-dihydro-4H-pyrazolo[3,4-d]pyrimidin-4-one | $^1$H NMR (CDCl$_3$) δ: 0.99 (6H, t, J = 7.4 Hz), 1.58-1.65 (2H, m), 1.68-1.77 (2H, m), 2.10 (6H, s), 2.28 (3H, s), 3.36 (3H, s), 3.86 (3H, s), 4.32-4.34 (1H, d, J= 7.8 Hz), 6.88 (2H, s). MS Calcd.: 367; Found: 368 (M + H). |
| 141 | 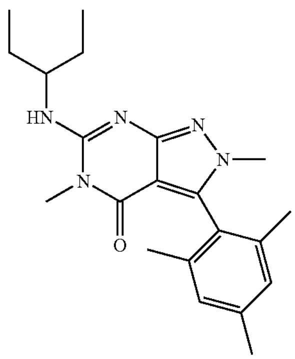 | 6-((1-ethylpropyl)amino)-3-mesityl-2,5-dimethyl-2,5-dihydro-4H-pyrazolo[3,4-d]pyrimidin-4-one | $^1$H NMR (CDCl$_3$) δ: 0.97 (6H, t, J=7.4 Hz), 1.55-1.62 (2H, m), 1.67-1.74 (2H, m), 2.02 (6H, s), 2.33 (3H, s), 3.36 (3H, s), 3.60 (3H, s), 4.21 (2H, br s), 6.96 (2H, s). MS Calcd.: 367; Found: 368 (M + H). |
| 142 | 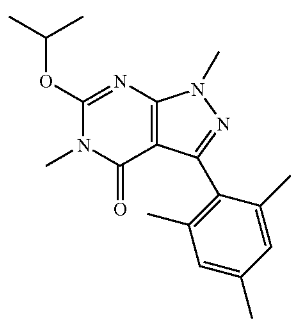 | 6-isopropoxy-3-mesityl-1,5-dimethyl-1,5-dihydro-4H-pyrazolo[3,4-d]pyrimidin-4-one | $^1$H NMR (CDCl$_3$) δ: 1.46 (6H, d, J=6.2 Hz), 2.09 (6H, s), 2.29 (3H, s), 3.36 (3H, s), 3.91 (3H, s), 5.44-5.50 (1H, m), 6.89 (2H, s). MS Calcd.: 340; Found: 341 (M + H). |
| 143 | 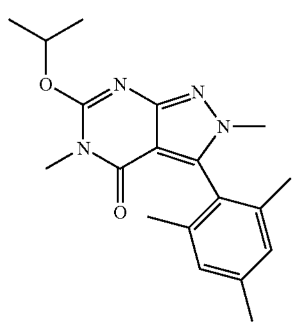 | 6-isopropoxy-3-mesityl-2,5-dimethyl-2,5-dihydro-4H-pyrazolo[3,4-d]pyrimidin-4-one | $^1$H NMR (CDCl$_3$) δ: 1.43 (6H, d, J=6.1 Hz), 2.00 (6H, s), 2.33 (3H, s), 3.35 (3H, s), 3.64 (3H, s), 5.47-5.53 (1H, m), 6.96 (2H, s). MS Calcd.: 340; Found: 341 (M + H). |

-continued

| Example | Structure | Name | Physical Data |
|---------|-----------|------|---------------|
| 144 | 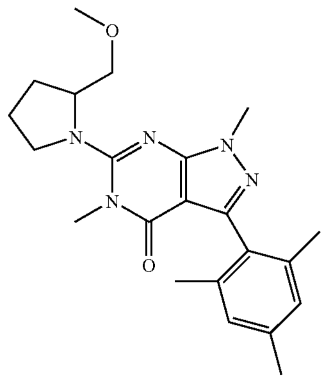 | 3-mesityl-6-[2-(methoxymethyl)pyrrolidin-1-yl]-1,5-dimethyl-1,5-dihydro-4H-pyrazolo[3,4-d]pyrimidin-4-one | MS Calcd.: 395; Found: 396 (M + H). |
| 145 | 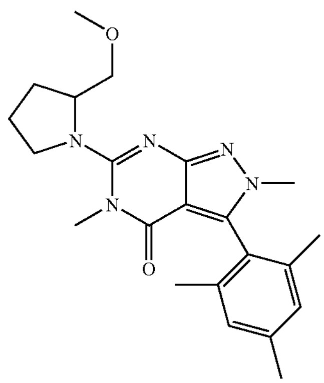 | 3-mesityl-6-[2-(methoxymethyl)pyrrolidin-1-yl]-2,5-dimethyl-2,5-dihydro-4H-pyrazolo[3,4-d]pyrimidin-4-one | MS Calcd.: 395; Found: 396 (M + H). |

Compounds of Examples 146-150 were prepared in a manner similar to that described in Example 21.

| Example | Structure | Name | Physical Data |
|---------|-----------|------|---------------|
| 146 | 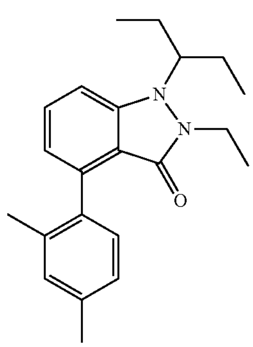 | 4-(2,4-dimethylphenyl)-2-ethyl-1-(1-ethylpropyl)-1,2-dihydro-3H-indazol-3-one | MS Calcd.: 336; MS Found: 337 (M + H) |

| | | | |
|---|---|---|---|
| 147 | 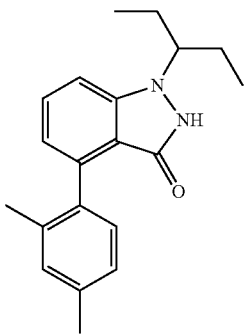 | 4-(2,4-dimethylphenyl)-1-(1-ethylpropyl)-1,2-dihydro-3H-indazol-3-one | $^1$H-NMR (CDCl$_3$) δ: 0.73 (6H, t, J=7.2 Hz), 1.73-1.82 (2H, m), 1.88-2.00 (2H, m), 2.16 (3H, s), 2.39 (3H, s), 4.00-4.13 (1H, m), 6.81 (1H, d, J=6.9 Hz), 7.08 (1H, d, J=7.5 Hz), 7.13 (1H, s), 7.21 (1H, t, J=7.5 Hz), 7.34 (1H, t, J=6.9 Hz), MS Calcd.: 308; Found: 309 (M + H). |
| 148 | 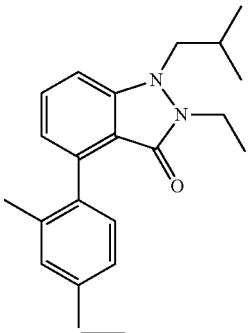 | 4-(2,4-dimethylphenyl)-2-ethyl-1-isobutyl-1,2-dihydro-3H-indazol-3-one | MS Calcd.: 322; MS Found: 323 (M + H) |
| 149 | 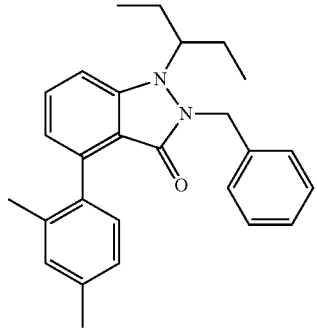 | 2-benzyl-4-(2,4-dimethylphenyl)-1-(1-ethylpropyl)-1,2-dihydro-3H-indazol-3-one | $^1$H-NMR (CDCl$_3$) δ: 0.69 (6H, t, J=7.2 Hz), 1.56-1.69 (4H, m), 2.17 (3H, s), 2.36 (3H, s), 3.55-3.58 (1H, m), 5.07 (2H, d, J=6.2 Hz), 6.92 (1H, d, J=7.2 Hz), 7.06-7.23 (9H, m), 7.46 (1H, t, J=7.2 Hz); MS Calcd.: 398; Found: 399 (M + H). |
| 150 | 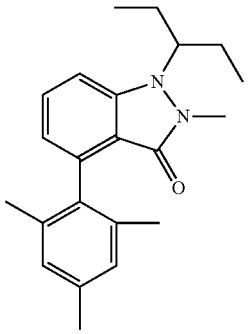 | 1-(1-ethylpropyl)-4-mesityl-2-methyl-1,2-dihydro-3H-indazol-3-one | $^1$H-NMR (CDCl$_3$) δ: 0.90 (6H, t, J=7.2 Hz), 1.65-1.82 (4H, m), 1.95 (3H, s), 2.31 (3H, s), 3.38 (3H, s), 3.65-3.69 (1H, m), 6.83 (1H, d, J=7.2 Hz), 6.92 (2H, s), 7.14 (1H, d, J=7.2 Hz), 7.49 (1H, t, J=7.2 Hz); MS Calcd.: 336; Found: 337 (M + H). |

Example 151

5-(2,4-dimethylphenyl)-4-oxo-1-(1-propylbutyl)-1,4-dihydroquinoline-3-carbonitrile

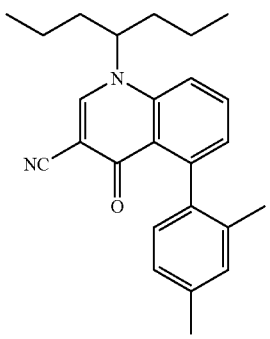

Methyl 2,6-dichlorobenzoate 2,6-Dichlorobenzoic acid (5.00 g, 26.2 mmol) was diluted in dimethylcarbonate (44 mL, 530 mmol). 1,8-Diazabicyclo[5.4.0]undec-7-ene (DBU) (3.91 mL, 26.2 mmol) was added last. The reacted was refluxed for 2 days. Upon cooling, the solution was diluted with ethyl acetate and water. The aqueous layer was removed and the organic layer was washed with water, 2N HCl (2×'s), sat. NaHCO$_3$ (2×'s), and twice with water. The organic layer was dried over sodium sulfate, filtered, and concentrated to yield 4.61 g (86%) of the desired compound as a clear oil.

$^1$H NMR (CDCl$_3$) δ: 4.5 (s, 3H), 7.28-7.38 (m, 3H).

3-(2,6-dichlorophenyl)-3-oxopropanenitrile n-Butyl lithium (20.1 mL, 32.2 mmol, 1.6M in hexanes) was added to THF (30 mL) and the solution was cooled to −78° C. Acetonitrile (1.7 mL, 32 mmol) was added dropwise and the reaction stirred at the temperature for 45 minutes. Methyl 2,6-dichlorobenzoate (1.00 g, 4.88 mmol) was dissolved in 2 mL THF and added to the reaction mixture. The reaction stirred at −78° C. for 0.5 hr. The solution was quenched with methanol and warmed to room temperature. The material was diluted with water and 1N HCl. The solution was then extracted with Ethyl acetate, dried, and concentrated to give 1.08 g of desired product at 85% purity. Material used as is in the next step.

$^1$H-NMR (CDCl$_3$) δ: 4.0 (s, 2H), 7.28-7.40 (m, 3H).

(E)-2-(2,6-dichlorobenzoyl)-3-(1-propylbutylamino)acrylonitrile

A mixture of 3-(2,6-dichlorophenyl)-3-oxopropanenitrile (0.200 g, 0.93 mmol), acetic anhydride (0.22 g, 2.20 mmol), and triethyl orthoformate (0.21 g, 1.40 mmol) was stirred at 150° C. for 1 hr. The solution was then concentrated and the residue redissolved in ethanol (5 mL). 4-heptylamine (0.16 g, 1.4 mmol) in 1 mL of tetrahydrofuran was added to the reaction mixture at 0° C. The reaction stirred for 30 minutes and was then concentrated. Flash chromatography (20% Ethyl acetate/hexanes) gave the desired compound (0.033 g, 10%).

$^1$H NMR (CDCl$_3$) δ: 0.98 (t, 6H), 1.20-1.57 (m, 4H), 1.57-70 (m, 4H), 3.23-3.37 (m, 1H), 7.24-7.35 (m, 3H), 7.47 (d, J=14 Hz, 1H), 10.58 (bs, 1H).

MS Calcd.: 338. Found: 339, 341 (M+H, M+3H).

5-choro-4-oxo-1-(1-propylbutyl)-1,4-dihydroquinoline-3-carbonitrile (E)-2-(2,6-dichlorobenzoyl)-3-(1-propylbutylamino)acrylonitrile (0.020 g, 0.059 mmol) was dissolved in dioxane (2 mL). Sodium hydride (0.007 g, 0.18 mmol, 60% wt. dispersion in mineral oil) was added in one portion. Reaction was heated overnight at 100° C. Solution was cooled and quenched with MeOH and concentrated. Flash chromatography gave the desired product (0.007 g, 40%)

$^1$H NMR (CDCl$_3$) δ: 0.93 (t, J=7.6 Hz, 6H), 1.23-1.35 (m, 4H), 1.75-1.95 (m, 4H), 4.63-4.73 (m, 1H), 7.45-7.57 (m, 3H), 7.97 (s, 1H).

MS Calcd.: 302. Found: 303 (M+H).

5-(2,4-dimethylphenyl)-4-oxo-1-(1-propylbutyl)-1,4-dihydroquinoline-3-carbonitrile 5-Choro-4-oxo-1-(1-propylbutyl)-1,4-dihydroquinoline-3-carbonitrile (0.015 g, 0.05 mmol), 2,4-dimethylbenzeneboronic acid (0.012 g, 0.079 mmol), and PdCl$_2$(PPh$_3$)$_2$ (0.010 g, 0.015 mmol) were suspended in toluene (1 mL). K$_3$PO$_4$ (0.074 mL, 0.15 mmol, 2M in water) was added last. The reaction was stirred at 90° C. with stirring overnight. The mixture was cooled, filtered through GF/F paper and concentrated. Flash chromatography (40% Ethyl acetate/hexanes) gave the desired product (0.009 g, 50%).

$^1$H NMR (CDCl$_3$) δ: 0.929-0.981 (m, 6H), 1.23-1.37 (m, 4H), 1.79-1.93 (m, 4H), 1.96 (s, 3H), 2.37 (s, 3H), 4.73-4.77 (m, 1H), 6.91 (d, J=8.0 Hz, 1H), 7.03 (d, J=8.0 Hz, 1H), 7.05 (s, 1H), 7.17 (d, J=6.8 Hz, 1H), 7.62-7.71 (m, 2H), 7.99 (s, 1H).

MS Calcd.: 372. Found: 373 (M+H).

Example 152

1-Benzyl-5-mesitylquinolin-4(1H)-one

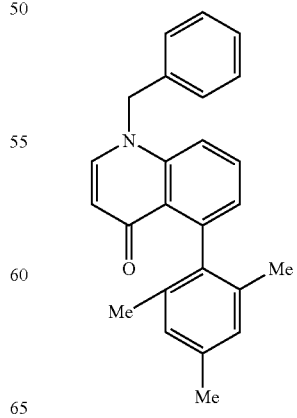

1-Benzyl-5-bromo-4-oxo-1,4-dihydroquinoline-3-carboxylic acid (A) and 1-benzyl-7-bromo-4-oxo-1,4-dihydroquinoline-3-carboxylic acid (B)

3-Bromoaniline (20.0 g, 116 mmol) and diethyl ethoxymethylenemalonate (25.6 g, 118 mmol) were stirred at 75° C. for 3 hr. The solution was cooled and polyphosphate ester (PPE) (150 mL) was added. The reaction stirred at 100° C. for 3 hr upon which LC/MS showed complete cyclization occurred. The solution was completely cooled and water was added to generate a precipitate. After stirring for 3 hr, the solid was filtered, washed with water, and dried under vacuum overnight to obtain 43 g of crude cyclized material. The solid was then suspended in NMP (400 mL), charged with potassium carbonate (40.0 g, 290 mmol), and stirred at 110° C. for 10 minutes. Benzyl bromide (69.0 mL, 580 mmol) was slowly added and the reaction continued to stir at 110° C. until alkylation went to completion. The mixture was then cooled and concentrated. The mixture was diluted with water and extracted with ethyl acetate. The organic layer was then washed with brine, dried over $Na_2SO_4$, and concentrated. The material was filtered through a silica plug (30% ethyl acetate/hexanes) and concentrated to obtain 76 g of the crude isomeric benzylated quinolinones. This material was then diluted in 48% HBr (150 mL) and heated at 115° C. for 2 days. The solution was cooled and poured into a 2 L flask and neutralized with sodium sulfate. The solution was extracted with dichloromethane (4x's), dried over $MgSO_4$, and concentrated to give the title compound acids (A) and (B) (65 g, 94%) as an isomeric mixture (ca. 1:1 ratio).

MS Calcd.: 357. Found: 358, 360 (M+H, M+3H).

1-Benzyl-5-bromoquinolin-4(1H)-one

A mixture (ca. 1:1 ratio) of 1-benzyl-5-bromo-4-oxo-1,4-dihydroquinoline-3-carboxylic acid and 1-benzyl-7-bromo-4-oxo-1,4-dihydroquinoline-3-carboxylic acid (1.22 g, 3.41 mmol), obtained by the procedure shown above, was dissolved in dimethylsulfoxide (10 mL). Potassium cyanide (2.22 g, 34.1 mmol) was added and the reaction was stirred at 120° C. for 4 hr. The solution was cooled, extracted with ethyl acetate, dried over sodium sulfate, and concentrated. Flash chromatography gave 0.154 g (14%) of the title compound.

$^1$H NMR (CDCl$_3$) δ: 5.27 (s, 2H), 6.31 (d, J=8.0 Hz, 1H), 7.12 (d, J=8.0 Hz, 2H), 7.21-7.23 (m, 2H), 7.31-7.37 (m, 3H), 7.52-7.57 (m, 2H). MS Calcd.: 313. Found: 314, 316 (M+H, M+3H).

1-Benzyl-5-mesitylquinolin-4(1H)-one

1-Benzyl-5-bromoquinolin-4(1H)-one (1.52 g, 4.84 mmol), 2,4,6-trimethylphenylboronic acid (1.19 g, 7.26 mmol), 2,8,9-trisobutyl-2,5,8,9-tetraaza-1-phosphabicyclo[3.3.3]undecane (0.331 g, 0.97 mmol), Pd(OAc)$_2$ (0.11 g, 0.48 mmol), and cesium carbonate (3.15 g, 9.68 mmol) were diluted in 25 mL of toluene and stirred for 3 hr. at 80° C. The solution was cooled and concentrated. Flash chromatography of the residue (50-75% Ethyl acetate/hexanes) gave the title compound as a white solid (0.52 g, 30%).

$^1$H NMR (CDCl$_3$) δ: 1.87 (s, 6H), 2.33 (s, 3H), 5.32 (s, 2H), 6.12 (d, J=8.0 Hz, 1H), 6.90 (s, 2H), 6.96 (d, J=6.8 Hz, 1H), 7.21 (d, J=8.4 Hz, 2H), 7.30-7.39 (m, 4H), 7.50-7.55 (m, 2H). MS Calcd.: 353. Found: 354 (M+H).

Example 153

1-Benzyl-3-bromo-5-mesitylquinolin-4(1H)-one

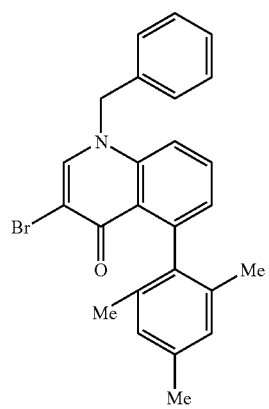

1-Benzyl-5-mesitylquinolin-4(1H)-one (0.52 g, 1.5 mmol) was dissolved in N,N-dimethylformamide (10 mL) and cooled to 0° C. N-bromosuccinimide (0.27 g, 1.5 mmol) was added and the reaction stirred for 1 hr. The reaction was quenched with water (100 mL) and the precipitate was collected by vacuum filtration. 0.57 g (90%) of the title compound was obtained as a yellow solid.

$^1$H NMR (CDCl$_3$) δ: 1.85 (s, 6H), 2.32 (s, 3H), 5.35 (s, 2H), 6.90 (s, 2H), 7.03 (d, J=7.6 Hz, 1H), 7.22 (d, J=8.4 Hz, 2H), 7.33-7.41 (m, 4H), 7.56 (t, J=7.2 Hz, 1H), 8.04 (s, 1H). MS Calcd.: 431. Found: 432, 434 (M+H, M+3H).

Example 154

1-Benzyl-5-mesityl-3-methylquinolin-4(1H)-one

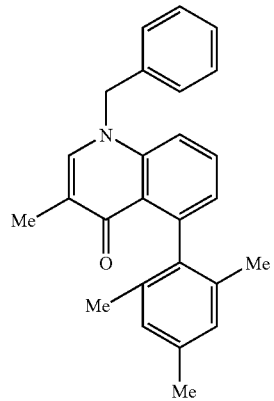

1-Benzyl-3-bromo-5-mesitylquinolin-4(1H)-one (0.277 g, 0.64 mmol), methyl boronic acid (0.384 g, 6.4 mmol), potassium carbonate (0.443 g, 3.2 mmol), and Pd(PPh$_3$)$_4$ (0.37 g, 0.32 mmol) were diluted in dioxane (4 mL). Water (0.11 mL, 6.4 mmol) was added and the reaction stirred at 95°

C. for 22 hr. The solution was then cooled and filtered through GF/F paper and concentrated. Flash chromatography (40% ethyl acetate/hexanes) gave the title compound as a white solid (0.14 g, 60%).

MS Calcd.: 367. Found: 368 (M+H).

Example 155

5-mesityl-3-methyl-1-(1-propylbutyl)quinolin-4(1H)-one (A) and 1-butyl-5-mesityl-3-methylquinolin-4(1H)-one (B)

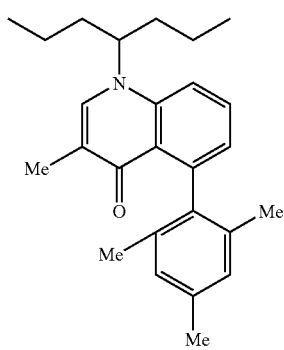
(A)

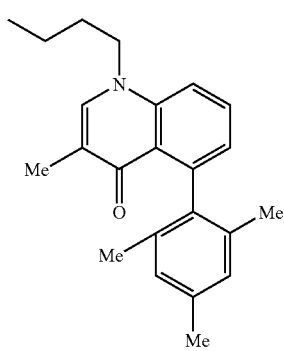
(B)

1-Benzyl-5-mesityl-3-methylquinolin-4(1H)-one (0.12 g, 0.327 mmol) was dissolved in ethanol (15 mL). 60 mg of Pd(OH)$_2$/C (20%, degussa type) was added followed by a hydrogen filled balloon. The reaction ran at room temperature for 3 hr. The balloon was removed and the solution was filtered through GF/F paper and concentrated to give the de-benzylated material as a white solid. The solid was then transferred to a sealed tube and suspended in 4-bromoheptane (10 mL) and sodium hydride (0.14 g, 3.4 mmol, 60% wt. dispersion in mineral oil) was added. The sealed tube reaction was stirred at 150° C. for 2.5 hr. The solution was cooled and quenched with water. The organics were extracted with ethyl acetate, dried, and concentrated. Flash chromatography (30% Ethyl acetate/hexanes) gave 0.054 g (50%) of 5-mesityl-3-methyl-1-(1-propylbutyl)quinolin-4(1H)-one (A) and 0.020 g (21%) of 1-butyl-5-mesityl-3-methylquinolin-4(1H)-one (B).

5-Mesityl-3-methyl-1-(1-propylbutyl)quinolin-4(1H)-one (A)

$^1$H NMR (acetone d$_6$) δ: 0.90 (t, J=7.2 Hz, 6H), 1.20-1.39 (m, 4H), 1.79 (s, 6H), 1.86-1.94 (m, 4H), 1.89 (s, 3H), 2.28 (s, 3H), 4.89-4.99 (m, 1H), 6.79-6.82 (m, 3H), 7.65 (t, J=8.0 Hz, 1H), 7.85 (s, 1H), 7.90 (d, J=9.2 Hz, 1H).

MS Calcd.: 375. Found: 376 (M+H).

1-Butyl-5-mesityl-3-methylquinolin-4(1H)-one (B)

$^1$H NMR (acetone d$_6$) δ: 0.99 (t, J=7.2 Hz, 6H), 1.43-1.53 (m, 2H), 1.79 (s, 6H), 1.85 (s, 3H), 1.85-1.91 (m, 2H), 2.28 (s, 3H), 4.27 (t, J=7.4 Hz, 2H), 6.799-6.82 (m, 3H), 7.66 (s, 2H), 7.78 (s, 1H).

MS Calcd.: 333. Found: 334 (M+H).

The following was prepared in an analogous manner:

| Example | Structure | Name | Physical Data |
|---------|-----------|------|---------------|
| 156 | 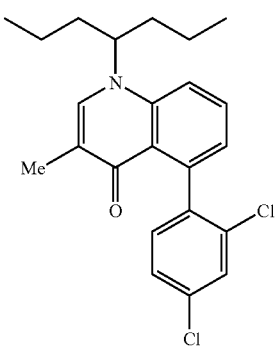 | 5-(2,4-dichlorophenyl)-3-methyl-1-(1-propylbutyl)quinolin-4(1H)-one | $^1$H NMR (acetone-d6) δ: 0.90-0.95 (m, 6H), 1.26-1.36 (m, 4H), 1.92 (s, 3H), 1.90-1.98 (m, 4H), 4.97-5.03 (m, 1H), 6.99 (d, J=7.2 Hz, 1H), 7.21 (d, J=8.4 Hz, 1H), 7.35 (dd, J=2.0, 8.0 Hz, 1H), 7.45 (d, J=1.6 Hz, 1H), 7.69-7.74 (m, 1H), 7.94 (s, 1H), 8.04 (d, J=8.8 Hz, 1H). MS Calcd.: 401, Found: 402, 404 (M + H, M + 3H). |

Example 157

5-(4-Chloro-2-methylphenyl)-2-(dipropylamino)-3,7-dimethyl-3,7-dihydro-4H-pyrrolo[2,3-d]pyrimidin-4-one

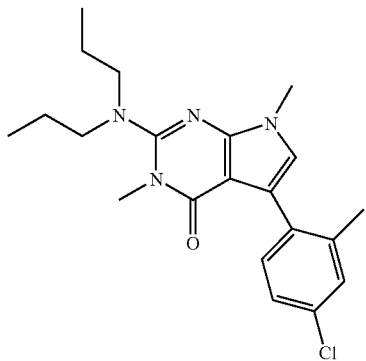

2-Amino-7-methyl-3,7-dihydro-4H-pyrrolo[2,3-d]pyrimidin-4-one

To a suspension of 2-amino-6-(methylamino)pyrimidin-4-ol (40.5 g, 289 mmol) in methanol (300 ml) was added 40% aqueous chloroacetoaldehyde (51.6 ml, 318 mmol) and potassium carbonate (44.0 g, 318 mmol), and the mixture was refluxed for 1 hour. After cooling, the resulting crystals were collected by filtration and washed with water to give 19.4 g (41%) of the title compound.

$^1$H NMR (DMSO-d$_6$) δ: 3.50 (3H, s), 6.18-6.20 (3H, m), 6.66 (1H, d, J=3.4 Hz), 10.23 (1H, s).

2,2-Dimethyl-N-(7-methyl-4-oxo-4,7-dihydro-3H-pyrrolo[2,3-d]pyrimidin-2-yl)propanamide To a suspension of 2-amino-7-methyl-3,7-dihydro-4H-pyrrolo[2,3-d]pyrimidin-4-one (4.82 g, 29.4 mmol) in pyridine (45 ml) was added pivaloyl chloride (11.6 ml, 94.0 mmol) at 0° C., and the mixture was stirred at 80° C. for 2 hours. After cooling, the reaction mixture was diluted with water and extracted with ethyl acetate (×1). The organic layer was washed with water (×1) and brine (×1), dried over sodium sulfate and concentrated in vacuo. The residual solids were suspended in methanol (45 ml), and concentrated aqueous ammonia (10 ml) was added at 0° C. The suspension was stirred at the same temperature for 30 minutes, before addition of water. After stirring at 0° C. for 2 hours, the resulting crystals were collected by filtration and washed with water to give 5.46 g (75%) of the title compound.

$^1$H NMR (DMSO-d$_6$) δ: 1.25 (9H, s), 3.67 (3H, s), 6.41 (1H, d, J=3.2 Hz), 7.00 (1H, d, J=3.2 Hz), 10.92 (1H, br s), 11.90 (1H, br s).

N-(5,6-Diiodo-7-methyl-4-oxo-4,7-dihydro-3H-pyrrolo[2,3-d]pyrimidin-2-yl)-2,2-dimethylpropanamide To a solution of 2,2-dimethyl-N-(7-methyl-4-oxo-4,7-dihydro-3H-pyrrolo[2,3-d]pyrimidin-2-yl)propanamide (682 mg, 2.75 mmol) in N,N-dimethylformamide (8 ml) was added N-iodosuccinimide (1.36 g, 6.04 mmol) at 0° C., and the mixture was stirred at room temperature for 5 hours in the dark. The reaction mixture was diluted with water and ethyl acetate, and the resulting crystals were collected by filtration to give 864 mg (63%) of the title compound.

$^1$H NMR (DMSO-d$_6$) δ: 1.24 (9H, s), 3.71 (3H, s), 10.99 (1H, s), 11.91 (1H, s).

N-(5-Iodo-7-methyl-4-oxo-4,7-dihydro-3H-pyrrolo[2,3-d]pyrimidin-2-yl)-2,2-dimethylpropanamide To a suspension of N-(5,6-diiodo-7-methyl-4-oxo-4,7-dihydro-3H-pyrrolo[2,3-d]pyrimidin-2-yl)-2,2-dimethylpropanamide (941 mg, 1.88 mmol) in acetic acid (9 ml) and water (2 ml) was added zinc powder (246 mg, 3.76 mmol), and the mixture was stirred at room temperature for 1 day. After addition of zinc (123 mg, 1.88 mmol), the mixture was stirred at room temperature for 1 day. The reaction mixture was diluted with water and stirred at 0° C. for 2 hours. The resulting crystals were collected by filtration, washed with water and dissolved in tetrahydrofuran. The solution was filtrated, and the filtrate was concentrated in vacuo. The residue was washed with diiopropyl ether to give 545 mg (78%) of the title compound.

$^1$H NMR (CDCl$_3$) δ: 1.34 (9H, s), 3.63 (3H, s), 6.80 (1H, s), 7.92 (1H, s), 11.65 (1H, br s).

2-Amino-5-iodo-7-methyl-3,7-dihydro-4H-pyrrolo[2,3-d]pyrimidin-4-one

To a solution of N-(5-iodo-7-methyl-4-oxo-4,7-dihydro-3H-pyrrolo[2,3-d]pyrimidin-2-yl)-2,2-dimethylpropanamide (17.9 g, 47.8 mmol) in tetrahydrofuran (150 ml) was added 2N aqueous solution of sodium hydroxide (57.4 ml, 115 mmol) at 0° C., and the mixture was refluxed for 5 hours After cooling, the solvent was evaporated in vacuo. The suspension was neutralized with 1N hydrochloric acid, and the resulting crystals were collected by filtration and washed with water to give 13.3 g (96%) of the title compound.

$^1$H NMR (DMSO-d$_6$) δ: 3.47 (3H, s), 6.27 (2H, br s), 6.86 (1H, s), 10.36 (1H, s).

2-Amino-5-iodo-3,7-dimethyl-3,7-dihydro-4H-pyrrolo[2,3-d]pyrimidin-4-one

To a solution of 2-amino-5-iodo-7-methyl-3,7-dihydro-4H-pyrrolo[2,3-d]pyrimidin-4-one (15.4 g, 53.1 mmol) in N,N-dimethylformamide (150 ml) was added sodium hydride (66% dispersion in oil, 1.93 g, 53.1 mmol) and iodomethane (3.31 ml, 53.1 mmol) at 0° C., and the mixture was stirred at the same temperature for 1 hour. The reaction mixture was diluted with water and extracted with ethyl acetate (×2) and ethyl acetate-tetrahydrofuran (×2). The combined organic layer was dried over sodium sulfate and concentrated in vacuo. The residue was purified by silica gel column chromatography eluting with a 50-100% hexane/ethyl acetate gradient mixture, and the desired fractions were concentrated in vacuo. The residual crystals were washed with diethyl ether to give 12.3 g (76%) of the title compound.

$^1$H NMR (DMSO-d$_6$) δ: 3.26 (3H, s), 3.47 (3H, s), 6.84 (2H, s), 6.87 (1H, s).

2-(Dipropylamino)-5-iodo-3,7-dimethyl-3,7-dihydro-4H-pyrrolo[2,3-d]pyrimidin-4-one To a solution of 2-amino-5-iodo-3,7-dimethyl-3,7-dihydro-4H-pyrrolo[2,3-d]pyrimidin-4-one (8.1 g, 26.6 mmol) in N,N-dimethylformamide (80 ml) was added sodium hydride (66% dispersion in oil, 2.13 g, 58.6 mmol) and 1-iodopropane (5.72 ml, 58.6 mmol) at 0° C., and the mixture was stirred at room temperature for 1 hour. After addition of sodium hydride (66% dispersion in oil, 193 mg, 5.30 mmol) and 1-iodopropane (0.52 ml, 5.30 mmol), the mixture was stirred at room temperature for 1 hour. The reaction mixture was diluted with ice-cold water and extracted with ethyl acetate (×2). The combined organic layer was washed with water (×1) and brine (×1), dried over sodium sulfate and concentrated in vacuo. The residue was purified by silica gel column chromatography eluting with a 3-10% hexane/ethyl acetate gradient mixture to give 8.10 g (78%) of the title compound.

$^1$H NMR (CDCl$_3$) δ: 0.87 (6H, t, J=7.3 Hz), 1.48-1.66 (4H, m), 3.06-3.14 (4H, m), 3.51 (3H, s), 3.63 (3H, s), 6.76 (1H, s).

5-(4-Chloro-2-methylphenyl)-2-(dipropylamino)-3,7-dimethyl-3,7-dihydro-4H-pyrrolo[2,3-d]pyrimidin-4-one A suspension of 2-(dipropylamino)-5-iodo-3,7-dimethyl-3,7-dihydro-4H-pyrrolo[2,3-d]pyrimidin-4-one (115 mg, 0.296 mmol), 4-chloro-2-methylphenylboronic acid (76 mg, 0.446 mmol), sodium carbonate (47 mg, 0.443 mmol) and tetrakis(triphenylphosphine)palladium (34 mg, 0.0294 mmol) in 1,2-dimethoxyethane (1.5 ml), ethanol (0.75 ml) and water (0.75 ml) was stirred at 80° C. for 4 hours. After cooling, the reaction mixture was diluted with water and ethyl acetate. The insoluble material was removed off by filtration. The filtrate was extracted with ethyl acetate (×2). The combined organic layer was washed with brine (×1), dried over sodium sulfate and concentrated in vacuo. The residue was purified by silica gel column chromatography eluting with a 10-18% hexane/ethyl acetate gradient mixture. The fractions containing the title compound were purified again by column chromatography eluting with 18% hexane/ethyl acetate using silica gel coated with amine. The desired fractions were concentrated in vacuo, and the resulting oil was crystallized from hexane and washed with pentane to give 12 mg (11%) of the title compound.

$^1$H NMR (CDCl$_3$) δ: 0.90 (6H, t, J=6.9 Hz), 1.53-1.66 (4H, m), 2.32 (3H, s), 3.09-3.14 (4H, m), 3.49 (3H, s), 3.69 (3H, s), 6.56 (1H, s), 7.13 (1H, dd, J=8.4, 1.2 Hz), 7.21 (1H, d, J=1.2 Hz), 7.24 (1H, d, J=8.4 Hz).

MS Calcd.: 386. Found: 387 (M+H).

Compounds of Examples 158-165 were prepared in a manner similar to that described in Example 157.

| Example | Structure | Name | Physical Data |
|---|---|---|---|
| 158 | 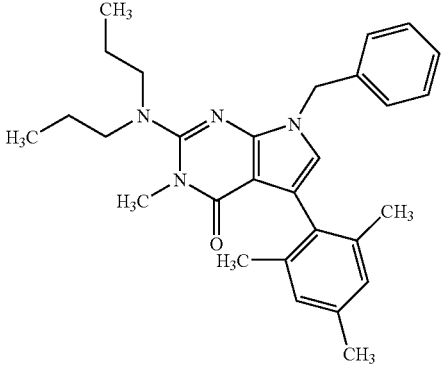 | 7-benzyl-2-(dipropylamino)-5-mesityl-3-methyl-3,7-dihydro-4H-pyrrolo[2,3-d]pyrimidin-4-one | $^1$H NMR (CDCl$_3$) δ: 0.87 (6H, t, J=7.4 Hz), 1.46-1.68 (4H, m), 2.09 (6H, s), 2.28 (3H, s), 3.08 (4H, t, J=7.4 Hz), 3.47 (3H, s), 5.26 (2H, s), 6.47 (1H, s), 6.89 (2H, s), 7.19-7.32 (5H, m). |
| 159 | 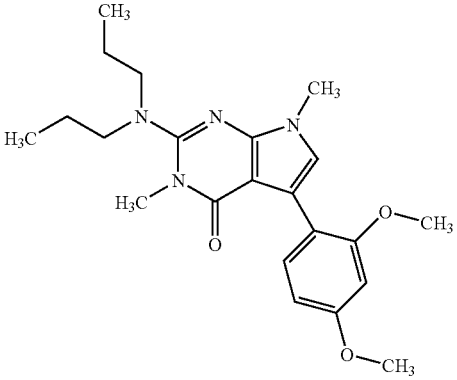 | 5-(2,4-dimethoxyphenyl)-2-(dipropylamino)-3,7-dimethyl-3,7-dihydro-4H-pyrrolo[2,3-d]pyrimidin-4-one | $^1$H NMR (CDCl$_3$) δ: 0.88 (6H, t, J=7.4 Hz), 1.53-1.66 (4H, m), 3.10 (2H, t, J=7.4 Hz), 3.11 (2H, t, J=7.4 Hz), 3.51 (3H, s), 3.68 (3H, s), 3.82 (3H, s), 3.83 (3H, s), 6.52-6.61 (2H, m), 6.93 (1H, s), 7.70 (1H, d, J=8.4 Hz) |

-continued

| Example | Structure | Name | Physical Data |
| --- | --- | --- | --- |
| 160 | 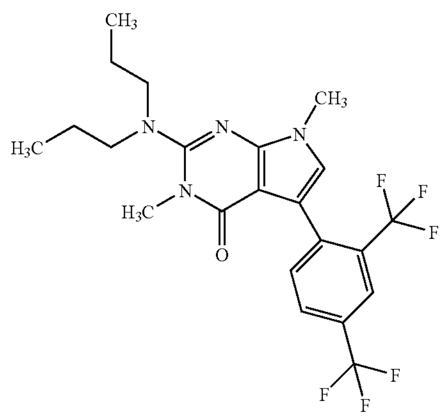 | 5-[2,4-bis(trifluoromethyl)phenyl]-2-(dipropylamino)-3,7-dimethyl-3,7-dihydro-4H-pyrrolo[2,3-d]pyrimidin-4-one | $^1$H NMR (CDCl$_3$) δ: 0.91 (6H, t, J=7.3 Hz) 1.52-1.71 (4H, m), 3.14 (2H, t, J= 7.5 Hz), 3.50 (2H, t, J= 7.4 Hz), 3.72 (3H, s), 6.76 (1H, s), 7.73 (1H, d, J= 9.0 Hz), 7.79 (1H, d, J= 9.1 Hz), 7.95 (1H, s). |
| 161 | 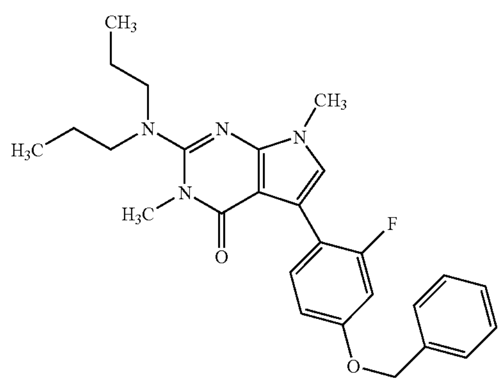 | 5-[4-(benzyloxy)-2-fluorophenyl]-2-(dipropylamino)-3,7-dimethyl-3,7-dihydro-4H-pyrrolo[2,3-d]pyrimidin-4-one | $^1$H NMR (CDCl$_3$) δ: 0.89 (6H, t, J=7.5 Hz), 1.50-1.69 (4H, m), 3.09-3.16 (2H, m), 3.53 (3H, s), 3.69 (3H, s), 5.07 (2H, s), 6.74 (1H, d, J= 12.6, 2.4 Hz), 6.84 (1H, J=8.8, 2.4 Hz), 6.92 (1H, d, J= 2.6 Hz), 7.27-7.46 (5H, m), 7.97 (1H, t, J= 8.8 Hz).; MS Calcd.: 462; Found: 463 (M + H). |
| 162 | 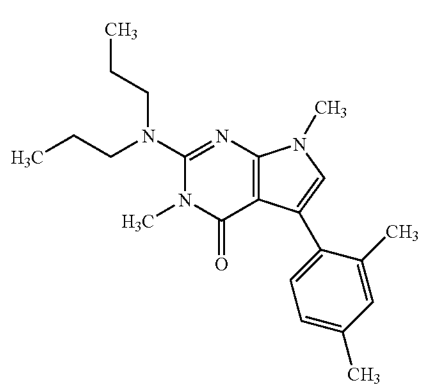 | 5-(2,4-dimethoxyphenyl)-2-(dipropylamino)-3,7-dimethyl-3,7-dihydro-4H-pyrrolo[2,3-d]pyrimidin-4-one | $^1$H NMR (CDCl$_3$) δ: 0.89 (6H, t, J=7.3 Hz), 1.51-1.69 (4H, m), 2.31 (3H, s), 2.33 (3H, s), 3.10 (2H, t, J= 7.5 Hz), 3.11 (2H, t, J= 7.5 Hz), 3.49 (3H, s), 3.69 (3H, s), 6.56 (1H, s) 6.99 (1H, d, J= 7.7 Hz), 7.06 (1H, s), 7.21 (1H, d, J= 7.7 Hz).; MS Calcd.: 366; Found: 367 (M + H). |

-continued

| Example | Structure | Name | Physical Data |
|---|---|---|---|
| 163 | 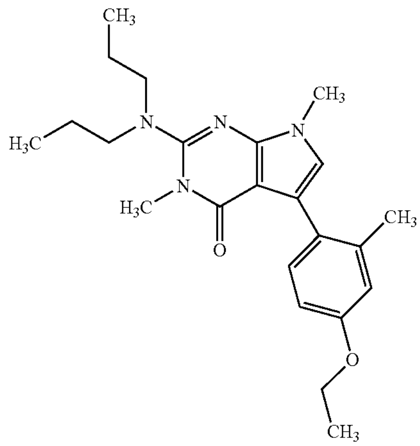 | 2-(dipropylamino)-5-(4-ethoxy-2-methylphenyl)-3,7-dimethyl-3,7-dihydro-4H-pyrrolo[2,3-d]pyrimidin-4-one | $^1$H NMR (CDCl$_3$) δ: 0.90 (6H, t, J=7.5 Hz), 1.41 (3H, t, J=7.2 Hz), 1.44-1.80 (4H, m), 2.32 (3H, s), 3.11 (4H, q, J=7.5 Hz), 3.49 (3H, s), 3.69 (3H, s), 4.04 (2H, q, J=7.2 Hz), 6.54 (1H, s), 6.73 (1H, dd, J=8.5, 2.5 Hz), 6.79 (1H, d, J=2.5 Hz), 7.23 (1H, d, J=8.5 Hz).; MS Calcd.: 396; Found: 397 (M + H). |
| 164 | 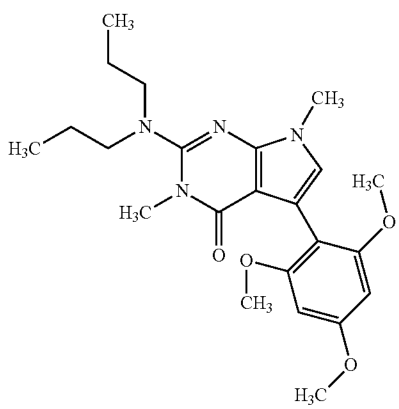 | 2-(dipropylamino)-3,7-dimethyl-5-(2,4,6-trimethoxyphenyl)-3,7-dihydro-4H-pyrrolo[2,3-d]pyrimidin-4-one | $^1$H NMR (CDCl$_3$) δ: 0.88 (6H, t, J=7.5 Hz), 1.48-1.67 (4H, m), 3.07 (4H, t, J=7.5 Hz), 3.46 (3H, s), 3.67 (3H, s), 3.75 (6H, s), 3.84 (3H, s), 6.22 (2H, s), 6.65 (1H, s).; MS Calcd.: 428; Found: 429 (M + H). |
| 165 | 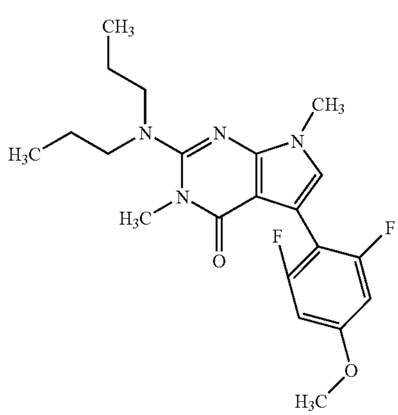 | 5-(2,6-difluoro-4-methoxyphenyl)-2-(dipropylamino)-3,7-dimethyl-3,7-dihydro-4H-pyrrolo[2,3-d]pyrimidin-4-one | $^1$H NMR (CDCl$_3$) δ: 0.89 (6H, t, J=7.3 Hz), 1.50-1.67 (4H, m), 3.07-3.14 (4H, m), 3.50 (3H, s), 3.70 (3H, s), 3.80 (3H, s), 6.54 (2H, d, J=9.4 Hz), 6.73 (1H, s).; MS Calcd.: 404; Found: 405 (M + H). |

| Example | Structure | Name | Physical Data |
|---|---|---|---|
| 166 | 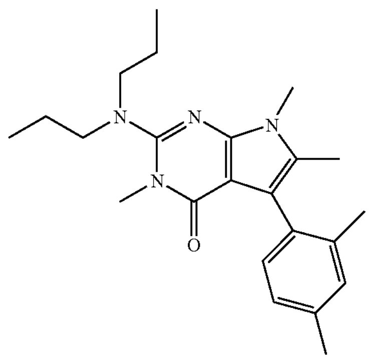 | 5-(2,4-dimethoxyphenyl)-2-(dipropylamino)-3,6,7-trimethyl-3,7-dihydro-4H-pyrrolo[2,3-d]pyrimidin-4-one | $^1$H NMR (CDCl$_3$) δ: 0.89 (6H, t, J=7.5 Hz), 1.50-1.65 (4H, m), 2.12 (3H, s), 2.17 (3H, s), 2.33 (3H, s), 3.00-3.15 (4H, m), 3.47 (3H, s), 3.62 (3H, s), 6.99 (1H, d, J=7.5 Hz), 7.06 (1H, d, J=7.5 Hz) 7.07 (1H, s). |
| 167 | 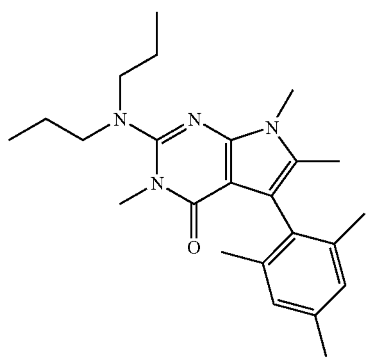 | 2-(dipropylamino)-5-mesityl-3,6,7-trimethyl-3,7-dihydro-4H-pyrrolo[2,3-d]pyrimidin-4-one | $^1$H NMR (CDCl$_3$) δ: 0.90 (6H, t, J=7.5 Hz), 1.50-1.65 (4H, m), 2.02 (9H, s), 2.30 (3H, s), 3.05-3.15 (4H, m), 3.46 (3H, s), 3.64 (3H, s), 6.90 (2H, s). |
| 168 | 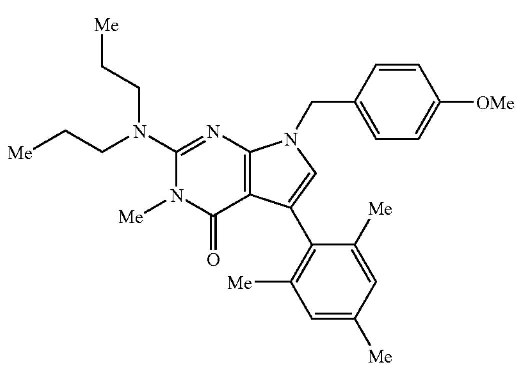 | 2-(dipropylamino)-5-mesityl-7-(4-methoxybenzyl)-3-methyl-3,7-dihydro-4H-pyrrolo[2,3-d]pyrimidin-4-one | $^1$H NMR (CDCl$_3$) δ: 0.90 (6H, t, J=7.2 Hz), 1.40-1.66 (4H, m), 2.11 (6H, s), 2.28 (3H, s), 3.08 (4H, t, J=7.2 Hz), 3.34 (3H, s), 3.48 (3H, s), 5.58 (2H, s), 6.47 (1H, s), 6.87 (2H, d, J=7.2 Hz), 6.93 (2H, s) 7.20 (2H, d, J=7.2 Hz). |

Example 169

2-(Dipropylamino)-5-(2-fluoro-4-hydroxyphenyl)-3,7-dimethyl-3,7-dihydro-4H-pyrrolo[2,3-d]pyrimidin-4-one

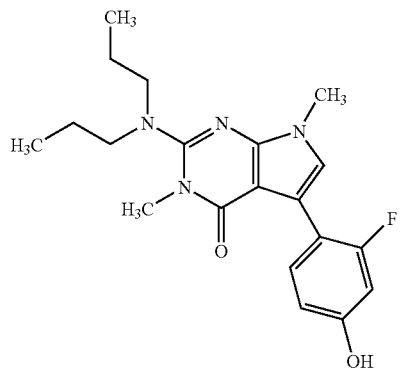

To a solution of 5-[4-(benzyloxy)-2-fluorophenyl]-2-(dipropylamino)-3,7-dimethyl-3,7-dihydro-4H-pyrrolo[2,3-d]pyrimidin-4-one (194 mg, 0.419 mmol) was added 10% palladium on carbon (50 mg), and the mixture was stirred at room temperature for 15 hours under hydrogen atmosphere. The catalyst was removed by filtration, and the filtrate was concentrated in vacuo. The residue was purified by silica gel column chromatography eluting with a 25% hexane/ethyl acetate mixture. The desired fractions were concentrated in vacuo, and the resulting crystals were washed with diethyl ether to give 42 mg (27%) of the title compound.

$^1$H NMR (CDCl$_3$) δ: 0.90 (6H, t, J=7.3 Hz), 1.45-1.70 (4H, m), 3.14 (4H, t, J=7.3 Hz), 3.58 (3H, s), 3.70 (3H, s), 6.64 (1H, dd, J=12.2, 2.6 Hz), 6.76 (1H, dd, J=8.4, 2.6 Hz), 6.91 (1H, d, J=2.2 Hz), 7.76 (1H, t, J=8.4 Hz). MS Calcd.: 372. Found: 373 (M+H).

Example 170

2-(Dipropylamino)-5-(2-fluoro-4-methoxyphenyl)-3,7-dimethyl-3,7-dihydro-4H-pyrrolo[2,3-d]pyrimidin-4-one

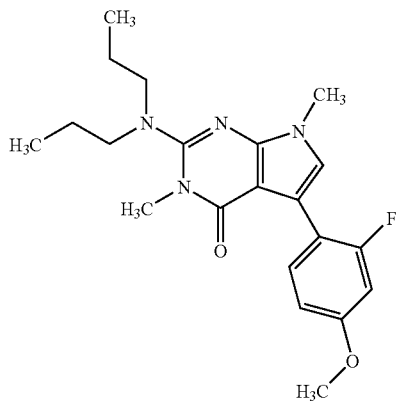

To a solution of 2-(dipropylamino)-5-(2-fluoro-4-hydroxyphenyl)-3,7-dimethyl-3,7-dihydro-4H-pyrrolo[2,3-d]pyrimidin-4-one (30 mg, 0.0805 mmol) in N,N-dimethylformamide (0.5 ml) were added sodium hydride (66% dispersion in oil; 3.2 mg, 0.0886 mmol) and iodomethane (0.006 ml, 0.0886 ml) at 0° C., and the mixture was stirred at the same temperature for 30 minutes. The reaction mixture was diluted with ice-cold water and extracted with ethyl acetate (×1). The organic layer was washed with water (×1) and brine (×1), dried over sodium sulfate and concentrated in vacuo. The residue was purified by silica gel column chromatography eluting with a 20% hexane/ethyl acetate mixture. The desired fractions were concentrated in vacuo to give 23 mg (74%) of the title compound as an oil.

$^1$H NMR (CDCl$_3$) δ: 0.89 (6H, t, J=7.3 Hz), 1.50-1.69 (4H, m), 3.12 (4H, t, J=7.5 Hz), 3.53 (3H, s), 3.69 (3H, s), 3.81 (3H, s), 6.67 (1H, dd, J=12.5, 2.6 Hz), 6.76 (1H, dd, J=8.8, 2.6 Hz), 6.92 (1H, d, J=2.6 Hz), 7.96 (1H, t, J=8.8 Hz).

MS Calcd.: 386. Found: 387 (M+H).

Compounds of Example 168-170 was prepared in a manner similar to that described in Example 41.

| Example | Structure | Name | Physical Data |
|---|---|---|---|
| 171 | ![structure] | 2-(dipropylamino)-7-ethyl-5-mesityl-3-methyl-3,7-dihydro-4H-pyrrolo[2,3-d]pyrimidin-4-one | $^1$H NMR (CDCl$_3$) δ: 0.90 (6H, t, J = 7.2 Hz), 1.43 (3H, t, J = 7.2 Hz), 1.52–1.70 (4H, m), 2.11 (6H, s), 2.29 (3H, s), 3.06–3.13 (4H, m), 3.47 (3H, s), 4.12 (2H, q, J = 7.2 Hz), 6.47 (1H, s), 6.90 (2H, s). |

Example 172

2-[Bis(cyclopropylmethyl)amino]-5-mesityl-3,7-dimethyl-3,7-dihydro-4H-pyrrolo[2,3-d]pyrimidin-4-one

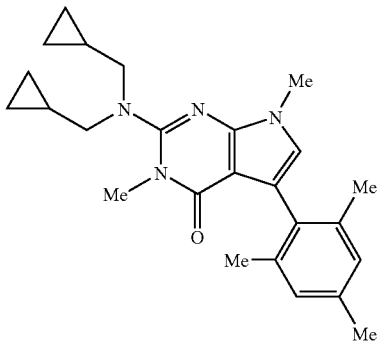

To a solution of 2-amino-5-mesityl-7-methyl-3,7-dihydro-4H-pyrrolo[2,3-d]pyrimidin-4-one (200 mg, 0.68 mmol) and N,N-dimethylformamide (5 ml) was added sodium hydride (60% in oil, 60 mg, 1.50 mmol) at 0° C. and stirred for 0.5 hour. After stirring at room temperature for 0.5 hour, to the mixture was added a solution of cyclopropylmethylbromide (202 mg, 1.50 mmol) and N,N-dimethylformamide (2 ml) at 0° C. and stirred for 0.5 hour. After stirring at 80° C. for 1 hour, the mixture was diluted with water (20 ml) and extracted with ethyl acetate (50 ml×3). The extracts were combined, washed with brine, dried over sodium sulfate and concentrated in vacuo. The residue was purified by silica gel chromatography eluting with hexane/ethyl acetate (4:1) to give 130 mg (47%) of the title compound.

$^1$H NMR (CDCl$_3$) δ: 0.12-0.17 (4H, m), 0.45-0.52 (4H, m), 1.01-1.10 (2H, m), 2.11 (6H, s), 2.29 (3H, s), 3.10 (4H, d, J=6.6 Hz), 3.52 (3H, s), 3.72 (3H, s), 6.45 (1H, s), 6.90 (2H, s).

Example 172

2-(Dipropylamino)-5-mesityl-3-methyl-3,7-dihydro-4H-pyrrolo[2,3-d]pyrimidin-4-one

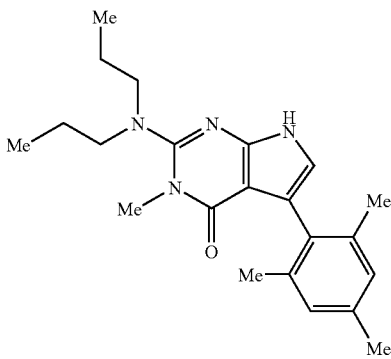

A Solution of 2-(dipropylamino)-5-mesityl-7-(4-methoxybenzyl)-3-methyl-3,7-dihydro-4H-pyrrolo[2,3-d]pyrimidin-4-one (100 mg, 0.21 mmol) in trifluoroacetic acid (3 ml) and anisole (0.1 ml) was refluxed for 3 days. The mixture was diluted with water (20 ml), neutralized with sodium hydrogen carbonate and extracted with ethyl acetate (20 ml×2). The extracts were combined, washed with brine, dried over sodium sulfate and concentrated in vacuo. The residue was purified by silica gel chromatography eluting with hexane/ethyl acetate (5:1) to give 12 mg (15%) of the title compound.

$^1$H NMR (CDCl$_3$) δ: 0.93 (6H, t, J=7.2 Hz), 1.22-1.40 (4H, m), 2.11 (6H, s), 2.29 (3H, s), 3.12 (4H, t, J=7.2 Hz), 3.70 (3H, s), 5.35 (1H, br), 6.13 (1H, s), 6.88 (2H, s).

Example 174

7-Acetyl-2-(dipropylamino)-5-mesityl-3-methyl-3,7-dihydro-4H-pyrrolo[2,3-d]pyrimidin-4-one

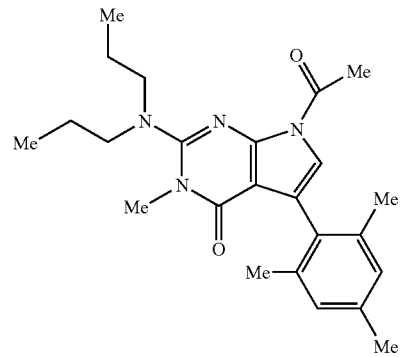

A solution of 2-(dipropylamino)-5-mesityl-3-methyl-3,7-dihydro-4H-pyrrolo[2,3-d]pyrimidin-4-one (20 mg, 0.054 mmol) in acetonitrile (1.5 ml) was added sodium hydride (60% in oil, 5 mg, 0.125 mmol) at 0° C. and stirred for 0.5 hour. After stirring at room temperature for 0.5 hour, to the mixture was added a solution of acetylchloride (20 mg, 0.25 mmol) and acetonitrile (0.5 ml) at 0° C. and stirred for 0.5 hour. After stirring at 80° C. for 1 hour, the mixture was diluted with water (20 ml) and extracted with ethyl acetate (20 ml×3). The extracts were combined, washed with brine, dried over sodium sulfate and concentrated in vacuo. The residue was purified by silica gel chromatography eluting with hexane/ethyl acetate (10:1) to give 17 mg (77%) of the title compound.

$^1$H NMR (CDCl$_3$) δ: 0.93 (6H, t, J=7.2 Hz), 1.31 (4H, m), 2.11 (6H, s), 2.22 (3H, s), 2.29 (3H, s), 3.12 (4H, t, J=7.2 Hz), 3.70 (3H, s), 6.34 (1H, s), 6.88 (2H, s).

Compounds of Examples 174-175 were prepared in a manner similar to that described in Example 173.

| Example | Structure | Name | Physical Data |
|---|---|---|---|
| 175 | 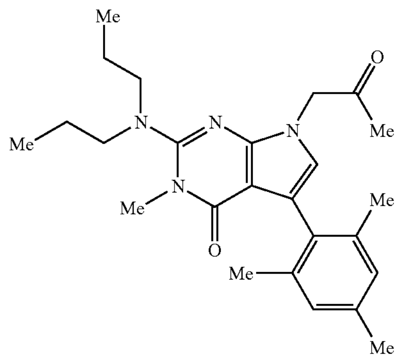 | 2-(dipropylamino)-5-mesityl-3-methyl-7-(2-oxopropyl)-3,7-dihydro-4H-pyrrolo[2,3-d]pyrimidin-4-one | $^1$H NMR (CDCl$_3$) δ: 0.90 (6H, t, J = 7.2 Hz), 1.20–1.40 (4H, m), 2.13 (6H, s), 2.25 (3H, s), 2.29 (3H, s), 3.12 (4H, t, J = 7.2 Hz), 3.70 (3H, s), 4.80 (2H, s), 6.34 (1H, s), 6.88 (2H, s).; MS Calcd.: 422; Found: 423 (M + H). |
| 176 | 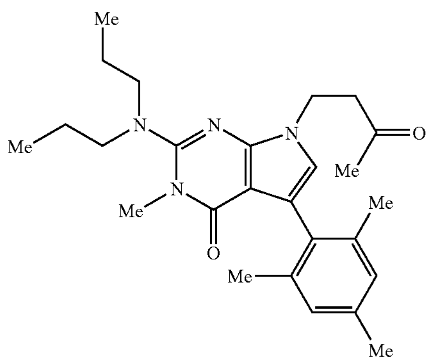 | 2-(dipropylamino)-5-mesityl-3-methyl-7-(3-oxobutyl)-3,7-dihydro-4H-pyrrolo[2,3-d]pyrimidin-4-one | $^1$H NMR (CDCl$_3$) δ: 0.90 (6H, t, J = 7.2 Hz), 1.21–1.39 (4H, m), 2.13 (6H, s), 2.25 (3H, s), 2.29 (3H, s), 3.12 (4H, t, J = 7.2 Hz), 3.66 (2H, t, J = 6.9 Hz), 3.70 (3H, s), 4.67 (2H, t, J = 6.9 Hz), 6.34 (1H, s), 6.88 (2H, s).; MS Calcd.: 436; Found: 437 (M + H). |

Compounds of Examples 176-180 were prepared in a manner similar to that described in Example 96.

| Example | Structure | Name | Physical Data |
|---|---|---|---|
| 177 | 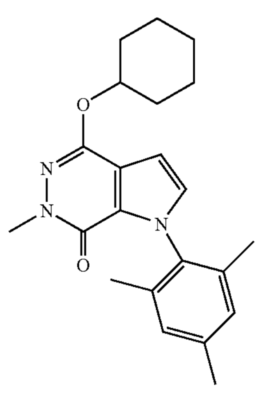 | 4-(cyclohexyloxy)-1-mesityl-6-methyl-1,6-dihydro-7H-pyrrolo[2,3-d]pyridazin-7-one | $^1$H NMR (CDCl$_3$) δ: 1.20–1.45 (3H, m), 1.50–1.60 (3H, m), 1.70–1.85 (2H, m), 1.81 (6H, s), 1.95–2.05 (2H, m), 2.29 (3H, s), 3.46 (3H, s), 4.80–4.90 (1H, s), 6.59 (1H, d, J = 3.0 Hz), 6.96 (2H, s), 7.32 (1H, d, J = 3.0 Hz). MS Calcd.: 365; Found: 366 (M + H). |

| Example | Structure | Name | Physical Data |
|---|---|---|---|
| 178 | 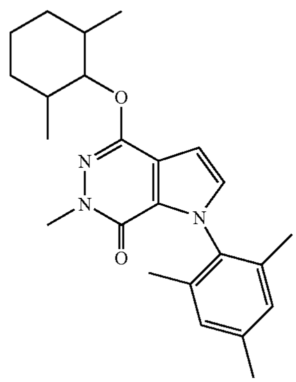 | 4-((2,6-dimethylcyclohexyl)oxy)-1-mesityl-6-methyl-1,6-dihydro-7H-pyrrolo[2,3-d]pyridazin-7-one | $^1$H NMR (CDCl$_3$) δ: 0.87 (3H, t, J = 7.2 Hz), 0.95 (3H, t, J= 7.2 Hz), 1.05–1.25 (2H, m), 1.35–1.60 (4H, m), 1.60–1.80 (2H, m), 1.81 (3H, s), 2.29 (3H, s), 3.44 (3H, s), 4.60–4.65 (1H, s), 6.60–6.65 (1H, m), 6.96 (2H, s), 7.31 (1H, d, J = 2.4 Hz). MS Calcd.: 393; Found: 394 (M + H). |
| 179 | 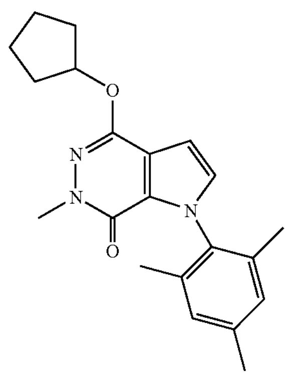 | 4-(cyclopentyloxy)-1-mesityl-6-methyl-1,6-dihydro-7H-pyrrolo[2,3-d]pyridazin-7-one | $^1$H NMR (CDCl$_3$) δ: 1.55–2.10 (8H, m), 1.92 (6H, s), 2.33 (3H, s), 3.62 (3H, s), 5.25–5.35 (1H, s), 6.59 (1H, d, J = 2.7 Hz), 6.94 (1H, d, J = 2.4 Hz), 6.95 (2H, s). MS Calcd.: 351; Found: 352 (M + H). |
| 180 | | 1-(2,4-dimethylphenyl)-4-(1-isopropyl-2-methylpropoxy)-6-methyl-1,6-dihydro-7H-pyrrolo[2,3-d]pyridazin-7-one | $^1$H NMR (CDCl$_3$) δ: 0.98 (12H, q, J = 6.6 Hz), 2.03 (3H, s), 2.00–2.10 (2H, m), 2.38 (3H, s), 3.60 (3H, s), 4.86 (1H, t, J = 6.0 Hz), 6.58 (1H, d, J = 3.0 Hz), 7.03 (1H, d, J = 3.0 Hz), 7.05–7.20 (3H, m). MS Calcd.: 367; Found: 368 (M + H). |
| 180 | | 4-{2-(dimethylamino)-1-[(dimethylamino)methyl]ethoxy}-1-(2,4-dimethylphenyl)-6-methyl-1,6-dihydro-7H-pyrrolo[2,3-d]pyridazin-7-one | $^1$H NMR (CDCl$_3$) δ: 2.00 (3H, s), 2.30–2.40 (15H, m), 2.65–2.70 (4H, m), 3.61 (3H, s), 5.25–5.35 (1H, m), 6.55 (1H, d, J = 2.0 Hz), 7.01 (1H, d, J = 2.0 Hz), 7.05–7.15 (3H, m). MS Calcd.: 397; Found: 398 (M + H). |

Example 181

5-(Dipropylamino)-3,6-dimethyl-1-(2,4,6-trichlorophenyl)-1,6-dihydro-7H-pyrazolo[4,3-d]pyrimidin-7-one (A) and 5-(Dimethylamino)-3,6-dimethyl-1-(2,4,6-trichlorophenyl)-1,6-dihydro-7H-pyrazolo[4,3-d]pyrimidin-7-one (B)

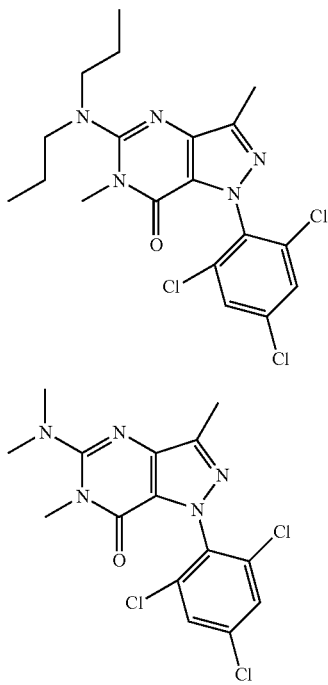

Ethyl 2-(methoxyimino)-4-oxopentanoate

A mixture of ethyl 2,4-dioxopentanoate (10.9 g, 68.7 mmol) and N-methoxyamine hydrochloride (4.01 g, 48.1 mmol) in ethanol (40 ml) was left to stand over molecular sieves 3A (25 g) for 18 h and diluted with dichloromethane (25 ml) The sieves was removed by filtration and the filtrate was concentrated under vacuum. The residue was purified by silica gel chromatography eluting with 5% ethyl acetate/n-hexane to give the title compound (12.9 g, 34%).

$^1$H NMR (CDCl$_3$) δ: 1.36 (t, J=7.2 Hz, 3H), 2.21 (s, 3H), 3.72 (s, 2H), 4.07 (s, 3H), 4.34 (q, J=7.2 Hz, 2H).

MS Calcd.: 187. Found: 188 (M+H).

Ethyl 3-methyl-1-(2,4,6-trichlorophenyl)-1H-pyrazole-5-carboxylate

A mixture of ethyl 2-(methoxyimino)-4-oxopentanoate (2.00 g, 10.7 mmol) and 2,4,6-trichlorophenylhydrazine hydrochloride (3.39 g, 16.0 mmol) in acetic acid (40 ml) and 2-methoxuethanol (20 ml) was stirred for 20 h at 105° C. The solvent was under vacuum and the residue was dissolved in ethyl acetate. The organic solution was washed with 0.2N HCl and water, dried over magnesium sulfate and concentrated under vacuum. The residue was purified by silica gel chromatography eluting with 10% ethyl acetate/n-hexane to give the title compound (1.50 g, 42%).

$^1$H NMR (CDCl$_3$) δ: 1.21 (t, J=7.2 Hz, 3H), 2.37 (s, 3H), 4.20 (q, J=7.2 Hz, 2H), 6.83 (s, 1H), 7.43 (s, 2H).

MS Calcd.: 332. Found: 333 (M+H), 335.

Ethyl 3-methyl-4-nitro-1-(2,4,6-trichlorophenyl)-1H-pyrazole-5-carboxylate

To a solution of ethyl 3-methyl-1-(2,4,6-trichlorophenyl)-1H-pyrazole-5-carboxylate (500 mg, 1.50 mmol) in trifluoroacetic acid (2.54 ml) was added trifluoroacetic anhydride (1.48 ml) followed by an addition of ammonium nitrate (240 mg, 3.00 mmol). The mixture was stirred for 20 h at room temperature and neutralized with aqueous potassium carbonate. The aqueous solution was extracted with ethyl acetate. The extract was dried over magnesium sulfate and concentrated under vacuum. The residue was purified by silica gel chromatography eluting with 3% ethyl acetate/n-hexane to give the title compound (372 mg, 66%).

$^1$H NMR (CDCl$_3$) δ: 1.22 (t, J=7.2 Hz, 3H), 2.58 (s, 3H), 4.29 (q, J=7.2 Hz, 2H), 7.43 (s, 2H).

N,3-Dimethyl-4-nitro-1-(2,4,6-trichlorophenyl)-1H-pyrazole-5-carboxamide

A mixture of ethyl 3-methyl-4-nitro-1-(2,4,6-trichlorophenyl)-1H-pyrazole-5-carboxylate (172 mg, 0.454 mmol), 1N NaOH (0.68 ml, 1.36 mmol) and ethanol (2 ml). The mixture was stirred for 18 h at room temperature. The solvent was evaporated under vacuum. The residue was neutralized with 1N HCl and extracted with ethyl acetate. The extract was washed with water, dried over magnesium sulfate and concentrated under vacuum to afford N,3-dimethyl-4-nitro-1-(2,4,6-trichlorophenyl)-1H-pyrazole-5-carboxylic acid. To a solution of the acid in dichloroethane (2 ml) was added thionyl chloride (0.044 ml, 0.599 mmol) and the mixture was refluxed for 3 h. The solvent was evaporated under vacuum. The residue was dissolved in dichloroethane (2 ml). Methyl amine (2M in tetrahydrofuran, 0.10 ml) was added. The mixture was stirred at room temperature for 18 h and diluted with water. The aqueous solution was extracted with ethyl acetate. The extract was washed with saturated sodium bicarbonate, dried over magnesium sulfate and concentrated under vacuum. The residue was purified by silica gel chromatography eluting with 50% ethyl acetate/hexane to give the title compound (47 mg, 65%).

$^1$H NMR (CDCl$_3$) δ: 2.62 (s, 3H), 2.93 (d, J=4.8 Hz, 3H), 7.44 (s, 2H), 8.19 (s, 1H).

MS Calcd.: 363. Found: 362 (M–H).

4-Amino-N,3-dimethyl-1-(2,4,6-trichlorophenyl)-1H-pyrazole-5-carboxamide

A mixture of N,3-dimethyl-4-nitro-1-(2,4,6-trichlorophenyl)-1H-pyrazole-5-carboxamide (42 mg, 0.116 mmol) and tin (II) chloride (110 mg, 0.578 mmol) was stirred at 80° C. for 3 h and diluted with saturated sodium bicarbonate. The aqueous solution was extracted with ethyl acetate. The extract was washed with brine, dried over magnesium sulfate and concentrated under vacuum. The residue was purified by silica gel chromatography eluting with 50% ethyl acetate/hexane to give the title compound (20 mg, 52%).

$^1$H NMR (CDCl$_3$) δ: 2.28 (s, 2H), 2.85 (s, 3H), 2.93 (s, 3H), 7.40 (s, 1H), 7.99 (s, 1H).

MS Calcd.: 332. Found: 333 (M+H), 335.

3,6-Dimethyl-1-(2,4,6-trichlorophenyl)-1H-pyrazolo[4,3-d]pyrimidine-5,7(4H,6H)-dione To a solution of 4 amino-N,3-dimethyl-1-(2,4,6-trichlorophenyl)-1H-pyrazole-5-carboxamide (20 mg, 0.0600 mmol) in tetrahydrofuran (1 ml) was added phosgene (20% solution in tetrahydrofuran, 0.048 ml) and the mixture was stirred at room temperature for 2 h. The solvent was evaporated under vacuum to give the title compound, which was used for the next step without further purification.

$^1$H NMR (CDCl$_3$) δ: 2.46 (s, 3H), 3.32 (s, 3H), 7.42 (s, 2H), 10.98 (s, 1H).

5-Chloro-3,6-dimethyl-1-(2,4,6-trichlorophenyl)-1,6-dihydro-7H-pyrazolo[4,3-d]pyrimidin-7-one A mixture of 3,6-dimethyl-1-(2,4,6-trichlorophenyl)-1H-pyrazolo[4,3-d]pyrimidine-5,7(4H,6H)-dione (20 mg, 0.0556 mmol), phosphorus oxychloride (0.52 ml) and N,N-diisopropylethylamine (0.21 ml) was stirred at 100° C. for 60 h. The solvent was evaporated under vacuum to give the title compound, which was used for the next step without further purification.

$^1$H NMR (CDCl$_3$) δ: 3.05 (s, 3H), 3.60 (s, 3H), 7.24 (s, 2H).

5-(Dipropylamino)-3,6-dimethyl-1-(2,4,6-trichlorophenyl)-1,6-dihydro-7H-pyrazolo[4,3-d]pyrimidin-7-one (A) and 5-(Dimethylamino)-3,6-dimethyl-1-(2,4,6-trichlorophenyl)-1,6-dihydro-7H-pyrazolo[4,3-d]pyrimidin-7-one (B)

A mixture of 5-Chloro-3,6-dimethyl-1-(2,4,6-trichlorophenyl)-1,6-dihydro-7H-pyrazolo[4,3-d]pyrimidin-7-one (20 mg, 0.0529 mmol) and dipropylamine (54 mg, 0.529 mmol) in N,N-dimethylformamide (1 ml) was stirred at 100° C. for 5 h and diluted with water. The aqueous solution was extracted with ethyl acetate. The extract was washed with brine, dried over magnesium sulfate and concentrated under vacuum. The residue was purified by silica gel chromatography eluting with 10% ethyl acetate/hexane to give the compound (A) (2.5 mg, 11%) and the compound (B) (8.1 mg, 40%).

Compound (A):
$^1$H-NMR (CDCl$_3$) δ: 0.84 (t, J=7.2 Hz, 6H), 1.45-1.57 (m, 4H), 2.46 (s, 3H), 3.00-3.06 (m, 4H), 3.46 (s, 3H), 7.39 (s, 2H).
MS Calcd.: 441. Found: 442 (M+H), 444.

Compound (B):
$^1$H-NMR (CDCl$_3$) δ: 2.53 (s, 3H), 2.86 (s, 6H), 3.51 (s, 3H), 7.45 (s, 2H).
MS Calcd.: 385. Found: 386 (M+H), 388.

Experiment 1

Measurement of Corticotropin-Releasing Factor (CRF) Binding Inhibitory Rate A receptor binding experiment was carried out using a human CRF receptor expressing CHO cellular membrane fraction and sheep CRF, [$^{125}$I]-tyr$^0$($^{125}$I-CRF). 100 nM of a test compound was incubated with 1 µg of human CRF receptor expressing CHO cellular membrane fraction and 50 pM of $^{125}$I-CRF in a binding assay buffer (50 mM Tris-HCl, 5 mM EDTA, 10 mM MgCl$_2$, 0.05% CHAPS, 0.1% BSA, 0.5 mM PMSF, 0.1 g/ml pepstatin, 20 µg/ml leupeptin, pH 7.5). In addition, for measuring nonspecific binding (NSB), 0.1 µM unlabelled human Urocortin was incubated with 1 µg of human CRF receptor expressing CHO cellular membrane fraction and 50 pM of $^{125}$I-CRF in a binding assay buffer. After a binding reaction was carried out at room temperature for 1 hour, the membrane was entrapped on a glass filter (UniFilter plate GF-C/Perkin Elmer) by suction filtration using a cell harvester (Perkin Elmer), and washed with ice-cooled 50 mM Tris-HCl (pH 7.5). After drying the glass filter, a liquid scintillation cocktail (Microscinti 0, Perkin Elmer) was added, and the radioactivity of $^{125}$I-CRF remaining on a glass filter was measured using Topcount (Perkin Elmer).

(TB-SB)/(TB-NSB)×100 (SB: radioactivity when a compound is added, TB: maximum binding radioactivity, NSB: nonspecific binding radioactivity) was calculated to obtain a binding inhibitory rate under the presence of 1,000 nM or 100 nM of each test substances.

Binding inhibitory rates of respective compounds measured by the aforementioned method are shown in Table 2.

TABLE 2

| Example No. | Binding inhibitory rate (%) 10 µM |
|---|---|
| 9 (A) | >80 |
| 24 | >80 |
| 28 | >80 |
| 41 | >80 |
| 96 | >80 |
| 112 | >80 |
| 150 | >80 |

INDUSTRIAL APPLICABILITY

Compound (I) of the present invention has an excellent CRF antagonistic activity, and therefore useful as drugs for treating or preventing affective disorder, depression, anxiety, and the like.

The invention claimed is:

1. A compound represented by the formula:

A-W—Ar     (I)

wherein, A is a group represented by the formula:

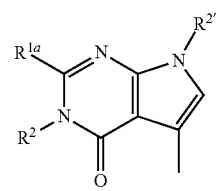

wherein R$^{1a}$ is
(1) an amino which is mono- or di-substituted with
  (i) a C$_{1-8}$ alkyl which may be substituted with a hydroxyl substituted with a C$_{1-8}$ alkyl,
  a C$_{3-7}$ cycloalkyl, a phenyl, a 4-methylphenyl, a hydroxyl substituted with a phenyl,
  a 2-chlorophenyl, a heterocyclic group, a 4-chlorophenyl, a 4-(benzyloxy)phenyl,
  a 3-methoxyphenyl, a 3-chlorophenyl, a 2'-cyanobiphenyl, a naphthyl, a 2,5-dimethoxyphenyl,
  a 3-fluoro-5-(trifluoromethyl)phenyl, an acyl, or an esterified or amidated carboxyl, (ii) a $C_{2-8}$ alkenyl,
(iii) a $C_{1-10}$ acyl, or
(iv) a $C_{3-7}$ cycloalkyl, or
(2) a cyclic amino;
$R^2$ is a hydrogen, a $C_{1-8}$ alkyl which may be substituted by a cyano or a phenyl;
$R^{2'}$ is
(1) a hydrogen,
(2) an acetyl, or
(3) a $C_{1-8}$ alkyl which may be substituted with a phenyl, a 4-methoxyphenyl or an acetyl;
W is a bond; and
Ar is a phenyl which is substituted with
(i) one or more $C_{1-8}$ alkyl which may be substituted with one or more halogen,
(ii) one or more alkoxy,
(iii) one or more halogen,
(iv) one or more benzyloxy, or
(v) one or more hydroxy;
or a salt thereof.

2. The compound according to claim 1, wherein the compound is 2-(dipropylamino)-5-mesityl-3,7-dimethyl-3,7-dihydro-4H-pyrrolo[2,3-d]pyrimidin-4-one.

3. A method for treating a disease wherein a CRF receptor is implicated, which comprises administering to a subject in need thereof an effective amount of a compound or salt according to claim 1, wherein the disease being treated is selected from the group consisting of affective disorder, depression and anxiety.

4. A pharmaceutical composition comprising the compound according to claim 1 or a salt thereof, and a pharmaceutically acceptable carrier.

5. The compound according to claim 1, wherein $R^{1a}$ is
(1) an amino which is mono- or di-substituted with
(i) a $C_{1-8}$ alkyl which may be substituted with a methoxy, a cyclopropyl, a phenyl,
a 4-methylphenyl, a phenoxy, a 2-chlorophenyl, a pyridyl, a 4-chlorophenyl,
a 4-(benzyloxy)phenyl, a 3-methoxyphenyl, a 3-chlorophenyl, a 2'-cyanobiphenyl, a pyrrolyl,
a naphthyl, a 2,5-dimethoxyphenyl, a quinolinyl, a 3-fluoro-5-(trifluoromethyl)phenyl,
a benzoyl, an ethoxycarbonyl, or an N,N-dimethylcarbamoyl,
(ii) a $C_{2-8}$ alkenyl,
(iii) a $C_{1-10}$ acyl, or
(iv) a $C_{3-7}$ cycloalkyl,
(2) a piperidinyl,
(3) a pyrrolidinyl, or
(4) a morpholinyl.

6. The compound according to claim 1, wherein $R^{1a}$ is an amino which is mono- or di-substituted with a $C_{1-8}$ alkyl.

7. The compound according to claim 1, wherein $R^2$ is a $C_{1-8}$ alkyl.

8. The compound according to claim 1, wherein $R^{2'}$ is a $C_{1-8}$ alkyl.

9. The compound according to claim 1, wherein Ar is a phenyl which is substituted with one or more $C_{1-8}$ alkyl.

10. The compound according to claim 1, wherein $R^{1a}$ is an amino group which is mono- or di-substituted with a $C_{1-8}$ alkyl;
$R^2$ is a $C_{1-8}$ alkyl;
$R^{2'}$ is a $C_{1-8}$ alkyl; and
Ar is a phenyl which is substituted with one or more $C_{1-8}$ alkyl.

* * * * *